(12) United States Patent
Sharma

(10) Patent No.: US 11,589,920 B2
(45) Date of Patent: *Feb. 28, 2023

(54) CATHETER WITH A DOUBLE BALLOON STRUCTURE TO GENERATE AND APPLY AN ABLATIVE ZONE TO TISSUE

(71) Applicant: Santa Anna Tech LLC, Santa Ana, CA (US)

(72) Inventor: Virender K Sharma, Paradise Valley, AZ (US)

(*) Notice: Subject to any disclaimer, the term of this patent is extended or adjusted under 35 U.S.C. 154(b) by 226 days.

This patent is subject to a terminal disclaimer.

(21) Appl. No.: 16/881,459

(22) Filed: May 22, 2020

(65) Prior Publication Data

US 2020/0352646 A1    Nov. 12, 2020

Related U.S. Application Data

(63) Continuation of application No. 15/600,670, filed on May 19, 2017, now Pat. No. 10,695,126, which is a
(Continued)

(51) Int. Cl.
*A61B 18/14* (2006.01)
*A61B 18/04* (2006.01)
(Continued)

(52) U.S. Cl.
CPC .......... *A61B 18/1492* (2013.01); *A61B 18/04* (2013.01); *A61B 90/39* (2016.02);
(Continued)

(58) Field of Classification Search
CPC ................ A61B 18/1492; A61B 18/04; A61B 2018/00357; A61B 2018/00791;
(Continued)

(56) References Cited

U.S. PATENT DOCUMENTS

| 408,899 A | 8/1889 | Small |
|---|---|---|
| 697,181 A | 4/1902 | Smith |

(Continued)

FOREIGN PATENT DOCUMENTS

| CN | 2757751 Y | 2/2006 |
|---|---|---|
| CN | 1803113 A | 7/2006 |

(Continued)

OTHER PUBLICATIONS

International Search Report for PCT/US21/13582, dated May 13, 2021.
(Continued)

*Primary Examiner* — Michael F Peffley
(74) *Attorney, Agent, or Firm* — Novel IP

(57) ABSTRACT

Ablation catheters and systems include coaxial catheter shafts with an inner lumen for delivering an ablative agent and an outer lumen for circulation of a cooling element about the catheter. Induction heating is used to heat a chamber and vaporize a fluid within by wrapping a coil about a ferromagnetic chamber and providing an alternating current to the coil. A magnetic field is created in the area surrounding the chamber which induces electric current flow in the chamber, heating the chamber and vaporizing the fluid inside. Positioning elements help maintain the device in the proper position with respect to the target tissue and also prevent the passage of ablative agent to normal tissues.

20 Claims, 114 Drawing Sheets

Related U.S. Application Data continuation-in-part of application No. 15/144,768, filed on May 2, 2016, now Pat. No. 10,064,697.

(60) Provisional application No. 62/425,144, filed on Nov. 22, 2016, provisional application No. 62/338,871, filed on May 19, 2016.

(51) Int. Cl.
| | |
|---|---|
| *A61B 90/00* | (2016.01) |
| *A61M 25/10* | (2013.01) |
| *A61B 5/0538* | (2021.01) |
| *A61B 5/00* | (2006.01) |
| *A61B 18/00* | (2006.01) |
| *A61B 17/00* | (2006.01) |
| *A61B 17/42* | (2006.01) |

(52) U.S. Cl.
CPC ....... *A61M 25/1018* (2013.01); *A61B 5/0538* (2013.01); *A61B 5/6853* (2013.01); *A61B 2017/00026* (2013.01); *A61B 2017/00044* (2013.01); *A61B 2017/00053* (2013.01); *A61B 2017/00084* (2013.01); *A61B 2017/00243* (2013.01); *A61B 2017/00274* (2013.01); *A61B 2017/00809* (2013.01); *A61B 2017/00818* (2013.01); *A61B 2017/4216* (2013.01); *A61B 2018/005* (2013.01); *A61B 2018/00023* (2013.01); *A61B 2018/00244* (2013.01); *A61B 2018/00285* (2013.01); *A61B 2018/00357* (2013.01); *A61B 2018/00488* (2013.01); *A61B 2018/00494* (2013.01); *A61B 2018/00541* (2013.01); *A61B 2018/00547* (2013.01); *A61B 2018/00559* (2013.01); *A61B 2018/00577* (2013.01); *A61B 2018/00642* (2013.01); *A61B 2018/00744* (2013.01); *A61B 2018/00791* (2013.01); *A61B 2018/00821* (2013.01); *A61B 2018/00839* (2013.01); *A61B 2018/00863* (2013.01); *A61B 2018/048* (2013.01); *A61B 2090/064* (2016.02); *A61B 2090/0811* (2016.02); *A61B 2090/3925* (2016.02); *A61B 2090/3966* (2016.02); *A61M 2205/3368* (2013.01)

(58) Field of Classification Search
CPC .... A61B 2018/048; A61B 2018/00023; A61B 2018/00244; A61B 2018/00285; A61B 2018/00488; A61B 2018/00494; A61B 2018/005; A61B 2018/00541; A61B 2018/00547; A61B 2018/00559; A61B 2018/00577; A61B 2018/00642; A61B 2018/00744; A61B 2018/00821; A61B 2018/00839; A61B 2018/00863; A61B 2090/065; A61B 2090/376; A61B 2090/064; A61B 2218/007; A61B 5/1076; A61B 5/6853; A61M 25/1018

See application file for complete search history.

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,289,138 A | 9/1981 | Halvorsen |
| RE32,204 E | 7/1986 | Halvorsen |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,828,544 A | 5/1989 | Lane |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,147,355 A | 9/1992 | Friedman |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,243,980 A | 9/1993 | Mehra |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,383,852 A | 1/1995 | Stevens-Wright |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,425,731 A | 6/1995 | Daniel |
| 5,425,931 A | 6/1995 | Arai |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Rath |
| 5,462,521 A | 10/1995 | Brucker |
| 5,462,527 A | 10/1995 | Stevens-Wright |
| 5,470,308 A | 11/1995 | Edwards |
| 5,470,309 A | 11/1995 | Edwards |
| 5,482,037 A | 1/1996 | Borghi |
| 5,484,400 A | 1/1996 | Edwards |
| 5,500,012 A | 3/1996 | Brucker |
| 5,503,638 A | 4/1996 | Cooper |
| 5,507,784 A | 4/1996 | Hill |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |

(56) References Cited

U.S. PATENT DOCUMENTS

| | | |
|---|---|---|
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,772 A | 11/1996 | Lennox |
| 5,575,803 A | 11/1996 | Cooper |
| 5,584,872 A | 12/1996 | LaFontaine |
| 5,588,432 A | 12/1996 | Crowley |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,609,151 A | 3/1997 | Mulier |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,630,837 A | 5/1997 | Crowley |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,674,217 A | 10/1997 | Wahlstrom |
| 5,681,282 A | 10/1997 | Eggers |
| 5,683,366 A | 11/1997 | Eggers |
| 5,685,878 A | 11/1997 | Falwell |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,715,817 A | 2/1998 | Stevens-Wright |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,759,158 A | 6/1998 | Swanson |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |
| 5,800,379 A | 9/1998 | Edwards |
| 5,800,482 A | 9/1998 | Pomeranz |
| 5,800,493 A | 9/1998 | Stevens |
| 5,807,249 A | 9/1998 | Qin |
| 5,810,764 A | 9/1998 | Eggers |
| 5,820,580 A | 10/1998 | Edwards |
| 5,824,703 A | 10/1998 | Clark, Jr. |
| 5,827,268 A | 10/1998 | Laufer |
| 5,830,179 A | 11/1998 | Mikus |
| 5,836,906 A | 11/1998 | Edwards |
| 5,840,031 A | 11/1998 | Crowley |
| 5,840,079 A | 11/1998 | Warman |
| 5,843,019 A | 12/1998 | Eggers |
| 5,843,073 A | 12/1998 | Sinofsky |
| 5,849,011 A | 12/1998 | Jones |
| 5,861,005 A | 1/1999 | Kontos |
| 5,871,469 A | 2/1999 | Eggers |
| 5,871,481 A | 2/1999 | Kannenberg |
| 5,873,855 A | 2/1999 | Eggers |
| 5,873,877 A | 2/1999 | McGaffigan |
| 5,879,295 A | 3/1999 | Li |
| 5,879,329 A | 3/1999 | Ginsburg |
| 5,885,243 A | 3/1999 | Capetan |
| 5,888,198 A | 3/1999 | Eggers |
| 5,891,095 A | 4/1999 | Eggers |
| 5,891,134 A | 4/1999 | Goble |
| 5,891,457 A | 4/1999 | Neuwirth |
| 5,895,417 A | 4/1999 | Pomeranz |
| 5,897,553 A | 4/1999 | Mulier |
| 5,902,272 A | 5/1999 | Eggers |
| 5,913,856 A | 6/1999 | Chia |
| 5,919,188 A | 7/1999 | Shearon |
| 5,931,835 A | 8/1999 | Mackey |
| 5,935,102 A | 8/1999 | Bowden |
| 5,938,660 A | 8/1999 | Swartz |
| 5,944,686 A | 8/1999 | Patterson |
| 5,944,715 A | 8/1999 | Goble |
| 5,954,714 A | 9/1999 | Saadat |
| 5,957,919 A | 9/1999 | Laufer |
| 5,957,922 A | 9/1999 | Imran |
| 5,964,752 A | 10/1999 | Stone |
| 5,964,756 A | 10/1999 | McGaffigan |
| 5,968,037 A | 10/1999 | Rizoiu |
| 5,976,123 A | 11/1999 | Baumgardner |
| 5,980,504 A | 11/1999 | Sharkey |
| 5,980,516 A | 11/1999 | Mulier |
| 5,986,662 A | 11/1999 | Argiro |
| 5,989,212 A | 11/1999 | Sussman |
| 5,989,238 A | 11/1999 | Ginsburg |
| 5,989,249 A | 11/1999 | Kirwan, Jr. |
| 5,989,445 A | 11/1999 | Wise |
| 5,993,462 A | 11/1999 | Pomeranz |
| 5,997,499 A | 12/1999 | Sussman |
| 6,002,955 A | 12/1999 | Willems |
| 6,004,269 A | 12/1999 | Crowley |
| 6,010,500 A | 1/2000 | Sherman |
| 6,014,581 A | 1/2000 | Whayne |
| 6,015,406 A | 1/2000 | Goble |
| 6,015,407 A | 1/2000 | Rieb |
| 6,016,809 A | 1/2000 | Mulier |
| 6,017,361 A | 1/2000 | Mikus |
| 6,024,733 A | 2/2000 | Eggers |
| 6,027,501 A | 2/2000 | Goble |
| 6,032,077 A | 2/2000 | Pomeranz |
| 6,032,674 A | 3/2000 | Eggers |
| 6,035,226 A | 3/2000 | Panescu |
| 6,036,713 A | 3/2000 | Kieturakis |
| 6,045,532 A | 4/2000 | Eggers |
| 6,045,549 A | 4/2000 | Smethers |
| 6,047,700 A | 4/2000 | Eggers |
| 6,053,172 A | 4/2000 | Hovda |
| 6,053,909 A | 4/2000 | Shadduck |
| 6,056,746 A | 5/2000 | Goble |
| 6,059,011 A | 5/2000 | Giolo |
| 6,063,079 A | 5/2000 | Hovda |
| 6,063,081 A | 5/2000 | Mulier |
| 6,064,902 A | 5/2000 | Haissaguerre |
| 6,066,132 A | 5/2000 | Chen |
| 6,066,134 A | 5/2000 | Eggers |
| 6,068,629 A | 5/2000 | Haissaguerre |
| 6,071,281 A | 6/2000 | Burnside |
| 6,074,358 A | 6/2000 | Andrew |
| 6,077,257 A | 6/2000 | Edwards |
| 6,080,128 A | 6/2000 | Sussman |
| 6,080,151 A | 6/2000 | Swartz |
| 6,083,255 A | 7/2000 | Laufer |
| 6,086,585 A | 7/2000 | Hovda |
| 6,095,149 A | 8/2000 | Sharkey |
| 6,099,251 A | 8/2000 | LaFleur |
| 6,102,046 A | 8/2000 | Weinstein |
| 6,102,885 A | 8/2000 | Bass |
| 6,105,581 A | 8/2000 | Eggers |
| 6,106,516 A | 8/2000 | Massengill |
| 6,109,268 A | 8/2000 | Thapliyal |
| 6,110,162 A | 8/2000 | Sussman |
| 6,112,123 A | 8/2000 | Kelleher |
| 6,113,593 A | 9/2000 | Tu |
| 6,113,597 A | 9/2000 | Eggers |
| 6,113,722 A | 9/2000 | Hoffman |
| 6,117,109 A | 9/2000 | Eggers |

(56) References Cited

U.S. PATENT DOCUMENTS

| | | |
|---|---|---|
| 6,119,041 A | 9/2000 | Pomeranz |
| 6,120,496 A | 9/2000 | Whayne |
| 6,126,682 A | 10/2000 | Sharkey |
| 6,129,669 A | 10/2000 | Panescu |
| 6,130,671 A | 10/2000 | Argiro |
| 6,139,538 A | 10/2000 | Houghton |
| 6,139,571 A | 10/2000 | Fuller |
| 6,149,620 A | 11/2000 | Baker |
| 6,152,144 A | 11/2000 | Lesh |
| 6,156,036 A | 12/2000 | Sussman |
| 6,159,194 A | 12/2000 | Eggers |
| 6,159,208 A | 12/2000 | Hovda |
| 6,162,232 A | 12/2000 | Shadduck |
| 6,168,594 B1 | 1/2001 | LaFontaine |
| 6,174,308 B1 | 1/2001 | Goble |
| 6,176,842 B1 | 1/2001 | Tachibana |
| 6,178,354 B1 | 1/2001 | Gibson |
| 6,179,805 B1 | 1/2001 | Sussman |
| 6,179,824 B1 | 1/2001 | Eggers |
| 6,179,836 B1 | 1/2001 | Eggers |
| 6,183,469 B1 | 2/2001 | Thapliyal |
| 6,190,381 B1 | 2/2001 | Olsen |
| 6,192,266 B1 | 2/2001 | Dupree |
| 6,194,066 B1 | 2/2001 | Hoffman |
| 6,196,989 B1 | 3/2001 | Padget |
| 6,200,333 B1 | 3/2001 | Laufer |
| 6,203,542 B1 | 3/2001 | Ellsberry |
| 6,206,847 B1 | 3/2001 | Edwards |
| 6,206,848 B1 | 3/2001 | Sussman |
| 6,210,402 B1 | 4/2001 | Olsen |
| 6,210,404 B1 | 4/2001 | Shadduck |
| 6,210,405 B1 | 4/2001 | Goble |
| 6,217,528 B1 | 4/2001 | Koblish |
| 6,217,607 B1 | 4/2001 | Alt |
| 6,219,059 B1 | 4/2001 | Argiro |
| 6,224,592 B1 | 5/2001 | Eggers |
| 6,228,078 B1 | 5/2001 | Eggers |
| 6,228,081 B1 | 5/2001 | Goble |
| 6,228,082 B1 | 5/2001 | Baker |
| 6,231,567 B1 | 5/2001 | Rizoiu |
| 6,234,178 B1 | 5/2001 | Goble |
| 6,235,020 B1 | 5/2001 | Cheng |
| 6,235,025 B1 | 5/2001 | Swartz |
| 6,238,389 B1 | 5/2001 | Paddock |
| 6,238,391 B1 | 5/2001 | Olsen |
| 6,241,666 B1 | 6/2001 | Pomeranz |
| 6,241,702 B1 | 6/2001 | Lundquist |
| 6,245,065 B1 | 6/2001 | Panescu |
| 6,254,597 B1 | 7/2001 | Rizoiu |
| 6,254,600 B1 | 7/2001 | Willink |
| 6,256,537 B1 | 7/2001 | Stoop |
| 6,258,087 B1 | 7/2001 | Edwards |
| 6,261,286 B1 | 7/2001 | Goble |
| 6,261,311 B1 | 7/2001 | Sharkey |
| 6,264,650 B1 | 7/2001 | Hovda |
| 6,264,651 B1 | 7/2001 | Underwood |
| 6,264,652 B1 | 7/2001 | Eggers |
| 6,264,654 B1 | 7/2001 | Swartz |
| 6,267,760 B1 | 7/2001 | Swanson |
| 6,270,476 B1 | 8/2001 | Santoianni |
| 6,270,515 B1 | 8/2001 | Linden |
| 6,277,112 B1 | 8/2001 | Underwood |
| 6,277,114 B1 | 8/2001 | Bullivant |
| 6,277,130 B1 | 8/2001 | Shadduck |
| 6,283,961 B1 | 9/2001 | Underwood |
| 6,283,989 B1 | 9/2001 | Laufer |
| 6,287,274 B1 | 9/2001 | Sussman |
| 6,287,301 B1 | 9/2001 | Thompson |
| 6,287,320 B1 | 9/2001 | Slepian |
| 6,290,715 B1 | 9/2001 | Sharkey |
| 6,293,942 B1 | 9/2001 | Goble |
| 6,296,636 B1 | 10/2001 | Cheng |
| 6,296,638 B1 | 10/2001 | Davison |
| 6,299,620 B1 | 10/2001 | Shadduck |
| 6,299,633 B1 | 10/2001 | Laufer |
| 6,300,150 B1 | 10/2001 | Venkatasubramanian |
| 6,306,129 B1 | 10/2001 | Little |
| 6,306,134 B1 | 10/2001 | Goble |
| 6,309,375 B1 | 10/2001 | Glines |
| 6,309,387 B1 | 10/2001 | Eggers |
| 6,312,408 B1 | 11/2001 | Eggers |
| 6,312,474 B1 | 11/2001 | Francis |
| 6,315,755 B1 | 11/2001 | Sussman |
| 6,319,222 B1 | 11/2001 | Andrew |
| 6,322,549 B1 | 11/2001 | Eggers |
| 6,327,505 B1 | 12/2001 | Medhkour |
| 6,331,171 B1 | 12/2001 | Cohen |
| 6,355,032 B1 | 3/2002 | Hovda |
| 6,356,790 B1 | 3/2002 | Maguire |
| 6,358,248 B1 | 3/2002 | Mulier |
| 6,363,937 B1 | 4/2002 | Hovda |
| 6,364,877 B1 | 4/2002 | Goble |
| 6,369,465 B1 | 4/2002 | Swanson |
| 6,375,635 B1 | 4/2002 | Moutafis |
| 6,379,350 B1 | 4/2002 | Sharkey |
| 6,379,351 B1 | 4/2002 | Thapliyal |
| 6,389,311 B1 | 5/2002 | Whayne |
| 6,391,025 B1 | 5/2002 | Weinstein |
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,505 B1 | 7/2002 | Fleischman |
| 6,416,507 B1 | 7/2002 | Eggers |
| 6,416,508 B1 | 7/2002 | Eggers |
| 6,416,509 B1 | 7/2002 | Goble |
| 6,419,673 B1 | 7/2002 | Edwards |
| 6,423,027 B1 | 7/2002 | Gonon |
| 6,428,537 B1 | 8/2002 | Swanson |
| 6,432,103 B1 | 8/2002 | Ellsberry |
| 6,434,424 B1 | 8/2002 | Igel |
| 6,438,407 B1 | 8/2002 | Ousdigian |
| 6,440,127 B2 | 8/2002 | McGovern |
| 6,443,950 B1 | 9/2002 | Sutton |
| 6,458,231 B1 | 10/2002 | Wapner |
| 6,461,296 B1 | 10/2002 | Desai |
| 6,461,350 B1 | 10/2002 | Underwood |
| 6,461,354 B1 | 10/2002 | Olsen |
| 6,461,356 B1 | 10/2002 | Patterson |
| 6,464,694 B1 | 10/2002 | Massengill |
| 6,464,695 B2 | 10/2002 | Hovda |
| 6,464,699 B1 | 10/2002 | Swanson |
| 6,464,700 B1 | 10/2002 | Koblish |
| 6,468,270 B1 | 10/2002 | Hovda |
| 6,468,271 B1 | 10/2002 | Wentzel |
| 6,468,272 B1 | 10/2002 | Koblish |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,488,680 B1 | 12/2002 | Francischelli |
| 6,491,710 B2 | 12/2002 | Satake |
| 6,493,589 B1 | 12/2002 | Medhkour |
| 6,494,880 B1 | 12/2002 | Swanson |
| 6,500,144 B1 | 12/2002 | Russell |
| 6,500,173 B2 | 12/2002 | Underwood |
| 6,508,816 B2 | 1/2003 | Shadduck |
| 6,510,854 B2 | 1/2003 | Goble |
| 6,514,245 B1 | 2/2003 | Holland |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,540,743 B2 | 4/2003 | Olson |
| 6,542,781 B1 | 4/2003 | Koblish |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |

(56) References Cited

U.S. PATENT DOCUMENTS

| | | |
|---|---|---|
| 6,551,274 B2 | 4/2003 | Heiner |
| 6,551,300 B1 | 4/2003 | McGaffigan |
| 6,551,309 B1 | 4/2003 | LePivert |
| 6,557,559 B1 | 5/2003 | Eggers |
| 6,558,314 B1 | 5/2003 | Adelman |
| 6,558,379 B1 | 5/2003 | Batchelor |
| 6,564,098 B1 | 5/2003 | Kerver |
| 6,566,636 B1 | 5/2003 | Bentley |
| 6,569,146 B1 | 5/2003 | Werner |
| 6,569,162 B2 | 5/2003 | He |
| 6,572,611 B1 | 6/2003 | Falwell |
| 6,575,929 B2 | 6/2003 | Sussman |
| 6,575,932 B1 | 6/2003 | OBrien |
| 6,575,968 B1 | 6/2003 | Eggers |
| 6,579,270 B2 | 6/2003 | Sussman |
| 6,579,288 B1 | 6/2003 | Swanson |
| 6,582,423 B1 | 6/2003 | Thapliyal |
| 6,585,639 B1 | 7/2003 | Kotmel |
| 6,585,732 B2 | 7/2003 | Mulier |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,084 B2 | 8/2003 | Acker |
| 6,605,087 B2 | 8/2003 | Swartz |
| 6,607,529 B1 | 8/2003 | Jones |
| 6,610,043 B1 | 8/2003 | Ingenito |
| 6,610,055 B1 | 8/2003 | Swanson |
| 6,613,046 B1 | 9/2003 | Jenkins |
| 6,620,130 B1 | 9/2003 | Ginsburg |
| 6,620,155 B2 | 9/2003 | Underwood |
| 6,620,159 B2 | 9/2003 | Hegde |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,638,278 B2 | 10/2003 | Falwell |
| 6,640,120 B1 | 10/2003 | Swanson |
| 6,647,300 B1 | 11/2003 | Balasubramanian |
| 6,648,847 B2 | 11/2003 | Sussman |
| 6,650,937 B2 | 11/2003 | Kerver |
| 6,652,555 B1 | 11/2003 | VanTassel |
| 6,652,594 B2 | 11/2003 | Francis |
| 6,653,525 B2 | 11/2003 | Ingenito |
| 6,656,174 B1 | 12/2003 | Hegde |
| 6,659,106 B1 | 12/2003 | Hovda |
| 6,659,981 B2 | 12/2003 | Stewart |
| 6,666,863 B2 | 12/2003 | Wentzel |
| 6,666,864 B2 | 12/2003 | Bencini |
| 6,668,195 B2 | 12/2003 | Warman |
| 6,669,685 B1 | 12/2003 | Rizoiu |
| 6,669,693 B2 | 12/2003 | Friedman |
| 6,669,694 B2 | 12/2003 | Shadduck |
| 6,673,071 B2 | 1/2004 | VanDusseldorp |
| 6,676,628 B2 | 1/2004 | Sussman |
| 6,676,629 B2 | 1/2004 | Andrew |
| 6,679,264 B1 | 1/2004 | Deem |
| 6,679,269 B2 | 1/2004 | Swanson |
| 6,679,879 B2 | 1/2004 | Shadduck |
| 6,682,520 B2 | 1/2004 | Ingenito |
| 6,692,491 B1 | 2/2004 | Phan |
| 6,692,494 B1 | 2/2004 | Cooper |
| 6,695,785 B2 | 2/2004 | Brisken |
| 6,695,839 B2 | 2/2004 | Sharkey |
| 6,699,244 B2 | 3/2004 | Carranza |
| 6,706,038 B2 | 3/2004 | Francischelli |
| 6,708,056 B2 | 3/2004 | Duchon |
| 6,711,444 B2 | 3/2004 | Koblish |
| 6,712,811 B2 | 3/2004 | Underwood |
| 6,712,812 B2 | 3/2004 | Roschak |
| 6,716,190 B1 | 4/2004 | Glines |
| 6,716,252 B2 | 4/2004 | Lazarovitz |
| 6,718,206 B2 | 4/2004 | Casavant |
| 6,719,738 B2 | 4/2004 | Mehier |
| 6,719,754 B2 | 4/2004 | Underwood |
| 6,719,755 B2 | 4/2004 | Sliwa, Jr. |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,740,082 B2 | 5/2004 | Shadduck |
| 6,745,080 B2 | 6/2004 | Koblish |
| 6,746,447 B2 | 6/2004 | Davison |
| 6,749,604 B1 | 6/2004 | Eggers |
| 6,755,790 B2 | 6/2004 | Stewart |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,788,969 B2 | 9/2004 | Dupree |
| 6,805,130 B2 | 10/2004 | Tasto |
| 6,813,520 B2 | 11/2004 | Truckai |
| 6,814,731 B2 | 11/2004 | Swanson |
| 6,824,515 B2 | 11/2004 | Suorsa |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,887,238 B2 | 5/2005 | Jahns |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,291 B2 | 5/2005 | Stoop |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,908,464 B2 | 6/2005 | Jenkins |
| 6,911,028 B2 | 6/2005 | Shadduck |
| 6,913,604 B2 | 7/2005 | Mihalik |
| 6,915,806 B2 | 7/2005 | Pacek |
| 6,916,317 B2 | 7/2005 | Falwell |
| 6,916,318 B2 | 7/2005 | Francischelli |
| 6,917,834 B2 | 7/2005 | Koblish |
| 6,918,903 B2 | 7/2005 | Bass |
| 6,921,385 B2 | 7/2005 | Clements |
| 6,926,712 B2 | 8/2005 | Phan |
| 6,926,714 B1 | 8/2005 | Sra |
| 6,929,640 B1 | 8/2005 | Underwood |
| 6,929,642 B2 | 8/2005 | Xiao |
| 6,939,350 B2 | 9/2005 | Phan |
| 6,949,096 B2 | 9/2005 | Davison |
| 6,949,097 B2 | 9/2005 | Stewart |
| 6,949,098 B2 | 9/2005 | Mulier |
| 6,950,689 B1 | 9/2005 | Willis |
| 6,952,615 B2 | 10/2005 | Satake |
| 6,955,674 B2 | 10/2005 | Eick |
| 6,955,675 B2 | 10/2005 | Jain |

(56) References Cited

U.S. PATENT DOCUMENTS

| | | |
|---|---|---|
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,974,464 B2 | 12/2005 | Quijano |
| 6,978,184 B1 | 12/2005 | Marcus |
| 6,979,329 B2 | 12/2005 | Burnside |
| 6,986,769 B2 | 1/2006 | Nelson |
| 6,989,010 B2 | 1/2006 | Francischelli |
| 6,991,028 B2 | 1/2006 | Comeaux |
| 6,991,631 B2 | 1/2006 | Woloszko |
| 6,994,092 B2 | 2/2006 | Van der Burg |
| 7,004,940 B2 | 2/2006 | Ryan |
| 7,004,941 B2 | 2/2006 | Tvinnereim |
| 7,008,401 B2 | 3/2006 | Thompson |
| 7,008,417 B2 | 3/2006 | Eick |
| 7,011,655 B2 | 3/2006 | Thompson |
| 7,011,671 B2 | 3/2006 | Welch |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,047,068 B2 | 5/2006 | Haissaguerre |
| 7,047,074 B2 | 5/2006 | Connelly |
| 7,058,443 B2 | 6/2006 | Struble |
| 7,079,892 B2 | 7/2006 | Dahl |
| 7,081,115 B2 | 7/2006 | Taimisto |
| 7,082,330 B2 | 7/2006 | Stadler |
| 7,083,612 B2 | 8/2006 | Littrup |
| 7,083,614 B2 | 8/2006 | Fjield |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,101,368 B2 | 9/2006 | Lafontaine |
| 7,104,986 B2 | 9/2006 | Hovda |
| 7,105,007 B2 | 9/2006 | Hibler |
| 7,107,098 B2 | 9/2006 | Sharma |
| 7,112,198 B2 | 9/2006 | Satake |
| 7,113,838 B2 | 9/2006 | Funk |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Gray |
| 7,153,301 B2 | 12/2006 | Swartz |
| 7,166,105 B2 | 1/2007 | Mulier |
| 7,169,143 B2 | 1/2007 | Eggers |
| 7,169,164 B2 | 1/2007 | Borillo |
| 7,172,589 B2 | 2/2007 | Lafontaine |
| 7,175,619 B2 | 2/2007 | Koblish |
| 7,175,734 B2 | 2/2007 | Stewart |
| 7,179,255 B2 | 2/2007 | Lettice |
| 7,181,273 B2 | 2/2007 | Havel |
| 7,182,764 B2 | 2/2007 | Jenkins |
| 7,186,234 B2 | 3/2007 | Dahla |
| 7,186,250 B2 | 3/2007 | Koblish |
| 7,189,227 B2 | 3/2007 | Lafontaine |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,225,040 B2 | 5/2007 | Eller |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,255,695 B2 | 8/2007 | Falwell |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,280,881 B2 | 10/2007 | Eller |
| 7,285,119 B2 | 10/2007 | Stewart |
| 7,297,143 B2 | 11/2007 | Woloszko |
| 7,297,145 B2 | 11/2007 | Woloszko |
| 7,303,558 B2 | 12/2007 | Swanson |
| 7,311,705 B2 | 12/2007 | Sra |
| 7,318,821 B2 | 1/2008 | Lalonde |
| 7,320,325 B2 | 1/2008 | Duchon |
| 7,321,794 B2 | 1/2008 | Thacker |
| 7,322,973 B2 | 1/2008 | Nahon |
| 7,331,958 B2 | 2/2008 | Falwell |
| 7,335,195 B2 | 2/2008 | Mehier |
| 7,335,197 B2 | 2/2008 | Sage |
| 7,338,434 B1 | 3/2008 | Haarstad |
| 7,340,307 B2 | 3/2008 | Maguire |
| 7,347,856 B2 | 3/2008 | Wittenberger |
| 7,347,858 B2 | 3/2008 | Francischelli |
| 7,347,859 B2 | 3/2008 | Garabedian |
| 7,357,800 B2 | 4/2008 | Swanson |
| 7,364,546 B2 | 4/2008 | Panescu |
| 7,364,578 B2 | 4/2008 | Francischelli |
| 7,364,579 B2 | 4/2008 | Mulier |
| 7,367,972 B2 | 5/2008 | Francischelli |
| 7,371,233 B2 | 5/2008 | Swanson |
| 7,410,486 B2 | 8/2008 | Fuimaono |
| 7,419,500 B2 | 9/2008 | Marko |
| 7,422,588 B2 | 9/2008 | Mulier |
| 7,422,591 B2 | 9/2008 | Phan |
| 7,429,262 B2 | 9/2008 | Woloszko |
| 7,435,250 B2 | 10/2008 | Francischelli |
| 7,438,714 B2 | 10/2008 | Phan |
| 7,450,996 B2 | 11/2008 | MacDonald |
| 7,455,669 B2 | 11/2008 | Swanson |
| 7,470,228 B2 | 12/2008 | Connors |
| 7,470,272 B2 | 12/2008 | Mulier |
| 7,474,909 B2 | 1/2009 | Phan |
| 7,488,289 B2 | 2/2009 | Suorsa |
| 7,503,904 B2 | 3/2009 | Choi |
| 7,512,445 B2 | 3/2009 | Truckai |
| 7,517,315 B2 | 4/2009 | Willis |
| 7,549,987 B2 | 6/2009 | Shadduck |
| 7,549,988 B2 | 6/2009 | Eberl |
| 7,559,367 B2 | 7/2009 | Vinegar |
| 7,582,084 B2 | 9/2009 | Swanson |
| 7,585,295 B2 | 9/2009 | Ben-Nun |
| 7,585,310 B2 | 9/2009 | Phan |
| 7,597,147 B2 | 10/2009 | Vitek |
| 7,597,704 B2 | 10/2009 | Frazier |
| 7,608,072 B2 | 10/2009 | Swanson |
| 7,610,078 B2 | 10/2009 | Willis |
| 7,633,502 B2 | 12/2009 | Willis |
| 7,647,124 B2 | 1/2010 | Williams |
| 7,650,186 B2 | 1/2010 | Hastings |
| 7,662,151 B2 | 2/2010 | Crompton, Jr. |
| 7,674,256 B2 | 3/2010 | Marrouche |
| 7,674,259 B2 | 3/2010 | Shadduck |
| 7,678,108 B2 | 3/2010 | Chrisitian |
| 7,678,111 B2 | 3/2010 | Mulier |
| 7,706,860 B2 | 4/2010 | McGee |
| 7,706,882 B2 | 4/2010 | Francischelli |
| 7,711,421 B2 | 5/2010 | Shafer |
| 7,713,282 B2 | 5/2010 | Frazier |
| 7,720,520 B2 | 5/2010 | Willis |
| 7,722,604 B2 | 5/2010 | Brown, III |
| 7,727,228 B2 * | 6/2010 | Abboud .......... A61M 25/1011 606/27 |
| 7,727,231 B2 | 6/2010 | Swanson |
| 7,734,346 B2 | 6/2010 | Van Bolhuis |
| 7,735,493 B2 | 6/2010 | Van der Burg |
| 7,740,623 B2 | 6/2010 | Nayak |
| 7,740,627 B2 | 6/2010 | Gammie |
| 7,753,871 B2 | 7/2010 | Mehier |
| 7,758,580 B2 | 7/2010 | Rothstein |
| 7,785,289 B2 | 8/2010 | Rios |
| 7,785,323 B2 | 8/2010 | Jenkins |
| 7,792,580 B2 | 9/2010 | Borowitz |
| 7,794,454 B2 | 9/2010 | Abboud |

(56) References Cited

U.S. PATENT DOCUMENTS

| | | |
|---|---|---|
| 7,794,460 B2 | 9/2010 | Mulier |
| 7,818,039 B2 | 10/2010 | Jahns |
| 7,824,399 B2 | 11/2010 | Francischelli |
| 7,831,133 B2 | 11/2010 | Vinegar |
| 7,837,676 B2 | 11/2010 | Sinelnikov |
| 7,846,157 B2 | 12/2010 | Kozel |
| 7,850,685 B2 | 12/2010 | Kunis |
| 7,861,725 B2 | 1/2011 | Swanson |
| 7,862,561 B2 | 1/2011 | Swanson |
| 7,862,562 B2 | 1/2011 | Eberl |
| 7,871,409 B2 | 1/2011 | Briscoe |
| 7,877,137 B2 | 1/2011 | Whitehurst |
| 7,892,229 B2 | 2/2011 | Shadduck |
| 7,896,871 B2 | 3/2011 | Bhushan |
| 7,913,698 B2 | 3/2011 | Barry |
| 7,922,714 B2 | 4/2011 | Stevens-Wright |
| 7,937,161 B2 | 5/2011 | Hastings |
| 7,938,828 B2 | 5/2011 | Koblish |
| 7,953,475 B2 | 5/2011 | Harlev |
| 7,955,325 B2 | 6/2011 | Wittenberger |
| 7,959,630 B2 | 6/2011 | Taimisto |
| 7,963,963 B2 | 6/2011 | Francischelli |
| 7,972,327 B2 | 7/2011 | Eberl |
| 7,972,359 B2 | 7/2011 | Kreidler |
| 7,975,703 B2 | 7/2011 | Jahns |
| 7,976,541 B2 | 7/2011 | McGee |
| 7,993,323 B2 | 8/2011 | Barry |
| 8,002,738 B2 | 8/2011 | White |
| 8,007,497 B2 | 8/2011 | Young |
| RE42,724 E | 9/2011 | Falwell |
| 8,014,711 B2 | 9/2011 | Ito |
| 8,016,822 B2 | 9/2011 | Swanson |
| 8,016,823 B2 | 9/2011 | Shadduck |
| 8,027,791 B2 | 9/2011 | Soykan |
| 8,050,774 B2 | 11/2011 | Kveen |
| 8,052,676 B2 | 11/2011 | Swanson |
| 8,052,715 B2 | 11/2011 | Quinn |
| 8,055,357 B2 | 11/2011 | Swanson |
| 8,057,466 B2 | 11/2011 | Soykan |
| RE43,007 E | 12/2011 | Lalonde |
| 8,080,006 B2 | 12/2011 | Lafontaine |
| 8,086,293 B2 | 12/2011 | Boseck |
| 8,092,444 B2 | 1/2012 | Lentz |
| 8,116,884 B2 | 2/2012 | Jung |
| 8,123,741 B2 | 2/2012 | Marrouche |
| 8,142,424 B2 | 3/2012 | Swanson |
| 8,142,470 B2 | 3/2012 | Quinn |
| 8,145,113 B2 | 3/2012 | Murakami |
| 8,147,532 B2 | 4/2012 | Barry |
| 8,162,929 B2 | 4/2012 | Lentz |
| 8,162,941 B2 | 4/2012 | Christian |
| 8,165,691 B2 | 4/2012 | Ellingson |
| 8,172,837 B2 | 5/2012 | Rothstein |
| 8,187,269 B2 | 5/2012 | Shadduck |
| 8,197,496 B2 | 6/2012 | Roue |
| 8,197,527 B2 | 6/2012 | Borillo |
| 8,216,224 B2 | 7/2012 | Morris |
| 8,221,402 B2 | 7/2012 | Francischelli |
| 8,221,411 B2 | 7/2012 | Francischelli |
| 8,221,445 B2 | 7/2012 | Van Tassel |
| 8,224,165 B2 | 7/2012 | Vinegar |
| 8,226,637 B2 | 7/2012 | Satake |
| 8,229,588 B2 | 7/2012 | Tsen |
| 8,231,617 B2 | 7/2012 | Satake |
| 8,235,976 B2 | 8/2012 | Lafontaine |
| 8,251,985 B2 | 8/2012 | Hoey |
| 8,260,422 B2 | 9/2012 | Ellingson |
| 8,272,383 B2 | 9/2012 | Hoey |
| 8,273,079 B2 | 9/2012 | Hoey |
| 8,273,084 B2 | 9/2012 | Kunis |
| 8,290,600 B2 | 10/2012 | Hastings |
| 8,298,219 B2 | 10/2012 | Lalonde |
| 8,306,612 B2 | 11/2012 | Macadam |
| 8,313,485 B2 | 11/2012 | Shadduck |
| 8,322,335 B2 | 12/2012 | Barry |
| 8,332,035 B2 | 12/2012 | Iaizzo |
| 8,333,757 B2 | 12/2012 | James |
| 8,333,764 B2 | 12/2012 | Francischelli |
| 8,353,900 B2 | 1/2013 | Jung |
| 8,355,623 B2 | 1/2013 | Vinegar |
| 8,361,059 B2 | 1/2013 | Abboud |
| 8,372,065 B2 | 2/2013 | Hoey |
| 8,388,611 B2 | 3/2013 | Shadduck |
| 8,401,644 B2 | 3/2013 | Gunderson |
| 8,414,573 B2 | 4/2013 | Francischelli |
| 8,419,723 B2 | 4/2013 | Shadduck |
| 8,425,456 B2 | 4/2013 | Mihalik |
| 8,437,840 B2 | 5/2013 | Patel |
| 8,437,870 B2 | 5/2013 | Tsai |
| 8,444,636 B2 | 5/2013 | Shadduck |
| 8,454,587 B2 | 6/2013 | Lalonde |
| 8,460,282 B2 | 6/2013 | Mcauley |
| 8,465,481 B2 | 6/2013 | James |
| 8,475,440 B2 | 7/2013 | Abboud |
| 8,480,664 B2 | 7/2013 | Watson |
| 8,504,132 B2 | 8/2013 | Friedman |
| 8,512,326 B2 | 8/2013 | Shadduck |
| 8,512,337 B2 | 8/2013 | Francischelli |
| 8,521,074 B2 | 8/2013 | Murakami |
| 8,521,281 B2 | 8/2013 | Patel |
| 8,527,027 B2 | 9/2013 | Falwell |
| 8,556,892 B2 | 10/2013 | Hong |
| 8,571,626 B2 | 10/2013 | Lau |
| 8,574,226 B2 | 11/2013 | Shadduck |
| 8,579,888 B2 * | 11/2013 | Hoey ............... A61B 18/1815 606/14 |
| 8,579,892 B2 | 11/2013 | Hoey |
| 8,579,893 B2 | 11/2013 | Hoey |
| 8,585,645 B2 | 11/2013 | Barry |
| 8,585,692 B2 | 11/2013 | Shadduck |
| 8,591,504 B2 | 11/2013 | Tin |
| 8,606,369 B2 | 12/2013 | Williams |
| 8,615,287 B2 | 12/2013 | Harlev |
| 8,617,149 B2 | 12/2013 | Lafontaine |
| 8,617,152 B2 | 12/2013 | Werneth |
| 8,623,010 B2 | 1/2014 | Ocel |
| 8,632,529 B2 | 1/2014 | Bencini |
| 8,632,530 B2 | 1/2014 | Hoey |
| 8,641,711 B2 | 2/2014 | Kelly |
| 8,642,747 B2 | 2/2014 | Sharma |
| 8,644,932 B2 | 2/2014 | Seifert |
| 8,647,336 B2 | 2/2014 | Werneth |
| 8,647,339 B2 | 2/2014 | Satake |
| 8,663,245 B2 | 3/2014 | Francischelli |
| 8,679,104 B2 | 3/2014 | Abboud |
| 8,682,436 B2 | 3/2014 | Ghosh |
| 8,685,055 B2 | 4/2014 | Vantassel |
| 8,688,469 B2 | 4/2014 | Ziegler |
| 8,700,120 B2 | 4/2014 | Koblish |
| 8,702,693 B2 | 4/2014 | Subramaniam |
| 8,702,696 B2 | 4/2014 | White |
| 8,706,260 B2 | 4/2014 | Stewart |
| 8,715,274 B2 | 5/2014 | Watson |
| 8,721,632 B2 | 5/2014 | Hoey |
| 8,727,983 B2 | 5/2014 | Kinnison |
| 8,734,380 B2 | 5/2014 | Barry |
| 8,744,578 B2 | 6/2014 | Ellingson |
| 8,744,601 B2 | 6/2014 | Spotnitz |
| 8,747,352 B1 | 6/2014 | Lalonde |
| 8,758,341 B2 | 6/2014 | Shadduck |
| 8,761,626 B2 | 6/2014 | Seo |
| 8,764,740 B2 | 7/2014 | Watson |
| 8,764,745 B2 | 7/2014 | Malewicz |
| 8,774,909 B2 | 7/2014 | Patel |
| 8,790,300 B2 | 7/2014 | Tun |
| 8,795,271 B2 | 8/2014 | Koblish |
| 8,798,706 B2 | 8/2014 | Kim |
| 8,801,702 B2 | 8/2014 | Hoey |
| 8,805,466 B2 | 8/2014 | Salahieh |
| 8,805,496 B2 | 8/2014 | Ellingson |
| 8,821,484 B2 | 9/2014 | Ingle |
| 8,821,485 B2 | 9/2014 | Heberer |
| 8,821,488 B2 | 9/2014 | Stewart |
| 8,827,952 B2 | 9/2014 | Subramaniam |

(56) References Cited

U.S. PATENT DOCUMENTS

| | | | |
|---|---|---|---|
| 8,838,254 B2 | 9/2014 | McClure |
| 8,845,558 B2 | 9/2014 | Macadam |
| 8,849,400 B2 | 9/2014 | Gunderson |
| 8,858,549 B2 | 10/2014 | Shadduck |
| 8,870,859 B2 | 10/2014 | Swanson |
| 8,886,296 B2 | 11/2014 | Patel |
| 8,900,223 B2 | 12/2014 | Shadduck |
| 8,911,430 B2 | 12/2014 | Hoey |
| 8,911,434 B2 | 12/2014 | Wittenberger |
| 8,926,602 B2 | 1/2015 | Pageard |
| 8,926,635 B2 | 1/2015 | Franischelli |
| 8,929,969 B2 | 1/2015 | Gillis |
| 8,945,116 B2 | 2/2015 | Macadam |
| 8,951,247 B2 | 2/2015 | Ding |
| 8,968,354 B2 | 3/2015 | Wang |
| 8,974,451 B2 | 3/2015 | Smith |
| 8,983,606 B2 | 3/2015 | Ellingson |
| 8,992,519 B2 | 3/2015 | Kim |
| 9,002,454 B2 | 4/2015 | Ghosh |
| 9,005,194 B2 | 4/2015 | Oral |
| 9,008,788 B2 | 4/2015 | Jenison |
| 9,028,486 B2 | 5/2015 | Collins |
| 9,034,006 B2 | 5/2015 | Quinn |
| 9,039,687 B2 | 5/2015 | Condie |
| 9,039,712 B2 | 5/2015 | Abboud |
| 9,050,074 B2 | 6/2015 | Joye |
| 9,061,155 B2 | 6/2015 | Gillberg |
| 9,072,516 B2 | 7/2015 | Sherman |
| 9,072,911 B2 | 7/2015 | Hastings |
| 9,089,272 B2 | 7/2015 | Thakur |
| 9,089,314 B2 | 7/2015 | Wittenberger |
| 9,095,321 B2 | 8/2015 | Phelan |
| 9,095,350 B2 | 8/2015 | Condie |
| 9,095,715 B2 | 8/2015 | Gillberg |
| 9,096,685 B2 | 8/2015 | Sharma |
| 9,113,858 B2 | 8/2015 | Barry |
| 9,113,911 B2 | 8/2015 | Sherman |
| 9,113,944 B2 | 8/2015 | Shadduck |
| 9,119,636 B2 | 9/2015 | Vegesna |
| 9,125,667 B2 | 9/2015 | Stone |
| 9,125,668 B2 | 9/2015 | Subramaniam |
| 9,149,198 B2 | 10/2015 | Werneth |
| 9,149,320 B2 | 10/2015 | Kuck |
| 9,155,590 B2 | 10/2015 | Mathur |
| 9,161,801 B2 | 10/2015 | Hoey |
| 9,168,080 B2 | 10/2015 | Wittenberger |
| 9,179,973 B2 | 11/2015 | Nabutovsky |
| 9,186,080 B2 | 11/2015 | Shuros |
| 9,198,708 B2 | 12/2015 | Hoey |
| 9,204,889 B2 | 12/2015 | Shadduck |
| 9,205,268 B2 | 12/2015 | Yoon |
| 9,211,156 B2 | 12/2015 | Kim |
| 9,233,193 B2 | 1/2016 | Truckai |
| 9,289,145 B2 | 3/2016 | Grenz |
| 9,295,513 B2 | 3/2016 | Watson |
| 9,314,612 B2 | 4/2016 | Dollimer |
| 9,320,564 B2 | 4/2016 | Avitall |
| 9,326,815 B2 | 5/2016 | Watson |
| 9,332,920 B2 | 5/2016 | Thakur |
| 9,333,023 B2 | 5/2016 | Wittenberger |
| 9,339,657 B2 | 5/2016 | Stancer |
| 9,345,507 B2 | 5/2016 | Hoey |
| 9,345,528 B2 | 5/2016 | Laske |
| 9,345,529 B2 | 5/2016 | Mihalik |
| 9,345,540 B2 | 5/2016 | Mallin |
| 9,351,783 B2 | 5/2016 | Jannicke |
| 9,351,789 B2 | 5/2016 | Novichenok |
| 9,370,329 B2 | 6/2016 | Tun |
| 9,387,032 B2 | 7/2016 | Martin |
| 9,387,310 B2 | 7/2016 | Satake |
| 9,433,457 B2 | 9/2016 | Shadduck |
| 9,456,867 B2 | 10/2016 | Lawrence |
| 9,463,064 B2 | 10/2016 | Subramaniam |
| 9,468,487 B2 | 10/2016 | Shadduck |
| 9,474,467 B2 | 10/2016 | Harlev |
| 9,474,516 B2 | 10/2016 | Clark |
| 9,486,280 B2 | 11/2016 | Koblish |
| 9,517,017 B2 | 12/2016 | Shuros |
| 9,526,434 B2 | 12/2016 | Harlev |
| 9,526,435 B2 | 12/2016 | Ghosh |
| 9,526,555 B2 | 12/2016 | Hoey |
| 9,532,725 B2 | 1/2017 | Laughner |
| 9,532,828 B2 | 1/2017 | Condie |
| 9,539,046 B2 | 1/2017 | Wittenberger |
| 9,554,848 B2 | 1/2017 | Stewart |
| 9,561,043 B2 | 2/2017 | Warnking |
| 9,566,113 B2 | 2/2017 | Werneth |
| 9,572,536 B2 | 2/2017 | Abboud |
| 9,579,034 B2 | 2/2017 | Thakur |
| 9,597,140 B2 | 3/2017 | Mihalik |
| 9,603,651 B2 | 3/2017 | Ghosh |
| 9,603,659 B2 | 3/2017 | Subramaniam |
| 9,610,045 B2 | 4/2017 | Du |
| 9,615,875 B2 * | 4/2017 | Shadduck ............ A61B 17/122 |
| 9,615,879 B2 | 4/2017 | Kim |
| 9,622,806 B2 | 4/2017 | Mihalik |
| 9,636,032 B2 | 5/2017 | Thakur |
| 9,636,172 B2 | 5/2017 | Hu |
| 9,642,555 B2 | 5/2017 | Bonner |
| 9,642,675 B2 | 5/2017 | Werneth |
| 9,643,024 B2 | 5/2017 | Reinke |
| 9,649,040 B2 | 5/2017 | Laughner |
| 9,655,666 B2 | 5/2017 | Markowitz |
| 9,655,667 B2 | 5/2017 | Hon |
| 9,655,668 B2 | 5/2017 | Ingle |
| 9,656,063 B2 | 5/2017 | Kelley |
| 9,662,470 B2 | 5/2017 | Roman |
| 9,675,263 B2 | 6/2017 | Deac |
| 9,675,270 B2 | 6/2017 | Sarkar |
| 9,675,806 B2 | 6/2017 | Ellingson |
| 9,681,817 B2 | 6/2017 | Maskara |
| 9,687,166 B2 | 6/2017 | Subramaniam |
| 9,693,819 B2 | 7/2017 | Franischelli |
| 9,730,600 B2 | 8/2017 | Thakur |
| 9,730,602 B2 | 8/2017 | Harlev |
| 9,737,223 B2 | 8/2017 | Du |
| 9,743,972 B2 | 8/2017 | Wittenberger |
| 9,743,973 B2 | 8/2017 | Pageard |
| 9,744,023 B2 | 8/2017 | Wang |
| 9,744,364 B2 | 8/2017 | Gordon |
| 9,750,556 B2 | 9/2017 | Lafontaine |
| 9,750,567 B2 | 9/2017 | Falwell |
| 9,750,570 B2 | 9/2017 | Condie |
| 9,757,191 B2 | 9/2017 | Avitall |
| 9,757,194 B2 | 9/2017 | Werneth |
| 9,757,535 B2 | 9/2017 | Rajagopalan |
| 9,763,625 B2 | 9/2017 | Laughner |
| 9,795,314 B2 | 10/2017 | Laughner |
| 9,814,523 B2 | 11/2017 | Condie |
| 9,844,641 B2 | 12/2017 | Rajagopalan |
| 9,848,795 B2 | 12/2017 | Marecki |
| 9,848,946 B2 | 12/2017 | Edmunds |
| 9,861,370 B2 | 1/2018 | Clark |
| 9,861,422 B2 | 1/2018 | Hareland |
| 9,861,423 B2 | 1/2018 | Lalonde |
| 9,872,717 B2 | 1/2018 | Bencini |
| 9,883,936 B2 | 2/2018 | Sutton |
| 9,907,599 B2 | 3/2018 | Hoey |
| 9,919,158 B2 | 3/2018 | Ellingson |
| 9,925,359 B2 | 3/2018 | Lalonde |
| 9,931,134 B2 | 4/2018 | Hissong |
| 9,931,152 B2 | 4/2018 | Wittenberger |
| 9,936,996 B2 | 4/2018 | Zachman |
| 9,936,999 B2 | 4/2018 | Lalonde |
| 9,956,401 B2 | 5/2018 | Hastings |
| 9,958,515 B2 | 5/2018 | Ellingson |
| 9,974,607 B2 | 5/2018 | Stone |
| 9,993,279 B2 | 6/2018 | Avitall |
| 10,010,368 B2 | 7/2018 | Laske |
| 10,010,716 B2 | 7/2018 | Ellingson |
| 10,022,538 B2 | 7/2018 | Drasler |
| 10,034,708 B2 | 7/2018 | Zarins |
| 10,039,467 B2 | 8/2018 | Stewart |
| 10,064,697 B2 | 9/2018 | Sharma |

(56) References Cited

U.S. PATENT DOCUMENTS

| | | |
|---|---|---|
| 10,179,019 B2 | 1/2019 | Chee |
| 10,299,857 B2 | 5/2019 | Rajagopalan |
| 10,864,352 B2 | 12/2020 | Rajagopalan |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1 | 6/2002 | Shadduck |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0143325 A1 | 10/2002 | Sampson |
| 2002/0156470 A1 | 10/2002 | Shadduck |
| 2002/0161326 A1 | 10/2002 | Sussman |
| 2002/0177846 A1 | 11/2002 | Mulier |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0059313 A1 | 3/2004 | Tachibana |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0015047 A1 | 1/2005 | Shah |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1 | 12/2005 | Truckai |
| 2005/0283143 A1 | 12/2005 | Rizoiu |
| 2006/0004400 A1 | 1/2006 | McGurk |
| 2006/0036237 A1 | 2/2006 | Davison |
| 2006/0041277 A1 | 2/2006 | Deem |
| 2006/0047291 A1 | 3/2006 | Barry |
| 2006/0085054 A1 | 4/2006 | Zikorus |
| 2006/0089636 A1 | 4/2006 | Christopherson |
| 2006/0095032 A1 | 5/2006 | Jackson |
| 2006/0100619 A1 | 5/2006 | McClurken |
| 2006/0130830 A1 | 6/2006 | Barry |
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1 | 10/2006 | Shadduck |
| 2006/0264832 A1 | 11/2006 | Skwarek |
| 2006/0276871 A1 | 12/2006 | Lamson |
| 2007/0032785 A1 | 2/2007 | Diederich |
| 2007/0036417 A1 | 2/2007 | Argiro |
| 2007/0049920 A1 | 3/2007 | McClurken |
| 2007/0083085 A1 | 4/2007 | Birnkrant |
| 2007/0091087 A1 | 4/2007 | Zuiderveld |
| 2007/0142846 A1 | 6/2007 | Catanese |
| 2007/0179496 A1 | 8/2007 | Swoyer |
| 2007/0225744 A1 | 9/2007 | Nobles |
| 2007/0225750 A1 | 9/2007 | Ren |
| 2007/0239197 A1 | 10/2007 | Dubey |
| 2007/0250056 A1 | 10/2007 | Vanney |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0183036 A1 | 7/2008 | Saadat |
| 2008/0208187 A1 | 8/2008 | Bhushan |
| 2008/0208189 A1 | 8/2008 | Van Wyk |
| 2008/0249399 A1 | 10/2008 | Appling |
| 2008/0275440 A1 | 11/2008 | Kratoska |
| 2008/0281267 A1 | 11/2008 | Mehier |
| 2008/0300571 A1 | 12/2008 | LePivert |
| 2009/0018553 A1 | 1/2009 | McLean |
| 2009/0054868 A1 | 2/2009 | Sharkey |
| 2009/0054869 A1 | 2/2009 | Sharkey |
| 2009/0054870 A1 | 2/2009 | Sharkey |
| 2009/0054871 A1 | 2/2009 | Sharkey |
| 2009/0082837 A1 | 3/2009 | Gellman |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0221998 A1 | 9/2009 | Epstein |
| 2009/0227998 A1 | 9/2009 | Aljuri |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1 | 3/2010 | Hoey |
| 2010/0094270 A1 | 4/2010 | Sharma |
| 2010/0114082 A1 | 5/2010 | Sharma |
| 2010/0114083 A1 | 5/2010 | Sharma |

(56) References Cited

U.S. PATENT DOCUMENTS

| | | |
|---|---|---|
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0168624 A1 | 7/2010 | Sliwa |
| 2010/0179416 A1 | 7/2010 | Hoey |
| 2010/0179528 A1 | 7/2010 | Shadduck |
| 2010/0204688 A1 | 8/2010 | Hoey |
| 2010/0262133 A1 | 10/2010 | Hoey |
| 2010/0274260 A1 | 10/2010 | DArpiany |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0172654 A1 | 7/2011 | Barry |
| 2011/0184400 A1 | 7/2011 | Pageard |
| 2011/0190751 A1 | 8/2011 | Ingle |
| 2011/0238144 A1 | 9/2011 | Hoey |
| 2011/0264090 A1 | 10/2011 | Shadduck |
| 2011/0276046 A1 | 11/2011 | Heimbecher |
| 2012/0065632 A1 | 3/2012 | Shadduck |
| 2012/0078078 A1 | 3/2012 | MacAdam |
| 2012/0101413 A1 | 4/2012 | Beetel |
| 2012/0116376 A1 | 5/2012 | Hoey |
| 2012/0197358 A1 | 8/2012 | Prescott |
| 2012/0232409 A1 | 9/2012 | Stahmann |
| 2012/0259271 A1 | 10/2012 | Shadduck |
| 2012/0323167 A1 | 12/2012 | Hoey |
| 2013/0006231 A1 | 1/2013 | Sharma |
| 2013/0030410 A1 | 1/2013 | Drasler |
| 2013/0074847 A1 | 3/2013 | Hoey |
| 2013/0079772 A1 | 3/2013 | Shadduck |
| 2013/0116683 A1 | 5/2013 | Shadduck |
| 2013/0165914 A1 | 6/2013 | Satake |
| 2013/0172867 A1 | 7/2013 | Shadduck |
| 2013/0197555 A1 | 8/2013 | Schaer |
| 2013/0237978 A1 | 9/2013 | Shadduck |
| 2013/0267939 A1 | 10/2013 | Barry |
| 2013/0296837 A1 | 11/2013 | Burnett |
| 2013/0345670 A1 | 12/2013 | Rajagopalan |
| 2014/0025057 A1 | 1/2014 | Hoey |
| 2014/0031805 A1 | 1/2014 | Shadduck |
| 2014/0107637 A1 | 4/2014 | Hoey |
| 2014/0114306 A1 | 4/2014 | Harada |
| 2014/0200569 A1 | 7/2014 | Shadduck |
| 2014/0200570 A1 | 7/2014 | Hoey |
| 2014/0276713 A1 | 9/2014 | Hoey |
| 2014/0288543 A1 | 9/2014 | Hoey |
| 2014/0324037 A1 | 10/2014 | Hoey |
| 2014/0357956 A1 | 12/2014 | Salahieh |
| 2014/0358137 A1 | 12/2014 | Hu |
| 2014/0371736 A1 | 12/2014 | Levin |
| 2015/0025515 A1 | 1/2015 | Hoey |
| 2015/0025516 A1 | 1/2015 | Hoey |
| 2015/0080883 A1 | 3/2015 | Haverkost |
| 2015/0126990 A1 | 5/2015 | Sharma |
| 2015/0148738 A1 | 5/2015 | Caplan |
| 2015/0182740 A1 | 7/2015 | Mickelsen |
| 2015/0265329 A1 | 9/2015 | Lalonde |
| 2016/0220297 A1 | 8/2016 | Kroon |
| 2016/0310200 A1 | 10/2016 | Wang |
| 2016/0354140 A1 | 12/2016 | Sharma |
| 2016/0354144 A1 | 12/2016 | Caplan |
| 2017/0165002 A1 | 6/2017 | Sharma |
| 2017/0231678 A1 | 8/2017 | Sharma |
| 2017/0333122 A1 | 11/2017 | Rajagopalan |
| 2017/0367755 A1 | 12/2017 | Sharma |
| 2019/0110830 A1 | 4/2019 | Hastings |
| 2019/0269449 A1 | 9/2019 | Hastings |
| 2019/0388133 A1 | 12/2019 | Sharma |

FOREIGN PATENT DOCUMENTS

| | | |
|---|---|---|
| CN | 102238920 | 9/2011 |
| CN | 102238920 A | 11/2011 |
| CN | 103582463 A | 2/2014 |
| CN | 105228547 A | 1/2016 |
| EP | 1602338 B1 | 12/2005 |
| EP | 2341859 | 7/2011 |
| FR | 2655548 | 6/1991 |
| WO | 1992010142 | 6/1992 |
| WO | 1995028198 A1 | 10/1995 |
| WO | 9902096 A | 1/1999 |
| WO | 1999053853 | 10/1999 |
| WO | 2000029055 | 5/2000 |
| WO | 2001024715 | 4/2001 |
| WO | 02069821 | 9/2002 |
| WO | 2002069821 | 9/2002 |
| WO | 2003070302 | 8/2003 |
| WO | 2003086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006019728 A2 | 2/2006 |
| WO | 2006055695 | 5/2006 |
| WO | 2006108974 | 10/2006 |
| WO | 2009009398 | 1/2009 |
| WO | 2009074844 A1 | 6/2009 |
| WO | 2010042461 | 4/2010 |
| WO | 2010042461 A1 | 4/2010 |
| WO | 2012167213 | 12/2012 |
| WO | 2012167213 A2 | 12/2012 |
| WO | 2013044182 A1 | 3/2013 |
| WO | 2013086461 A1 | 6/2013 |
| WO | 2013152119 A1 | 10/2013 |
| WO | 2014113724 | 7/2014 |
| WO | 2014113724 A2 | 7/2014 |
| WO | 2017201504 A1 | 11/2017 |
| WO | 2018089773 A1 | 5/2018 |

OTHER PUBLICATIONS

Written Opinion of the International Searching Authority for PCT/US21/13582, dated May 13, 2021.

International Search Report for PCT/US20/48419, dated Dec. 18, 2020.

Written Opinion of the International Searching Authority for PCT/US20/48419, dated Dec. 18, 2020.

International Search Report for PCT/US19/50662, dated Jan. 7, 2020.

Written Opinion of the International Searching Authority for PCT/US19/50662, dated Jan. 7, 2020.

Tanaka, et al. "A New Radiofrequency Thermal Balloon Catheter for Pulmonary Vein Isolation", Journal of the American College of Cargiology, 2001, vol. 38, No. 7, Dec. 2001: 2079-86; ISSN 0735-109, PII S0735-1097.

Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.

International Search Report for PCT/US2017/033693, dated Oct. 2, 2017.

Thibeau; AW-06995-001; Text, Manual, Novasure, V1, EN, US; Aug. 26, 2011; pp. 1-23; Hologic, Inc.

Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.

International Search Report for PCT/US2016/012840, dated Aug. 18, 2016.

Sharma et al; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.

(56) References Cited

OTHER PUBLICATIONS

Sanfilippo et al; Update: Options in Endometrial Ablation; Supplement to OBG Management; Dec. 2009; pp. S1-S24; Dowden Health Media.

United States FDA; Summary of Safety and Effectiveness Data: Cryogen, Inc.: Her Option Uterine Cryoablation Therapy System; PMA P000032; Sep. 14, 2001; pp. 1-22.

American Medical Systems, Inc.; heroption office cryoablation therapy Resource Guide; 2007; pp. 1-29; American Medical Systems, Inc.. 10700 Bren Road West, Minnetonka, MN 55343 USA.

Boston Scientific; HTA System Endometrial Ablation System; 2006; BVU 1090 Rev. A 10M Sep. 6-Sep. 8; Boston Scientific Corporation, One Boston Scientific Place, Natick, MA 01760-1537.

Ethicon Women's Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.

Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.

Carter; Endometrial Ablation: More Choices, More Options; The Female Patient; 2005; pp. 35-40; 30(12).

"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/ cpu.aspx>.

HAI; Photoselective Vaporization Prostatectomy: A Palliative Treatment Option for Men with Urinary Obstruction Secondary to Prostate Cancer; PCRI Prost. Cancer Rsrch. Inst. Reprint, from PCRI Insights Nov. 2005, vol. 8(4); pp. 4.

Van De Velde; Vapo-cauterization of the uterus; Amer. J. Med. Sci.; vol. CXVII; 1899.

Blacker; Vaporization of the uterus; J. Obstet. & Gyn.; pp. 488-511; 1901.

Neuwirth et al; The endometrial ablator: a new instrument; Obst. & Gyn.; vol. 83; No. 5; part 1; pp. 792-796; 1994.

Prior et al.; Treatment of mennorrhagia by radiofrequency heating; Int. J. Hyperthermia; vol. 7; No. 2; pp. 213-220; 1991.

International Search Report for PCT/US19/34991, dated Sep. 20, 2019.

Written Opinion of the International Searching Authority for PCT/US19/34991, dated Sep. 20, 2019.

Kim, J. W, Kim, D. H., Roh, Y. K Ju, S. Y., Nam, H. Y., Nam, G. E., Kim, D. W., Lee, S. H., Lee, C. W., Han, K., & Park, Y. G. (2015). Serum Ferritin Levels Are Positively Associated With Metabolically Obese Normal Weight: A Nationwide Population-Based Study. Medicine, 94(52), e2335 (Year: 2015).

Läpädat, A. M., Gheonea, D. I., Florescu, L. M., & Gheonea, I. A. (2019). Before and After Treatment Quantitative Assessment of Hepatic Steatosis in a Romanian Population Using Magnetic Resonance Liver Spectroscopy. Current health sciences journal, 45(3) 258-262 (Year: 2019).

Stål P. (2015). Liver fibrosis in non-alcoholic fatty liver disease—diagnostic challenge with prognostic significance. World journal of gastroenterology, 21(39), 11077-11087 (Year: 2015).

Singh, S., Allen, A. M., Wang, Z., Prokop, L. J., Murad, M. H., & Loomba, R. (2015). Fibrosis progression [ . . . ] and meta-analysis of paired-biopsy studies. Clinical gastroenterology and hepatology : the official clinical practice journal of the American Gastroenterological Association, 13(4), 643-e40 (Year: 2015).

El-Zefzafy, W, Eltokhy, H., Mohamed, N. A., & Abu-Zahab, Z. (2015). Significance of Serum Cytokeratin-18 in Prediction of U Hepatocellular Carcinoma in Chronic Hepatitis C Infected Egyptian Patients. Open access Macedonian journal of medical sciences, 3(1), 117-123 (Year: 2015).

Lee, D. H., Lee, J. M., Yoon, J. H., Kim, Y. J., Lee, J. H., Yu, S. J., & Han, J. K. (2018). Liver Stiffness Measured by Two-Dimensional Shear-Wave Elastography: Prognostic Value after Radiofrequency Ablation for Hepatocellular Carcinoma. Liver cancer, 7(1), 65-75 (Year: 2018).

International Search Report for PCT/US2021/071778, dated Feb. 14, 2022.

* cited by examiner

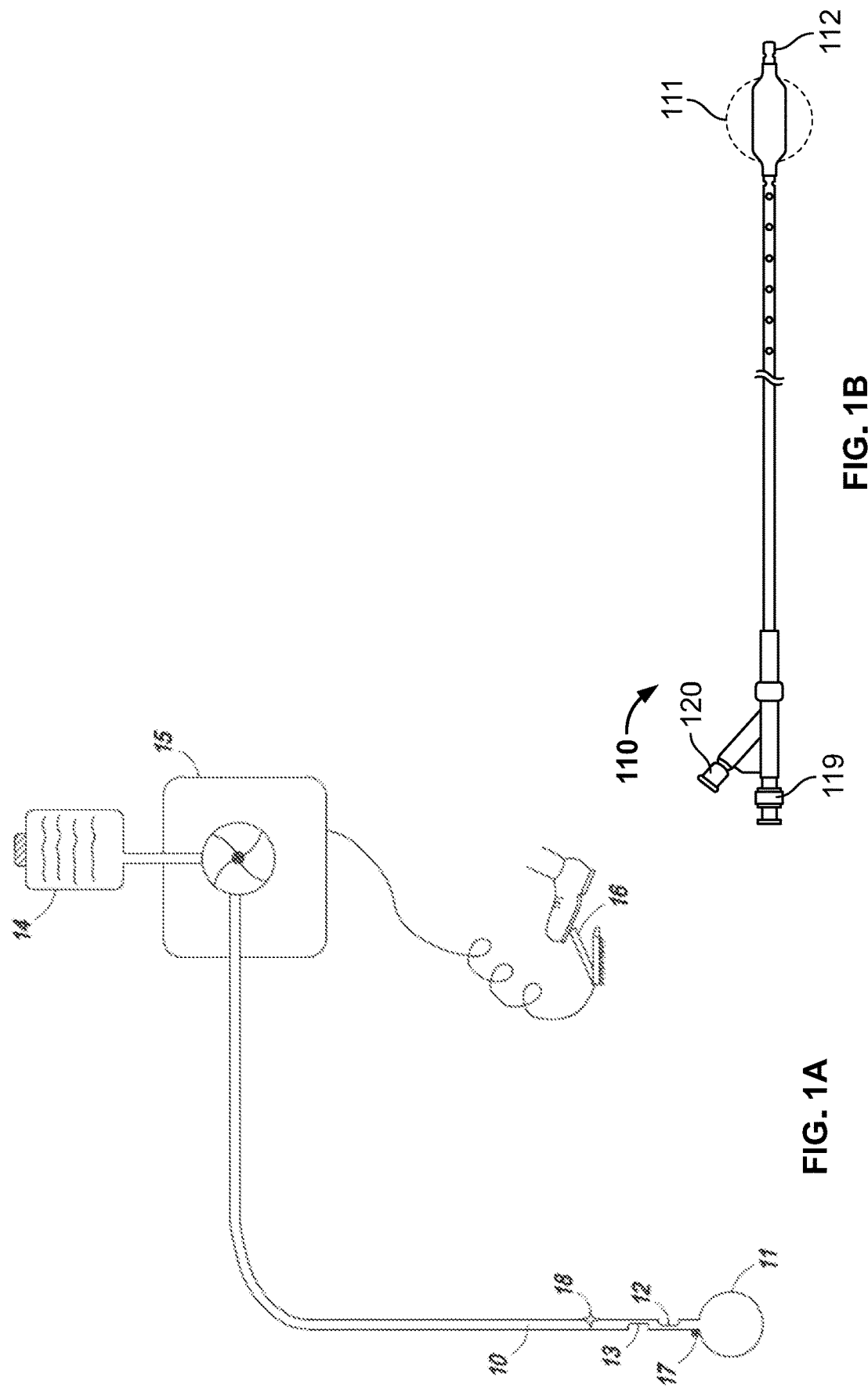

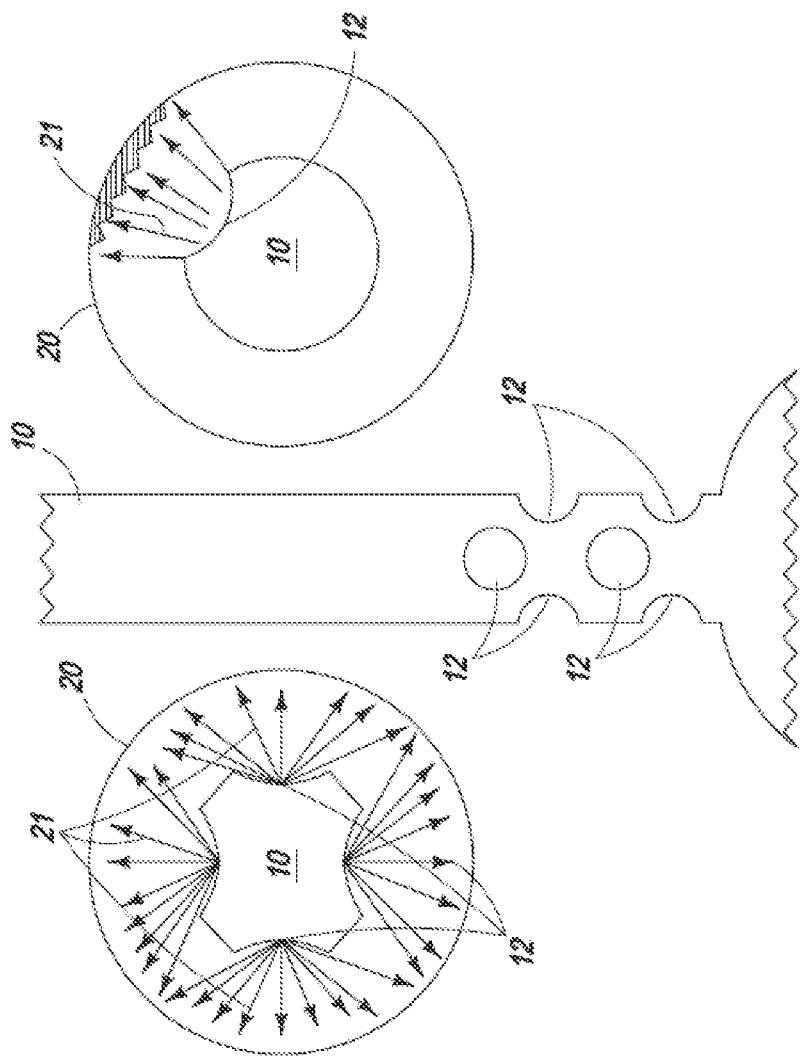

651

Ablation Catheter Having a Plurality of Lumens is Inserted into a Body Lumen, Wherein the Catheter Includes At Least One Vapor Delivery Port in Fluid Communication with a First Lumen of Said Plurality of Lumens, Such that Said At Least One Delivery Port is Positioned Proximate a Tissue to be Ablated

652

Vapor is Delivered to the Tissue to be Ablated Through Said First Lumen and Said At Least One Vapor Delivery Port While Simultaneously a Fluid at a Temperature in a Range of 0 to 60°c is Delivered Through a Second Lumen of Said Plurality of Lumens and Through a Cooling Fluid Delivery Port of Said Catheter to a Site Away from the Tissue Being Ablated

653

Optionally, Fluid is Simultaneously Suctioned Through a Fluid Suction Port of Said Catheter and a Third Lumen of Said Plurality of Lumens from a Site Away from the Tissue Being Ablated

654

Optionally, Fluid is Alternatingly Delivered and Suctioned Through Said Cooling Fluid Delivery Port and Said Second Lumen.

FIG. 6C

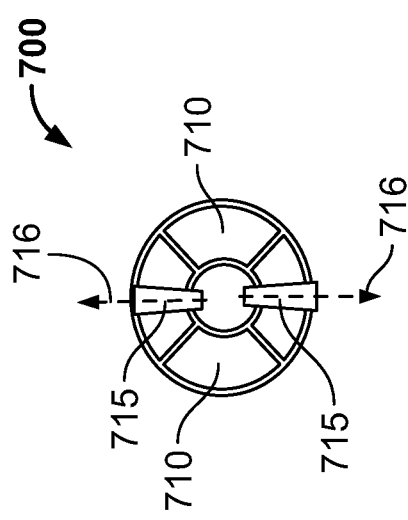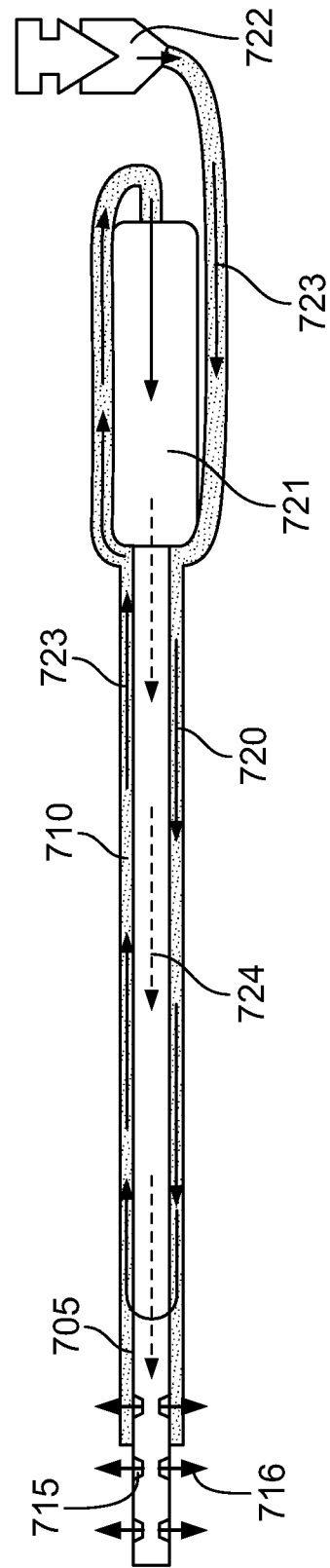
FIG. 7B
FIG. 7A

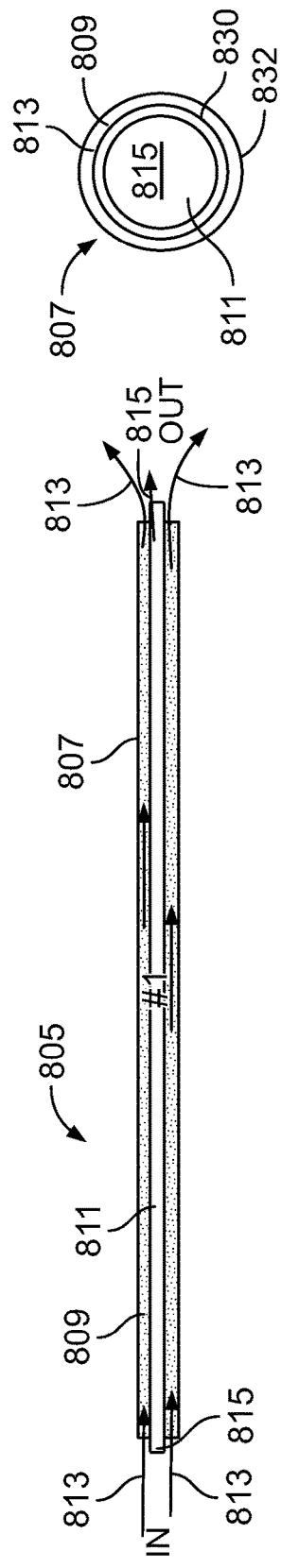
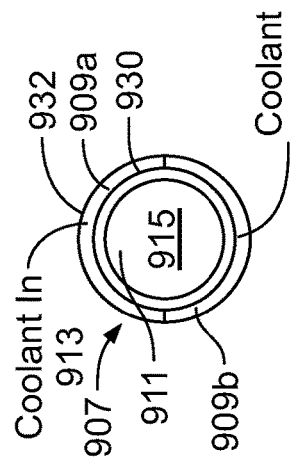
FIG. 8A
FIG. 8B
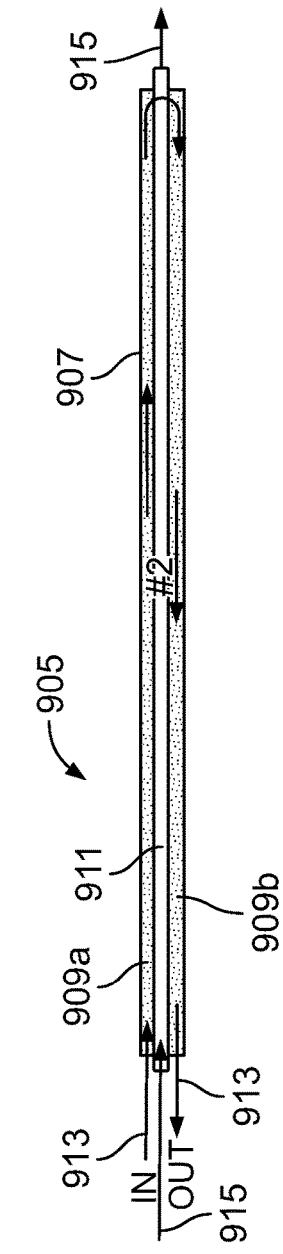
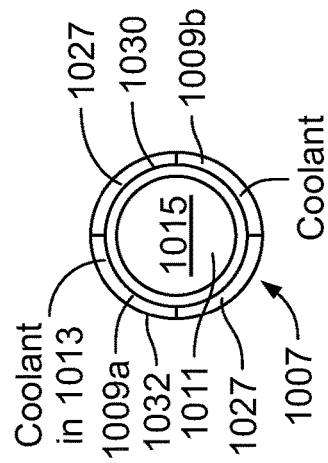
FIG. 9A
FIG. 9B
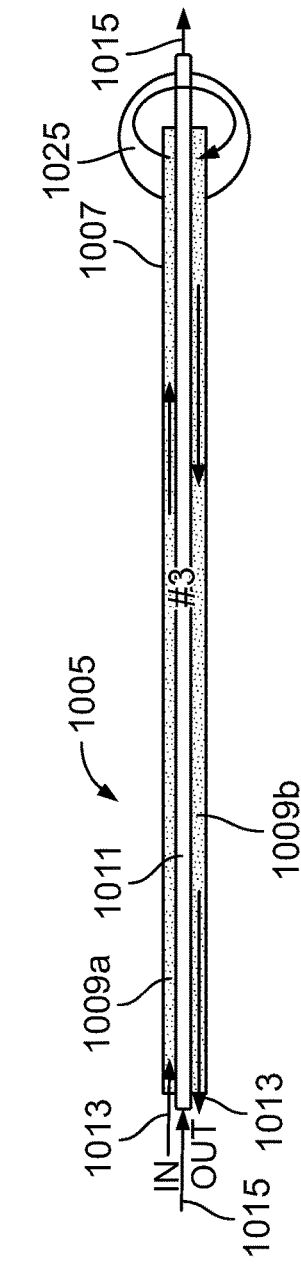
FIG. 10A
FIG. 10B

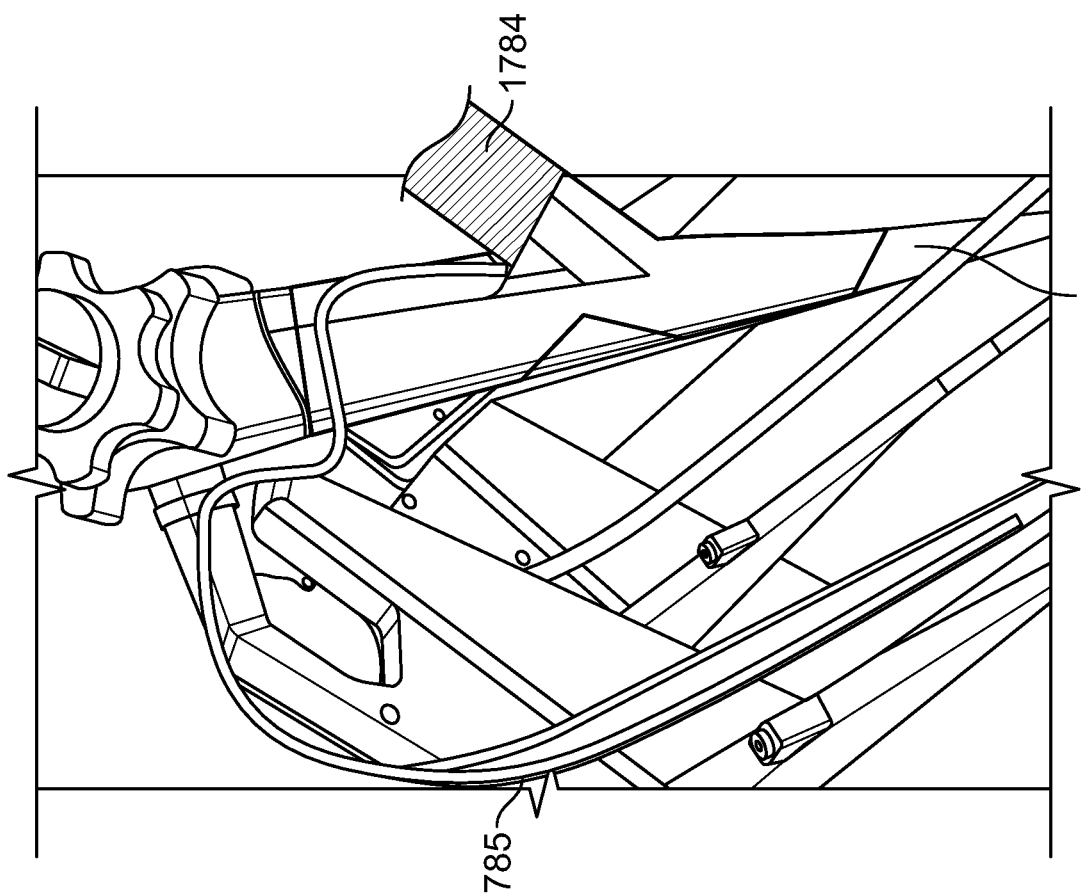
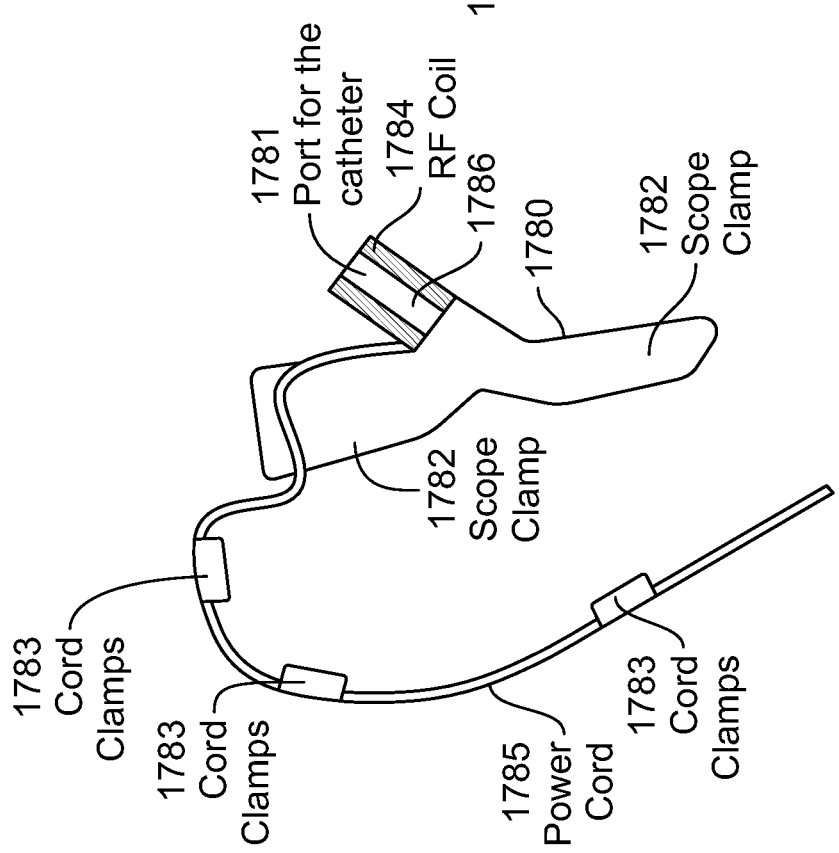
FIG. 17B
FIG. 17A

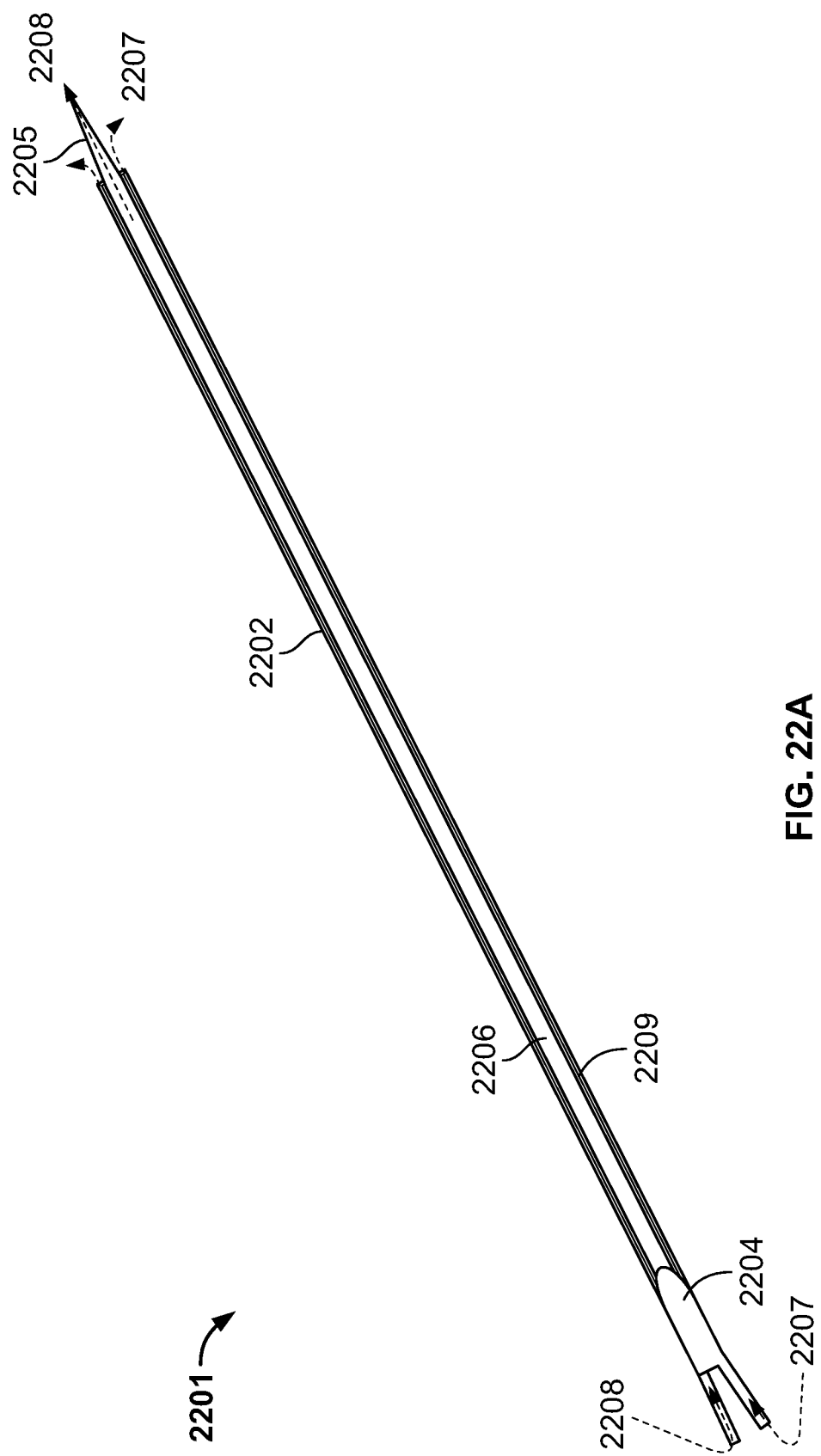

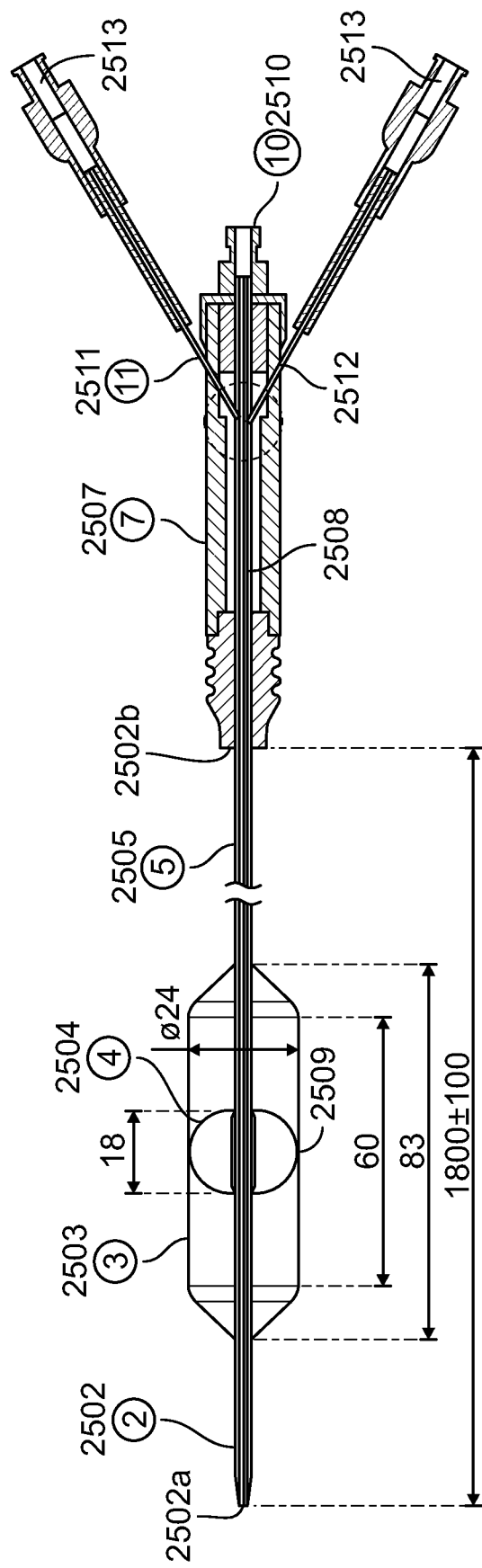
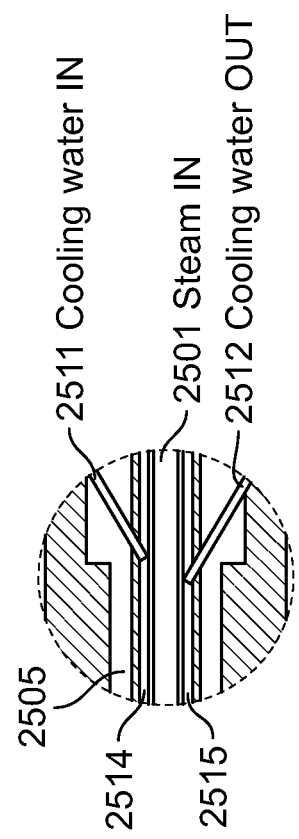
FIG. 25A
FIG. 25B

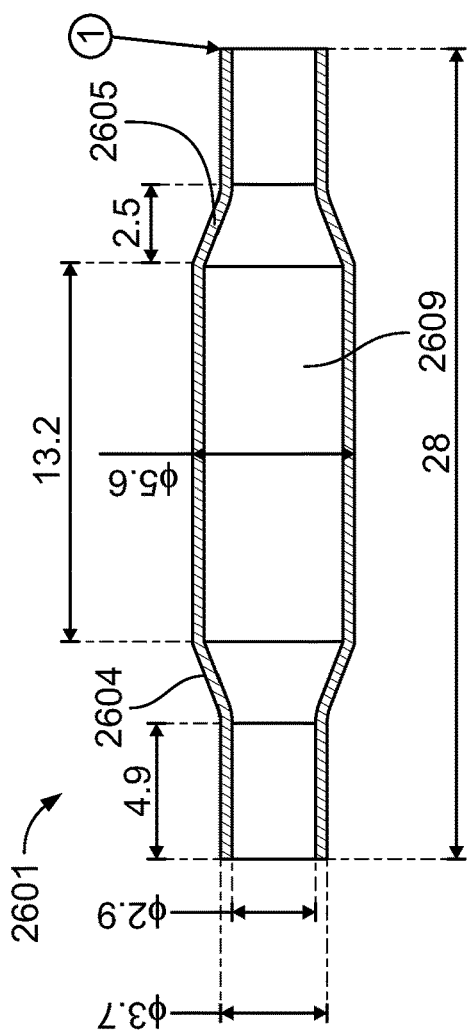
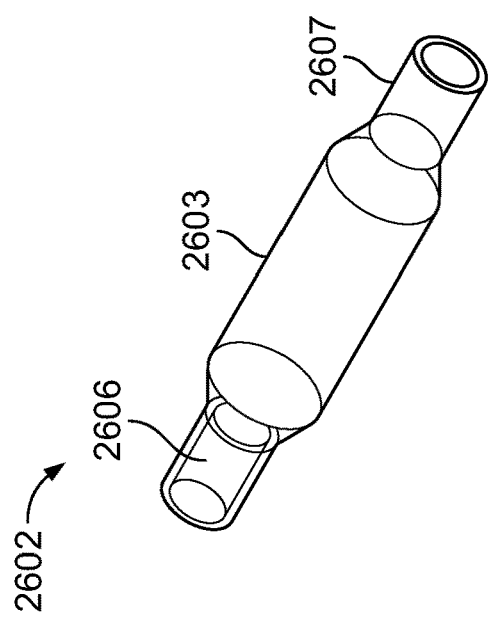
FIG. 26A

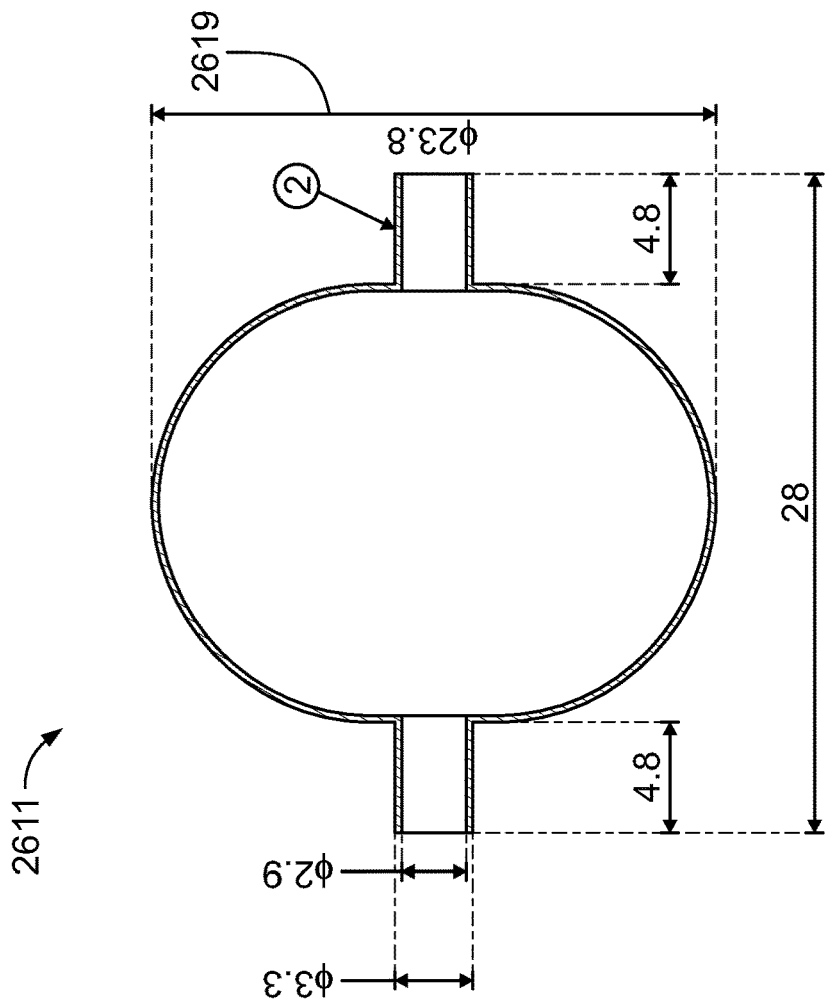
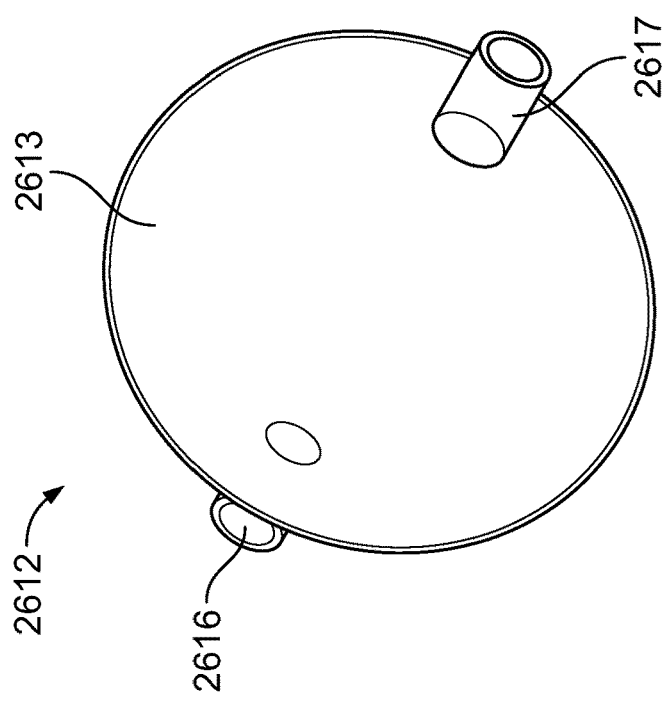
FIG. 26B

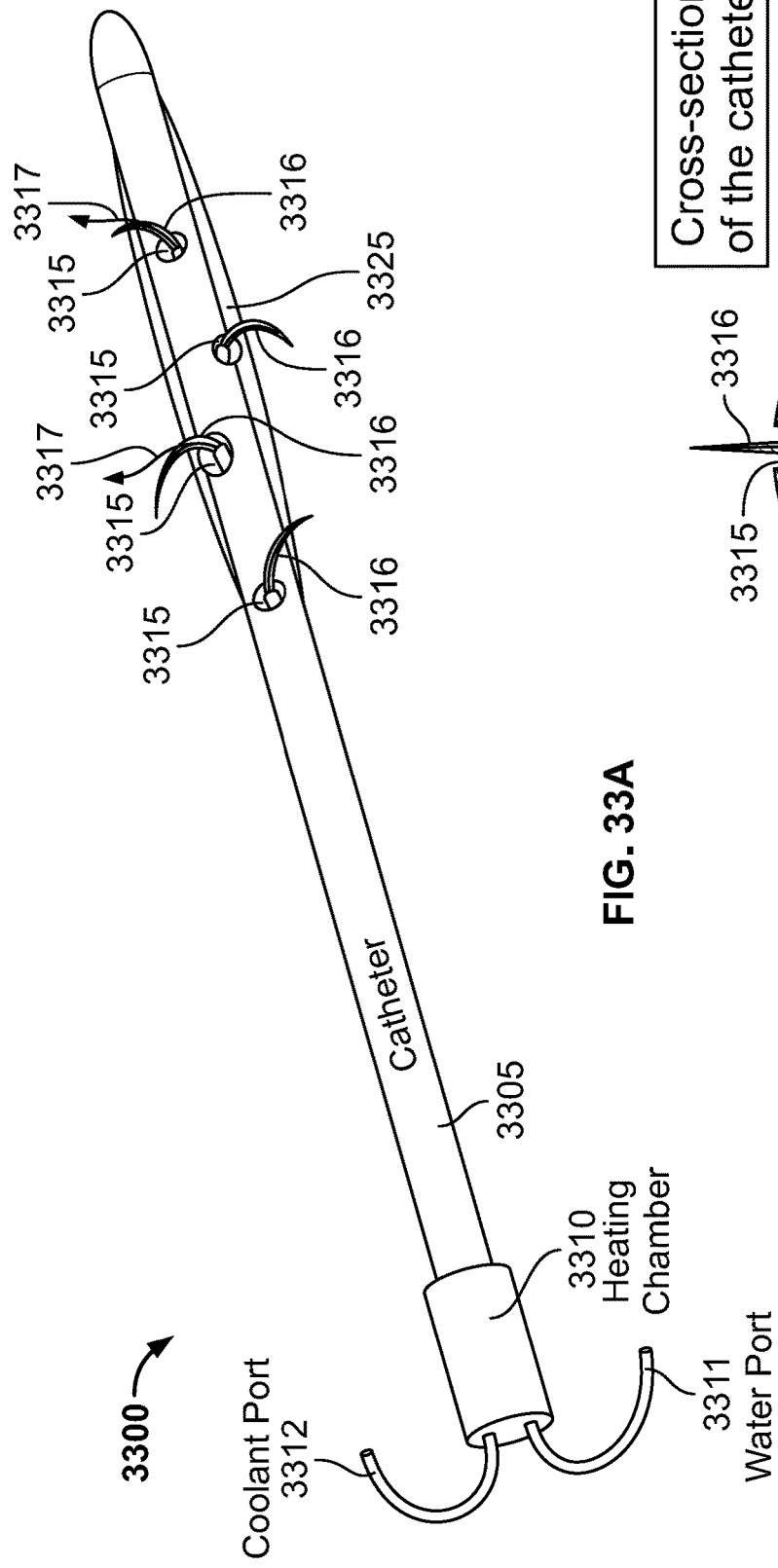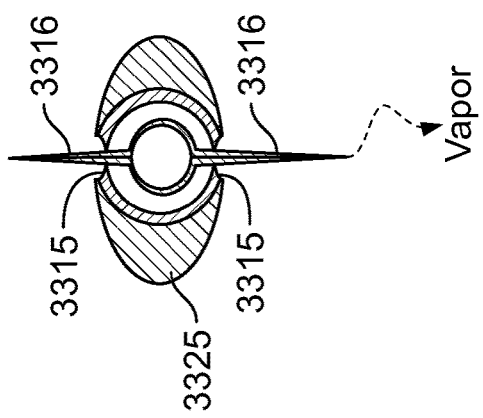

3340

Insert Ablation Catheter into Urethra and Advance Until the Openings for Delivering Vapor are Positioned Proximate the Prostatic Tissue to be Ablated

3342

Inflate the Cooling Balloon with Coolant to Fix the Catheter Within Prostatic Urethra and Maintain Ambient Temperature of the Surface of the Prostatic Tissue to be Ablated

3344

Advance Needles into the Prostatic Tissue and Deliver Vapor Through the Openings in the Needles to Ablate the Prostatic Tissue at a Desired Depth Without Ablating the Surface of the Prostatic Tissue; Modulate Coolant Flow to Maintain Temperature of the Surface of the Prostatic Tissue Below 60 Degree C

FIG. 33D

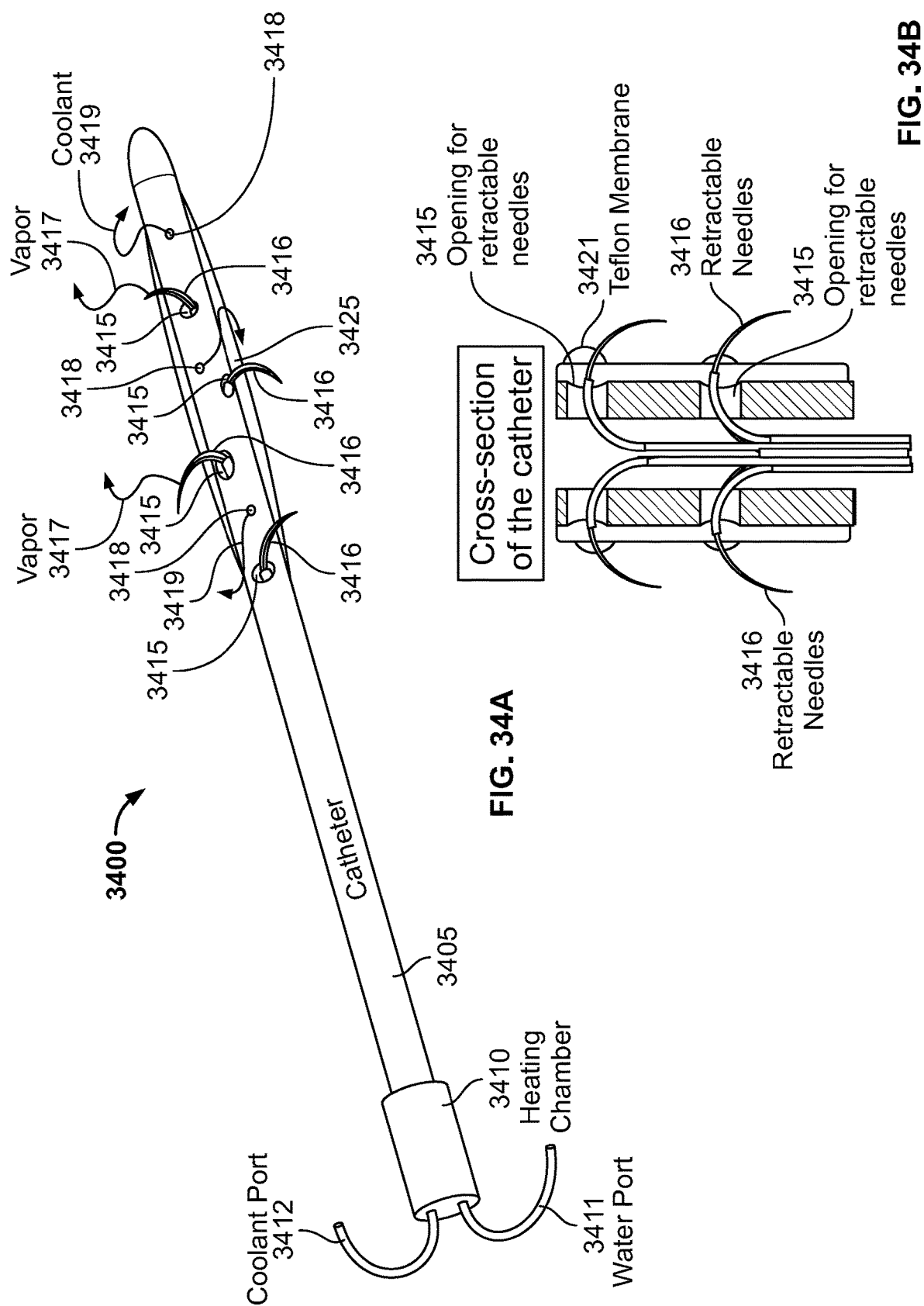

3440

Insert Ablation Catheter into Urethra and Advance Until the First Plurality of Openings for Delivering Vapor are Positioned Proximate the Prostatic Tissue to be Ablated

3442

Inflate the Cooling Balloon with Coolant to Fix the Catheter Within Prostatic Urethra and Maintain Ambient Temperature of the Surface of the Prostatic Tissue to be Ablated

3444

Advance Needles into the Prostatic Tissue, Perforating the Overlying Insulating Membrane, and Deliver Vapor Through the Openings in the Needles to Ablate the Prostatic Tissue at a Desired Depth Without Ablating the Surface of the Prostatic Tissue;

3446

A Coolant is Administered to the Prostatic Urethra Through the Second Plurality of Openings to Maintain Ambient Temperature of the Surface of the Prostatic Tissue to be Ablated; Modulate Coolant Flow to Maintain Temperature of the Surface of the Prostatic Tissue Below 60 Degree C

FIG. 34D

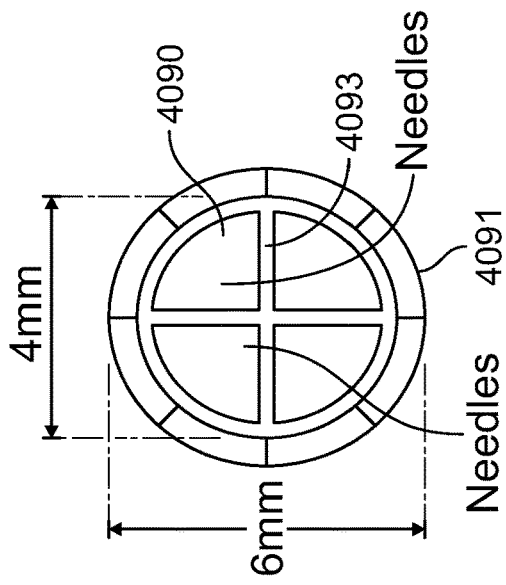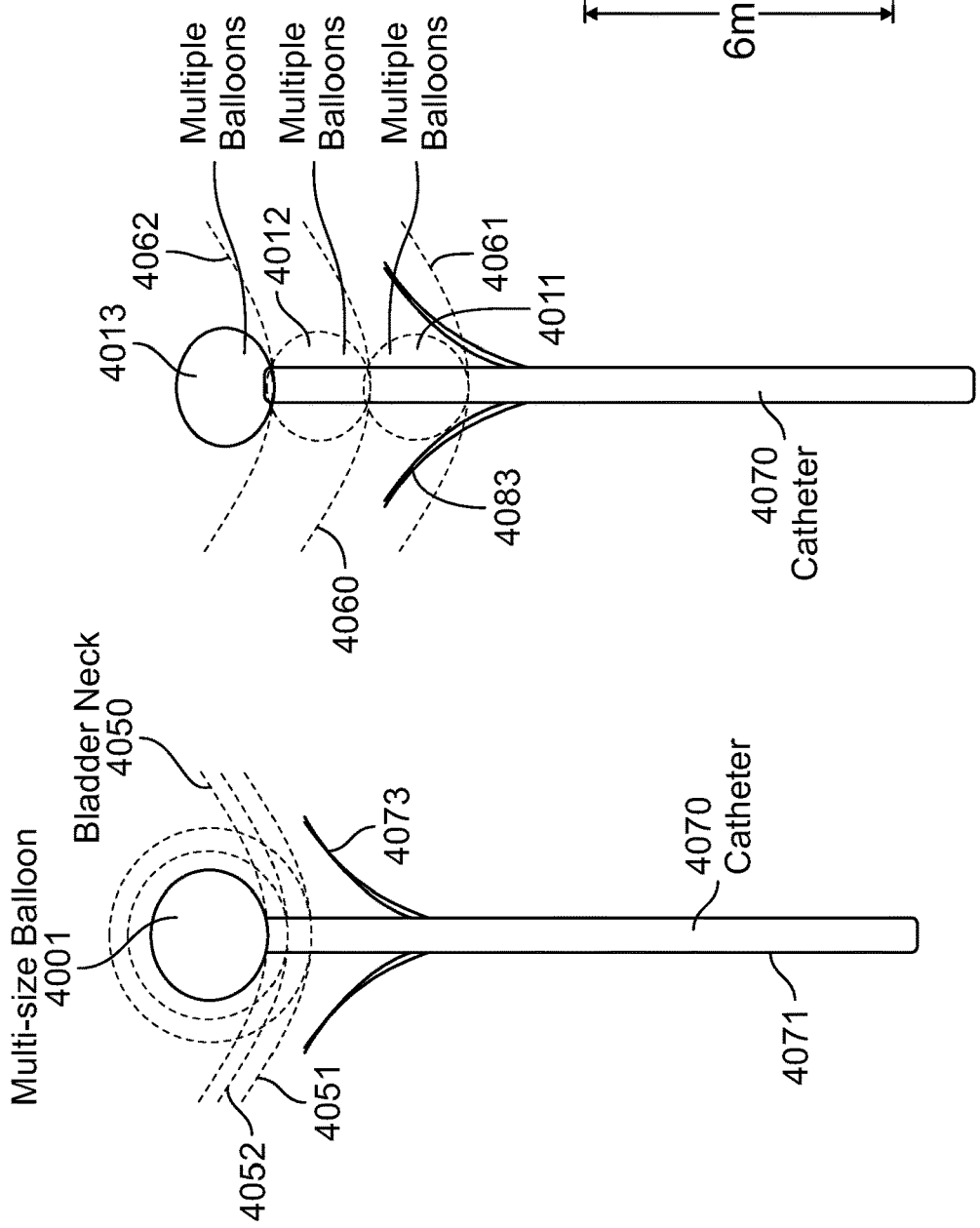

International Prostate Symptom Score questionnaire

| In the past month | Not at all | Less than 1 in 5 times | Less than half of the time | About half of the time | More than half of the time | Almost always | Your score |
|---|---|---|---|---|---|---|---|
| 1. Incomplete emptying<br>How often have you had the sensation of not emptying your bladder? 4380 | 0 | 1 | 2 | 3 | 4 | 5 | 4381 |
| 2. Frequency<br>How often have you had to urinate less than every 2 hours? | 0 | 1 | 2 | 3 | 4 | 5 | |
| 3. Intermittency<br>How often have you found you stopped and started again several times when you urinated? | 0 | 1 | 2 | 3 | 4 | 5 | |
| 4. Urgency<br>How often have you found it difficult to postpone urination? | 0 | 1 | 2 | 3 | 4 | 5 | |
| 5. Weak stream<br>How often have you had a weak urinary stream? | 0 | 1 | 2 | 3 | 4 | 5 | |
| 6. Straining<br>How often have you had to strain to start urination? | 0 | 1 | 2 | 3 | 4 | 5 | |
| | None | 1 time | 2 times | 3 times | 4 times | 5 times | Your score |
| 7. Nocturia<br>How many times did you typically get up at night to urinate? | 0 | 1 | 2 | 3 | 4 | 5 | |
| Total IPSS score<br>Quality of life due to urinary symptoms | Delighted | Pleased | Mostly satisfied | Mixed | Mostly dissatisfied | Unhappy | Terrible |
| If you were to spend the rest of your life with your urinary condition the way it is now, how would you feel about that? | 0 | 1 | 2 | 3 | 4 | 5 | 6 |

FIG. 43A

Benign Prostatic Hypertrophy Impact Index questionnaire

1. During the last month, how much physical discomfort did any urinary problems cause you? — 4385

None (0) — 4386    Only a little (1)    Some (2)    A lot (3)

2. During the last month, how much did you worry about your health because of any urinary problems?

None (0)    Only a little (1)    Some (2)    A lot (3)

3. Overall, how bothersome has any trouble with urination been during the last month?

Not at all (0)    A little (1)    Some (2)    A lot (3)

4. During the last month, how much of the time has any urinary problem kept you from doing the kinds of things you would usually do?

None (0)    A little (1)    Some of the time (2)    Most of the time (3)    All the time (4)

FIG. 43B

CATHETER WITH A DOUBLE BALLOON STRUCTURE TO GENERATE AND APPLY AN ABLATIVE ZONE TO TISSUE

CROSS-REFERENCE

The present application is a continuation application of U.S. patent application Ser. No. 15/600,670, entitled "Catheter with a Double Balloon Structure to Generate and Apply a Heated Ablative Zone to Tissue", filed on May 19, 2017, and issued as U.S. Pat. No. 10,695,126 on Jun. 30, 2020, which relies on U.S. Provisional Patent Application No. 62/425,144, entitled "Methods and Systems for Ablation" and filed on Nov. 22, 2016, and U.S. Provisional Patent Application No. 62/338,871, entitled "Cooled Coaxial Ablation Catheter" and filed on May 19, 2016, for priority.

U.S. patent application Ser. No. 15/600,670 is also a continuation-in-part application of U.S. patent application Ser. No. 15/144,768, entitled "Vapor Based Ablation System for Treating Various Indications", filed on May 2, 2016, and issued as U.S. Pat. No. 10,064,697 on Sep. 4, 2018.

All of the above referenced applications are herein incorporated by reference in their entirety.

FIELD

The present specification relates to systems and methods configured to generate and deliver vapor for ablation therapy. More particularly, the present specification relates to systems and methods comprising a cooled catheter and vapor generation for delivering ablation therapy to specific organ systems.

BACKGROUND

Ablation, as it pertains to the present specification, relates to the removal or destruction of a body tissue, via the introduction of a destructive agent, such as radiofrequency energy, laser energy, ultrasonic energy, cyroagents, or steam. Ablation is commonly used to eliminate diseased or unwanted tissues, such as, but not limited to cysts, polyps, tumors, hemorrhoids, and other similar lesions.

Steam-based ablation systems, such as the ones disclosed in U.S. Pat. Nos. 9,615,875, 9,433,457, 9,376,497, 9,561,068, 9,561,067, and 9,561,066, disclose ablation systems that controllably deliver steam through one or more lumens toward a tissue target. One problem that all such steam-based ablation systems have is the potential overheating or burning of healthy tissue. Steam passing through a channel within a body cavity heats up surfaces of the channel and may cause exterior surfaces of the medical tool, other than the operational tool end itself, to become excessively hot. As a result, physicians may unintentionally burn healthy tissue when external portions of the device, other than the distal operational end of the tool, accidentally contacts healthy tissue. U.S. Pat. Nos. 9,561,068, 9,561,067, and 9,561,066 are hereby incorporated herein by reference.

Furthermore, it is often desirable to rapidly cool a treatment area after the application of steam or some other ablative agent. Current systems largely rely, however, on a natural cooling process that prolongs treatment time. Alternatively, current medical treatment methods may flush an area with fluid, but that requires implementing a separate medical tool, thereby complicating the procedure and also prolonging treatment times.

It is therefore desirable to have steam-based ablation devices that integrate into the device itself safety mechanisms which prevent unwanted burning during use. It is further desirable to be able to provide a way to augment the natural cooling process to thereby decrease treatment time. Finally, it is desirable to provide an easy to implement cooling mechanism that does not rely on a separate medical tool to deliver fluid to cool the treatment area.

SUMMARY

The present specification discloses a catheter adapted to ablate cardiac tissue comprising: a first shaft having an external surface and a first lumen extending from a proximal end of the catheter to a first point positioned before a distal end of the catheter; a second shaft having a second lumen extending from the proximal end of the catheter to a second point at or before the distal end of the catheter, wherein the second shaft is positioned within the first shaft; a balloon positioned between said first point and said second point; and a channel extending through said first shaft, wherein the channel is in fluid communication with the balloon.

Optionally, the catheter further comprises a plurality of sensors positioned at a distal end of the catheter wherein the plurality of sensors are adapted to generate a signal representative of cardiac tissue associated with an arrhythmia. Optionally, the second point is positioned between said balloon and said plurality of sensors.

Optionally, the second shaft and channel extend beyond the first point after the external surface of the first shaft terminates at the first point.

The present specification also discloses an ablation system adapted to ablate cardiac tissue comprising: a vapor generation system adapted to generate vapor; a catheter comprising: a first shaft having a first lumen extending from a proximal end of the catheter to a first point positioned before a distal end of the catheter; a second shaft having a second lumen extending from the proximal end of the catheter to a second point at or before the distal end of the catheter, wherein the second shaft is positioned within the first shaft; a balloon positioned between said first point and said second point; and a channel extending through said first shaft, wherein the channel is in fluid communication with the balloon and in fluid communication with the vapor generation system; and a controller in data communication with the vapor generation system, wherein the controller is adapted to control an amount of vapor passed into the channel.

Optionally, the controller is further adapted to control at least one of an amount of pressure in said balloon and an amount of air passing out from the balloon and through the channel.

Optionally, the ablation system further comprises a plurality of sensors positioned at a distal end of the catheter wherein the plurality of sensors are adapted to generate a signal representative of cardiac tissue associated with an arrhythmia.

Optionally, the controller is adapted to cause an amount of air to be delivered from an air source through the channel to cause the balloon to inflate to a first pressure. Optionally, the controller is adapted to cause an amount of vapor to be delivered from the vapor generation system through the channel to cause the balloon to inflate to a second pressure, wherein the second pressure is different from the first pressure. Optionally, the controller is adapted to cause an amount of air to be removed from said balloon to maintain said second pressure within a range of 25% of said first pressure.

Optionally, the ablation system further comprises a water reservoir, wherein the controller is further adapted to control an amount of water passing from said water reservoir and through the first shaft. Optionally, the controller is further adapted to control an amount of water passing from said water reservoir and through the second shaft.

The present specification also discloses a method of ablating cardiac tissue comprising: positioning a distal end of a catheter proximate cardiac tissue, wherein the catheter comprises: an outer shaft having a first lumen extending from a proximal end of the catheter to a first point positioned before the distal end of the catheter; an inner shaft having a second lumen extending from the proximal end of the catheter to a second point at or before the distal end of the catheter, wherein the inner shaft is positioned within the outer shaft; a balloon positioned between said first point and said second point; and a vapor channel extending through said first shaft, wherein the vapor channel is in fluid communication with the balloon and in fluid communication with the vapor generation system; activating a controller to cause said balloon to inflate to a first pressure; and activating the controller to cause vapor to pass from a vapor generation system into the vapor channel and into the balloon.

Optionally, the method further comprises determining an area of the cardiac tissue associated with an arrhythmia using a plurality of sensors positioned at a distal end of the catheter.

Optionally, activating the controller to cause vapor to pass from the vapor generation system into the vapor channel further comprises activating the controller to cause the balloon to inflate to a second pressure, wherein the second pressure is different from the first pressure. Optionally, the method further comprises, using the controller, causing an amount of air to be removed from said balloon to maintain said second pressure within a range of 25% of said first pressure.

Optionally, the method further comprises applying said balloon containing the vapor to the cardiac tissue. Optionally, the method further comprises activating the controller to cause water to pass from a water source into at least one of the outer shaft and inner shaft. Optionally, the method further comprises activating the controller to cause water to pass from a water source into both the outer shaft and inner shaft.

Optionally, the method further comprises, using the controller, modulating an amount of vapor passing from the vapor generation system into the balloon, via the vapor channel, to maintain said second pressure within a range of 25% of said first pressure.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 1A illustrates an ablation device, in accordance with an embodiment of the present specification;

FIG. 1B illustrates another embodiment of a catheter for use with the ablation device of FIG. 1A;

FIG. 2A illustrates a longitudinal section of an ablation device with ports distributed thereon;

FIG. 2B illustrates a cross section of a port on the ablation device, in accordance with an embodiment of the present specification;

FIG. 2C illustrates a cross section of a port on the ablation device, in accordance with another embodiment of the present specification;

FIG. 6C is a flowchart illustrating a method of ablation for a body tissue, according to yet another embodiment of the present specification;

FIG. 7A is an illustration of a water cooled catheter, in accordance with one embodiment of the present specification;

FIG. 7B is a cross-section view of the shaft of the water cooled catheter of FIG. 7A;

FIG. 8A illustrates a first ablation catheter in accordance with an embodiment of the present specification;

FIG. 8B is a cross sectional view of a shaft or elongate body of the catheter of FIG. 8A;

FIG. 9A illustrates a second ablation catheter in accordance with an embodiment of the present specification;

FIG. 9B is a cross sectional view of a shaft or elongate body of the catheter of FIG. 9A;

FIG. 10A illustrates a third ablation catheter in accordance with an embodiment of the present specification;

FIG. 10B is a cross sectional view of a shaft or elongate body of the catheter of FIG. 10A;

FIG. 17A illustrates an exemplary handle mechanism comprising an RF coil for use with the ablation catheters, in accordance with one embodiment;

FIG. 17B illustrates the handle mechanism of FIG. 17A attached to an endoscope, in accordance with one embodiment;

FIG. 22A illustrates a cardiac ablation catheter with a first distal attachment, in accordance with an embodiment;

FIG. 25A illustrates a side cross section view of an embodiment of a cardiac ablation catheter, where the distal attachment comprises an inner balloon lying within an outer balloon;

FIG. 25B illustrates the channels within the catheter of FIG. 25A, in accordance with one embodiment;

FIG. 26A illustrates a side cross section view and a perspective view of the inner balloon, when the balloon is in unexpanded state, according to one embodiment.

FIG. 26B illustrates a side cross section view and a perspective view of the inner balloon, when the balloon is in expanded state, according to one embodiment;

FIG. 30B is a flowchart illustrating a method of ablating a uterine fibroid in accordance with one embodiment of the present specification;

FIG. 31A is an illustration of a water cooled catheter, in accordance with another embodiment of the present specification;

FIG. 31B is a cross-section view of a tip section of the water cooled catheter of FIG. 31A;

FIG. 32A illustrates prostate ablation being performed on an enlarged prostrate in a male urinary system by using the device, in accordance with an embodiment of the present specification;

FIG. 32B is an illustration of transurethral prostate ablation being performed on an enlarged prostrate in a male urinary system using an ablation device, in accordance with one embodiment of the present specification;

FIG. 32C is an illustration of transurethral prostate ablation being performed on an enlarged prostrate in a male urinary system using an ablation device, in accordance with another embodiment of the present specification;

FIG. 32D is a flow chart listing the steps involved in a transurethral enlarged prostate ablation process using an ablation catheter, in accordance with one embodiment of the present specification;

FIG. 32E is an illustration of transrectal prostate ablation being performed on an enlarged prostrate in a male urinary system using an ablation device, in accordance with one embodiment of the present specification;

FIG. 32F is an illustration of transrectal prostate ablation being performed on an enlarged prostrate in a male urinary system using a coaxial ablation device having a positioning element, in accordance with another embodiment of the present specification;

FIG. 32G is a close-up illustration of the distal end of the catheter and needle tip of the ablation device of FIGS. 32E and 32F;

FIG. 32H is a flow chart listing the steps involved in a transrectal enlarged prostate ablation process using an ablation catheter, in accordance with one embodiment of the present specification;

FIG. 33A is an illustration of an ablation catheter, in accordance with an embodiment of the present specification;

Figure 33C:
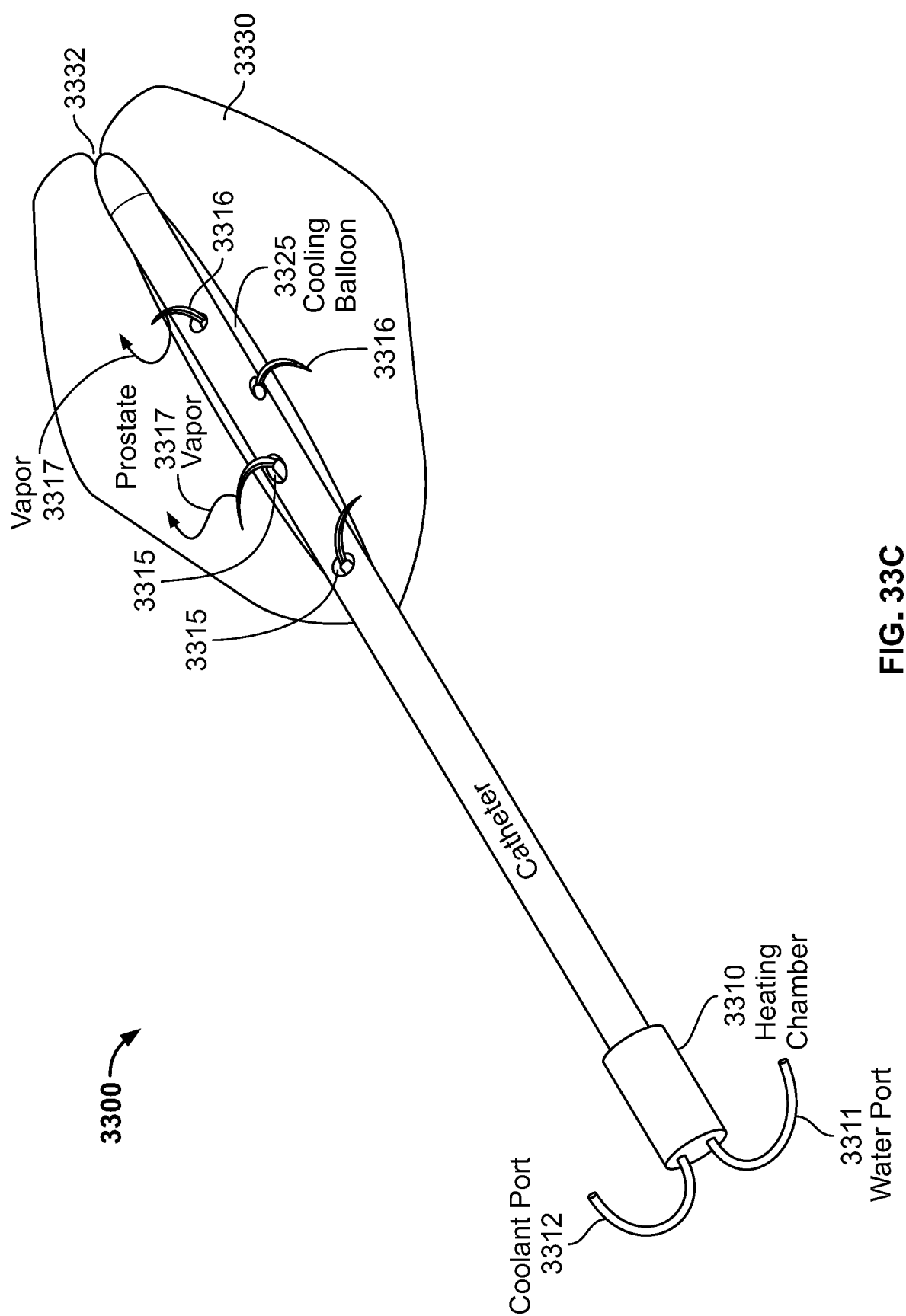
Figure 34C:
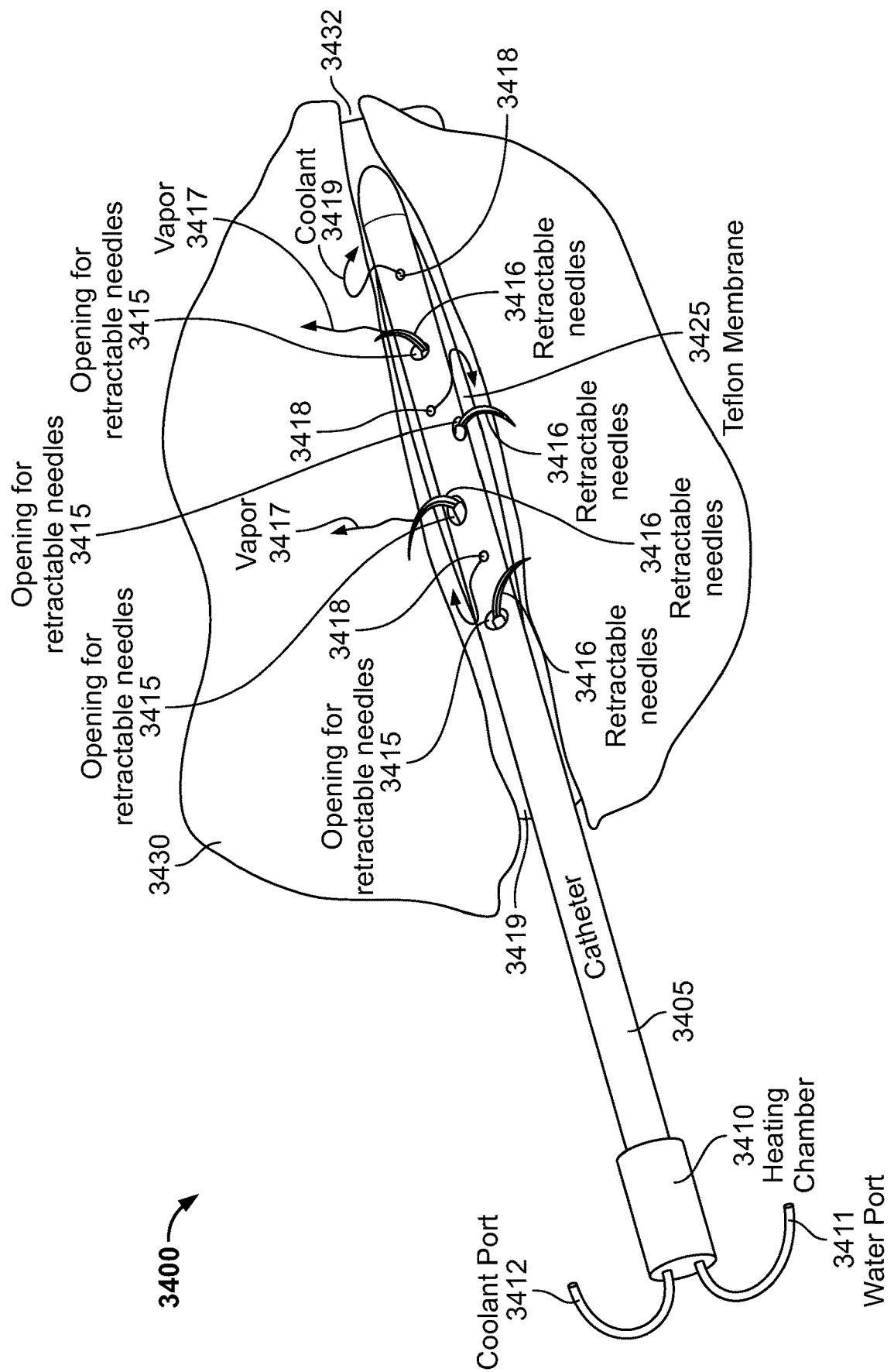

FIG. 33B is a cross-section view of a tip of the ablation catheter of FIG. 33A;

FIG. 33C is an illustration of transurethral prostate ablation being performed using the ablation catheter of FIG. 33A, in accordance with an embodiment;

FIG. 33D is a flow chart listing the steps involved in a transurethral enlarged prostate ablation process, in accordance with an embodiment;

FIG. 34A is an illustration of an ablation catheter, in accordance with another embodiment of the present specification;

FIG. 34B is a cross-section view of a tip of the ablation catheter of FIG. 34A;

FIG. 34C is an illustration of transurethral prostate ablation being performed using the ablation catheter of FIG. 34A, in accordance with an embodiment;

FIG. 34D is a flow chart listing the steps involved in a transurethral enlarged prostate ablation process, in accordance with an embodiment.

Figure 35A:
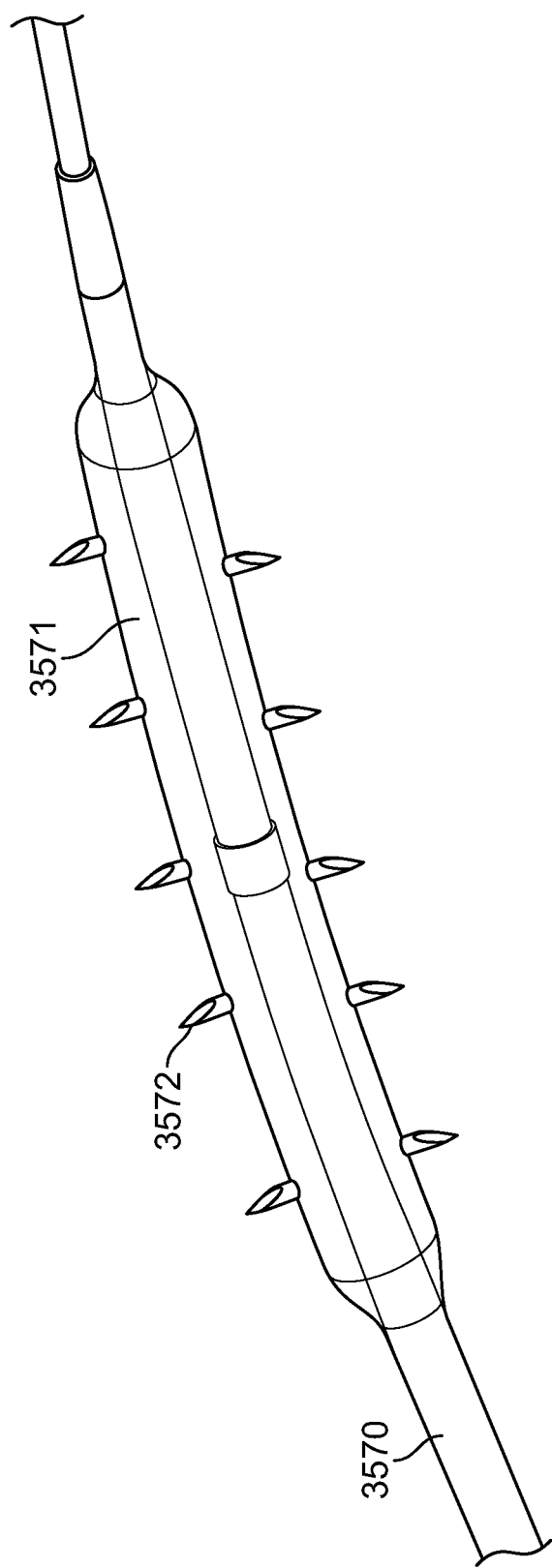
Figure 35B:
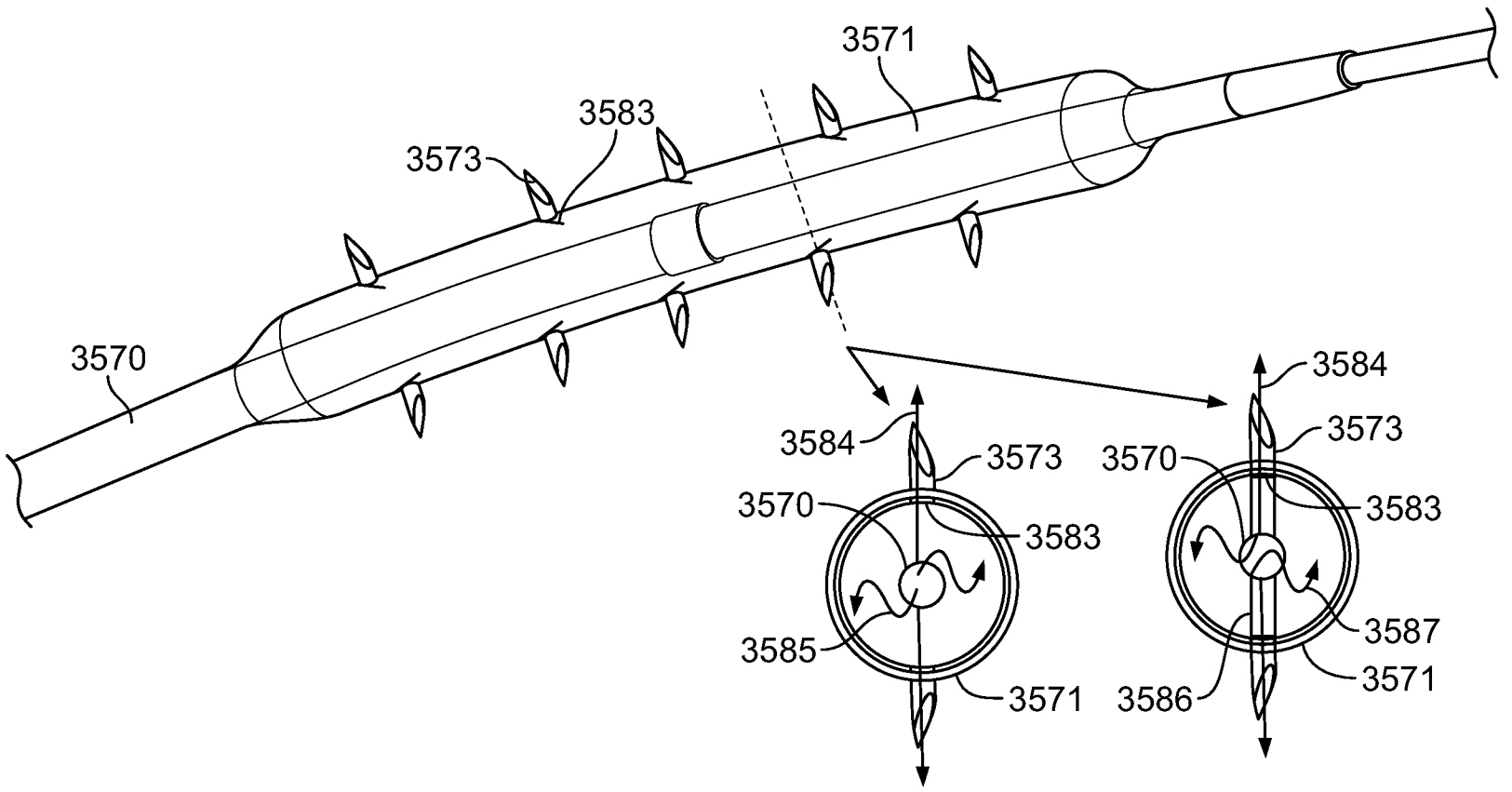
Figure 36:
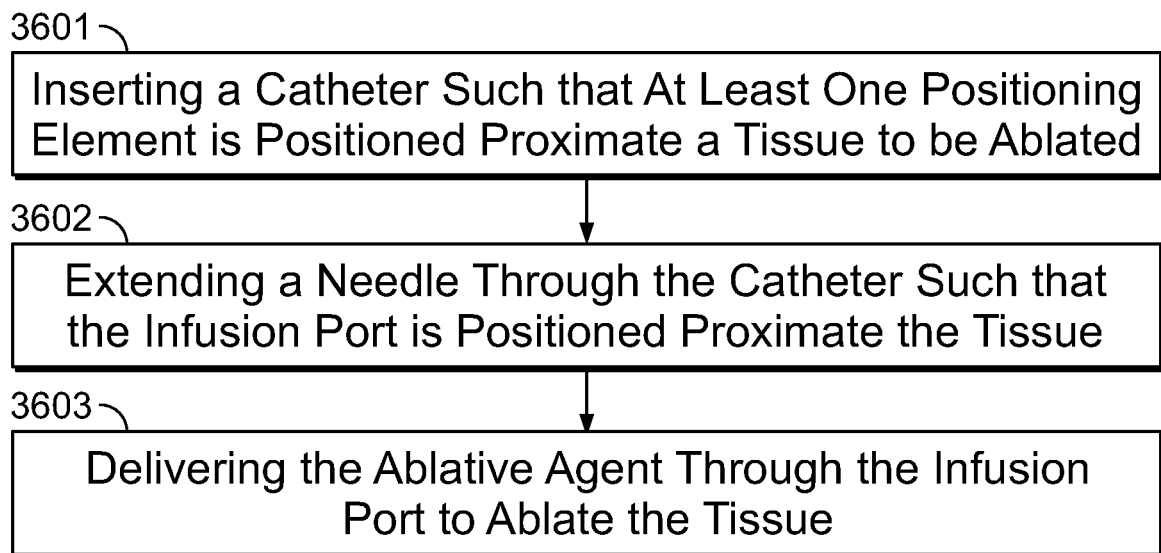
Figure 37:
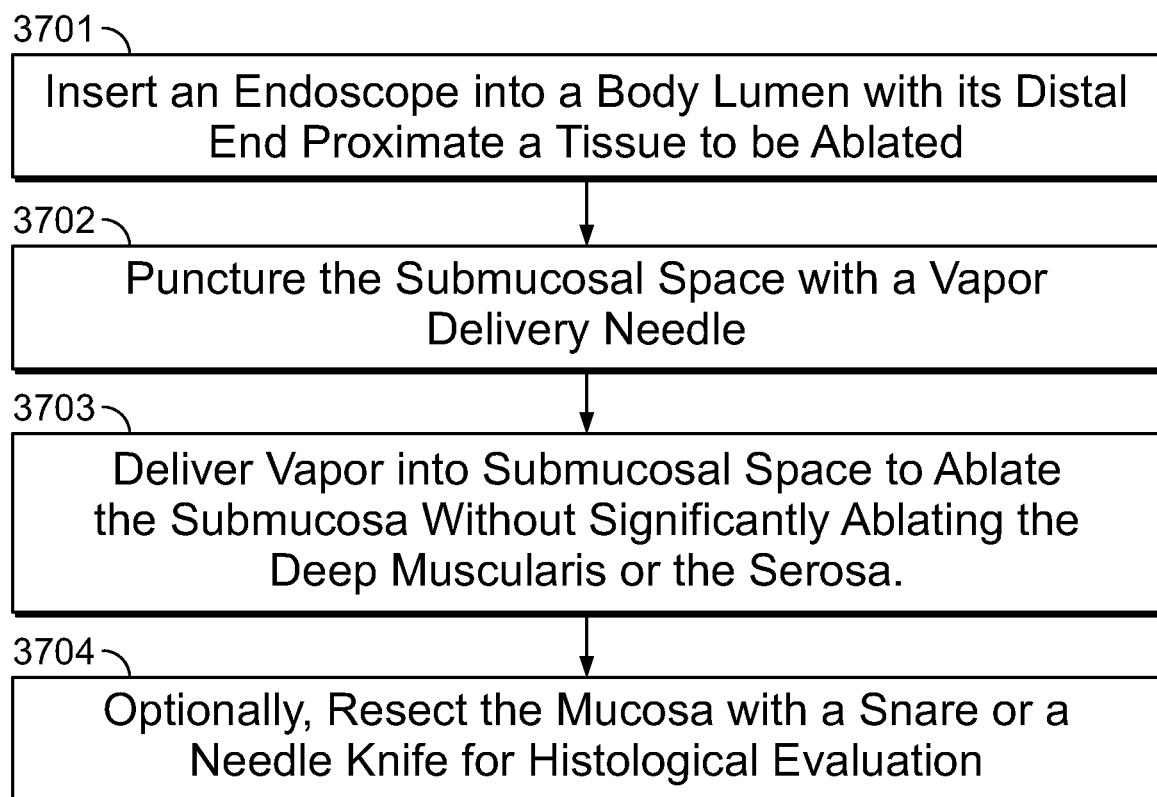
Figure 38:
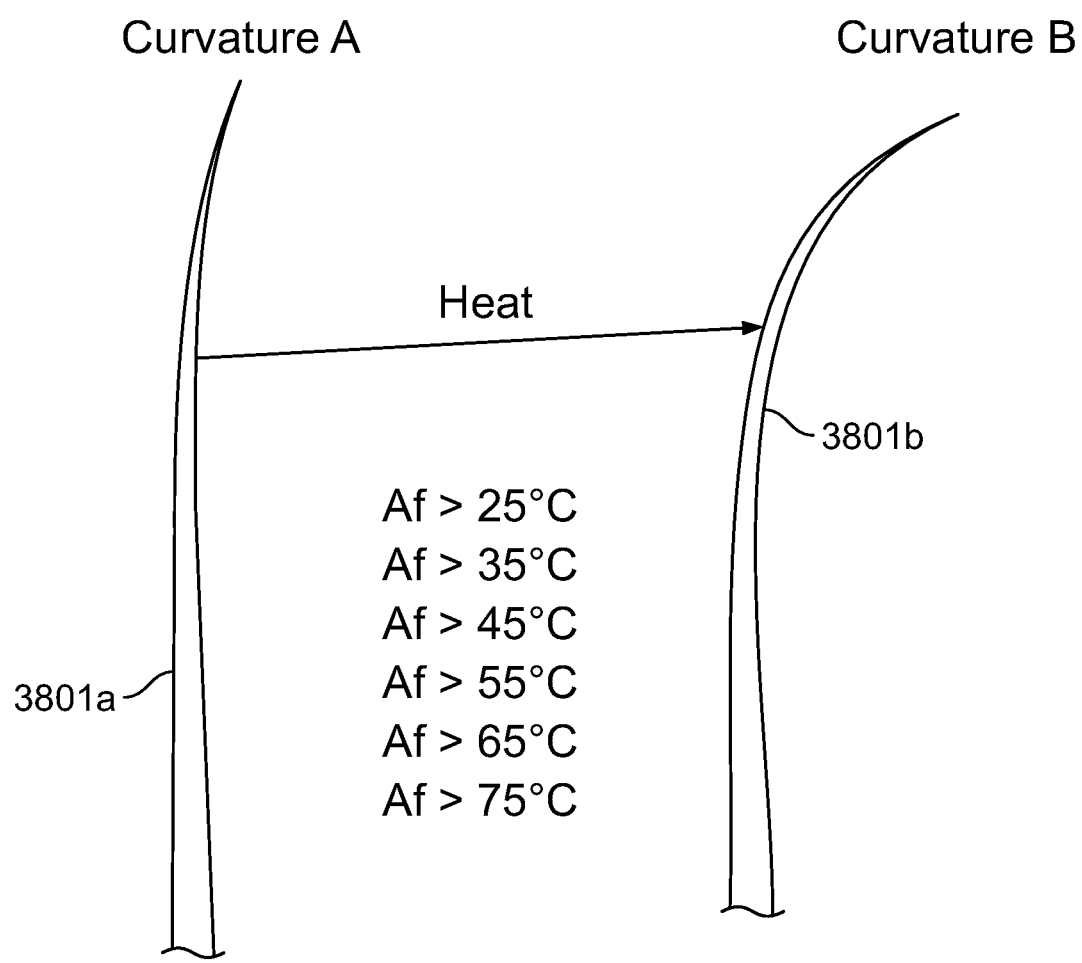
Figure 39:
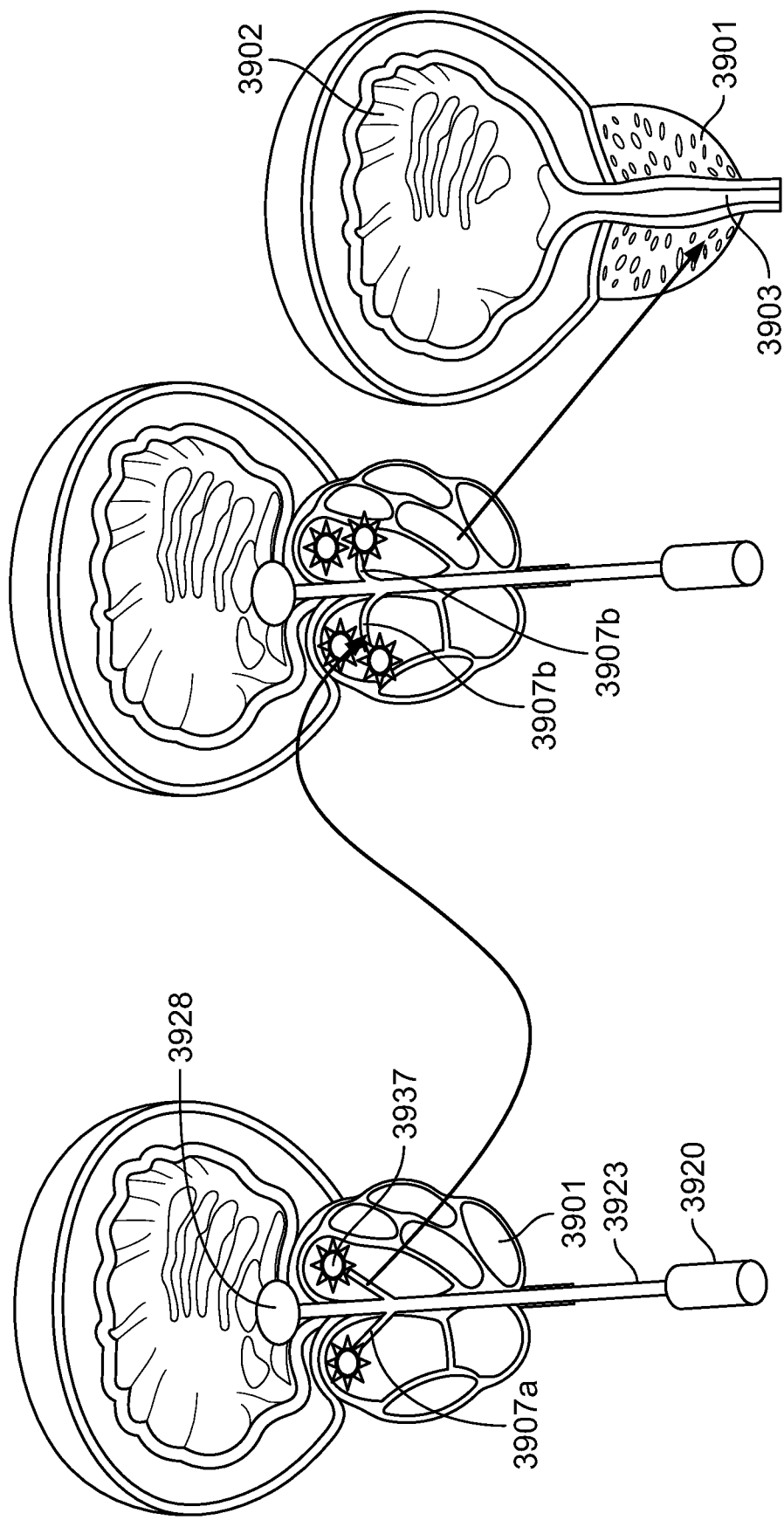
Figure 41:
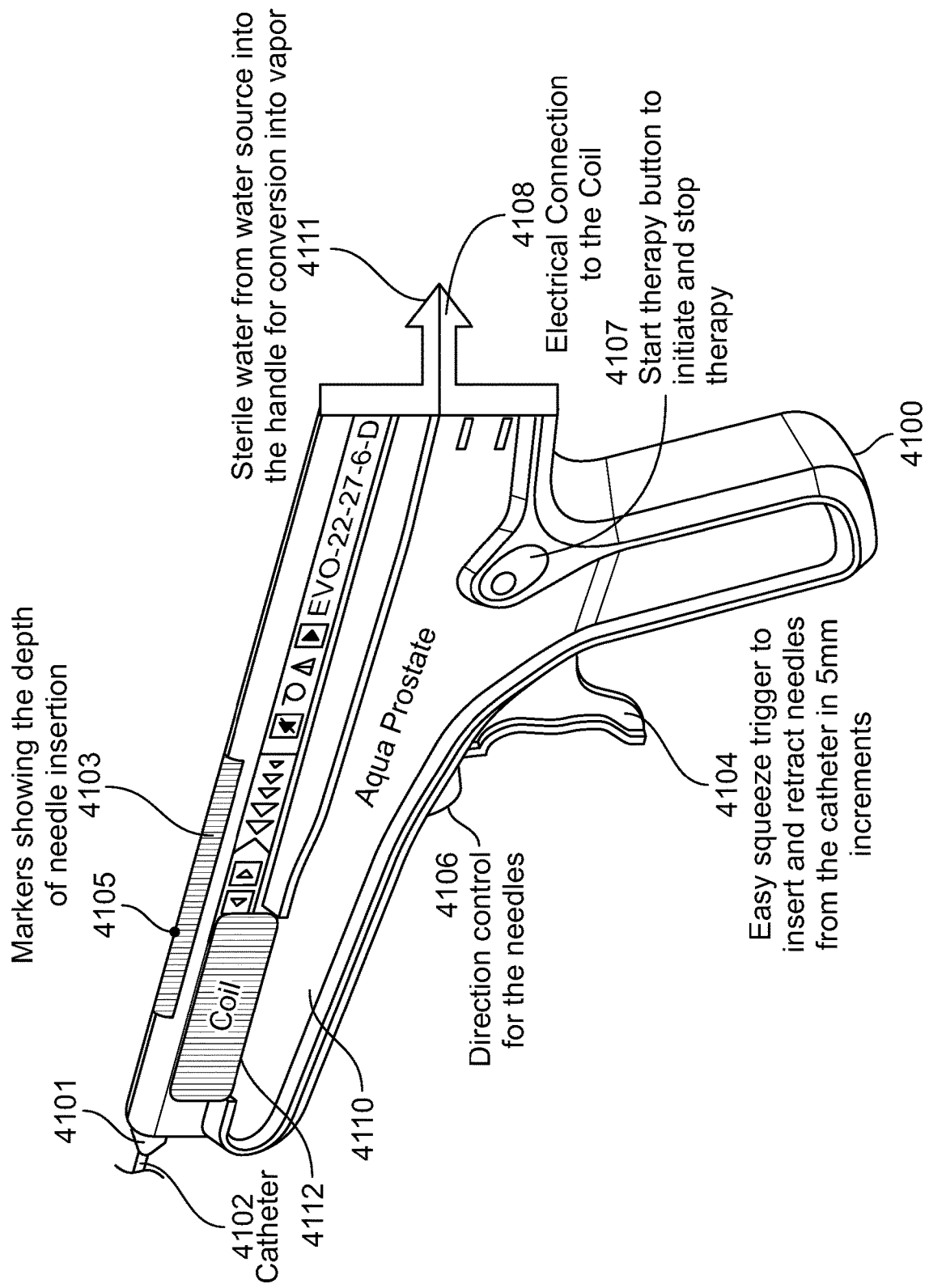
Figure 42A:
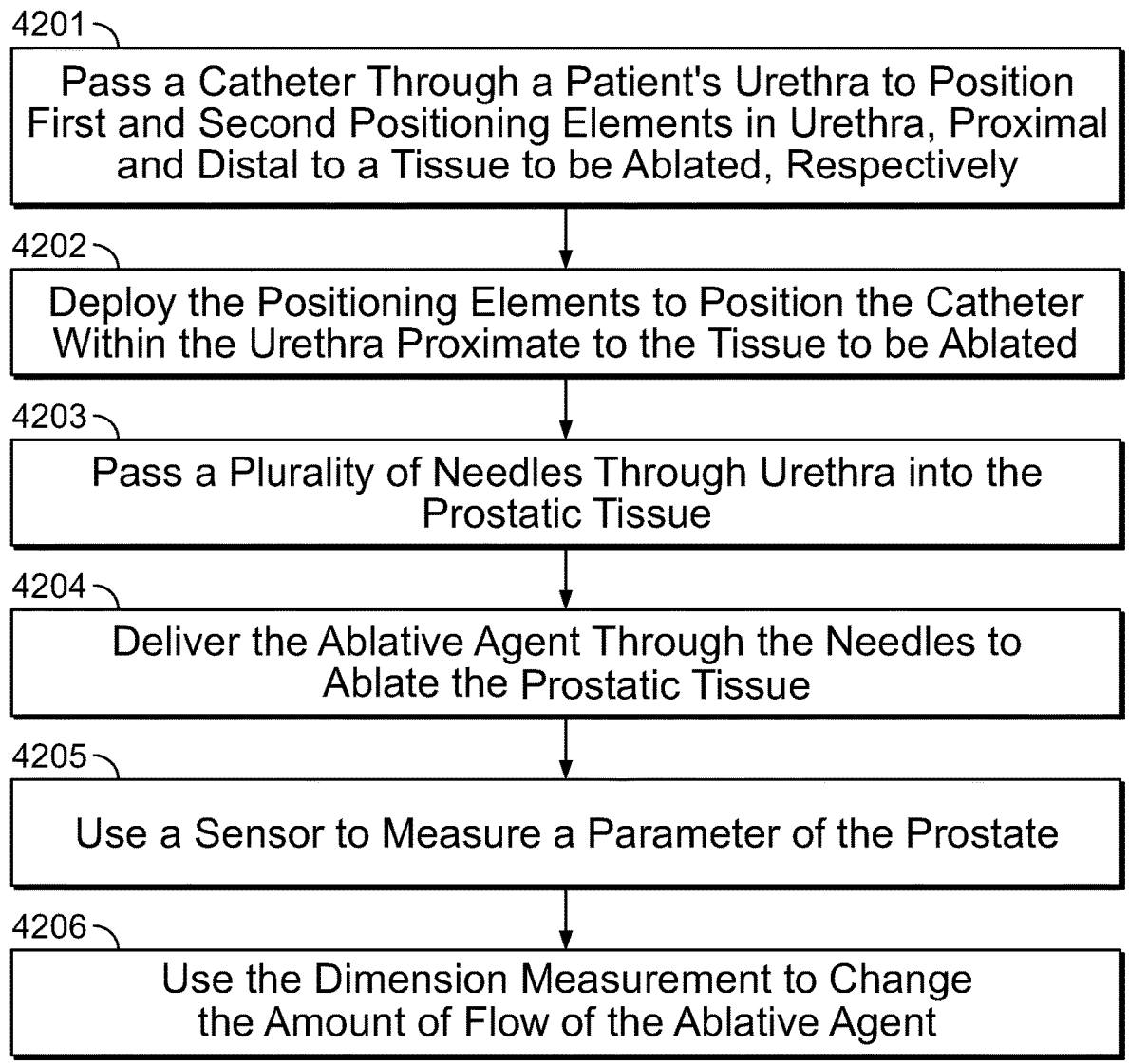
Figure 42B:
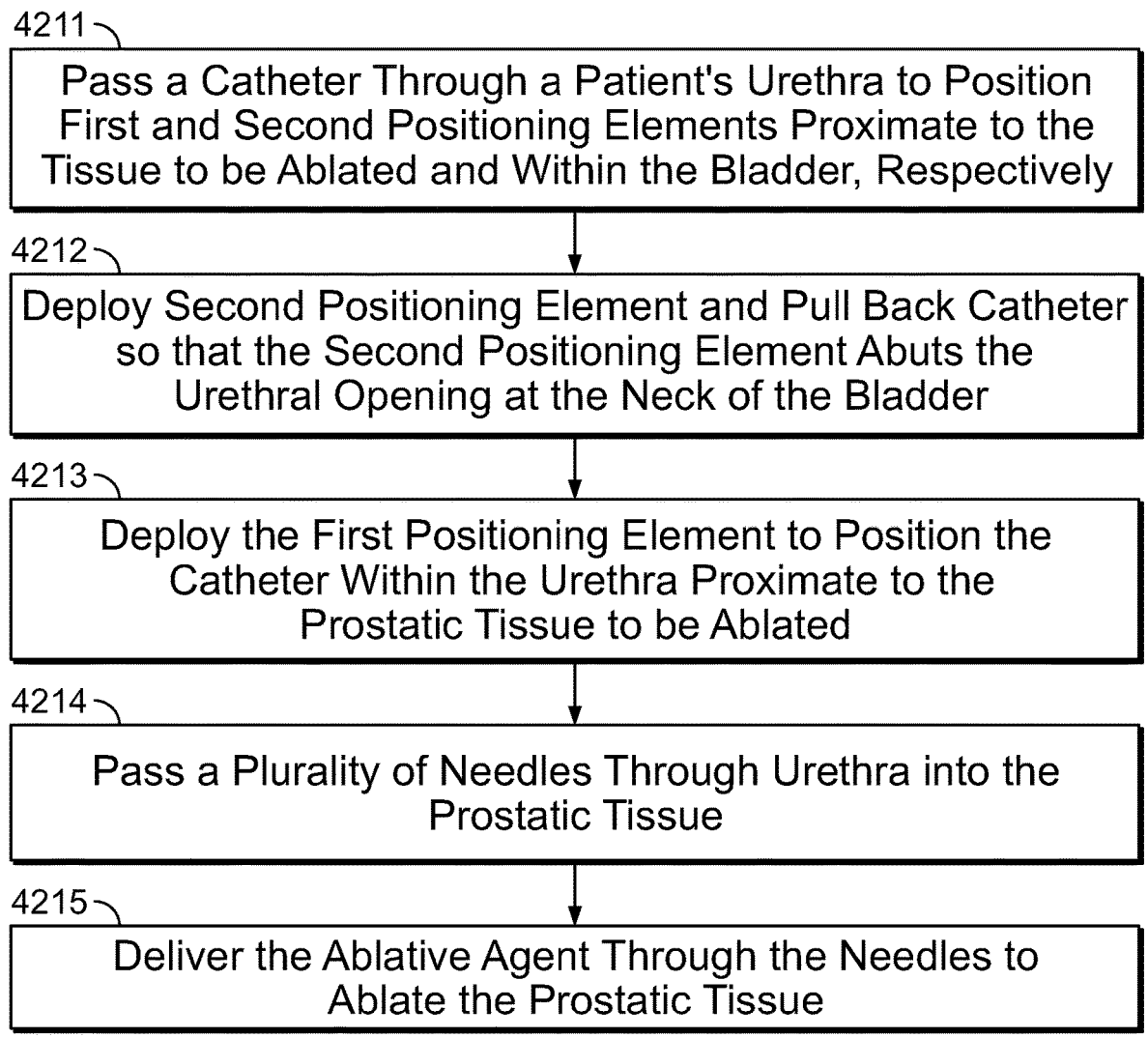

FIG. 35A is an illustration of one embodiment of a positioning element of an ablation catheter, depicting a plurality of thermally conducting elements attached thereto;

FIG. 35B is an illustration of one embodiment of a positioning element of an ablation catheter, depicting a plurality of hollow thermally conducting elements attached thereto;

FIG. 36 is a flowchart illustrating one embodiment of a method of ablation of a tissue using a needle catheter device;

FIG. 37 is a flowchart illustrating a method of ablation of a submucosal tissue using a needle catheter device, according to one embodiment of the present specification;

FIG. 38 is an exemplary illustration of shape changing needles, according to one embodiment of the present specification;

FIG. 39 is an illustration of transurethral prostate ablation being performed using an ablation device, in accordance with one embodiment of the present specification;

FIG. 40A is an illustration of one embodiment of a positioning element of an ablation catheter with needles attached to the catheter body;

FIG. 40B is an illustration of another embodiment of positioning elements for an ablation catheter;

FIG. 40C illustrates a cross section of the distal tip of a catheter, in accordance with an embodiment of the present specification;

FIG. 41 illustrates one embodiment of a handle mechanism that may be used for deployment and retrieval of ablation needles at variable depths of insertion;

FIG. 42A is a flowchart illustrating a method of ablation of prostatic tissue in accordance with one embodiment of the present specification;

FIG. 42B is a flowchart illustrating a method of ablation of prostatic tissue in accordance with another embodiment of the present specification;

FIG. 43A is an International Prostate Symptom Score (IPSS) Questionnaire; and

FIG. 43B is a Benign Prostatic Hypertrophy Impact Index Questionnaire (BPHIIQ).

DETAILED DESCRIPTION

In various embodiments, the ablation devices and catheters described in the present specification are used in conjunction with any one or more of the heating systems described in U.S. patent application Ser. No. 14/594,444, entitled "Method and Apparatus for Tissue Ablation", filed on Jan. 12, 2015 and issued as U.S. Pat. No. 9,561,068 on Feb. 7, 2017, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. The terms "comprises" and variations thereof do not have a limiting meaning where these terms appear in the description and claims.

Unless otherwise specified, "a," "an," "the," "one or more," and "at least one" are used interchangeably and mean one or more than one.

The term "controller" refers to an integrated hardware and software system defined by a plurality of processing elements, such as integrated circuits, application specific integrated circuits, and/or field programmable gate arrays, in data communication with memory elements, such as random access memory or read only memory where one or more processing elements are configured to execute programmatic instructions stored in one or more memory elements.

The term "vapor generation system" refers to any or all of the heater or induction-based approaches to generating steam from water described in this application.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of cardiac arrhythmias, Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferromagnetic materials can be incorporated into the catheter to help with magnetic navigation.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

FIG. 1A illustrates an ablation device, in accordance with an embodiment of the present specification. The ablation device comprises a catheter 10 having a distal centering or positioning attachment which is an inflatable balloon 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. In one embodiment, the infusion ports 12 can direct the ablative agent at different angles. Ablative agent is stored in a reservoir 14 connected to the catheter 10. Delivery of the ablative agent is controlled by a microprocessor 15 and initiation of the treatment is controlled by a treating physician using an input device, such as a foot-paddle 16. In other embodiments, the input device could be a voice recognition system (that is responsive to commands such as "start", "more", "less", etc.), a mouse, a switch, footpad, or any other input device known to persons of ordinary skill in the art. In one embodiment, microprocessor 15 translates signals from the input device, such as pressure being placed on the foot-paddle or vocal commands to provide "more" or "less" ablative agent, into control signals that determine whether more or less ablative agent is dispensed. Optional sensor 17 monitors changes in an ablative tissue or its vicinity to guide flow of ablative agent. In one embodiment, optional sensor 17 also includes a temperature sensor. Optional infrared, electromagnetic, acoustic or radiofrequency energy emitters and sensors 18 measure the dimensions of the hollow organ.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

In one embodiment, the inflatable balloon has a diameter of between 1 mm and 10 cm. In one embodiment, the inflatable balloon is separated from the ports by a distance of 1 mm to 10 cm. In one embodiment, the size of the port openings is between 1 μm and 1 cm. It should be appreciated that the inflatable balloon is used to fix the device and therefore is configured to not contact the ablated area. The inflatable balloon can be any shape that contacts the hollow organ at 3 or more points. One of ordinary skill in the art will recognize that, using triangulation, one can calculate the distance of the catheter from the lesion. Alternatively, the infrared, electromagnetic, acoustic or radiofrequency energy emitters and sensors 18 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. It should be appreciated that the emitter and sensor 18 can be incorporated into a single transceiver that is capable of both emitting energy and detecting the reflected energy.

FIG. 1B illustrates another embodiment of a catheter 110 for use with the ablation device of FIG. 1A. The catheter 110 includes an inlet port 119 and an insufflation port 120 at its proximal end. An ablative agent is introduced into the catheter 110 via the inlet port 119 and is delivered to a target region by at least one delivery port 112 at the distal end of the catheter 110. Air is introduced at the insufflation port 120 to inflate at least one positioning element 111 at the distal end of the catheter. In one embodiment, the at least one positioning element 111 is a balloon.

FIG. 2A illustrates a longitudinal section of the ablation device, depicting a distribution of infusion ports. FIG. 2B illustrates a cross section of a distribution of infusion ports on the ablation device, in accordance with an embodiment of the present specification. The longitudinal and cross sectional views of the catheter 10 as illustrated in FIGS. 2A and 2B respectively, show one arrangement of the infusion ports 12 to produce a uniform distribution of ablative agent 21 in order to provide a circumferential area of ablation in a hollow organ 20. FIG. 2C illustrates a cross section of a distribution of infusion ports on the ablation device, in accordance with another embodiment of the present specification. The arrangement of the infusion ports 12 as illustrated in FIG. 2C produce a focal distribution of ablative agent 21 and a focal area of ablation in a hollow organ 20.

For all embodiments described herein, it should be appreciated that the size of the port, number of ports, and distance between the ports will be determined by the volume of ablative agent needed, pressure that the hollow organ can withstand, size of the hollow organ as measured by the distance of the surface from the port, length of the tissue to be ablated (which is roughly the surface area to be ablated), characteristics of the tissue to be ablated and depth of ablation needed. In one embodiment, there is at least one port opening that has a diameter between 1 μm and 1 cm. In another embodiment, there are two or more port openings that have a diameter between 1 μm and 1 cm and that are equally spaced around the perimeter of the device. In some embodiments, the ports optionally have valves for the control of release of the ablative agent. In various embodiments, the valves are regulated either by pressure, temperature, or both.

Figure 2D:
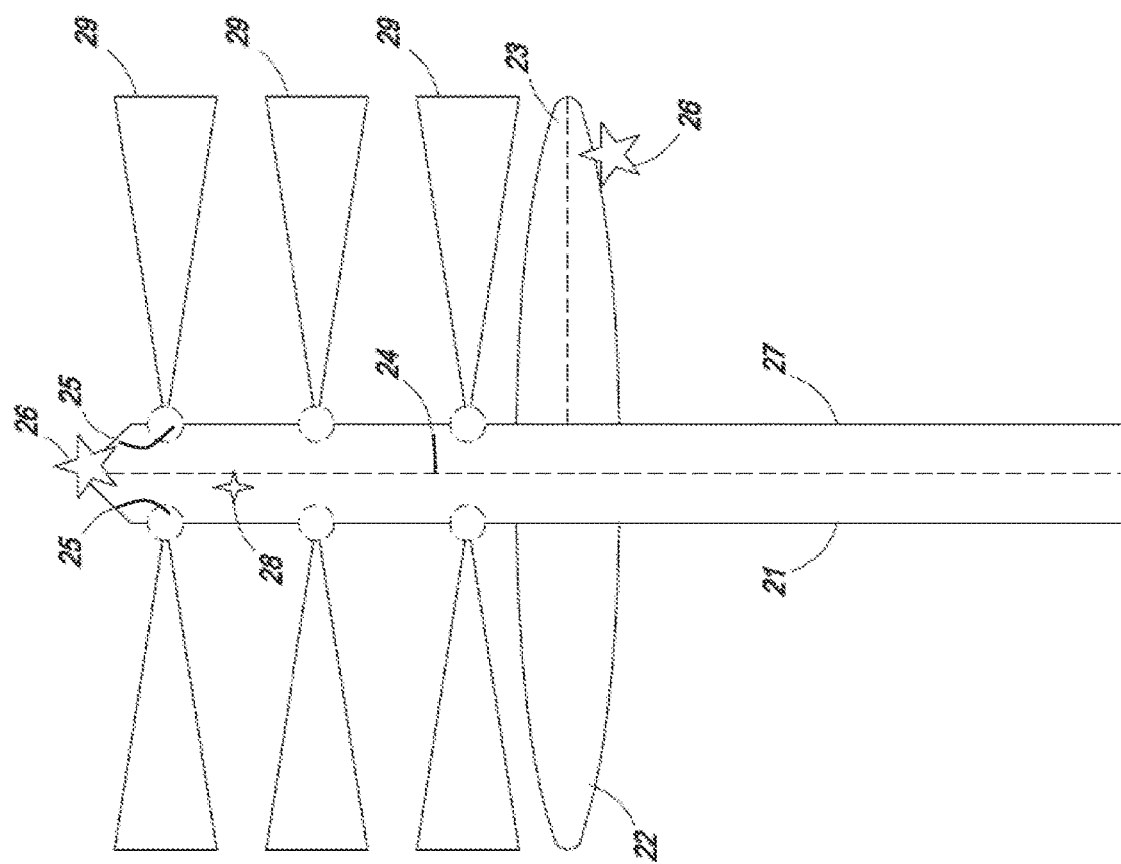
FIG. 2D illustrates a catheter of the ablation device, in accordance with an embodiment of the present specification.

FIG. 2D illustrates another embodiment of the ablation device. The vapor ablation catheter comprises an insulated catheter 21 with one or more positioning attachments 22 of known length 23. The vapor ablation catheter has one or more vapor infusion ports 25. The length 24 of the vapor ablation catheter 21 with infusion ports 25 is determined by the length or area of the tissue to be ablated. Vapor 29 is delivered through the vapor infusion ports 25. The catheter 21 is preferably positioned in the center of the positioning attachment 22, and the infusion ports 25 are arranged circumferentially for circumferential ablation and delivery of vapor. In another embodiment, the catheter 21 can be positioned toward the periphery of the positioning attachment 22 and the infusion ports 25 can be arranged non-circumferentially, preferably linearly on one side for focal ablation and delivery of vapor. The positioning attachment 22 is one of an inflatable balloon, a wire mesh disc with or without an insulated membrane covering the disc, a cone shaped attachment, a ring shaped attachment or a freeform attachment designed to fit the desired hollow body organ or hollow body passage, as further described below. Optional infrared, electromagnetic, acoustic or radiofrequency energy emitters and sensors 28 are incorporated to measure the dimensions of the hollow organ.

The vapor ablation catheter may also comprise an optional coaxial sheet 27 to restrain the positioning attachment 22 in a manner comparable to a coronary metal stent. In one embodiment, the sheet is made of memory metal or memory material with a compressed linear form and a non-compressed form in the shape of the positioning attachment. Alternatively, the channel of an endoscope may perform the function of restraining the positioning attachment 22 by, for example, acting as a constraining sheath. Optional sensor 26 is deployed on the catheter to measure changes associated with vapor delivery or ablation. The sensor is one of temperature, pressure, photo or chemical sensor.

Optionally, one or more, infrared, electromagnetic, acoustic or radiofrequency energy emitters and sensors 28 can measure the dimensions of the hollow organ. The infrared, electromagnetic, acoustic or radiofrequency energy is emitted from the emitter 28 and is reflected back from the tissue to the detector in the emitter 28. The reflected data can be used to determine the dimension of the hollow cavity. The measurement is performed at one or multiple points to get an accurate estimate of the dimension of the hollow organ. The data can also be used to create a topographic representation of the hollow organ. Additional data from diagnostic tests can be used to validate or add to the data from the above measurements.

Figure 2E:
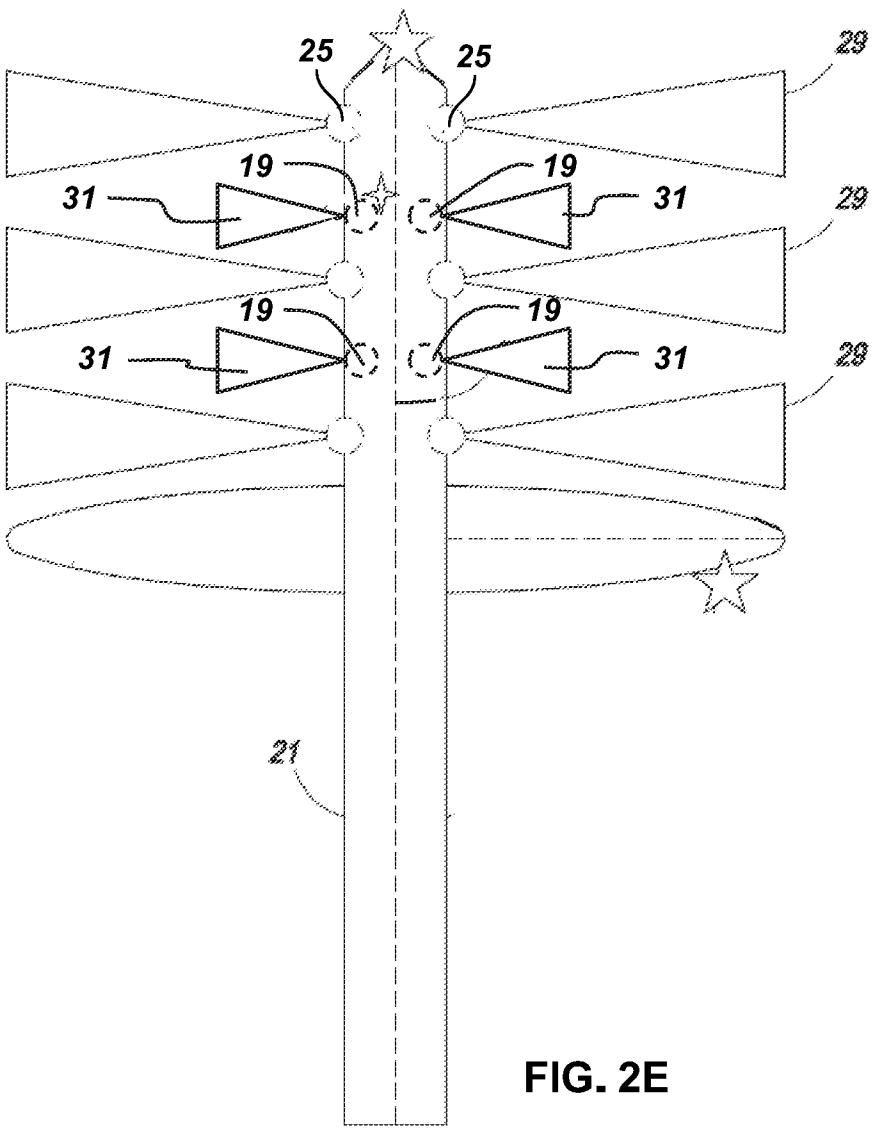
FIG. 2E illustrates a catheter of the ablation device, in accordance with another embodiment of the present specification.

FIG. 2E illustrates a catheter 21 of the ablation device, in accordance with another embodiment of the present specification. The catheter 21 is similar to that described with reference to FIG. 2D, however, the catheter 21 of FIG. 2E additionally includes at least one port 19 for the delivery of a conductive medium 31. In one embodiment, the conductive medium 31 is injected into the hollow tissue or organ prior to the introduction of the ablative agent 29. Once the tissue has been filled to an appropriate level with the conductive medium 31, ablative agent 29 is then delivered into the conductive medium 31 filled tissue. The conductive medium 31 acts to evenly distribute the ablative agent 29, resulting in more consistent and effective ablation of the target tissue.

Figure 2F:
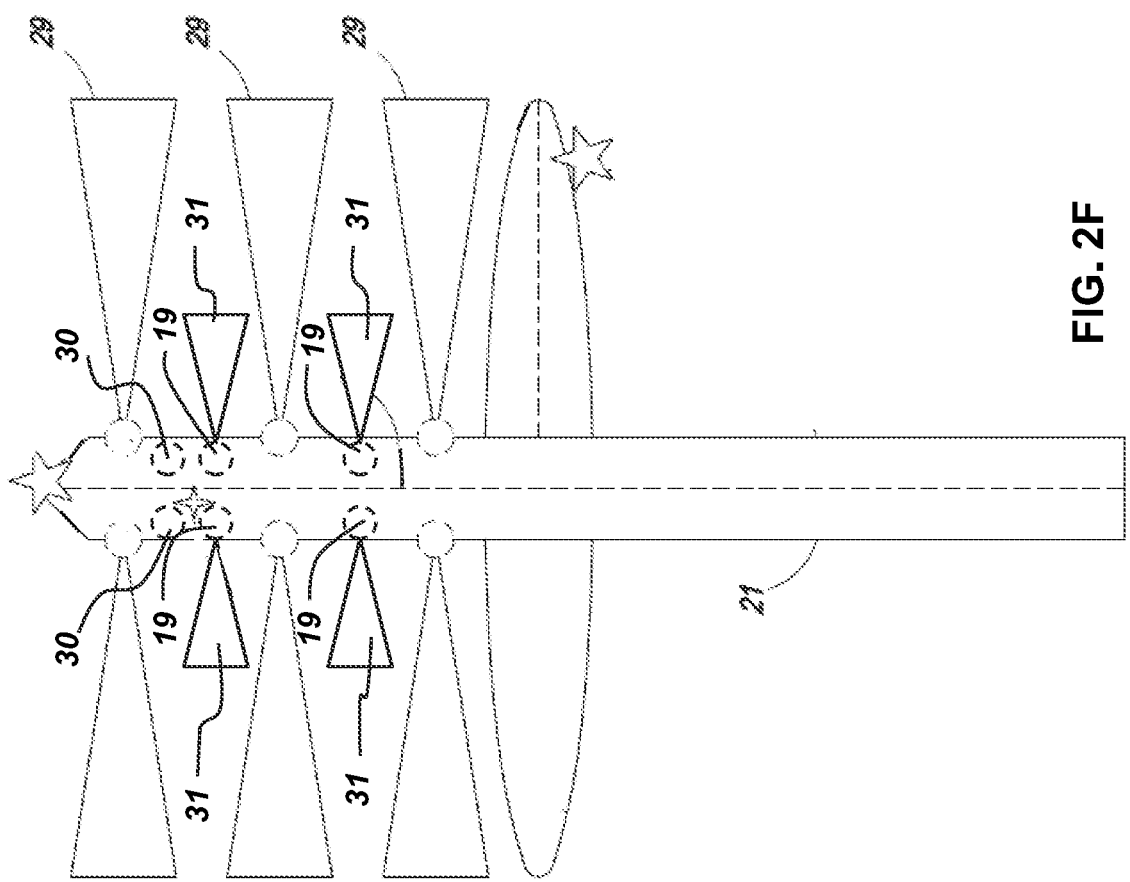
FIG. 2F illustrates a catheter of the ablation device, in accordance with yet another embodiment of the present specification.

FIG. 2F illustrates a catheter 21 of the ablation device, in accordance with yet another embodiment of the present specification. The catheter 21 is similar to that described with reference to FIG. 2E, however, the catheter 21 of FIG. 2F additionally includes at least one port 30 for the removal via suction of the natural contents of the hollow tissue or organ. In one embodiment, the natural contents of the hollow tissue or organ are removed prior to the introduction of the conductive medium 31 or the ablative agent 29.

In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the ablative agent delivery port 25. In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the conductive medium delivery port 19. In yet another embodiment, as depicted in FIG. 2D, the conductive medium can be delivered, and, the natural contents of the hollow tissue or organ can be removed via suction, using the ablative agent delivery port 25. In various embodiments, after ablation of the target tissue(s), the remaining contents of the hollow tissue or organ are removed via suction using one or more of the ports described above.

In various embodiments, with respect to the catheters depicted in FIGS. 2A-2F, the ablative agent can be any one of steam, liquid nitrogen, or any other suitable ablative agent.

Figure 2G:
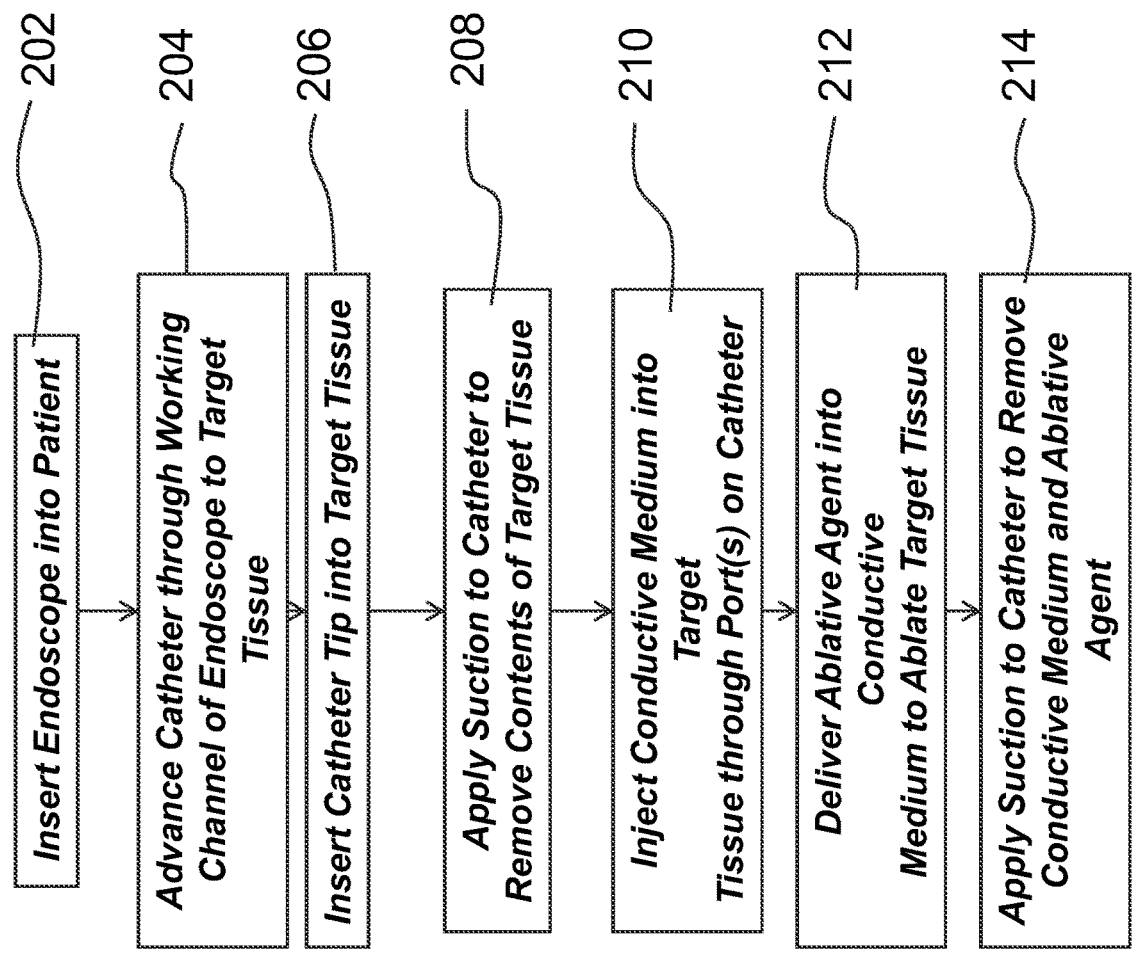
FIG. 2G is a flow chart listing the steps involved in a hollow tissue or organ ablation process using an ablation device, in accordance with one embodiment of the present specification.

FIG. 2G is a flow chart listing the steps involved in a hollow tissue or organ ablation process using the ablation device, in accordance with one embodiment of the present specification. At step 202, an endoscope is inserted into a patient. An ablation device comprising a catheter in accordance with one embodiment of the present specification, is advanced through a working channel of the endoscope and to a target tissue at step 204. At step 206, the distal end or tip of the catheter is inserted into the target hollow tissue or organ. Then, at step 208, suction is applied at the proximal end of the catheter to remove the natural contents of the hollow tissue or organ. A conductive medium is then injected, at step 210, into the hollow tissue or organ via at least one port on the distal end of the catheter. At step 212, an ablative agent is delivered into the conductive medium for ablation of the target tissue. At step 214, the remaining contents of the tissue, including conductive medium and ablative agent, are removed via suction using the catheter. In another embodiment, step 214 is optional, and the remaining contents of the hollow tissue or organ are reabsorbed by the body. In another embodiment, the removal of the natural contents of the hollow tissue or organ at step 208 is optional, and the procedure moves directly to the injection of conductive medium at step 210 from entering the target tissue with the catheter at step 206. Optionally, in some embodiments, the natural contents of the hollow organ can be used as the conductive media.

Figure 2H:
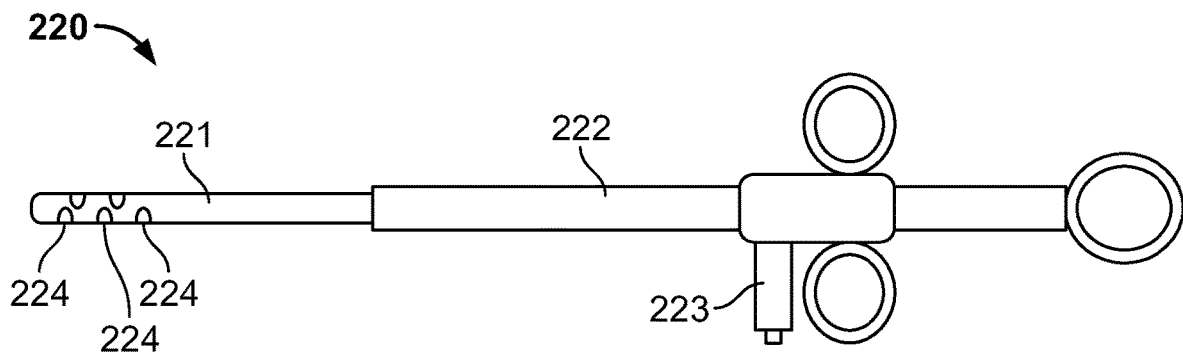
FIG. 2H illustrates an ablation device in the form of a catheter extending from a conventional snare handle, in accordance with an embodiment of the present specification.

FIG. 2H illustrates an ablation device 220 in the form of a catheter 221 extending from a conventional handle 222, in accordance with an embodiment of the present specification. The catheter 221 is of a type as described above and extends from and attaches to the handle 222. In one embodiment, the catheter 221 is insulated to protect the user from burns that could result from hot vapor heating the catheter. In one embodiment, the catheter is composed of a material that will ensure that the outer temperature of the catheter will remain below 60° C. during use. The handle 222 includes a pressure resistant port at the point of attachment with the catheter 221. The handle 222 also includes a flow channel within that directs vapor through to the catheter 221.

In one embodiment, the snare handle 222 includes a single attachment port 223 for the connection of a vapor stream and an RF feed. In another embodiment (not shown), the snare handle includes two separate attachment ports for the connection of a vapor stream and an RF feed. The attachment port 223 interfaces with the vapor supply cord via pressure-resistant connectors. In one embodiment, the connectors are of a luer lock type. In one embodiment, the catheter 221 is a dual lumen catheter. The first lumen serves to deliver vapor to the site of ablation. In one embodiment, the vapor is released through small ports 224 positioned proximate the distal end of the catheter 221. The distal end of the catheter 221 is designed so that it can puncture the tissue to deliver vapor to the desired depth and location within the target tissue. In one embodiment, the distal end of the catheter 221 tapers to a point. The second lumen houses the electrode used for RF ablation. In one embodiment, the delivery of vapor or RF waves is achieved through the use of a microprocessor. In another embodiment, the user can release vapor or subject the target tissue to RF waves by the use of actuators (not shown) on the handle 222. In one embodiment, the catheter has varying or differential insulation along its length. In one embodiment, the ablation device 220 includes a mechanism in which a snare to grasp the tissue to be ablated and sizing the tissue in the snare is used to determine the amount of vapor to be delivered.

Figure 2I:
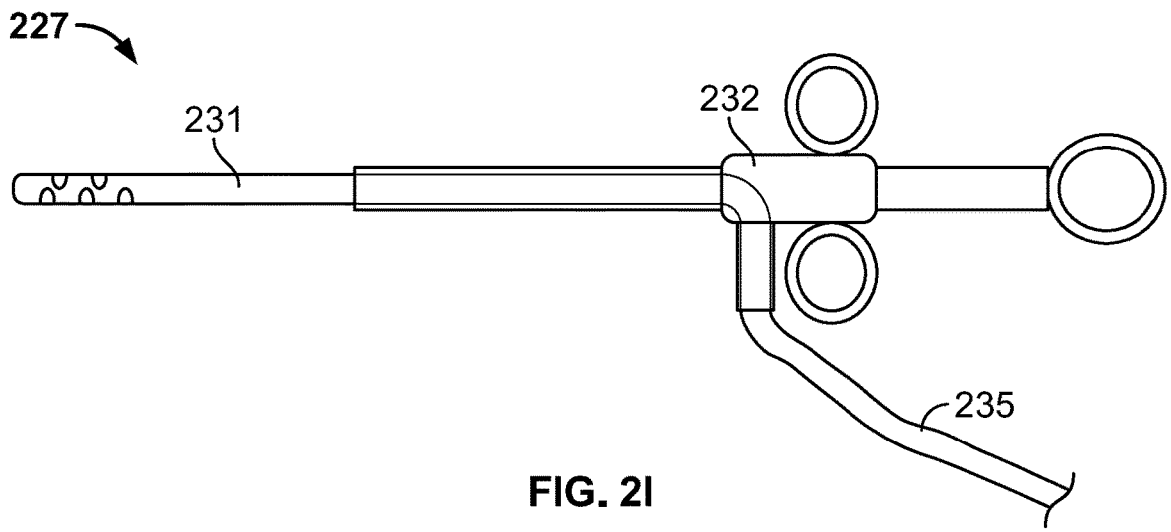
FIG. 2I illustrates a cross section of an ablation device in the form of a catheter extending from a conventional snare handle with a pre-attached cord, in accordance with another embodiment of the present specification.

FIG. 2I illustrates a cross section of an ablation device 227 in the form of a catheter 231 extending from a conventional handle 232 with a pre-attached cord 235, in accordance with another embodiment of the present specification. The cord 235 attaches directly to the vapor delivery system, eliminating one interface between the system and the ablation device and thereby decreasing the chance of system failure as a result of disconnection. In this embodiment, the handle 232 includes a separate attachment port (not shown) for the RF or an electric feed.

Figure 2J:
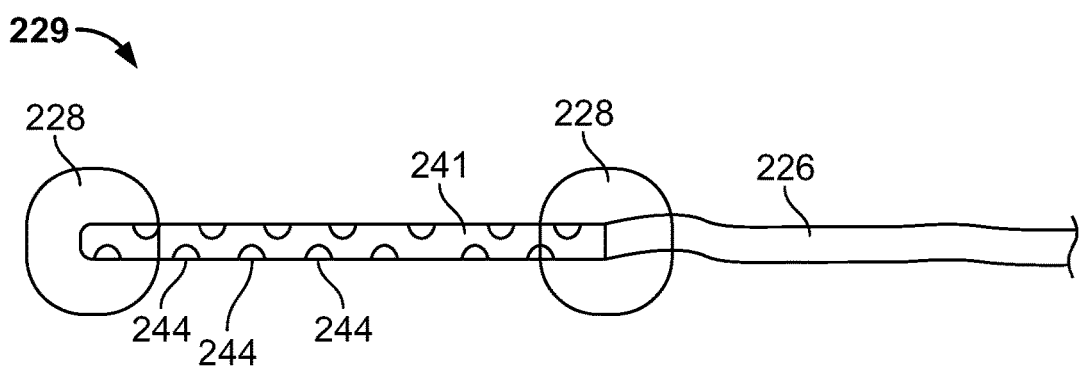
FIG. 2J illustrates an ablation device in the form of a catheter extending from a conventional esophageal probe, in accordance with an embodiment of the present specification.

FIG. 2J illustrates an ablation device 229 in the form of a catheter 241 extending from a conventional esophageal probe 226, in accordance with an embodiment of the present specification. In one embodiment, the catheter 241 is insulated and receives vapor from a flow channel contained within the probe 226. The catheter 241 includes a multitude of small ports 244 for the delivery of vapor to the target tissue. The delivery of vapor is controlled by a microprocessor. In one embodiment, the catheter 241 also includes two inflatable balloons 228, one at its distal end beyond the last vapor port 244, and one at its proximal end, proximate the catheter's 241 attachment to the probe 226. All vapor ports are positioned between these two balloons. Once the device 229 is inserted within the esophagus, the balloons 228 are inflated to keep the catheter 241 positioned and to contain the vapor within the desired treatment area. In one embodiment, the balloons must be separated from the ablation region by a distance of greater than 0 mm, preferably 1 mm and ideally 1 cm. In one embodiment, the diameter of each balloon when inflated is in the range of 10 to 100 mm, preferably 15-40 mm, although one of ordinary skill in the art would appreciate that the precise dimensions are dependent on the size of the patient's esophagus.

In one embodiment, the catheter 241 attached to the esophageal probe 226 is a dual lumen catheter. The first lumen serves to deliver vapor to the site of ablation as described above. The second lumen houses the electrode used for RF ablation.

In various embodiments, ablation therapy provided by the vapor ablation systems of the present specification is delivered to achieve the following general therapeutic endpoints: maintain a tissue temperature between 45° C. and 100° C. for a time period lasting longer than 1 sec; maintain a tissue temperature at 100° C. or less to cause coagulation of intracellular proteins without carbonization of intracellular sugars; exert a pressure on a tissue to be ablated equal to or less than 125% of a pre-treatment pressure of the tissue; and exert a pressure on a tissue to be ablated which is less than a patient's mean arterial pressure so as not to impede perfusion to the tissue.

Figure 3:
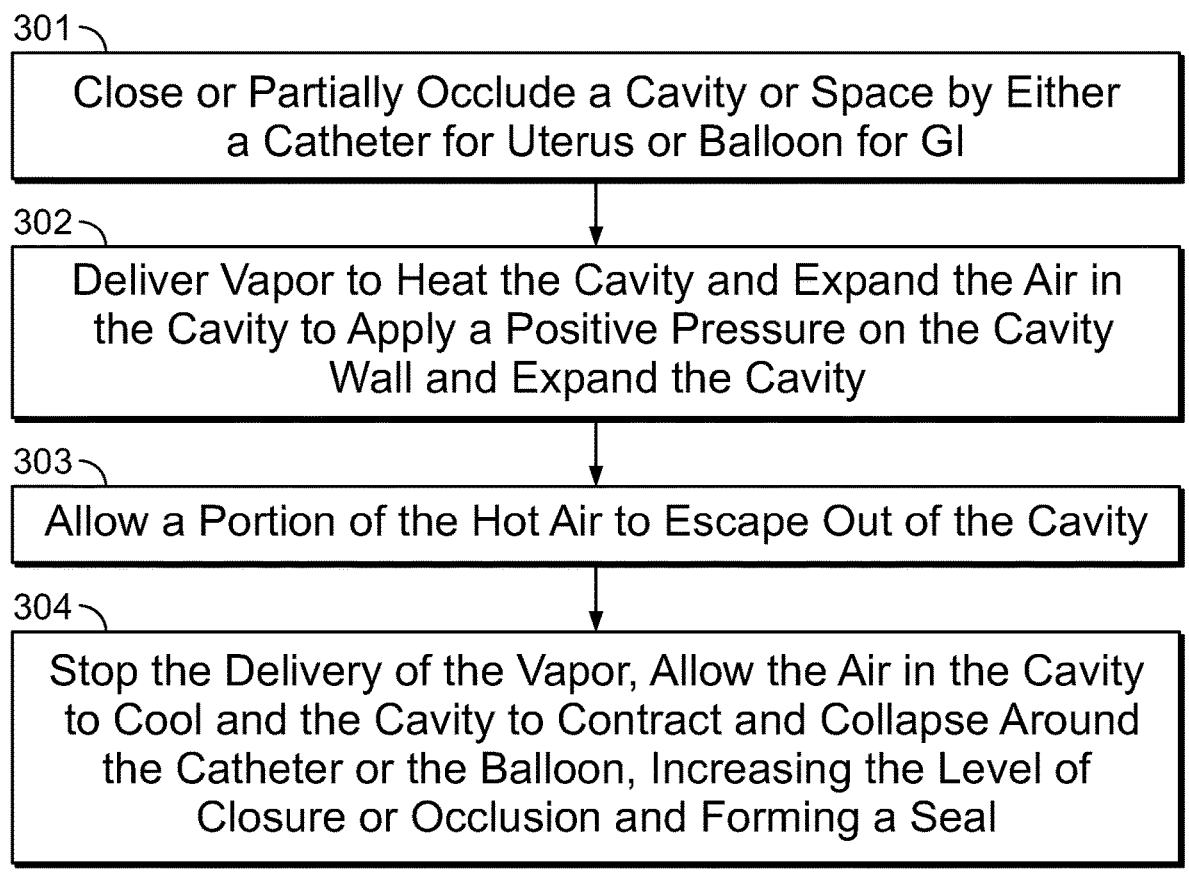
FIG. 3 is a flowchart detailing the steps involved in one embodiment of a method of tissue ablation.

FIG. 3 is a flowchart detailing the steps involved in one embodiment of a method of tissue ablation. In the first step 301, a body lumen, cavity or space where the tissue to be ablated is located, is either partially or completely occluded or closed. This closure or occlusion can be achieved by passing a catheter, such as in case of ablation in the uterus of a patient, or by means of a balloon, such as when ablation is performed in the GI tract of a patient. In the next step 302, vapor is delivered to heat the cavity, which in turn expands the air in the cavity. The expanding air acts to increase the pressure in the cavity and applies a positive pressure on the cavity wall. This in turn expands the body cavity. In the next step 303, a portion of the hot air in the body cavity is allowed to escape out of the cavity. Next, in step 304, the delivery of the vapor is stopped and the air in the cavity is allowed to cool. This contracts the air in the cavity and decreases the pressure in the cavity. This in turn allows the cavity to contract and collapse around the catheter or the balloon, thereby increasing the level of closure or occlusion and forming a seal. As the body cavity seals around the inserted catheter or balloon, it does not allow the expelled air to reenter the cavity. This creates a negative pressure in the cavity and this negative pressure is applied to the cavity wall. The negative pressure in turn may increase the blood flow to the cavity wall, cooling the cavity wall. Additionally, allowing for the heated air to escape the cavity allows for pressure on the cavity wall to be relieved during cessation of flow of the ablative agent between cycles of ablation, thereby allowing for capillary blood flow and cooling of the ablation zone.

Figure 4A:
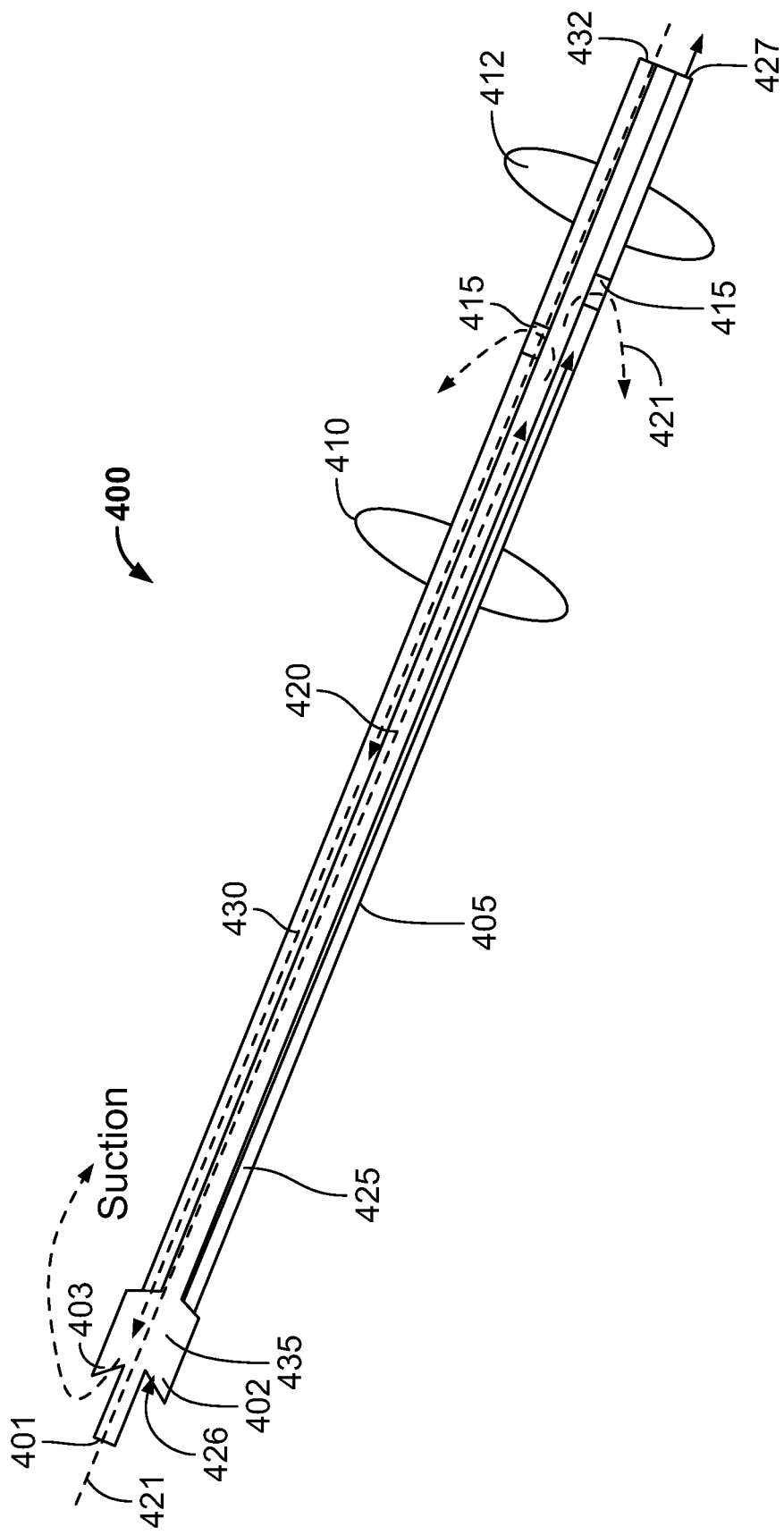
FIG. 4A illustrates a multi-lumen ablation catheter, in accordance with an embodiment.

FIG. 4A illustrates a multiple lumen ablation catheter 400 in accordance with an embodiment of the present specification. The catheter 400 includes an elongate body 405 with a proximal end and a distal end. The catheter 400 includes at least one positioning element proximate its distal end. In various embodiments, the positioning element is a balloon. In some embodiments, the catheter includes more than one positioning element.

In the embodiment depicted in FIG. 4A, the catheter 400 includes two positioning balloons 410, 412 proximate its distal end with a plurality of infusion ports 415 located on the body 405 between the two balloons 410, 412. A fluid delivery port 427 and a suction port 432 are located at the distal end of the body 405. The body 405 includes a first lumen 420 in fluid communication with the plurality of infusion ports 415, a second lumen 425 in fluid communication with the fluid delivery port 427, and a third lumen 430 in fluid communication with the suction port 432. The first, second and third lumens 420, 425, 430 extend along the length of the body 405 through a handle 435 at the proximal end to the distal end. An ablative agent 421 is introduced into the first lumen 420 at an ablative agent input port 401 at the proximal end of the catheter 400 and exits through the infusion ports 415 for ablation. In one embodiment, the ablative agent 421 is steam.

A fluid 426 is introduced into the second lumen 425 at a fluid input port 402 at the proximal end of the catheter 400 and exits through the fluid delivery port 427. In one embodiment, the fluid 426 is a coolant. In one embodiment, the coolant is water and is in a temperature range of 0 degrees C. to 60 degrees C. Negative pressure is applied, using a pump, to the third lumen 430 at a suction input port 403 at the proximal end of the catheter 400 to enable suction of the fluid, delivered from the fluid delivery port 427 and the infusion ports 415 respectively, via the suction port 432. In various embodiments, the fluid delivery port 427 and a suction port 432 can be located at various locations along the length of the catheter 400 distal to positioning balloon 412 or proximal to positioning balloon 410.

Figure 4B:
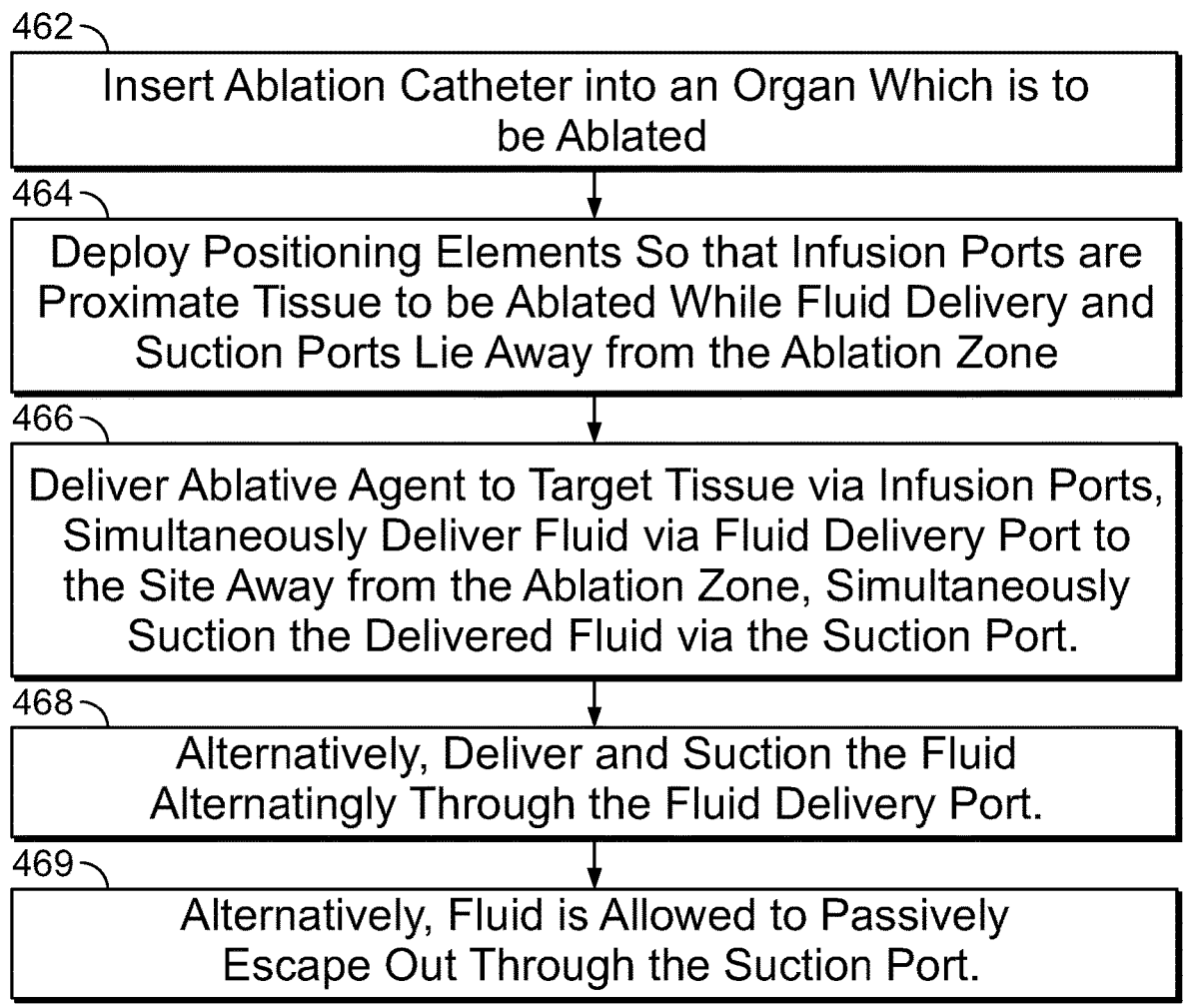
FIG. 4B is a flowchart illustrating the basic procedural steps for using the ablation catheter of FIG. 4A, in accordance with an embodiment of the present specification.

FIG. 4B is a flowchart illustrating the basic procedural steps for using the ablation catheter 400 of FIG. 4A, in accordance with an embodiment of the present specification. Referring now to FIGS. 4A and 4B, at step 462, the body 405 of the ablation catheter 400 is inserted into an organ which is to be ablated. For example, in order to perform ablation in a Barrett's esophagus of a patient, the catheter is inserted into the Barrett's esophagus via the esophagus of the patient.

At step 464, the positioning elements or balloons 410, 412 are deployed such that the plurality of infusion ports 415 lie proximate to the tissue to be ablated while the fluid delivery port 427 and the suction port 432 are positioned at a site away from the ablation zone. Thereafter, at step 466, an ablative agent (such as steam) is delivered through a first lumen, via infusion ports 415, to the target tissue to be ablated while simultaneously a fluid is delivered through a second lumen, via fluid delivery port 427, at the site away from the tissue being ablated such that the delivery of the fluid does not significantly interfere with the delivery of the ablative agent. In accordance with some embodiments, the fluid is delivered at a temperature ranging from 0 to 60° C. Also, simultaneously, the delivered fluid is suctioned out through the suction port 432 and third lumen 430 from the site away from the tissue being ablated such that the suction of the fluid does not result in suction of the delivered ablative agent. In accordance with alternative embodiments, at step 468, the fluid is alternatingly delivered and suctioned, respectively, through the fluid delivery port 427 and second lumen 425. In another embodiment, at step 469, the fluid is allowed to passively escape out through suction port 432.

Figure 5A:
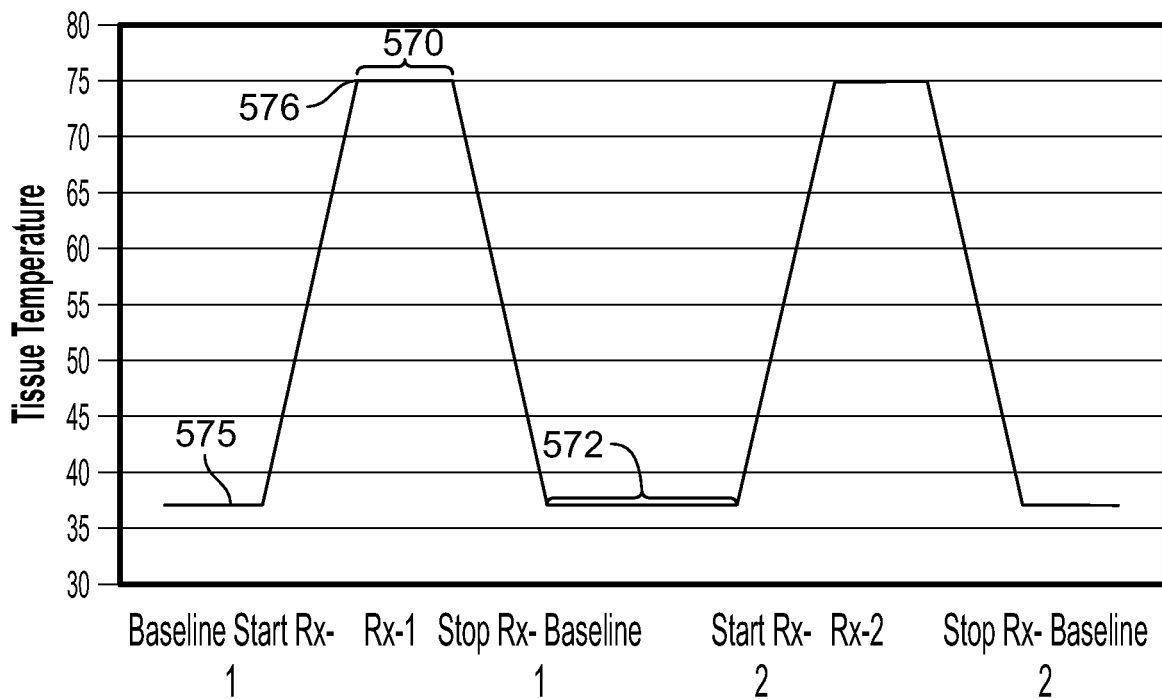
FIG. 5A is a first graph illustrating a process of ablating tissue in accordance with an embodiment.
Figure 5B:
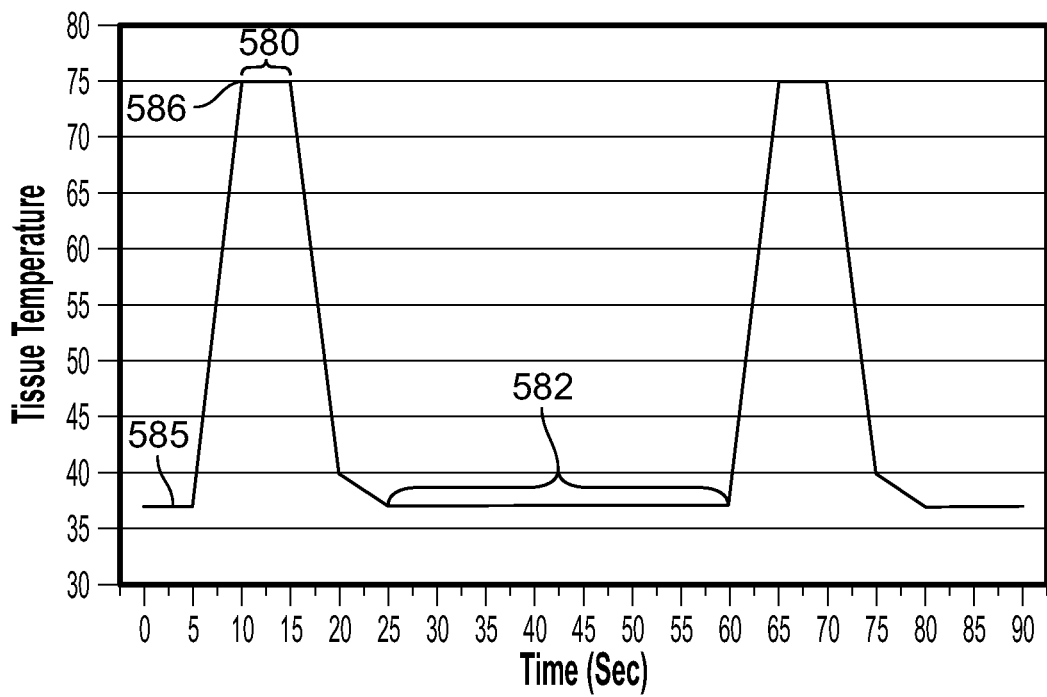
FIG. 5B is a second graph illustrating a process of ablating tissue in accordance with another embodiment.

FIG. 5A is a first graph illustrating a process of ablating tissue in accordance with an embodiment. As shown in FIG. 5A, ablative agent, such as vapor, is delivered to a target tissue for a first period of time 570 as a result of which the temperature of the target tissue rises to a first temperature 576. The target tissue temperature is maintained at the first temperature 576 for the first period of time 570. After completion of the first period of time 570, the delivery of vapor is turned off and the target tissue temperature is allowed to cool down to a base temperature 575. After a second period of time 572, the vapor delivery is resumed to the target tissue and the ablation process cycle is repeated. FIG. 5B is a second graph illustrating a process of ablating tissue in accordance with another embodiment. As shown in FIG. 5B, ablative agent, such as vapor, is delivered to a target tissue for a third period of time 580 as a result of which the temperature of the target tissue rises to a second temperature 586. The target tissue temperature is maintained at the second temperature 586 for the third period of time 580. After completion of the third period of time 580, the delivery of vapor is turned off and the target tissue temperature is allowed to cool down to a base temperature 585. After a fourth period of time 582, the vapor delivery is resumed to the target tissue and the ablation process cycle is repeated. In various embodiments, the first and second periods of time 570, 572 may or may not be equal. Similarly, in various embodiments, the third and fourth periods of time 580, 582 may or may not be equal. In still other embodiments, the first and third periods of time 570 and 580 are not equal and the second and fourth periods of time 572 and 582 are also not equal.

In various embodiments, the first and third time periods 570, 580 range from 1 to 180 seconds while the second and fourth time periods 572, 582 range from 1 to 1800 seconds. Also, in various embodiments, the base temperature 575, 585 ranges from 37 to 45 degree C. while the first and second temperatures 576, 586 range from 60 to 100 degrees C.

Figure 5C:
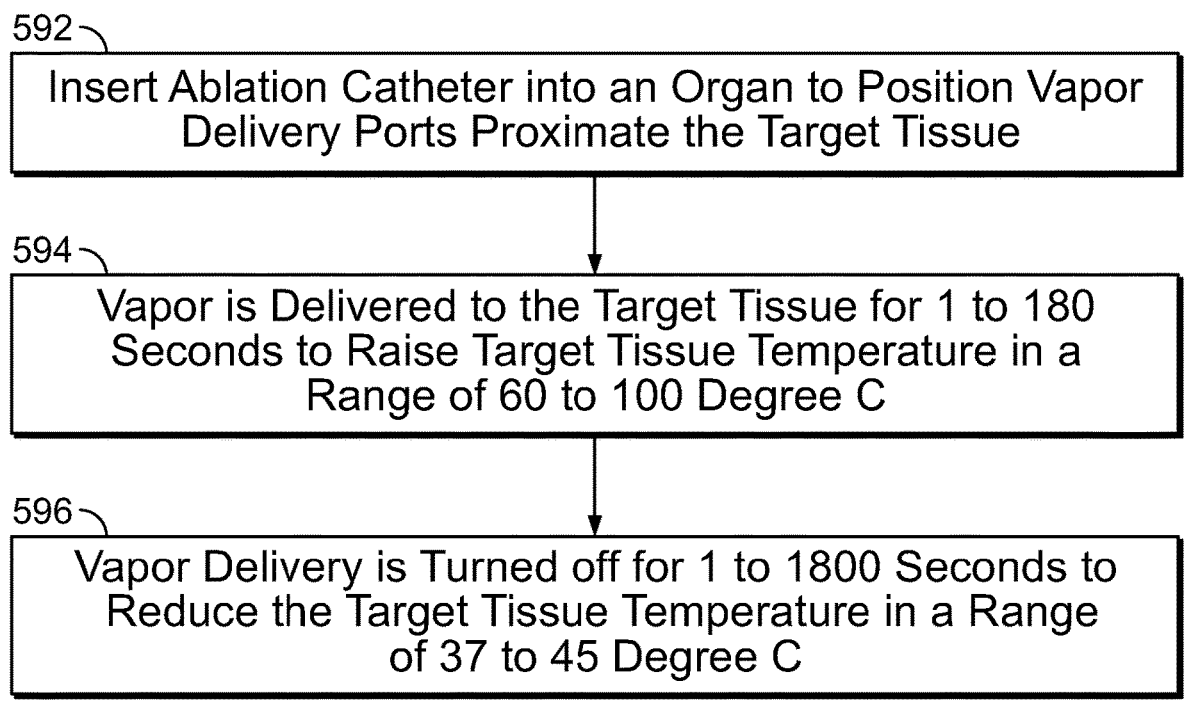
FIG. 5C is a flow chart illustrating a plurality of steps associated with the ablation processes of FIGS. 5A and 5B.

FIG. 5C is a flow chart illustrating a plurality of steps associated with the ablation processes of FIGS. 5A and 5B. At step 592, an ablation catheter is inserted into an organ so that the vapor delivery ports are positioned proximate the target tissue for ablation. At step 594, vapor is delivered to the target tissue for a heating period of time, ranging from 1 to 180 second, as a result of which the target tissue temperature rises, in a range of 60 to 100 degrees C. At step 596, the vapor delivery is turned off for a cooling off period of time, ranging from 1 to 1800 seconds, as a result of which the target tissue temperature reduces to be in a range of 37 to 45 degree C. After completion of the cooling off period of time, the steps 592 and 594 are repeated.

Figure 6A:
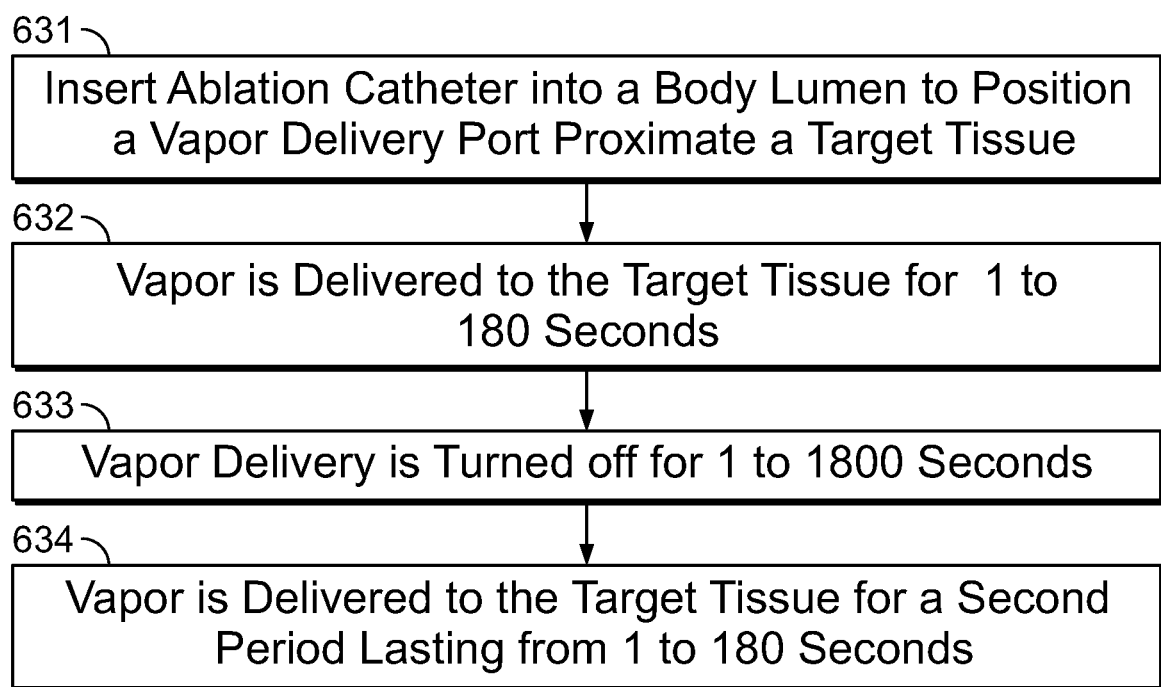
FIG. 6A is a flowchart illustrating a method of ablation for a body tissue, according to one embodiment of the present specification.

FIG. 6A is a flowchart illustrating a method of ablation of a body tissue according to one embodiment of the present specification. Referring to FIG. 6A, the first step 631 includes inserting an ablation catheter into a body lumen such that a vapor delivery port of the catheter is positioned proximate a target tissue. Next, in step 632, vapor is delivered for a period of 1-180 seconds. Thereafter, vapor delivery is turned off for a period of 1-1800 seconds in step 633. Vapor is then delivered again for a second period lasting from 1-180 seconds in step 634.

Figure 6B:
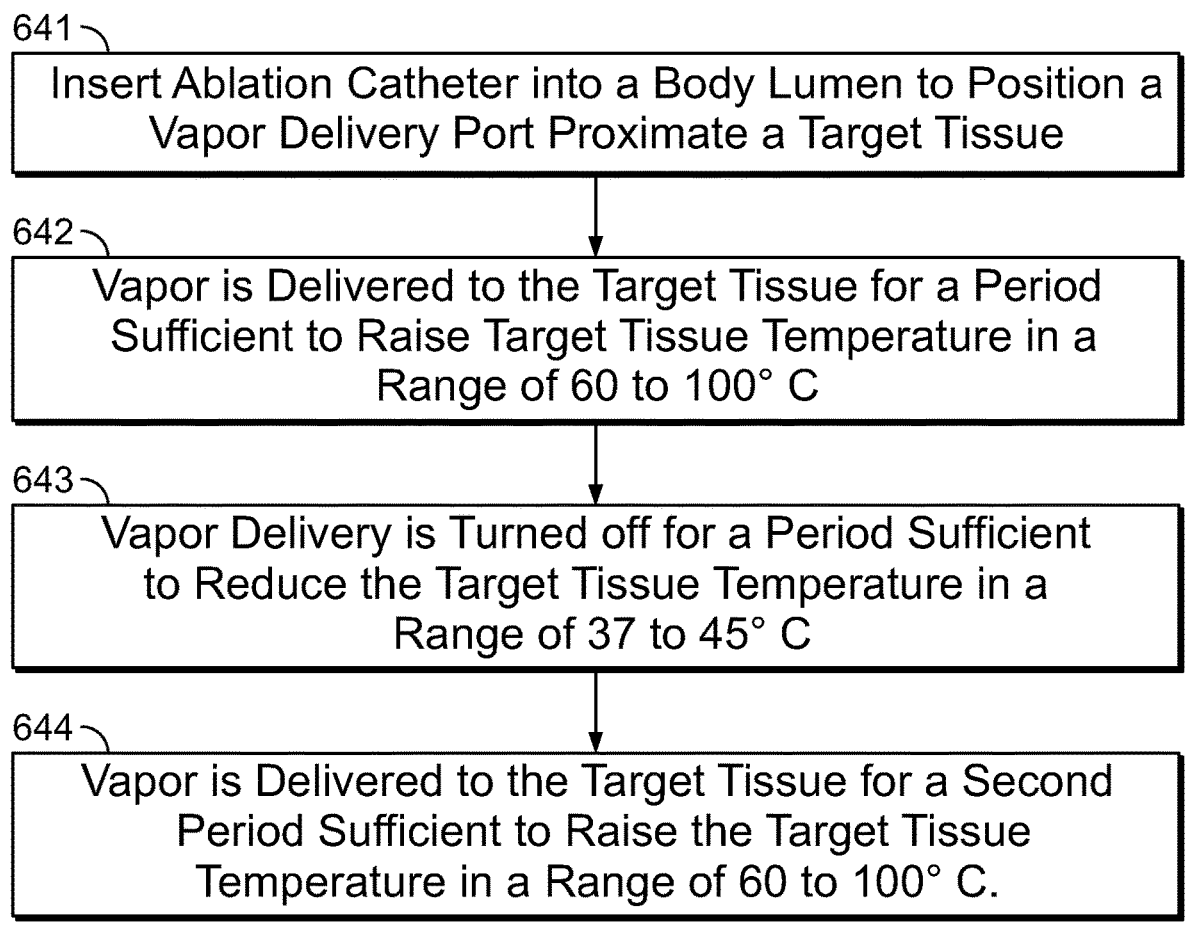
FIG. 6B is a flowchart illustrating a method of ablation for a body tissue, according to another embodiment of the present specification.

FIG. 6B is a flowchart illustrating a method of ablation of a body tissue according to another embodiment of the present specification. Referring to FIG. 6B, the first step 641 includes inserting an ablation catheter into a body lumen such that a vapor delivery port of the catheter is positioned proximate a target tissue. Next, in step 642, vapor is delivered for a period sufficient to raise a temperature of the target tissue to a temperature in a range of 60° C. to 100° C. Thereafter, vapor delivery is turned off for a period sufficient to allow cooling of the target tissue to a temperature in a range of 37° C. to 45° C. in step 643. Vapor is then delivered again for a second period sufficient to raise a temperature of the target tissue to a temperature in a range of 60° C. to 100° C. in step 644.

FIG. 6C is a flowchart illustrating a method of ablation of a body tissue in accordance with yet another embodiment of the present specification. Referring to FIG. 6C, the first step 651 includes inserting an ablation catheter having a plurality of lumens into a body lumen, wherein the catheter includes at least one vapor delivery port in fluid communication with a first lumen of said plurality of catheter lumens, such that said at least one delivery port is positioned proximate a tissue to be ablated. In step 652, vapor is delivered to the tissue to be ablated through said first lumen and said at least one vapor delivery port while simultaneously a fluid at a temperature in a range of 0 to 60° C. is delivered through a second lumen of said plurality of lumens and through a cooling fluid delivery port of said catheter to a site away from the tissue being ablated. Optionally, in step 653, fluid is simultaneously suctioned through a fluid suction port of said catheter and a third lumen of said plurality of lumens from a site away from the tissue being ablated. Further, optionally as shown in step 654, fluid is alternatingly delivered and suctioned through said cooling fluid delivery port and said second lumen.

FIG. 7A is an illustration of a water cooled catheter 700, in accordance with one embodiment of the present specification, and FIG. 7B is a cross-section view of the shaft of the water cooled catheter of FIG. 7A. The catheter 700 comprises an elongate body 705 having a proximal end and a distal end. The distal end includes a plurality of infusion ports 715 for the delivery of an ablative agent 716, such as steam or vapor for tissue ablation. A sheath 710 comprising cooling channels extends along the body 705 of the catheter 700. In some embodiments, the sheath 710 extends along the catheter body 705 to a point distal to or proximate the ports 715. In these embodiments, the sheath 710 is positioned such that it does not cover the ports 715, allowing ablative agent 716 to exit the catheter 700 through said ports 715, as depicted in FIG. 7B. In other embodiments, the sheath extends along the catheter body to a point proximal to the ports. During use, water 720 from a water source 722 is circulated through the sheath 710 to cool the catheter 700. The water 710 for cooling is then fed into chamber 721 where it is heated to turn into vapor 716 to be delivered through the elongate body 705 and through the infusion ports 715. Vapor 716 for ablation and water 720 for cooling are supplied to the catheter 700 at its proximal end. Arrows 723 show the path of water 710 through the sheath and into the chamber 721. Arrows 724 show the path of vapor 716 through the elongate body 705 and out the infusion ports 715.

FIG. 8A illustrates an ablation catheter 805 while FIG. 8B is a cross-sectional view of an elongate body or shaft 807 of the catheter 805, in accordance with an embodiment of the present specification. The elongate body or shaft 807 has a distal end, a proximal end and includes an outer lumen 809 and a coaxial inner lumen 811. In accordance with an aspect, a coolant 813, such as, but not limited to, air, water or saline, passes from the proximal end of the body or shaft 807 into the outer lumen 809 and is discharged through the distal end of the body or shaft 807. Similarly, vapor 815 passes from the proximal end of the body or shaft 807 into the inner lumen 811 to emanate from the distal end of the body or shaft 807 while the body or shaft 807 is kept cooled by the circulating coolant 813.

FIG. 9A illustrates an ablation catheter 905 while FIG. 9B is a cross-sectional view of an elongate body or shaft 907 of the catheter 905, in accordance with an embodiment of the present specification. The elongate body or shaft 907 has a distal end, a proximal end and includes first and second outer lumens 909a, 909b and a coaxial inner lumen 911. In accordance with an aspect, a coolant 913, such as, but not limited to, air, water or saline, passes from the proximal end of the body or shaft 907 into the first outer lumen 909a and is discharged through the second outer lumen 909b, also at the proximal end of the body or shaft 907, after having been circulated through the body or shaft 907. Vapor 915 passes from the proximal end of the body or shaft 907 into the inner lumen 911 to emanate from the distal end of the body or shaft 907 while the body or shaft 907 is kept cooled by the recirculating coolant 913. In embodiments, where the coolant 913 is air, the air may be released or discharged via a handle attached at the proximal end of the body or shaft 907 thereby cooling the handle. In embodiments, where the coolant 913 is water, the water enters the shaft 907 through the first outer lumen 909a and is fed, through the second outer lumen 909b, into a heating chamber enclosed within the handle attached at the proximal end of the body or shaft 907. The water fed into the heating chamber is converted into vapor 915 that then enters the inner lumen 911.

FIG. 10A illustrates an ablation catheter 1005 while FIG. 10B is a cross-sectional view of an elongate body or shaft 1007 of the catheter 1005, in accordance with an embodiment of the present specification. The elongate body or shaft 1007 has a distal end, a proximal end and includes first and second outer lumens 1009a, 1009b and a coaxial inner lumen 1011. At least one balloon 1025 is attached at the distal end of the body or shaft 1007 and is in fluid communication with the first and second outer lumens 1009a, 1009b. In some embodiments, the elongate body or shaft 1007 optionally includes one or more additional outer lumens 1027 (FIG. 10B) to function as accessory channels such as for various sensors. In accordance with an aspect, a coolant 1013, preferably air, passes from the proximal end of the body or shaft 1007 into the first outer lumen 1009a and is discharged through the second outer lumen 1009b, also at the proximal end of the body or shaft 1007, after having inflated the balloon 1025 to a desired pressure while maintaining the air circulation in the body or shaft 1007 to maintain the shaft temperature below 60 degrees C., and preferably below 40 degrees C. The desired pressure, within the balloon 1025, is maintained by a pressure valve (or an e-valve controlled by a micro-controller) positioned at the proximal end of the second outer lumen 1009b wherein the pressure valve maintains air flow and opens when the desired pressure is rated. Similarly, vapor 1015 passes from the proximal end of the body or shaft 1007 into the inner lumen 1011 to emanate from the distal end of the body or shaft 1007 while the body or shaft 1007 is kept cooled by the circulating coolant 1013. It should be appreciated that in some embodiments the inner lumen 1011 is in fluid communication with another balloon positioned and freely movable within the balloon 1025.

Thus, in accordance with an aspect, a coolant, such as water, circulates within the outer lumen of the elongate body and is then fed into a heating chamber for conversion to vapor—as described with reference to FIGS. 9A, 9B. In accordance with another aspect a coolant, such as air, is circulated in a balloon back and forth through the outer lumen of the elongate body to cool the elongate body or shaft—as described with reference to FIGS. 10A, 10B.

Referring now to FIGS. 8B, 9B and 10B, in accordance with an aspect of the present specification, an inner layer 830, 930, 1030 of the catheter shaft 807, 907, 1007 is thicker in comparison to an outer layer 832, 932, 1032 to prevent heat loss or minimize energy transfer from inside to the outside of the catheter. This is in contrast to prior art cooled shaft catheters where the purpose is to maximize transfer of cold temperature from inside the catheter to the outside of the catheter.

Figure 11:
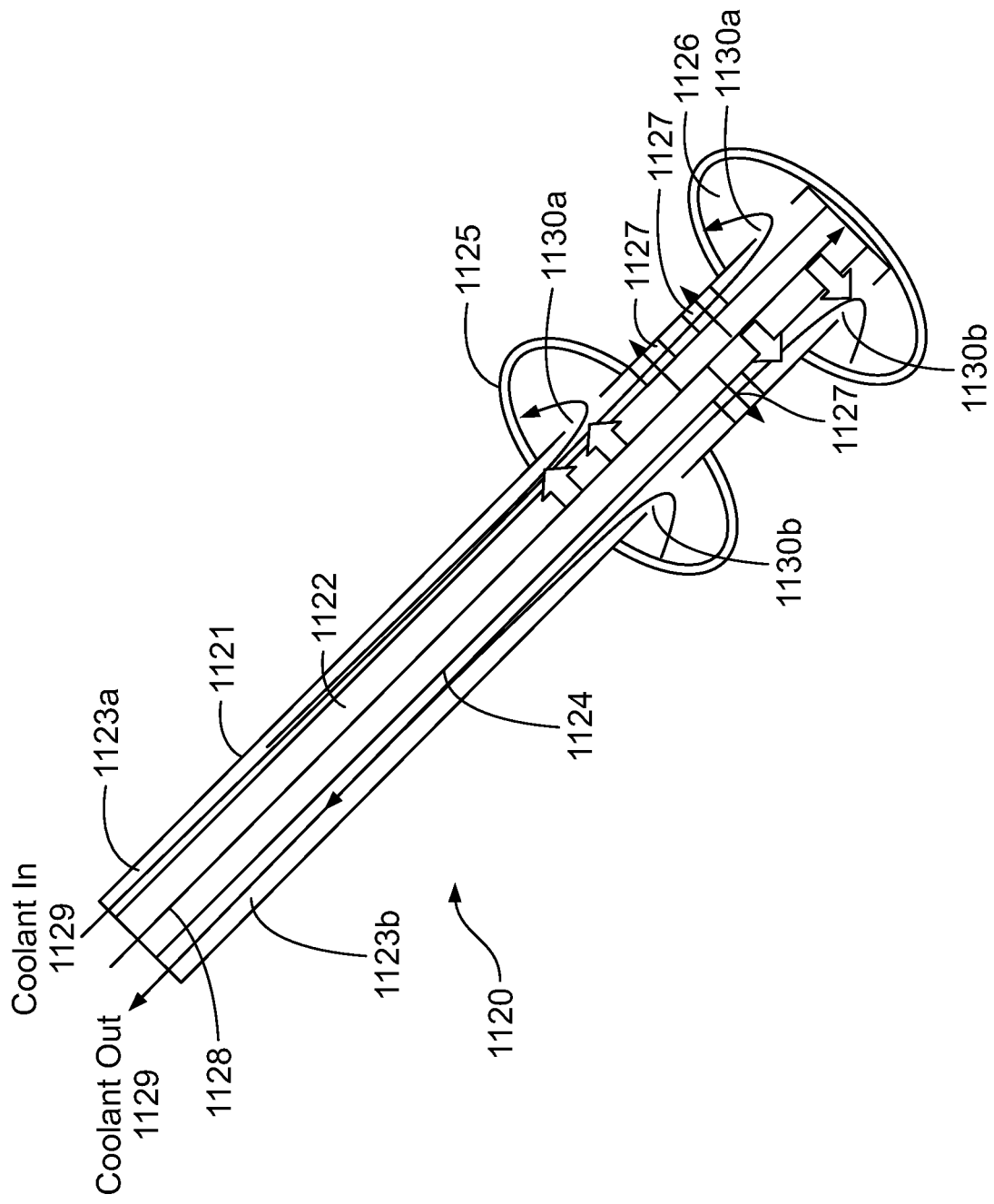
FIG. 11 illustrates an ablation catheter is accordance with an embodiment of the present specification.

FIG. 11 illustrates an ablation catheter 1120 in accordance with one embodiment of the present specification. The catheter 1120 includes an elongate body 1121 with a proximal end and a distal end. In one embodiment, the catheter body 1121 includes an inner lumen 1122, a first outer lumen 1123a and a second outer lumen 1123b. The inner lumen 1122 is separated from the outer lumens 1123a, 1123b by a thermally semi-permeable wall 1124 which allows a portion of the thermal energy to pass from the inner lumen 1122 to the outer lumens 1123a, 1123b. The catheter also includes at least one positioning element or balloon at its distal end. In the embodiment depicted in FIG. 11, the catheter 1120 includes two positioning balloons 1125, 1126 at its distal end with a plurality of delivery ports 1127 located on the catheter body 1121 between the two balloons 1125, 1126. The delivery ports 1127 are in fluid communication with the inner lumen 1122. An ablative agent 1128 is introduced into the inner lumen 1122 at the proximal end of the catheter 1120 and exits through the delivery ports 1127 into an organ, such as an esophagus, for ablation. In one embodiment, the ablative agent 1128 is steam. Coolant, such as air 1129, is introduced into the first outer lumen 1123a at the proximal end of the catheter 1120 and travels through inflation ports 1130a into the balloons 1125, 1126 to inflate said balloons 1125, 1126 and thereafter exits the balloons 1125, 1126 via exit ports 1130b into the second outer lumen 1123b and finally exits at the proximal end of the catheter, allowing for the air 1129 to circulate a length of the catheter 1120 and through one or more of the balloons 1125, 1126.

Figure 12:
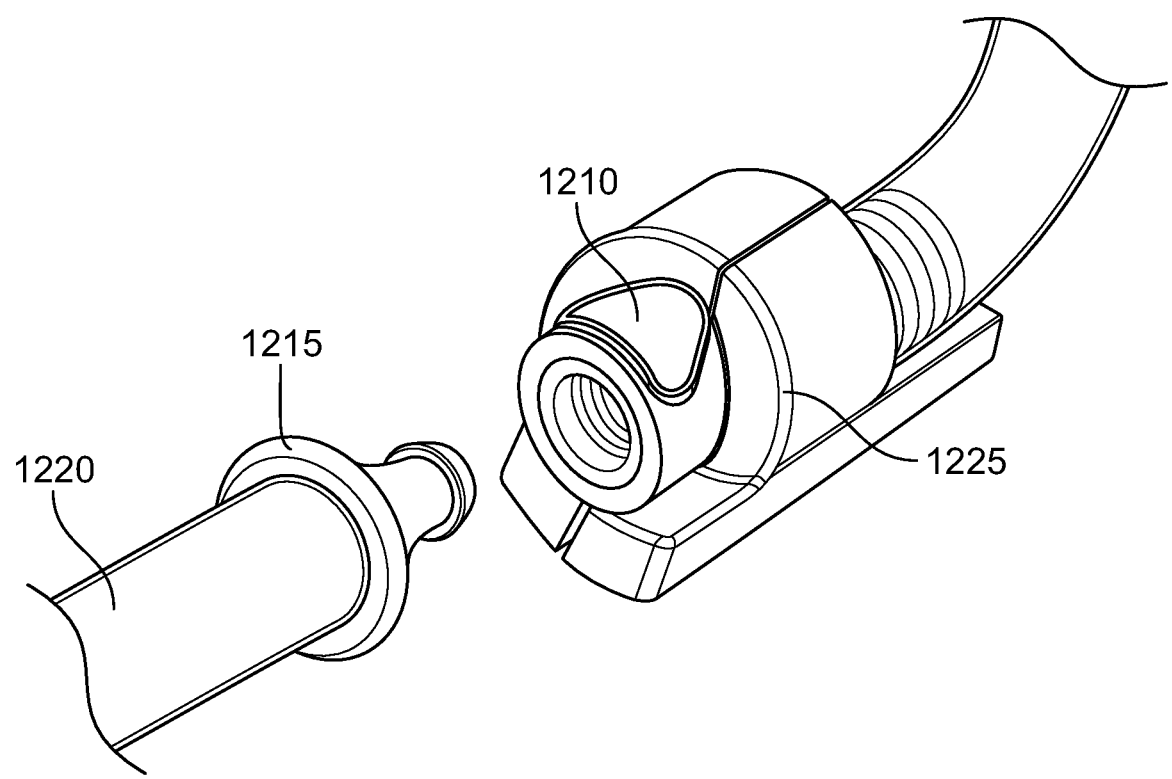
FIG. 12 illustrates a connection between a syringe and a catheter, in accordance with an embodiment of the present specification.

FIG. 12 illustrates a connection between a syringe 1220 and a catheter 1210, in accordance with an embodiment. As shown in FIG. 12, a proximal end of a catheter 1210 is configured to receive a distal end of a connector component 1215 in order to form a fluid seal when the distal end of the connector component 1215 is inserted into the proximal end of the catheter 1210. A syringe 1220 is coupled to a proximal end of the connector component 1215 to supply water to the catheter 1210 through the connector component 1215 coupled to the catheter 1210. In various embodiments, a radio frequency identification component 1225 is included at the proximal end of the catheter 1210 to communicate successful fluid connection between the catheter 1210 and the syringe 1220.

Figure 13A:
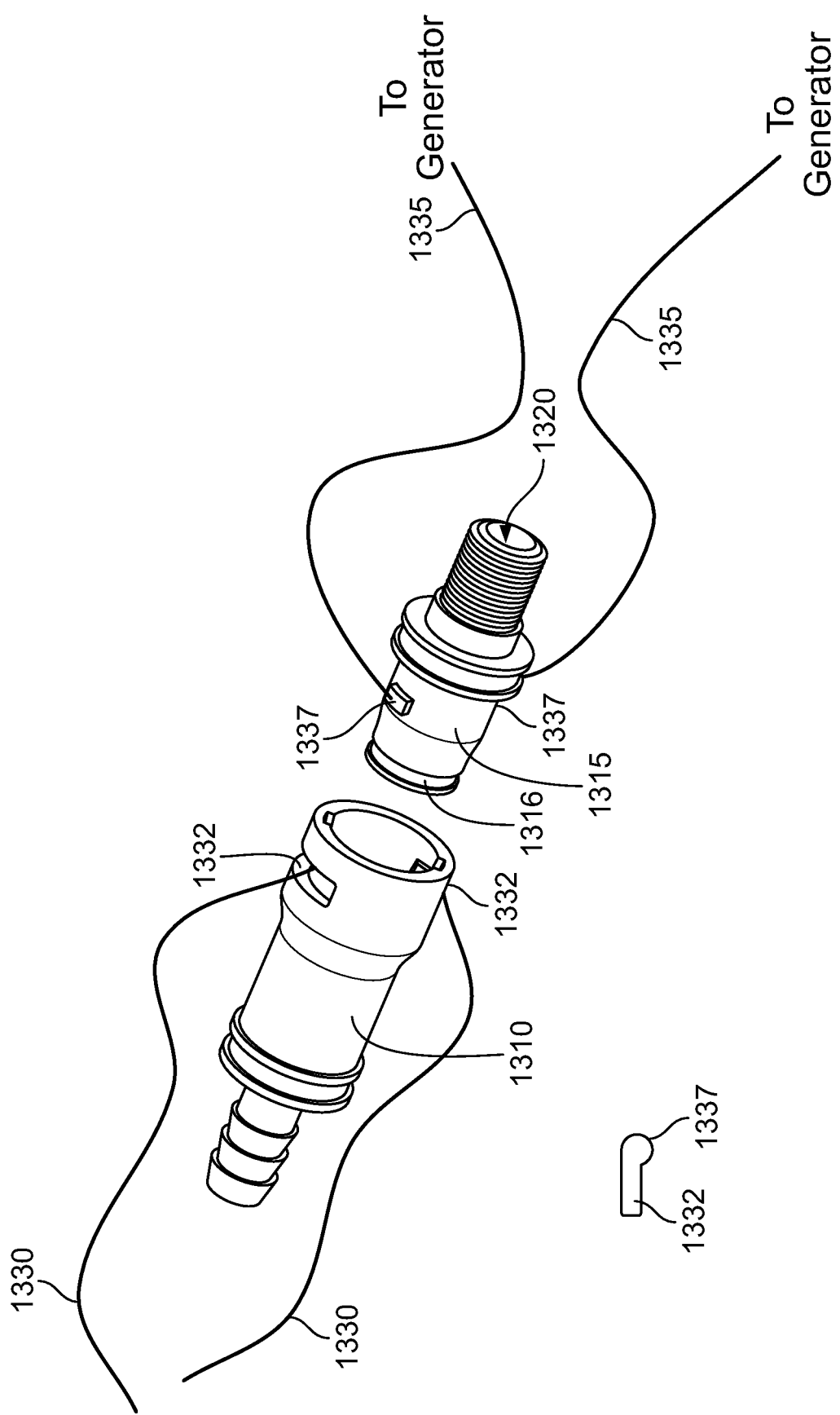
FIG. 13A is an illustration of a connector and a heating chamber of a catheter, in accordance with another embodiment of the present specification.
Figure 13B:
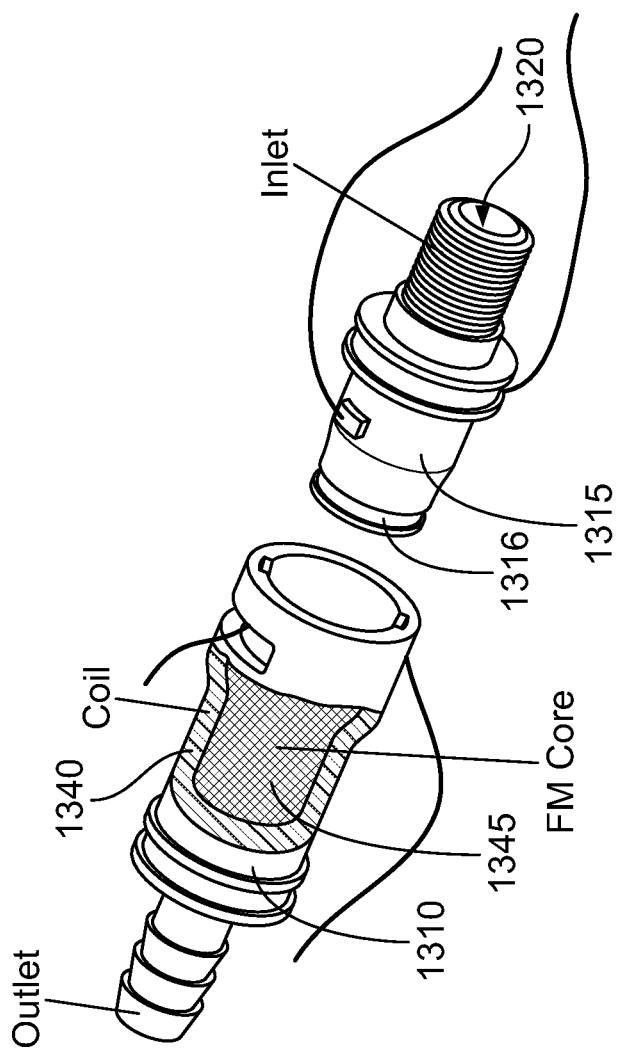
FIG. 13B illustrates a coil and ferromagnetic core positioned within the heating chamber shown in FIG. 13A.
Figure 13C:
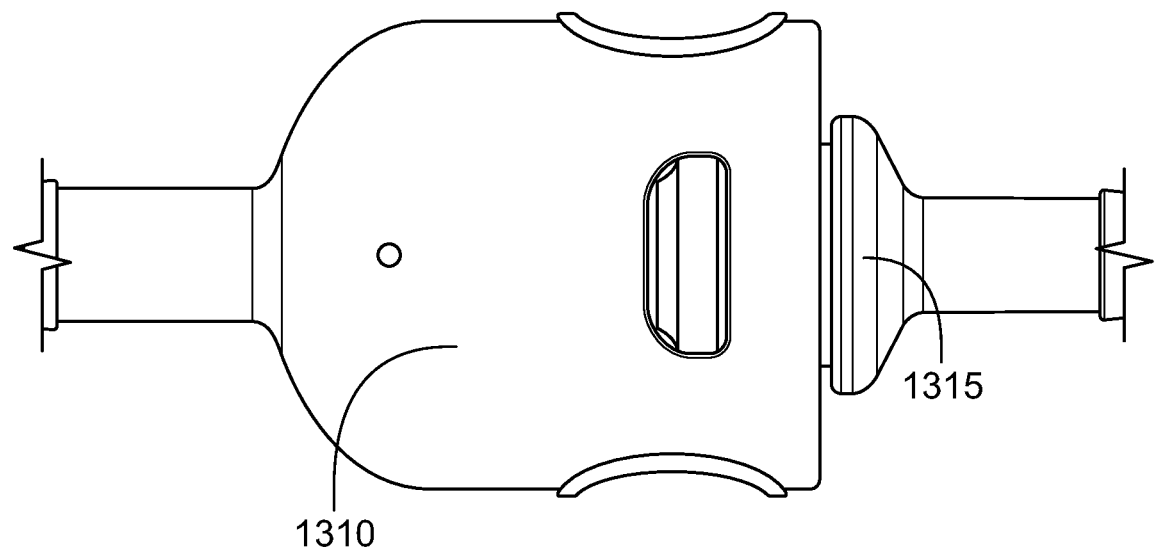
FIG. 13C is an assembled view of the connector and the heating chamber of FIG. 13A.

FIG. 13A illustrates a connector for coupling a heating chamber and a water supply, such as a syringe pump, in accordance with another embodiment, while FIG. 13B illustrates a heating coil and a ferromagnetic core within the heating chamber. Referring now to FIGS. 13A and 13B, a proximal end of a heating chamber 1310 is configured to receive a distal end of a connector component 1315. The distal end of the connector component 1315 includes an O Ring 1316 to form a tight fluid seal when the distal end of the connector component 1315 is inserted into the proximal end of the heating chamber 1310. The connector component 1315 has an inlet port 1320 at its proximal end that is coupled to a syringe pump, for example, to supply water. The heating chamber 1310 includes a coil 1340 wound around a ferromagnetic core 1345. Wires 1330 are attached to the coil 1340 for providing the coil 1340 with radiofrequency (RF) energy. Wires 1335 are attached to a generator to supply electrical energy. In accordance with an embodiment, the electrical contacts 1332 of wires 1330 are coupled to the electrical contacts 1337 of wires 1335 when the distal end of the connector component 1315 is inserted into the proximal end of the heating chamber 1310, thereby forming an electrical connection. FIG. 13C illustrates a perspective assembled view of the heating chamber 1310 in fluid connection with the connector component 1315. In various embodiments, the fluid connection is configured to withstand fluid pressure ranging from 5 to 500 psi.

Figure 13D:
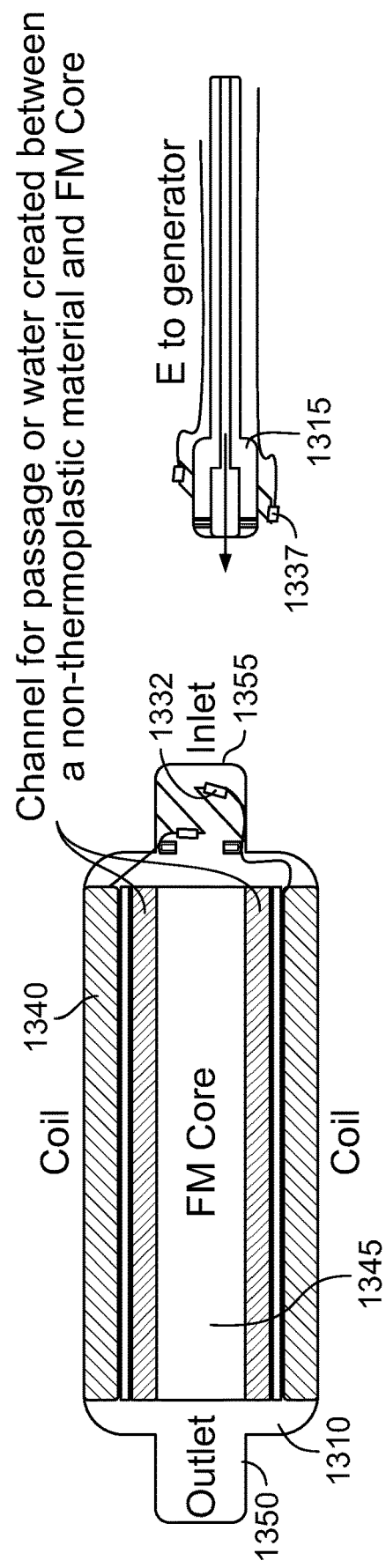
FIG. 13D is a cross-section view of the connector and heating chamber of FIG. 13A.

FIG. 13D illustrates a cross-section view of the heating chamber 1310 comprising a channel for passage of water created between a non-thermoplastic material and the ferromagnetic core 1345. The coil 1340 is wound around the ferromagnetic core 1345. The heating chamber 1310 includes an outlet port 1350 at its distal end for delivering vapor and an inlet port 1355 at its proximal end to receive water. Also shown are the electrical contacts 1332, on the heating chamber 1310, corresponding to the wires (1330 in FIG. 13A), and the electrical contacts 1337, on the connector component 1315, corresponding to the wires (1335 in FIG. 13A) for providing electrical energy from the generator. When the distal end of the connector component 1315 is inserted into the proximal end of the heating chamber 1310, forming a fluid connection and electrical connection, the coupling of the electrical contacts 1332 and 1337 enables electrical connection of the coil 1340 with the generator and provides a fail-safe as incomplete fluid connection would result in no electrical connection and the induction heating would not be switched on.

Figure 14A:
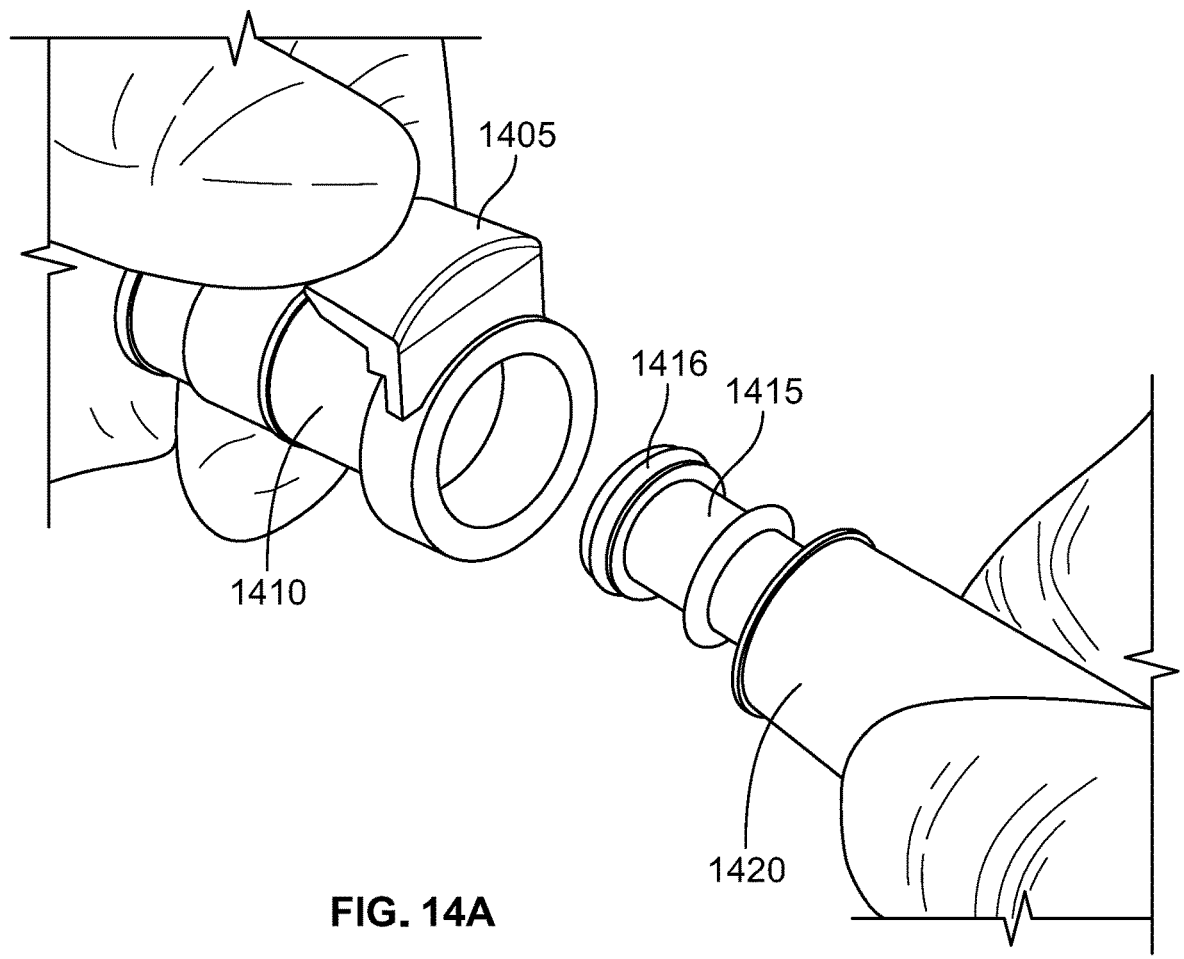
FIG. 14A is an illustration of a connector and a heating chamber of a catheter, in accordance with another embodiment of the present specification.
Figure 14B:
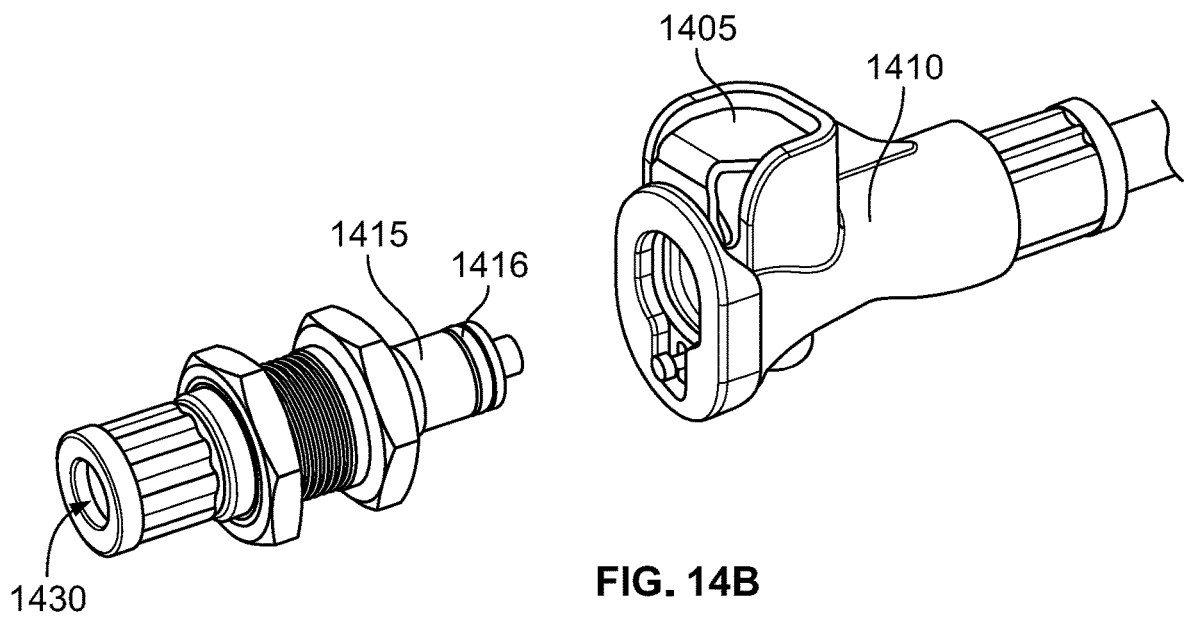
FIG. 14B is an illustration of a connector and a heating chamber of a catheter, in accordance with still another embodiment of the present specification.

FIGS. 14A and 14B show a spring loaded mechanism 1405 on a heating chamber 1410. A proximal end of the heating chamber 1410 is configured to receive a distal end of the connector component 1415. The distal end of the connector component 1415 includes an O-ring 1416 to form a fluid seal when the distal end of the connector component 1415 is inserted into the proximal end of the heating chamber 1410. The spring loaded mechanism 1405, when pressed, allows easy insertion of the distal end of the connector component 1415 into the proximal end of the heating chamber 1410 to form a fluid coupling. When released, the spring loaded mechanism 1405 further secures the fluid coupling. In FIG. 14A, a proximal end of the connector component 1415 includes a syringe pump 1420 to supply water. FIG. 14B shows a water inlet port 1430 at the proximal end of the connector component 1415 for supplying water.

In various embodiments, the connectors described in the present specification are composed of thermoplastics including ABS, acetal, nylon (poly amide), and polyetheretherketone (PEEK), and fluoropolymers including polyvinylidene difluoride (PVDF). In various embodiments, the O-rings are composed of fluorocarbon (FKM) or silicone.

Figure 15A:
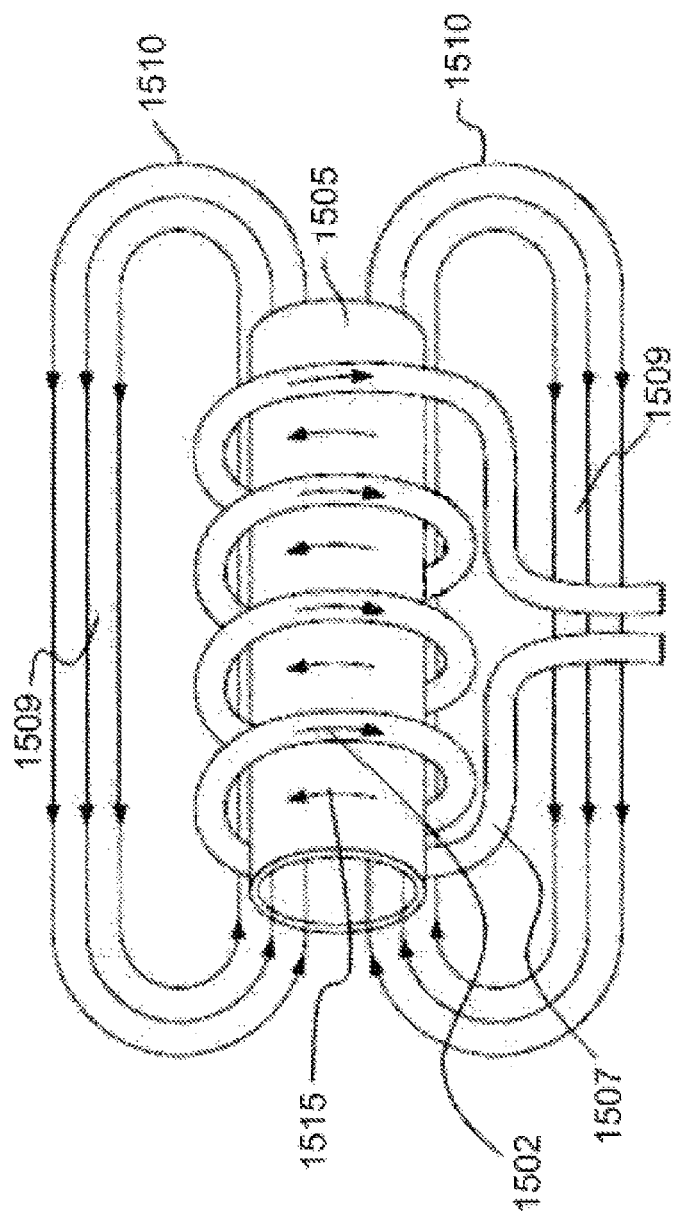
FIG. 15A illustrates the use of induction heating to heat a chamber.

FIG. 15A illustrates the use of induction heating to heat a chamber 1505. When an alternating electric current 1502 is passed through a coil 1507 of wire within the chamber 1505, the coil 1507 creates a magnetic field 1509. Magnetic lines of flux 1510 of the magnetic field 1509 cut through the air around the coil 1507. When the chamber 1505 is composed of a ferrous material, such as, iron, stainless steel, or copper, electrical currents known as eddy currents 1515 are induced to flow in the chamber 1505 as a result of the presence of the alternating current 1502 and magnetic field 1509 with lines of flux 1510. The eddy currents 1515 cause localized heating of the chamber 1505. When the chamber 1505 is filled with a fluid, such as water, the heat is transferred from the chamber to the fluid inside, resulting in vaporization of said fluid. In the embodiment depicted in FIG. 15A, the coil 1507 is looped about the chamber 1505 with four loops and spaced a distance away from said chamber 1505 to assist with visualization. The design of the chamber and coil in FIG. 15A depicts only one possible embodiment and is not intended to be limiting. Those skilled in the art will understand many different design configurations are possible with respect to the chamber and coil. In various embodiments, the coil includes at least one loop about the chamber and is looped about said chamber such that the coil is in physical contact with said chamber. In other embodiments, the coil includes at least one loop about the chamber and is looped about said chamber such that the coil is spaced away a specific distance from said chamber with a layer of air or other insulating material between said coil and said chamber. In various embodiments, the loops of the coil are arranged closely together such that they are in contact with one another. In other embodiments, the loops of the coil are arranged with a specific distance between one another. In one embodiment, the loops of the coil extend along the entire length of the chamber. In various embodiments, the loops of the coil extend beyond the length of the chamber. In other embodiments, the loops of the coil extend along a portion of the length of the chamber that is less than the chamber's total length.

Figure 15B:
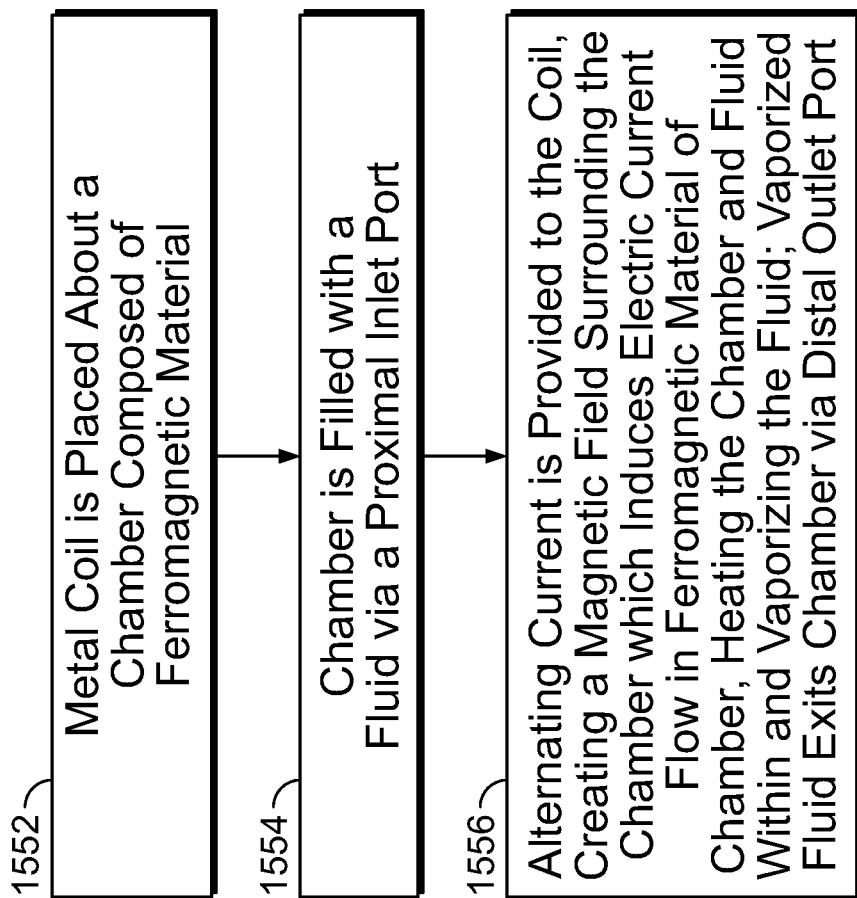
FIG. 15B is a flow chart listing the steps involved in using induction heating to heat a chamber.

FIG. 15B is a flow chart listing the steps involved in using induction heating to heat a chamber. At step 1552, a metal coil is placed about a chamber composed of a ferromagnetic material such that the coil surrounds the chamber. Then, at step 1554, the chamber is filled with a fluid via a proximal inlet port on said chamber. At step 1556, an alternating current is provided to the coil, creating a magnetic field in the area surrounding the chamber. The magnetic field induces electric (eddy) current flow in the ferromagnetic material which heats the chamber. The heat is transferred to the fluid inside the chamber and vaporizes the fluid. The vaporized fluid exits the chamber via the distal outlet port.

Figure 16A:
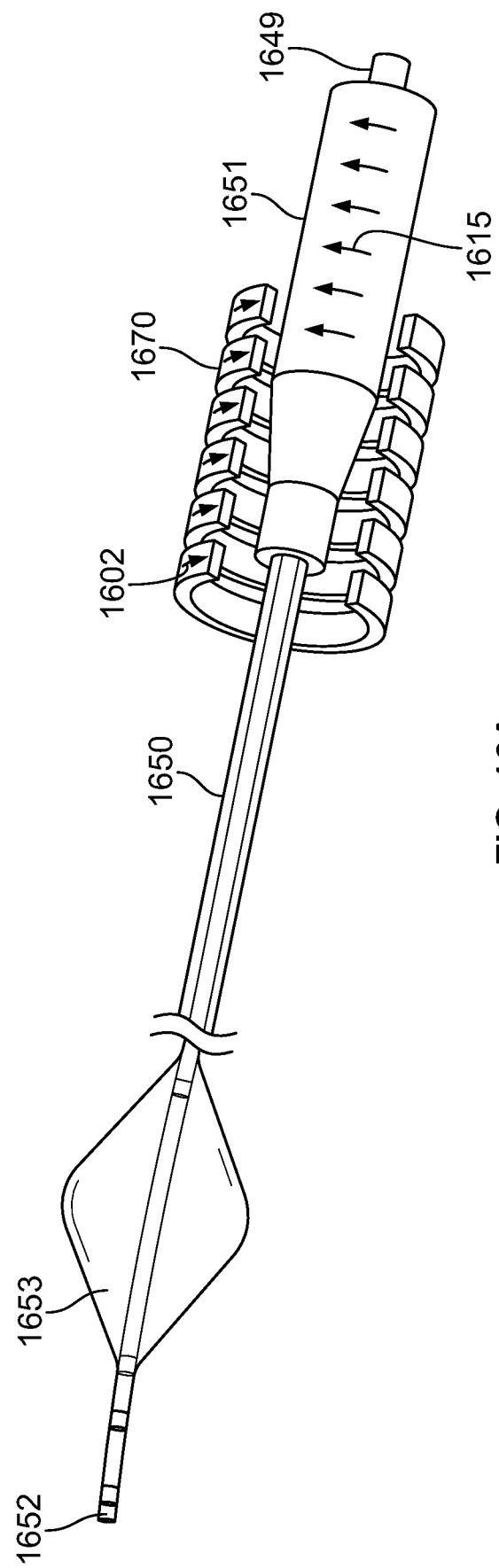
FIG. 16A illustrates one embodiment of a coil used with induction heating in a vapor ablation system of the present specification.

FIG. 16A illustrates one embodiment of a coil 1670 used with induction heating in the vapor ablation system of the present specification. A section of the coil 1670 has been cut away to assist with visualization. The coil 1670 is positioned surrounding the catheter fluid heating chamber 1651. An alternating current 1602 passing through the coil 1670 creates a magnetic field which induces eddy currents 1615 to flow in the chamber 1670 as described above. The flow of eddy currents 1615 results in heating of the catheter fluid heating chamber 1651. The heated chamber heats the fluid within, converting it into a vapor, which passes into the catheter 1650 for use in the ablation procedure. The catheter 1650 includes at least one delivery port 1652 at its distal end for the delivery of vapor. Optionally, the catheter 1650 includes at least one positioning element 1653 proximate its distal end. In one embodiment, the at least one positioning element 1653 is an inflatable balloon. The coil 1670 itself does not heat, making it safe to touch. A luer fitting coupler 1649 is provided at the proximal end of the catheter fluid heating chamber 1651 for connecting a tube supplying sterile water. In one embodiment, a one-way valve (not shown) is included at the proximal end of the catheter fluid heating chamber 1651, distal to the luer fitting 1649, to prevent the passage of vapor toward the water supply. In one embodiment, thermal insulating material (not shown) is positioned between the coil 1670 and the heating chamber 1651. In another embodiment, the chamber 1651 is suspended in the center of the coil 1670 with no physical contact between the two. In this embodiment, the intervening air acts as a thermally insulating material. The design of the chamber is optimized to increase its surface area to maximize contact and heat transfer, in turn resulting in more efficient vapor generation. In one embodiment, the coil 1670 is constructed in a 'clamshell' style design, similar to the heat exchange unit 1660 depicted in FIG. 16A, and opens and closes about the heating chamber 1651.

Figure 16B:
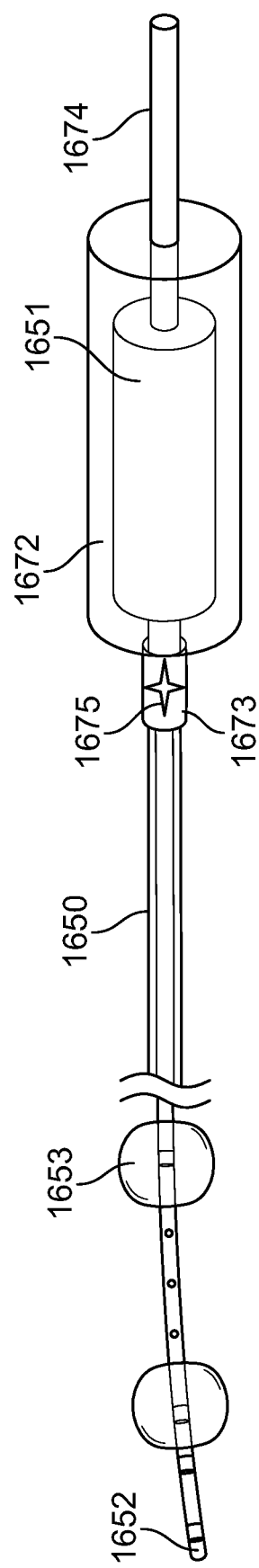
FIG. 16B illustrates one embodiment of a catheter handle used with induction heating in a vapor ablation system of the present specification.

FIG. 16B illustrates one embodiment of a catheter handle 1672 used with induction heating in the vapor ablation system of the present specification. The handle 1672 is thermally insulated and incorporates an induction coil. In one embodiment, the handle 1672 includes an insulated tip 1673 at its distal end that engages with an endoscope channel after the catheter is inserted into the endoscope. The catheter 1650 is connected to the heating chamber 1651 which in turn is connected with the pump via an insulated connector 1674. In one embodiment, the heating chamber 1651 length and diameter are less than those of the handle 1672 and the induction coil, thus the heating chamber 1651 can slide inside the handle 1672 in a coaxial fashion while maintaining a constant position within the magnetic field generated by the induction coil. The operator can manipulate the catheter 1650 by grasping on the insulated connector 1674 and moving it in and out of the handle 1672 which in turn moves the catheter tip in and out of the distal end of the endoscope. In this design, the heated portions of the catheter 1650 are within the channel of the endoscope and in the insulated handle 1672, thus not coming into contact with the operator at anytime during the operation. An optional sensor 1675 on the insulated tip 1673 can sense when the catheter is not engaged with the endoscope and temporarily disable the heating function of the catheter to prevent accidental activation and thermal injury to the operator. With respect to FIG. 16B, the catheter 1650 and heating chamber 1651 are the heated components of the system while the handle 1672, insulated tip 1673, and insulated connector 1674 are the cool components and therefore safe to touch by the user. The catheter 1650 includes at least one delivery port 1652 at its distal end for the delivery of vapor. Optionally, the catheter 1650 includes at least one positioning element 1653 proximate its distal end. In one embodiment, the at least one positioning element 1653 is an inflatable balloon.

Figure 16C:
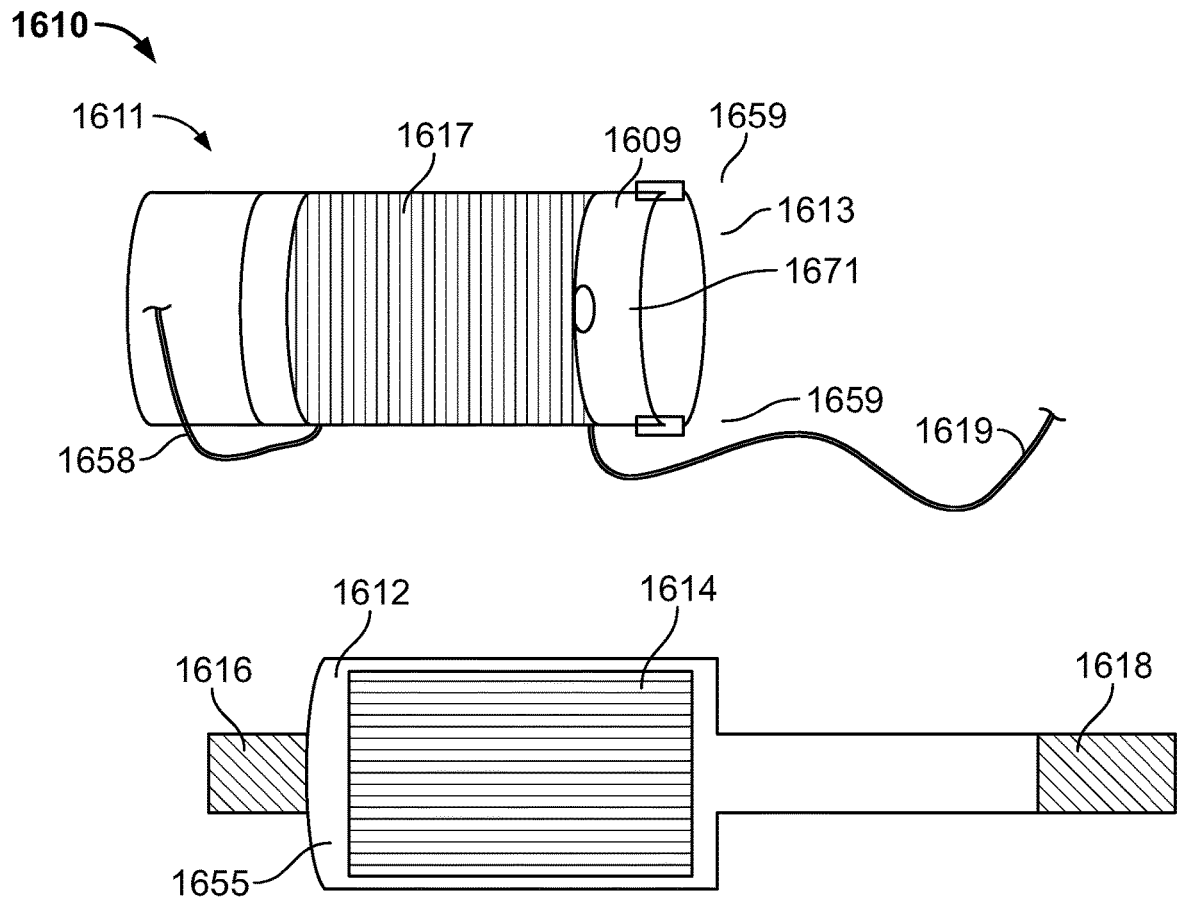
FIG. 16C illustrates a disassembled coil component and heating chamber of an induction heating system in accordance with one embodiment of the present specification.

FIG. 16C illustrates a disassembled coil component 1611 and heating chamber 1612 of an induction heating system 1610 in accordance with one embodiment of the present specification. In some embodiments, the coil component 1611 comprises an outer shell or bobbin 1609 with an electromagnetic coil 1617 wrapped thereabout. In other embodiments, the coil component 1611 comprises only a coil 1617. In some embodiments, the coil 1617 comprises solid copper wire. In other embodiments, the coil 1617 comprises copper tubing to allow for water cooling through the tubing. In various embodiments, the copper wire or copper tubing is mechanically self-supporting (no bobbin required) due to the stiffness of the wire or tubing and has few windings. In some embodiments, the copper wire or copper tubing has 10 winding with space between each winding so that insulation may be omitted. In still other embodiments, the coil 1617 comprises multi-strand litz wire having hundreds of individual strands insulated from one another to counter the skin effect and allow for low-loss high-frequency operation. In some embodiments, the individual wires are AWG46 strands. In embodiments where the coil 1617 comprises multi-strand litz wire, a bobbin 1609 is required for supporting and winding the coil 1617 thereabout. A wire 1619 is attached to the coil 1617 for providing the coil 1617 with radiofrequency (RF) energy. In some embodiments, the wire 1619, providing an electrical connection to the induction heating system 1610, is coupled with a fluid connector supplying fluid to the vapor delivery system. Coupling the electrical connection with the fluid connection simultaneously provides a mechanically stable fluid connection and connection of the RF coil with wires from a generator to complete an electrical circuit. This coupling functions as a failsafe as incomplete fluid connection would result in no electrical connection and the induction heating would not be switched on. The coil component 1611 has an elongate shape with a proximal end and a distal end and further includes an opening 1613 at its proximal end configured to receive the heating chamber 1612. The heating chamber 1612 comprises an inner electrically conducting or ferromagnetic core 1614 and includes an inlet port 1618 at its proximal end for connecting to a fluid source and an outlet port 1616 at its distal end for the delivery of generated steam. A space 1655 is present between the core 1614 and the walls of the heating chamber 1612 where heat energy from the core 1614 is transferred to fluid within the chamber 1612 to convert the fluid to steam.

Figure 16D:
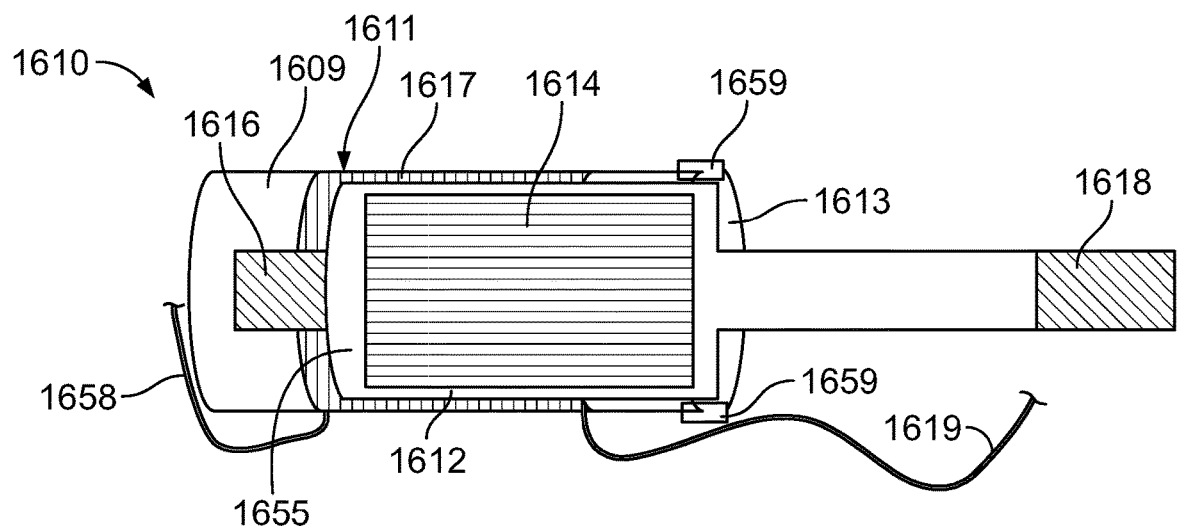
FIG. 16D illustrates an assembled induction heating system comprising the coil component and heating chamber of FIG. 16C.

FIG. 16D illustrates an assembled induction heating system 1610 comprising the coil component 1611 and heating chamber 1612 of FIG. 16C. The heating chamber 1612 has been inserted through opening 1613 and is movable longitudinally within the coil component 1611. RF energy supplied by the wire 1619 to the coil 1617 is converted to a magnetic field about the coil 1617 which, through eddy current losses and magnetic hysteresis losses, induces the creation of heat energy within the core 1614. Fluid supplied at input port 1618 is converted to steam by the heat energy in space 1655 within the heating chamber 1612 and exits via outlet port 1616.

In some embodiments, referring to FIGS. 16C and 16D simultaneously, the induction heating system 1610 further includes a mechanism for maintaining the heating chamber 1612 within the coil component 1611 once assembled, while still allowing for some coaxial movement of the heating chamber 1612 within the coil component. In some embodiments, referring to FIG. 16C, a first stopping mechanism 1658 comprises a portion of the coil 1617 which has been positioned in a plane defined by opening 1613. The first stopping mechanism 1658 functions as a mechanical limiter so that the heating chamber 1612 may be slid into the coil component 1611 from a proximal end and then comes against the stopping mechanism 1658 at the distal end, preventing further movement in a distal direction. In other embodiments, a second stopping mechanism 1659 is provided on the proximal end of the bobbin 1609. In various embodiments, the second stopping mechanism comprises a luer lock or other connector. In some embodiments, the second stopping mechanism 1659 is similar to the spring loaded connector depicted in FIGS. 16R and 16S. A portion of the second stopping mechanism 1659 extends into opening 1613. To insert the heating chamber 1612 into the coil component 1611, the second stopping mechanism 1659 is depressed, causing said extending portion to retract and providing a complete opening 1613. The heating chamber 1612 is slid into the coil component 1611 through the opening 1613 at the proximal end of the coil component 1611 while the second stopping mechanism 1659 is depressed. Once the heating chamber 1612 has been fully inserted, the second stopping mechanism 1659 is released and the extending portion extends again into opening 1613, acting as a stopper for the heating chamber 1612 in the proximal direction. In some embodiments, the induction heating system 1610 includes both a first stopping mechanism 1658 and a second stopping mechanism 1659 wherein a distance between said first stopping mechanism 1658 and said second stopping mechanism 1659 is greater than a length of the heating chamber 1612 to allow for some coaxial movement of the heating chamber 1612 within the coil component 1611. In other embodiments, the induction heating system 1610 includes only a first stopping mechanism 1658. In still other embodiments, the induction heating system 1610 includes only a second stopping mechanism 1659. In various embodiments, the heating chamber 1612 can move coaxially within the coil component 1611 a distance equal to at least 5% of a length of the coil 1617. In various embodiments, the coil component 1611 and heating chamber 1612 can move coaxially within a handle, such as handle 1672 of FIG. 16B, a distance equal to at least 5% of a length of the handle. In some embodiments, one or both of the heating chamber 1612 and coil component 1611 are disposable. In some embodiments, the heating induction system 1610 further includes a sensor 1671 configured to sense a parameter of the system 1610 and inform a user that it is safe to disconnect the heating chamber 1612 from the coil component 1611. For example, in an embodiment, the sensor 1671 is a temperature sensor which senses a temperature of the heating induction system 1610 and signals the user when the system temperature has decreased sufficiently that the heating chamber 1612 is safe to touch without burn risk and can be removed from the coil component 1611. In various embodiments, other heating chamber and coil component embodiments discussed below also include first stopping mechanisms, second stopping mechanisms, and sensors as described with reference to FIGS. 16C and 16D. In some embodiments, the heating chamber and coil of FIGS. 16C and 16D are similar to those described with reference to FIGS. 16K through 16M.

Figure 16F:
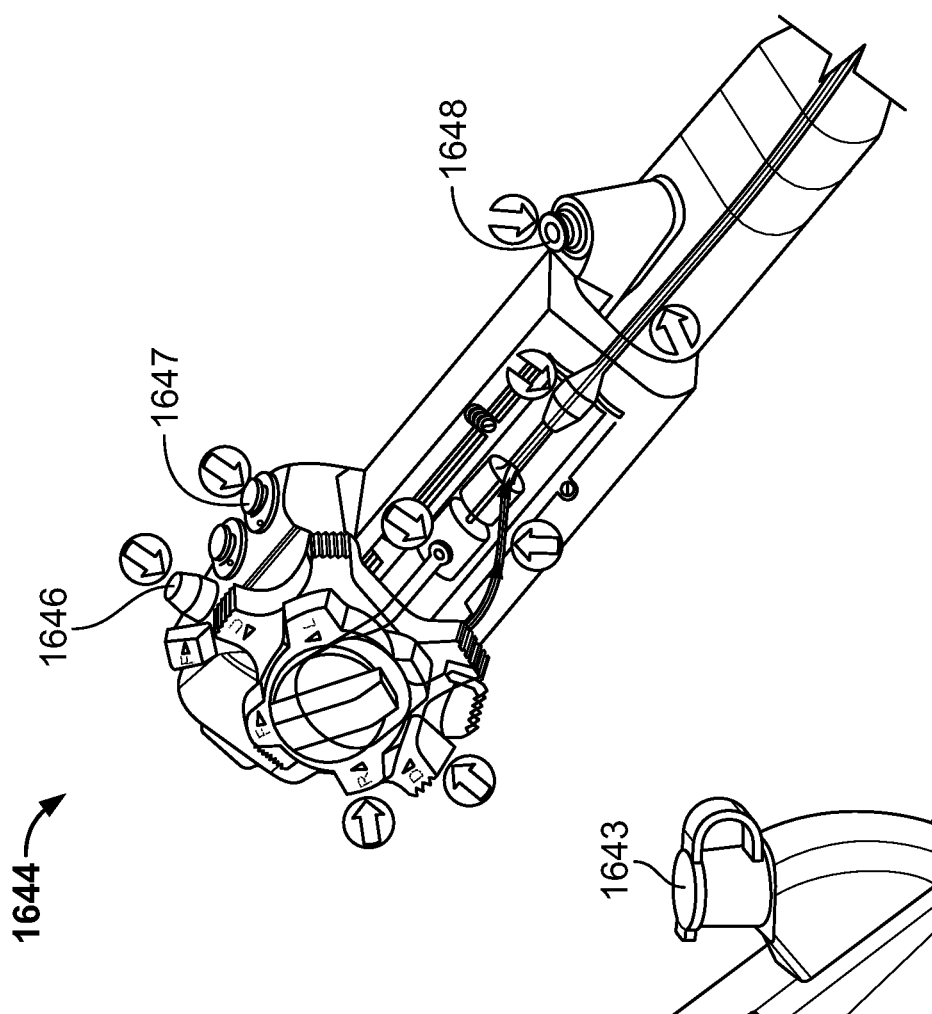
FIG. 16F illustrates a second conventional endoscope handle for use with an induction heating system of the present specification.
Figure 16E:
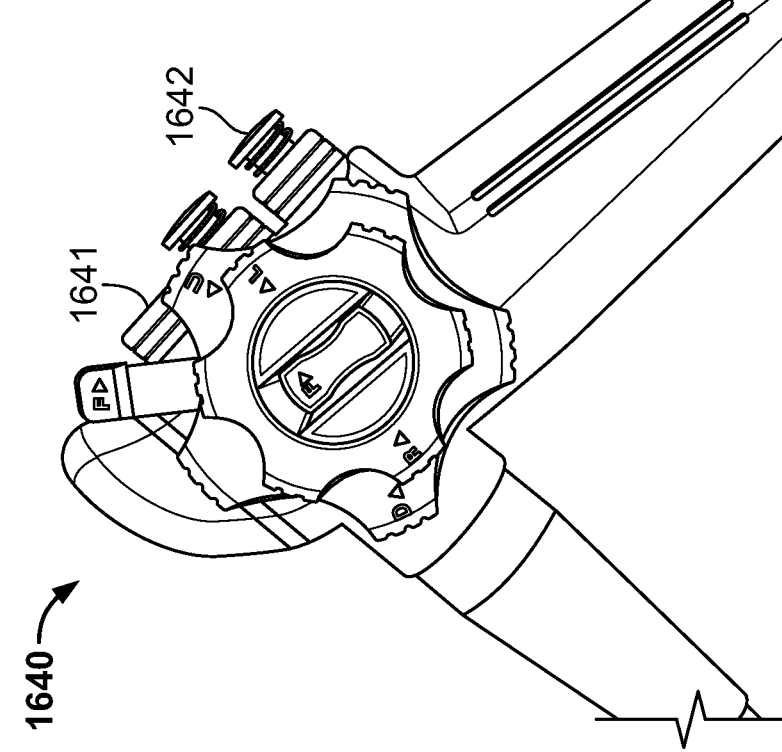
FIG. 16E illustrates a first conventional endoscope handle for use with an induction heating system of the present specification.

FIGS. 16E and 16F illustrate a first conventional endoscope handle 1640 and a second conventional endoscope handle 1644 respectively, for use with an induction heating system of the present specification. The endoscope handles 1640, 1644 include, among other controls, an air/water button 1641, 1646 to provide air or fluid to a body lumen, a suction button 1642, 1647 to provide suction to a body lumen, and a biopsy or working channel 1643, 1648 for the insertion of working tools and removal or body tissues. In various embodiments of the present specification, an induction heating system, such as those discussed below with reference to FIGS. 16G through 16S, is connected to the biopsy or working channel 1643, 1648 to provide steam to a body lumen.

Figure 16G:
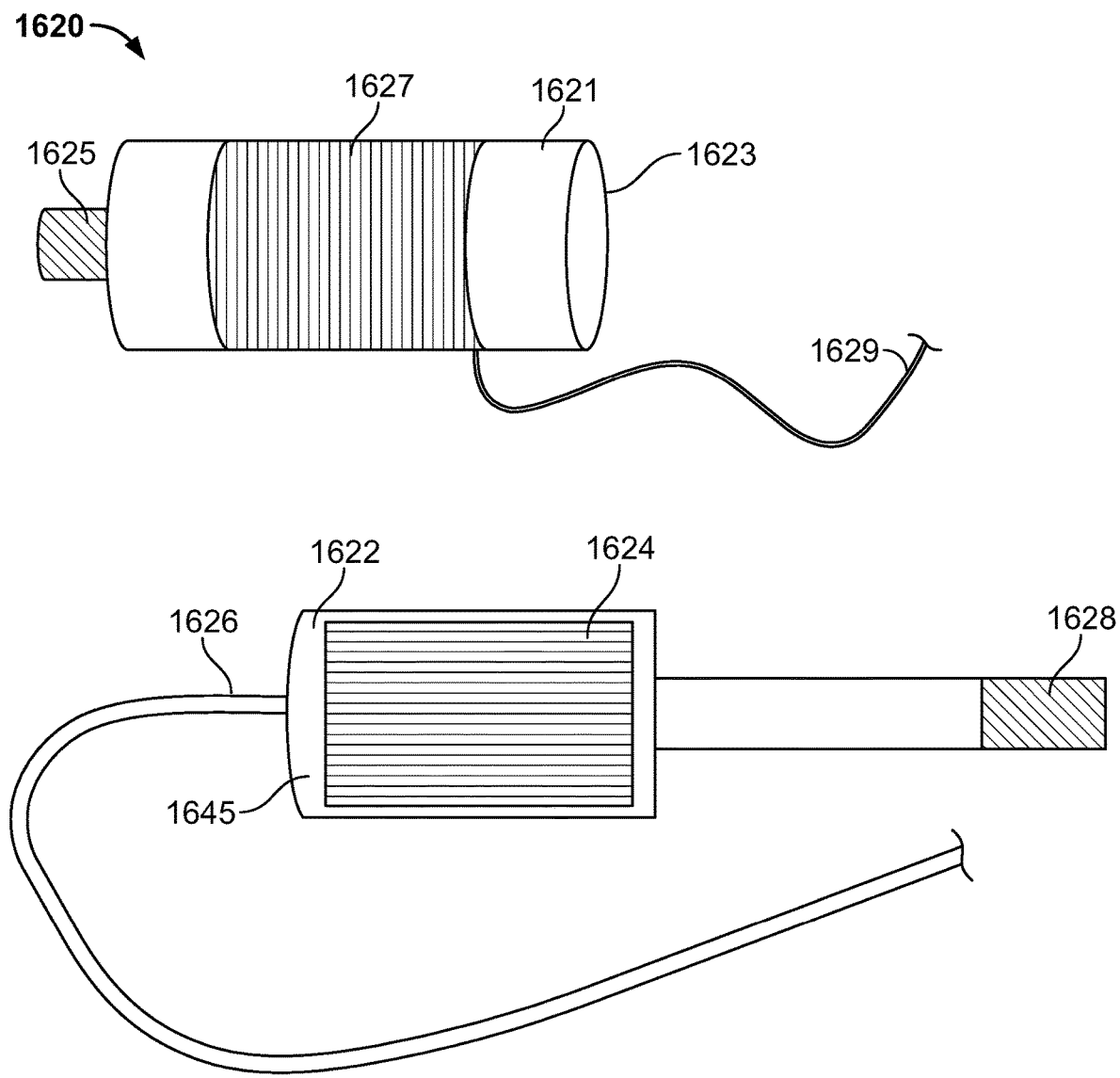
FIG. 16G illustrates a dissembled coil component and heating chamber of an induction heating system for use with an endoscope, in accordance with one embodiment of the present specification.

FIG. 16G illustrates a dissembled coil component 1621 and heating chamber 1622 of an induction heating system 1620 for use with an endoscope, in accordance with one embodiment of the present specification. In some embodiments, the coil component 1621 comprises an outer shell with an electromagnetic coil 1627. In other embodiments, the coil component 1621 comprises only a coil 1627. A wire 1629 is attached to the coil 1627 for providing the coil 1627 with radiofrequency (RF) energy. The coil component 1621 has an elongate shape with a proximal end and a distal end and further includes an opening 1623 at its proximal end configured to receive the heating chamber 1622 and a connector 1625 at its distal end configured to attach to a working channel port of an endoscope. The heating chamber 1622 comprises an inner electrically conducting or ferromagnetic core 1624 and includes an inlet port 1628 at its proximal end for connecting to a fluid source and a catheter 1626 at its distal end for the delivery of generated steam. A space 1645 is present between the core 1624 and the walls of the heating chamber 1622 where heat energy from the core 1624 is transferred to fluid within the chamber 1622 to convert the fluid to steam.

Figure 16H:
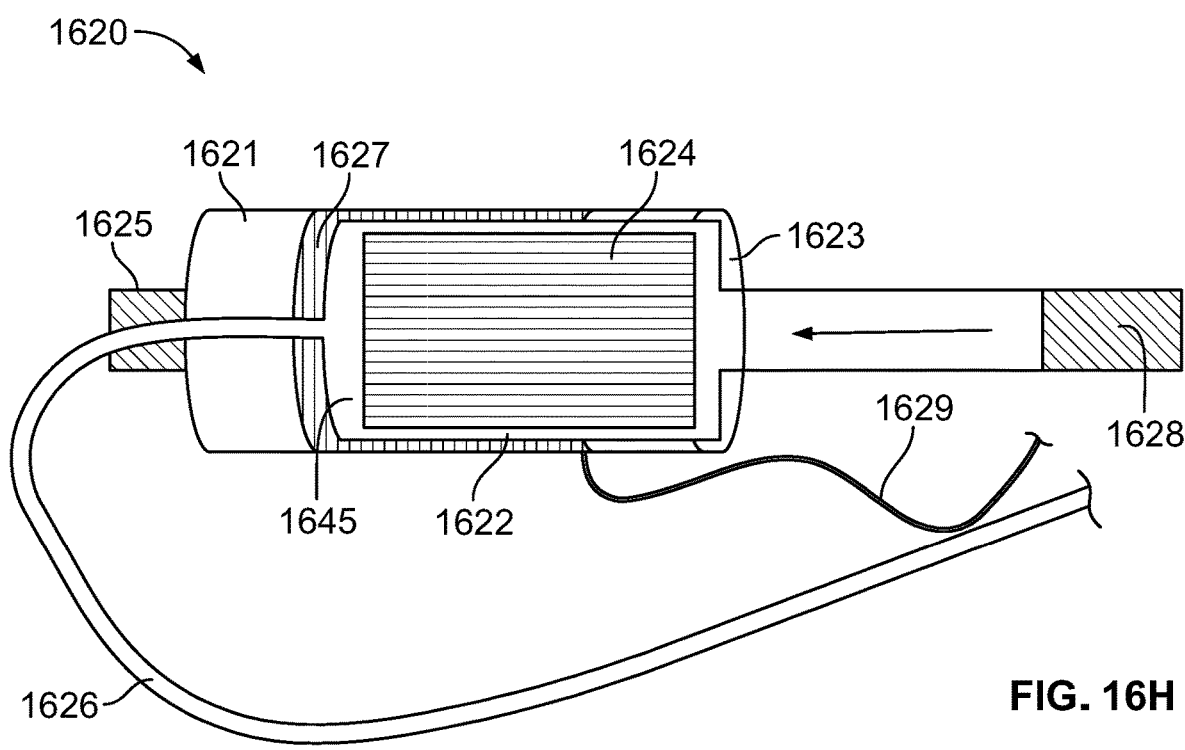
FIG. 16H illustrates an assembled induction heating system for use with an endoscope comprising the coil component and heating chamber of FIG. 16G.

FIG. 16H illustrates an assembled induction heating system 1620 for use with an endoscope comprising the coil component 1621 and heating chamber 1622 of FIG. 16G. The heating chamber 1622 has been inserted through opening 1623 and is movable longitudinally within the coil component 1621. The catheter 1626 has been passed through connector 1625 and is configured to extend along the length of the working channel of an endoscope. Movement of the heating chamber 1622 relative to the coil component 1621 allows for positioning of the catheter 1626 within a body lumen. RF energy supplied by the wire 1629 to the coil 1627 is converted to a magnetic field about the coil 1627 which, through eddy current losses and magnetic hysteresis losses, induces the creation of heat energy within the core 1624. Fluid supplied at input port 1628 is converted to steam by the heat energy in space 1645 within the heating chamber 1622 and exits via catheter 1626.

Figure 16I:
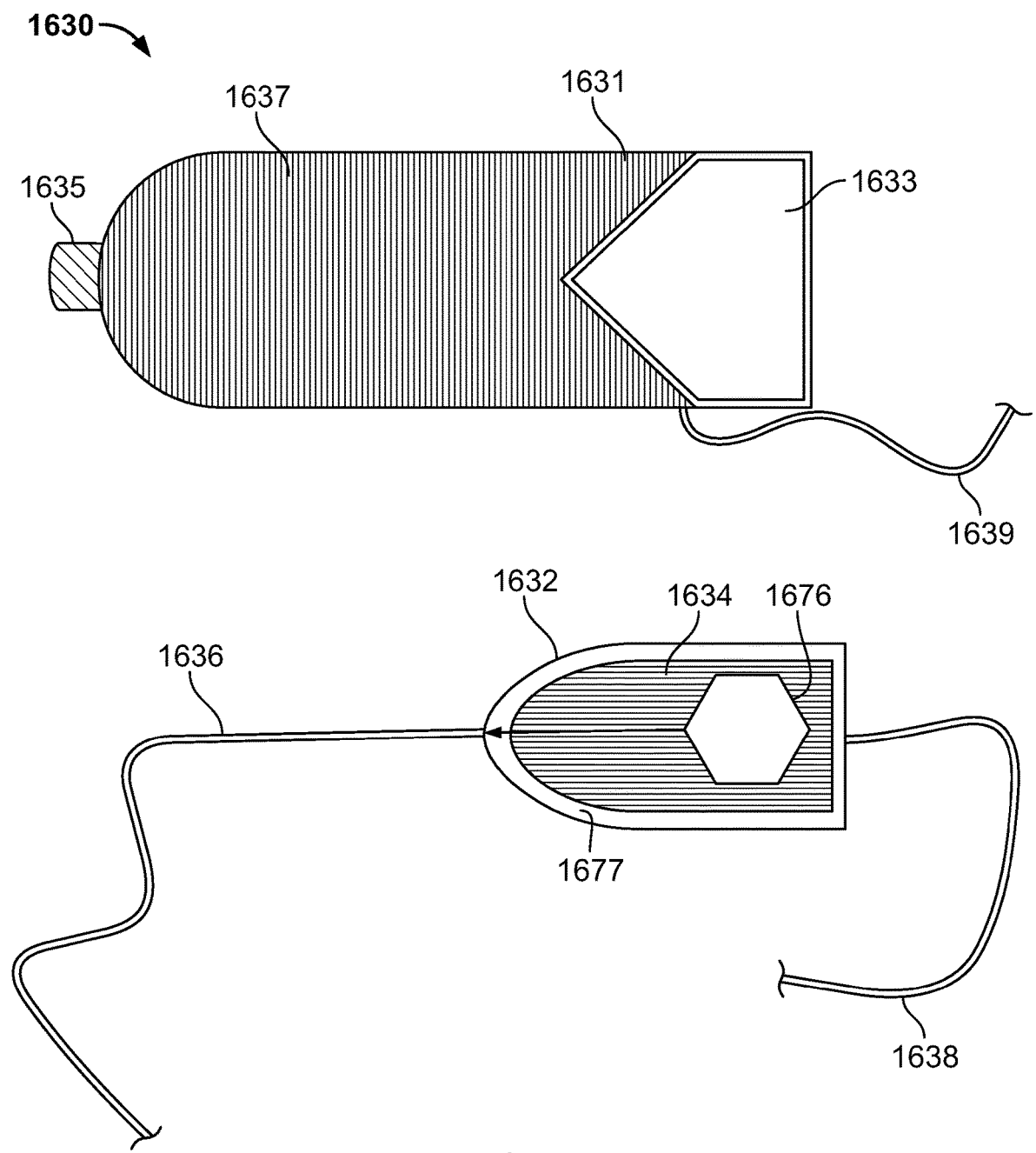
FIG. 16I illustrates a dissembled coil component and heating chamber of an induction heating system for use with an endoscope, in accordance with another embodiment of the present specification.

FIG. 16I illustrates a dissembled coil component 1631 and heating chamber 1632 of an induction heating system 1630 for use with an endoscope, in accordance with another embodiment of the present specification. In some embodiments, the coil component 1631 comprises an outer shell with an electromagnetic coil 1637. In other embodiments, the coil component 1631 comprises only a coil 1637. A wire 1639 is attached to the coil 1637 for providing the coil 1637 with radiofrequency (RF) energy. The coil component 1621 has an elongate shape with a proximal end and a rounded distal end and further includes an opening 1633 at its proximal end configured to receive the heating chamber 1632 and a connector 1635 at its distal end configured to attach to a working channel port of an endoscope. The heating chamber 1632 comprises an inner electrically conducting or ferromagnetic core 1634 and includes an inlet port 1638 at its proximal end for connecting to a fluid source and a catheter 1636 at its distal end for the delivery of generated steam. The distal end of the heating chamber 1632 is rounded to fit within the rounded distal end of the coil component 1631. A space 1677 is present between the core 1634 and the walls of the heating chamber 1632 where heat energy from the core 1634 is transferred to fluid within the chamber 1632 to convert the fluid to steam. The heating chamber 1632 further includes a grasper 1676 for manipulating the chamber 1632 and moving the chamber 1632 and core 1634 relative to the coil component 1631.

Figure 16J:
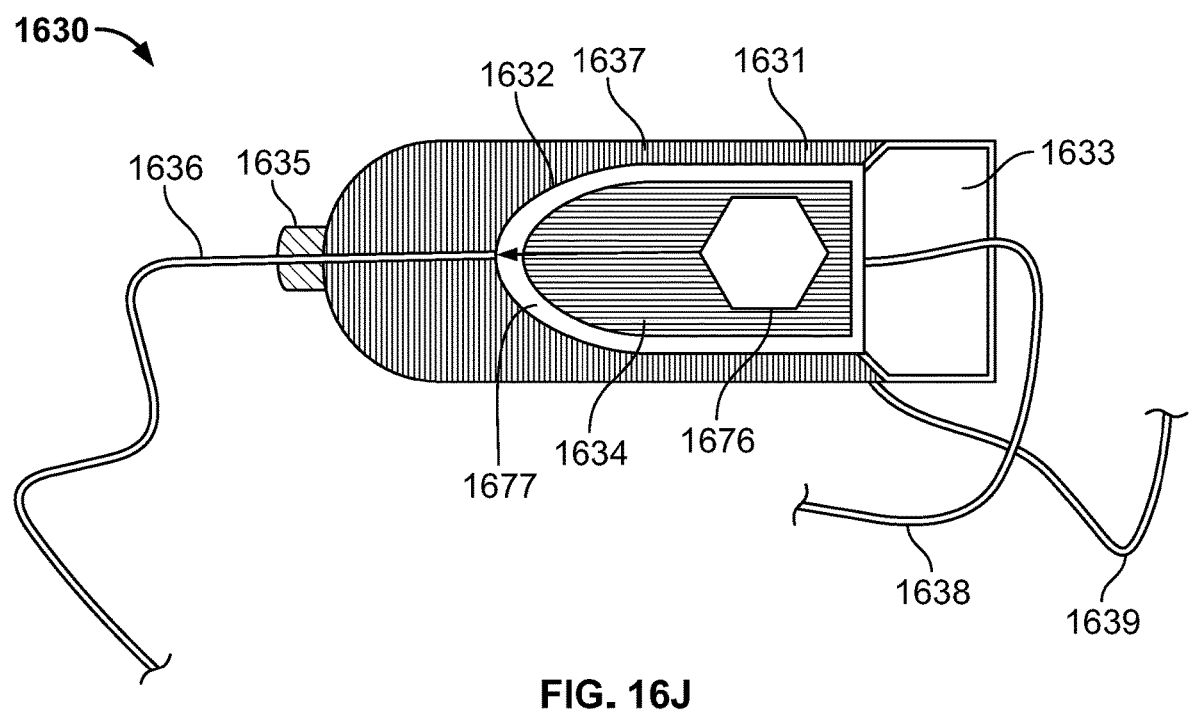
FIG. 16J illustrates an assembled induction heating system for use with an endoscope comprising the coil component and heating chamber of FIG. 16I.

FIG. 16J illustrates an assembled induction heating system 1630 for use with an endoscope comprising the coil component 1631 and heating chamber 1632 of FIG. 16I. The heating chamber 1632 has been inserted through opening 1633 and is movable longitudinally within the coil component 1631. The catheter 1636 has been passed through connector 1635 and is configured to extend along the length of the working channel of an endoscope. Movement of the heating chamber 1632 relative to the coil component 1631 via manipulation of the grasper 1676 allows for positioning of the catheter 1636 within a body lumen. RF energy supplied by the wire 1639 to the coil 1637 is converted to a magnetic field about the coil 1637 which, through eddy current losses and magnetic hysteresis losses, induces the creation of heat energy within the core 1634. Fluid supplied at input port 1638 is converted to steam by the heat energy in space 1677 within the heating chamber 1632 and exits via catheter 1636.

Figure 16L:
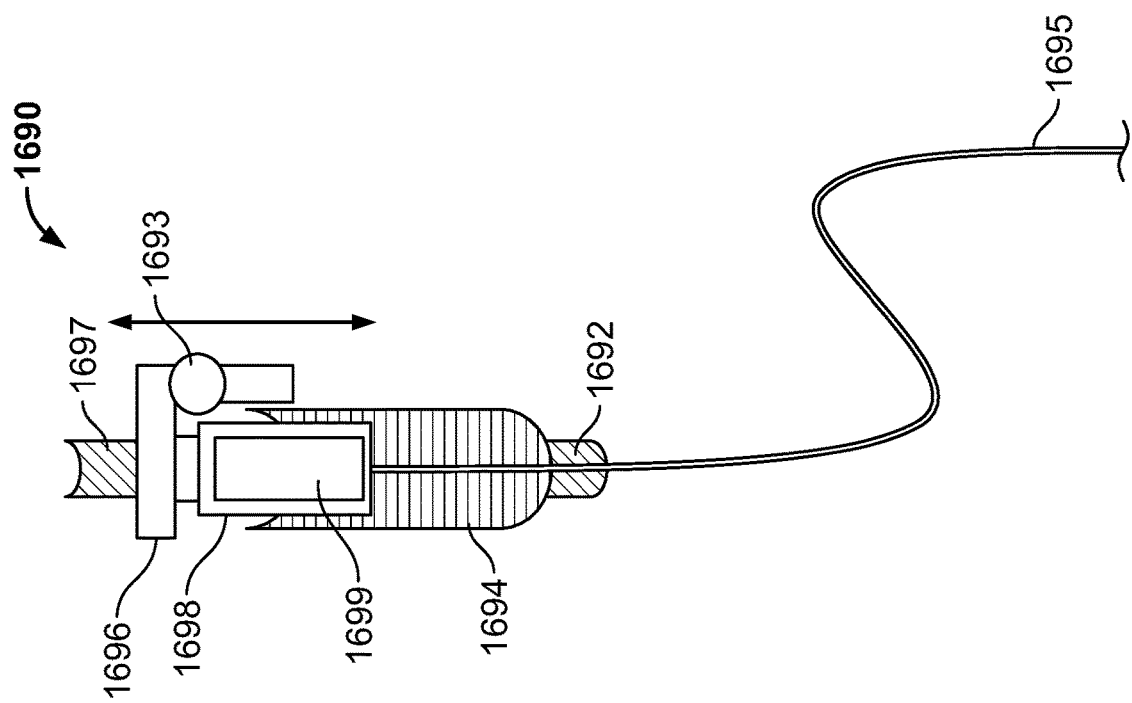
FIG. 16L is a cross-sectional illustration of an induction heating system comprising a handle and having a wheel mechanism for moving a coil component relative to a heating chamber, in accordance with one embodiment of the present specification.
Figure 16K:
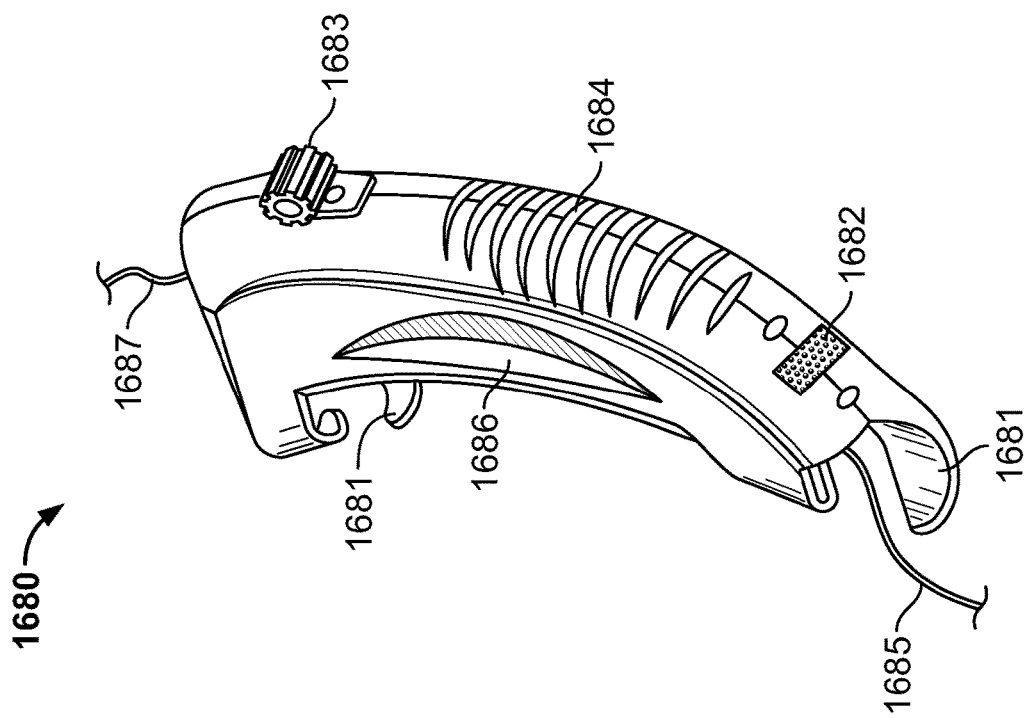
FIG. 16K illustrates an induction heating system comprising a handle configured to be attached to a conventional endoscope handle, in accordance with one embodiment of the present specification.

FIG. 16K illustrates an induction heating system 1680 comprising a handle 1686 configured to be attached to a conventional endoscope handle, in accordance with one embodiment of the present specification. The induction heating system handle 1686 includes at least one clamp 1681 for securing the induction heating system 1680 to an endoscope handle. In one embodiment, the inductions heating system includes two clamps 1681, one each at a proximal and distal end of the handle 1686. The coil component 1684 is embedded within the handle 1686 and movable longitudinally about a heating chamber (not shown) by manipulation of a wheel mechanism 1683 on the handle 1686. In one embodiment, a spring loaded connector 1682 at the distal end of the handle 1686 attaches the induction heating system 1680 to a working channel port of the endoscope handle. A catheter 1685 extends from a distal end of the heating chamber and is configured to pass through the working channel of the endoscope. An inlet port 1687 extends from a proximal end of the heating chamber for connection to a fluid source.

FIG. 16L is a cross-sectional illustration of an induction heating system 1690 comprising a handle 1696 and having a wheel mechanism 1693 for moving a coil component 1694 relative to a heating chamber 1698, in accordance with one embodiment of the present specification. The coil component 1694 is embedded within the handle 1696 and movable longitudinally about the heating chamber 1698 and core 1699 by manipulation of a wheel mechanism 1693 on the handle 1696. A connector 1692 at the distal end of the coil component 1694 attaches the induction heating system 1690 to a working channel port of an endoscope handle. In various embodiments, the connector 1692 is a luer lock connector or spring loaded connector. A catheter 1695 extends from a distal end of the heating chamber 1698, passes through connector 1692, and is configured to extend through the working channel of the endoscope. An inlet port 1697 extends from a proximal end of the heating chamber 1698 for connection to a fluid source. In some embodiments, handle 1696 includes at least one mechanism, similar to clamps 1681 of FIG. 16K, for attaching the induction heating system 1690 to an endoscope handle.

Figure 16N:
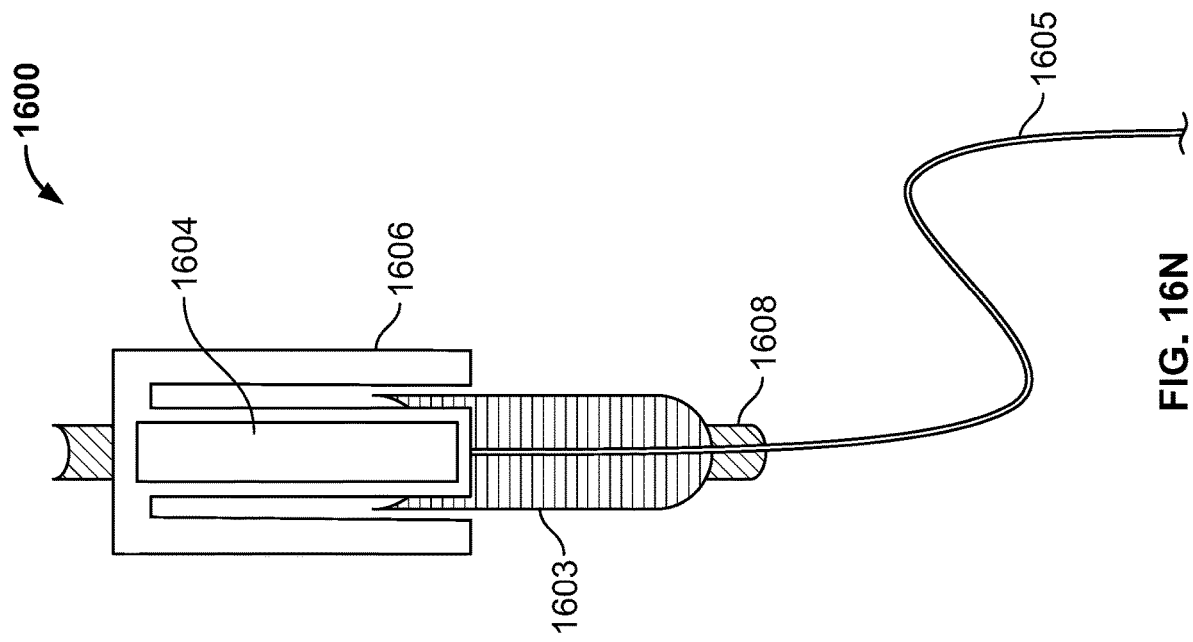
FIG. 16N illustrates the induction heating system of FIG. 16M with the heating chamber in a second position relative to the coil component.
Figure 16M:
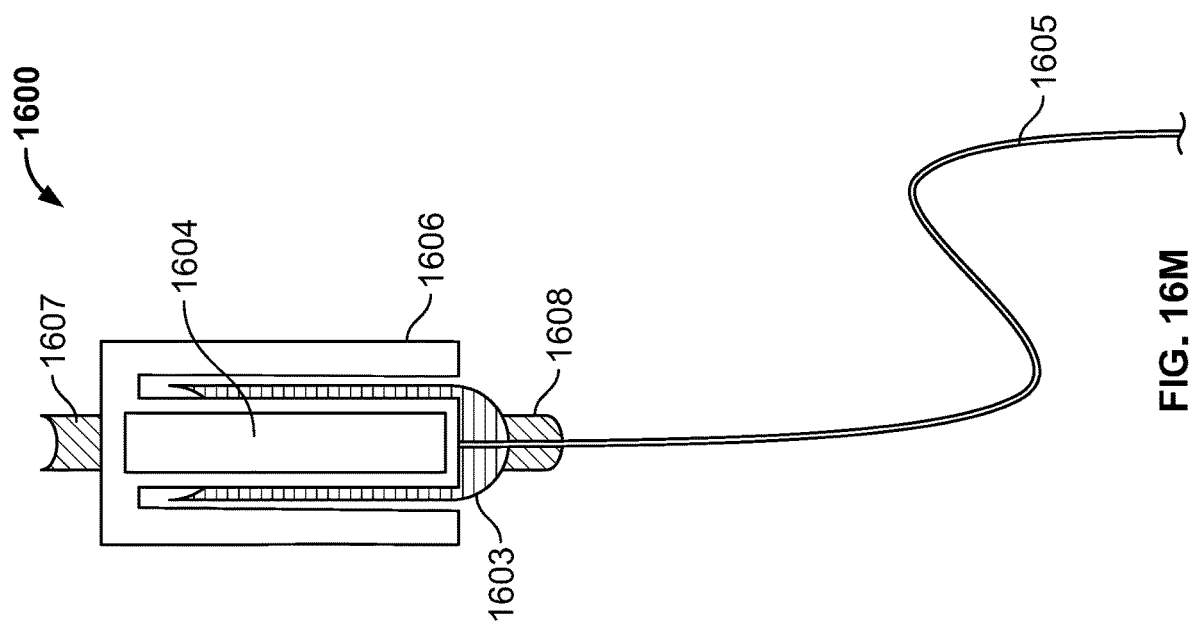
FIG. 16M illustrates an induction heating system comprising a heating chamber in a first position relative to a coil component, in accordance with one embodiment of the present specification.

FIG. 16M illustrates an induction heating system 1600 comprising a heating chamber 1604 in a first position relative to a coil component 1603, in accordance with one embodiment of the present specification. In the first position, the heating chamber 1604 is located in a most distal position relative to the coil component 1603. The induction heating system 1600 includes a handle 1606 for manipulation of the heating chamber 1604 relative to the coil component 1603. A connector 1608 is positioned at the distal end of the coil component 1603 for attaching the induction heating system 1600 to a working channel port of an endoscope. The heating chamber 1604 includes an inlet port 1607 at its proximal end for providing a fluid to the heating chamber 1604 and a catheter 1605 at its distal end configured to extend through the working channel of the endoscope. FIG. 16N illustrates the induction heating system 1600 of FIG. 16M with the heating chamber 1604 in a second position relative to the coil component 1603. In the second position, the heating chamber 1604 has been moved proximally relative to the coil component 1603 via manipulation of the handle 1606. The coil component 1603 position remains fixed as the coil component 1603 is attached to an endoscope handle via connector 1608. Movement of the heating chamber 1604 results in similar movement of the attached catheter 1605 and fine-tune positioning of the distal end of the catheter 1605 within a body lumen.

Figure 16O:
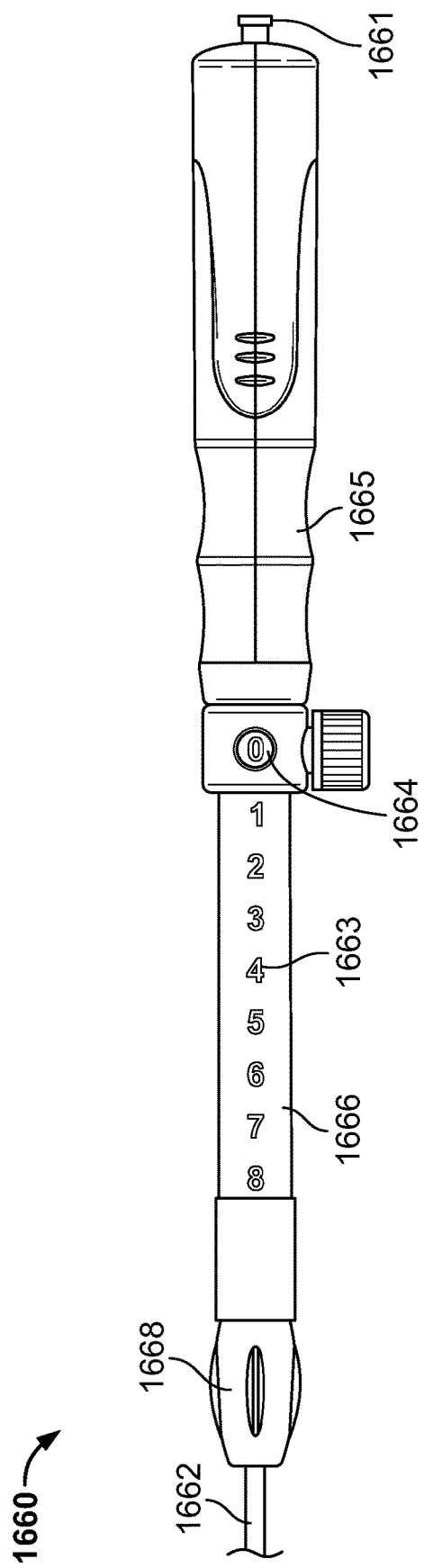
FIG. 16O illustrates an induction heating system comprising a first handle component in a first position relative to a second handle component, in accordance with one embodiment of the present specification.
Figure 16P:
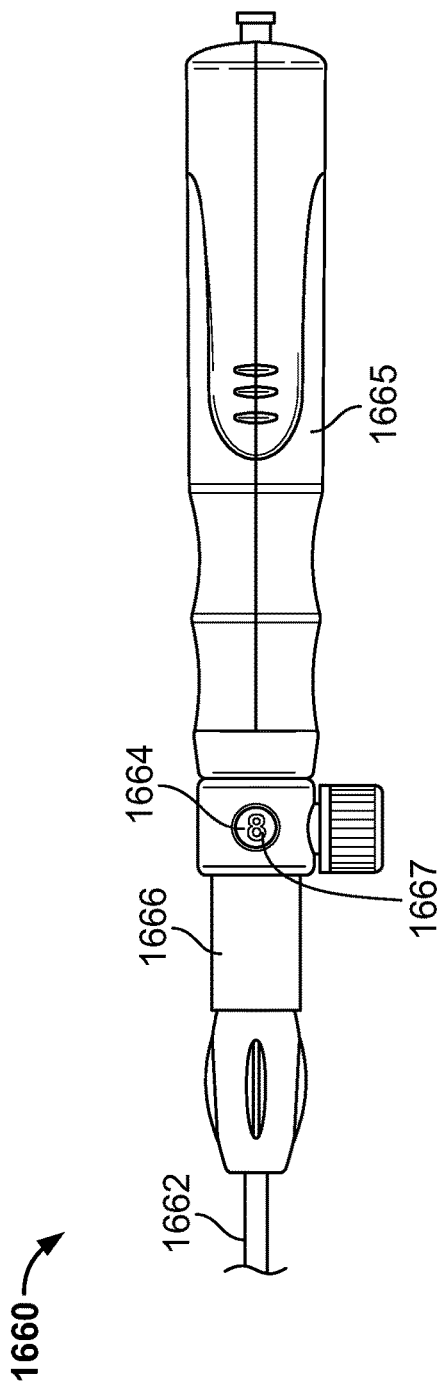
FIG. 16P illustrates the induction heating system of FIG. 16O with the first handle component in a second position relative to the second handle component.

FIG. 16O illustrates an induction heating system 1660 comprising a first handle component 1665 in a first position relative to a second handle component 1666, in accordance with one embodiment of the present specification. In one embodiment, the first handle component 1665 has an elongate body with a proximal end and distal end and comprises a heating chamber within. In one embodiment, the second handle component 1666 has an elongate body with a proximal end and a distal end and comprises a coil within. The second handle component 1666 telescopes in and out of the distal end of the first handle component 1665. An inlet port 1661 is included at the proximal end of the first handle component 1665 for providing the heating chamber with fluid. A connector 1668 is included at the distal end of the second handle component 1666 for attaching the induction heating system 1660 to a working channel port of an endoscope handle. A catheter 1662 extends through the second handle component 1666 and is in fluid communication with the heating chamber within the first handle component 1665. In the first position depicted in FIG. 16O, the first handle component 1665 is positioned most proximally relative to the second handle component 1666. The second handle component 1666 includes a plurality of markings 1663 along its body. In one embodiments, the markings 1663 are numbers. The first handle component 1665 includes a window 1664 proximal its distal end which aligns with one of said markings as the first handle component 1665 is moved longitudinally relative to the second handle component 1666. The marking 1663 in the window 1664 indicates the length of the catheter 1662 extended beyond the distal end of the working channel of the endoscope and into a body lumen of a patient. FIG. 16P illustrates the induction heating system 1660 of FIG. 16O with the first handle component 1665 in a second position relative to the second handle component 1666. The marking 1667 in window 1664 indicates to an operator that the first handle component 1665 is in its most distal position relative to the second handle component 1666 and that the catheter 1662 is fully extended within the body lumen of the patient.

Figure 16Q:
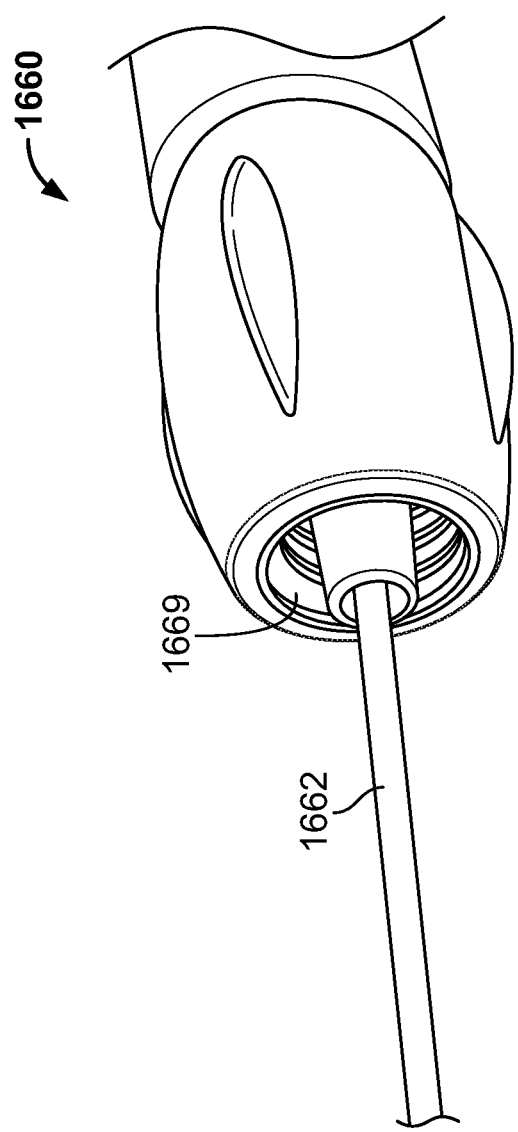
FIG. 16Q illustrates a luer lock mechanism at a distal end of a handle of an induction heating system, in accordance with one embodiment of the present specification.

FIG. 16Q illustrates a luer lock mechanism 1669 at a distal end of a handle of an induction heating system 1660, in accordance with one embodiment of the present specification. A catheter 1662 exists through the luer lock mechanism 1669 and is configured to extend through a working channel of an endoscope. The luer lock mechanism 1669 is configured to attach to a corresponding connector at a working channel port of an endoscope handle.

Figure 16R:
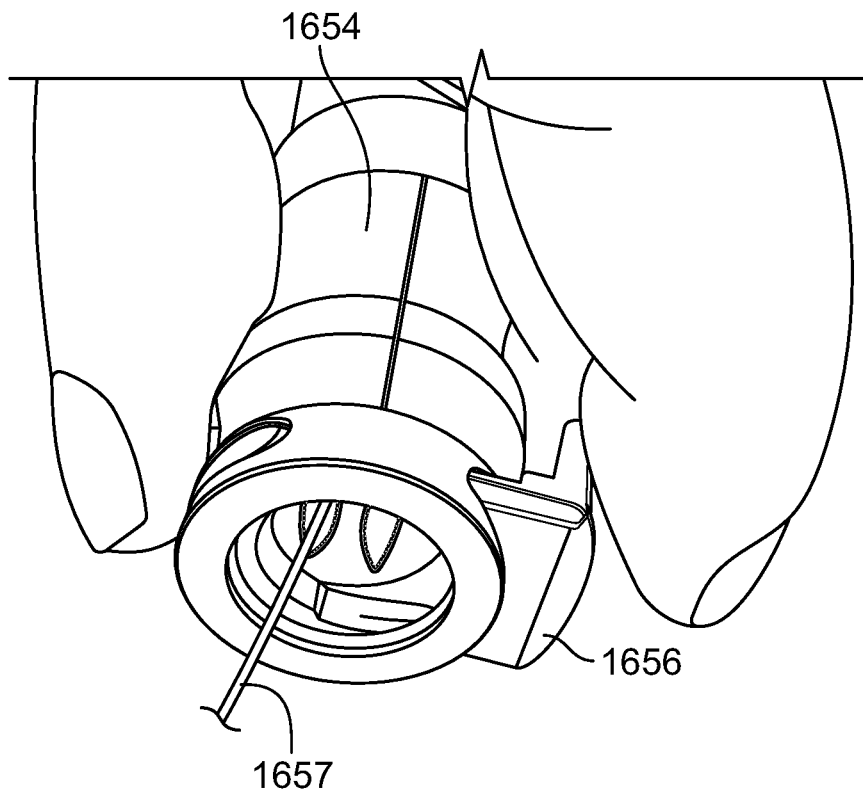
FIG. 16R illustrates a spring loaded connector in a first position at a distal end of a handle of an induction heating system, in accordance with one embodiment of the present specification.
Figure 16S:
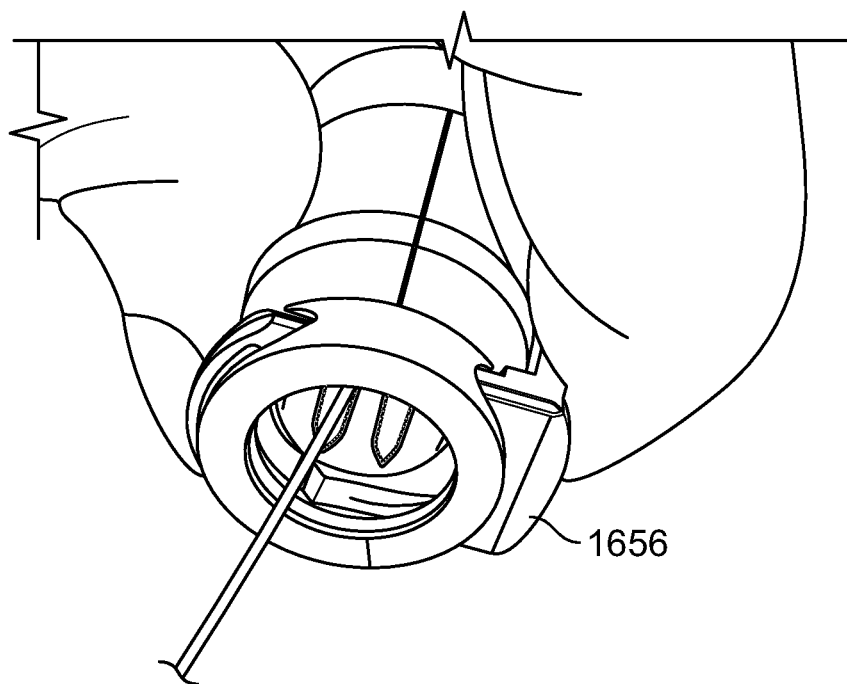
FIG. 16S illustrates the spring loaded connector of FIG. 16R in a second position.

FIG. 16R illustrates a spring loaded connector 1656 in a first position at a distal end of a handle of an induction heating system 1654, in accordance with one embodiment of the present specification. In the first position, the spring loaded connector 1656 is locked and secured to a working channel port of an endoscope handle. A catheter 1657 extends through the distal end of the induction heating system handle. FIG. 16S illustrates the spring loaded connector 1656 of FIG. 16R in a second position, wherein the connector 1656 is depressed and open for connecting to a working channel port of an endoscope handle.

Figure 16T:
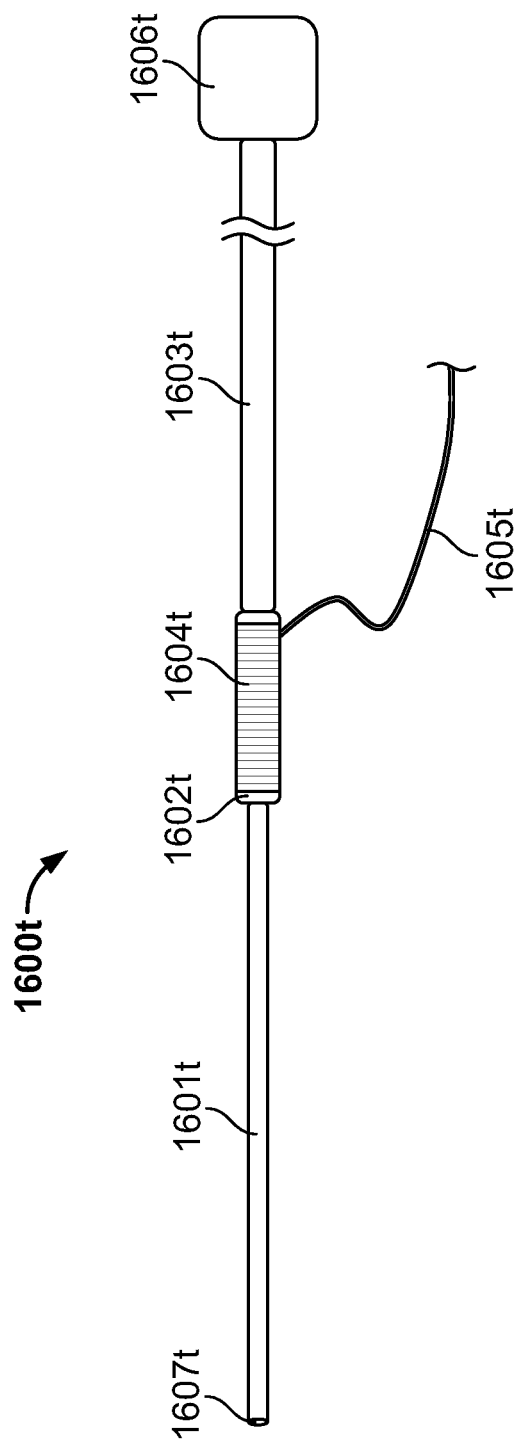
FIG. 16T illustrates a closed loop vapor delivery system for use with an endoscope, in accordance with one embodiment of the present specification.

FIG. 16T illustrates a closed loop vapor delivery system 1600*t* for use with an endoscope, in accordance with one embodiment of the present specification. A closed loop catheter 1601*t*, heating chamber 1602*t*, and fluid channel 1603*t* (from a fluid source 1606*t*) is provided. In various embodiments, the fluid channel 1603*t* comprises a solid tube or housing and acts as a handle to be held and manipulated by a physician. The catheter 1601*t* is configured to be inserted in the working channel of an endoscope, such as working channel 1643 of FIG. 16E. The heating chamber 1602*t* is positioned within an induction coil support structure 1604*t* which in turn, is attached via wire 1605*t*, to driving circuitry to power the coil and generate induction heating. Fluid is provided from fluid source 1606*t* through fluid channel 1603*t* and into heating chamber 1602*t* where it is converted into steam through induction heating provided by induction coil support structure 1604*t*. The steam travels through catheter 1601*t* and is delivered to a target tissue via one or more openings 1607*t* at the distal end of the catheter 1601*t*. In some embodiments, the catheter 1601*t* further includes one or more positioning elements, for example inflatable balloons, for positioning the catheter 1601*t* within a body cavity. The induction coil support structure 1604*t* moves with the heating chamber 1602*t*. A physician holds the fluid channel 1603*t*, which doubles as a handle, and moves the catheter 1601*t* as needed via the endoscope. Using this closed loop system 1600*t* to deliver vapor for ablation therapy comprises simply inserting the catheter 1601*t* into the endoscope and moving back and forth.

Figure 16U:
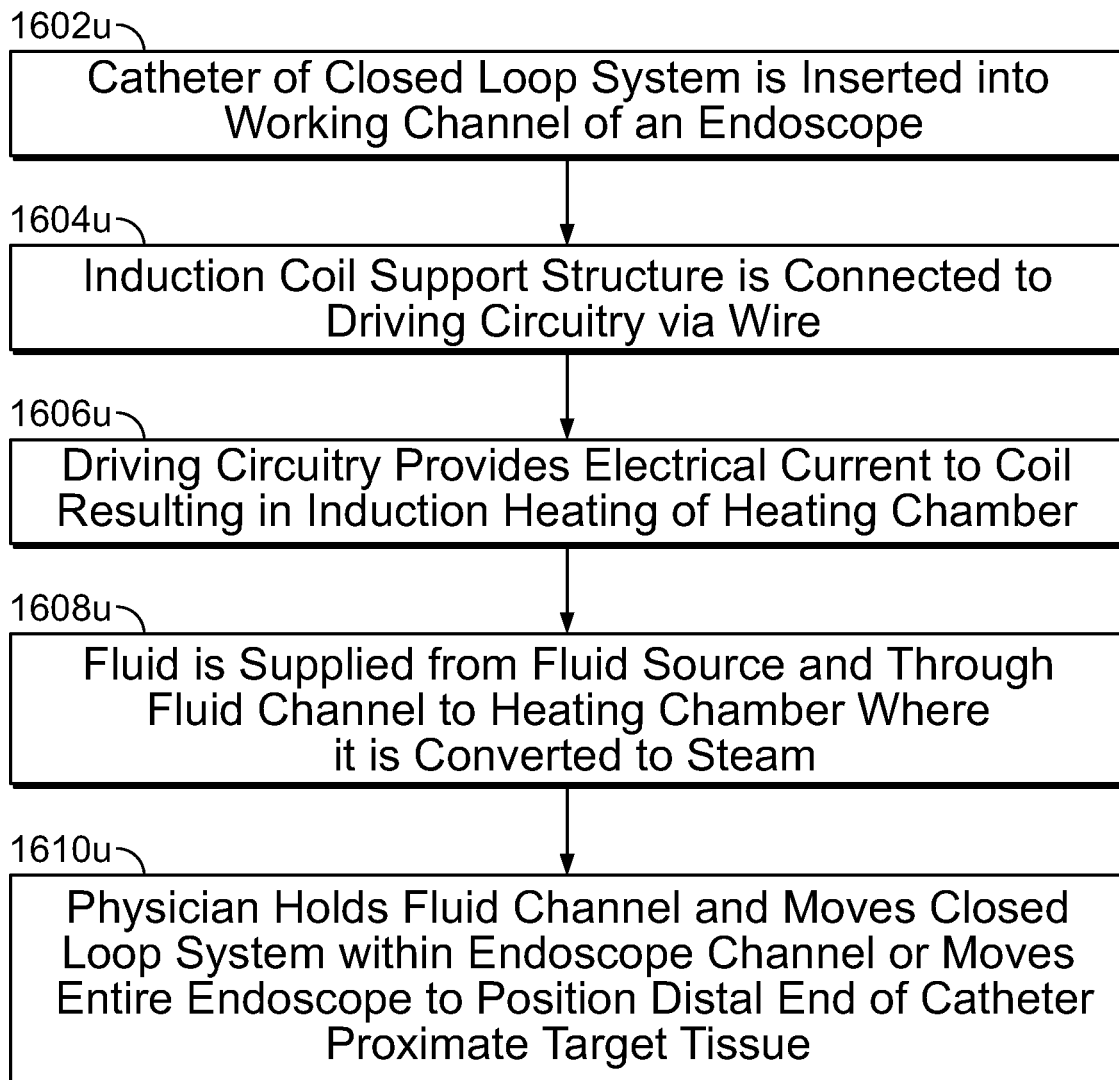
FIG. 16U is a flowchart illustrating the steps involved in one embodiment of a method of providing vapor ablation therapy using the vapor delivery system of FIG. 16T.

FIG. 16U is a flowchart illustrating the steps involved in one embodiment of a method of providing vapor ablation therapy using the vapor delivery system of FIG. 16T. At step 1602*u*, the catheter of the closed loop vapor delivery system in inserted into a working channel of an endoscope. The induction coil support structure is then connected to driving circuitry via a wire at step 1604*u*. The driving circuitry provides electrical current to the coil at step 1606*u* resulting in induction heating of the heating chamber. At step 1608*u*, fluid is supplied from the fluid source and through the fluid channel to the heating chamber where it is converted to steam. The physician holds the fluid channel at step 1610*u* and moves the closed loop system within the endoscope channel or moves the entire endoscope to position the distal end of the catheter proximate a target tissue for vapor ablation.

Figure 16V:
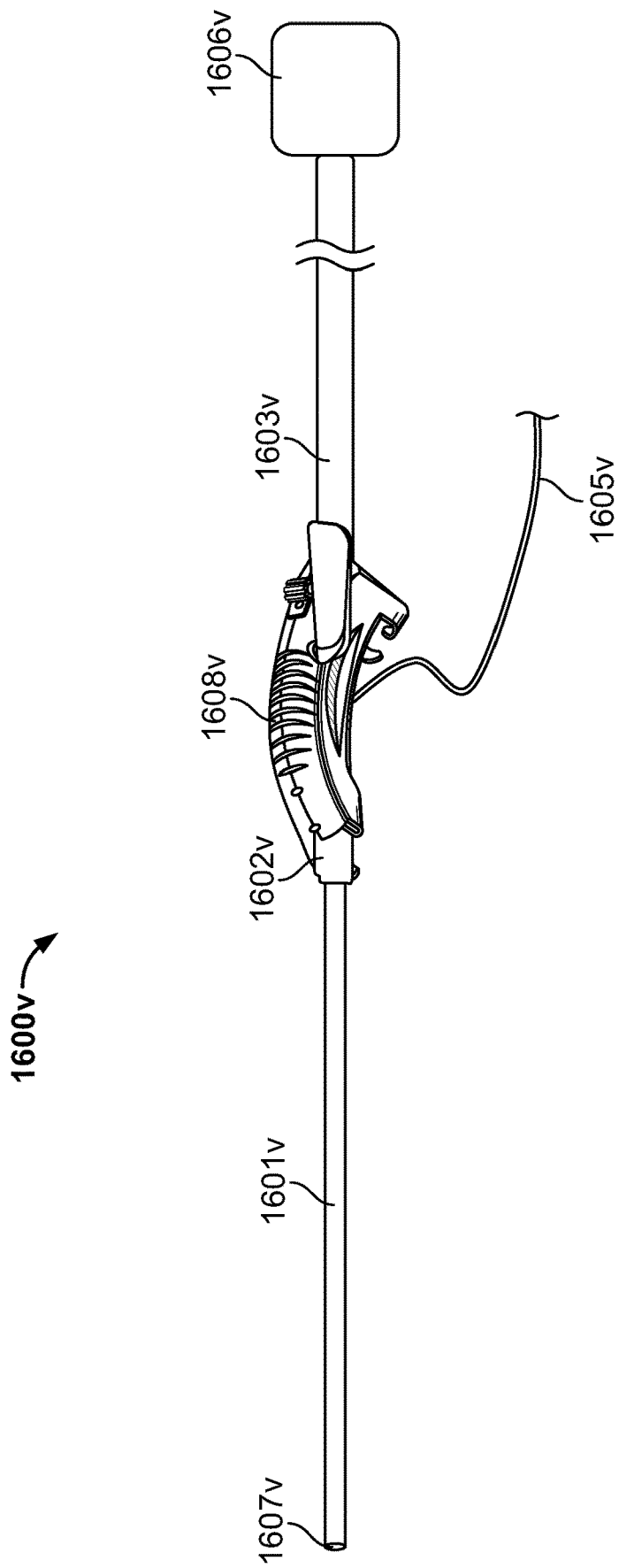
FIG. 16V illustrates a closed loop vapor delivery system for use with an endoscope, in accordance with another embodiment of the present specification.

FIG. 16V illustrates a closed loop vapor delivery system 1600*v* for use with an endoscope, in accordance with another embodiment of the present specification. A closed loop catheter 1601*v*, heating chamber 1602*v*, and fluid channel 1603*v* (from a fluid source 1606*v*) is provided. In various embodiments, the fluid channel 1603*v* comprises a solid tube or housing and acts as a handle to be held and manipulated by a physician. In this embodiment, the heating chamber 1602*v* is too big to be moved back and forth without support. Therefore, the system 1600*v* includes an endoscope handle attachment 1608*v*, similar to the handle 1686 shown in FIG. 16K. The catheter 1601*v* is configured to be inserted into the working channel of an endoscope, such as working channel 1643 of FIG. 16E, with the heating chamber 1602*v* and handle portion of the fluid channel 1603*v* being positioned within the endoscope handle attachment 1608*v*. In the embodiment depicted in FIG. 16V, the endoscope handle attachment 1608*v* has the induction coil built-in. The built-in coil is in turn attached to driving circuitry via wire 1605*v* to power the coil and generate induction heating. Fluid is provided from fluid source 1606*v* through fluid channel 1603*v* and into heating chamber 1602*v* where it is converted into steam through induction heating provided by the built-in coil of the endoscope handle attachment 1608*v*. The steam travels through catheter 1601*v* and is delivered to a target tissue via one or more openings 1607*v* at the distal end of the catheter 1601*v*. In some embodiments, the catheter 1601*v* further includes one or more positioning elements, for example inflatable balloons, for positioning the catheter 1601*v* within a body cavity. The endoscope handle attachment 1608*v* does not move with the heating chamber 1602*v*. A physician toggles a switch on the endoscope handle attachment 1608*v* which manipulates the fluid channel 1602*v*, which doubles as a handle, and moves the catheter 1601*v* as needed via the endoscope. In this embodiment, the closed loop system 1600*v* inserted into the endoscope is moved back and forth and the heating chamber 1602*v* remains in the field generated by the stationary induction coil in the endoscope handle attachment 1608*v*.

Figure 16W:
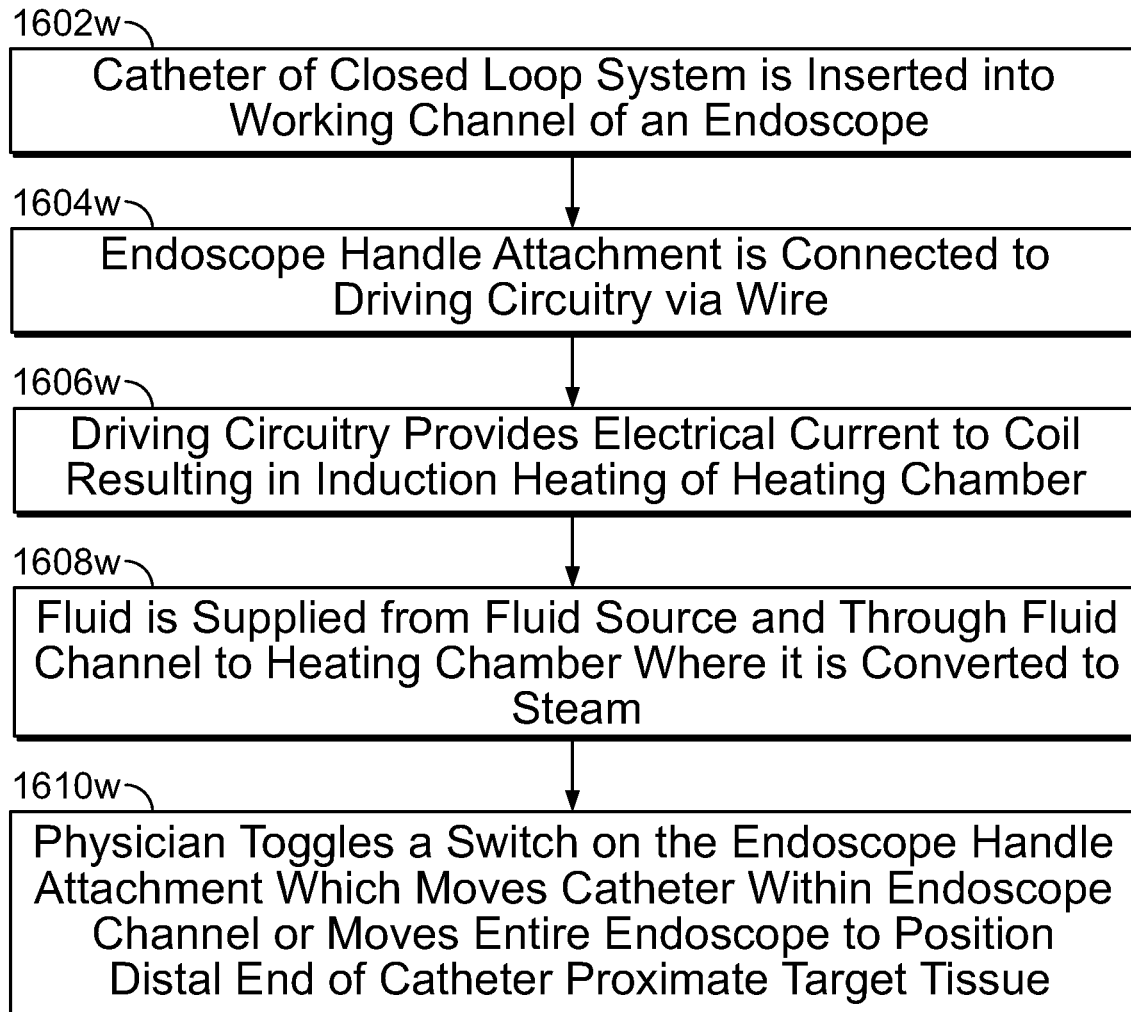
FIG. 16W is a flowchart illustrating the steps involved in one embodiment of a method of providing vapor ablation therapy using the vapor delivery system of FIG. 16V.

FIG. 16W is a flowchart illustrating the steps involved in one embodiment of a method of providing vapor ablation therapy using the vapor delivery system of FIG. 16V. At step 1602*w*, the catheter of the closed loop vapor delivery system in inserted into a working channel of an endoscope. The endoscope handle attachment, containing the built-in coil, is then connected to driving circuitry via a wire at step 1604*w*. The driving circuitry provides electrical current to the coil at step 1606*w* resulting in induction heating of the heating chamber. At step 1608*w*, fluid is supplied from the fluid source and through the fluid channel to the heating chamber where it is converted to steam. The physician toggles a switch on the endoscope handle attachment at step 1610*w* which moves the catheter within the endoscope channel or moves the entire endoscope to position the distal end of the catheter proximate a target tissue for vapor ablation.

Figure 16X:
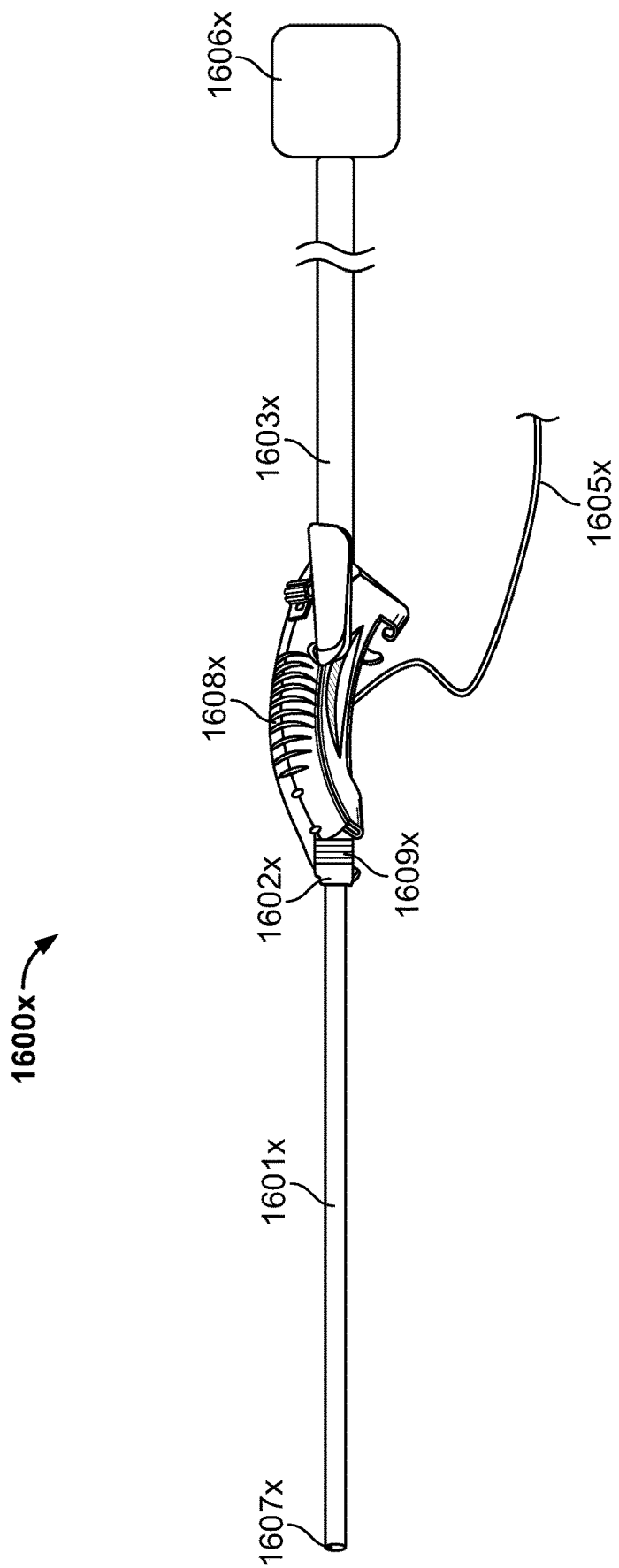
FIG. 16X illustrates a closed loop vapor delivery system for use with an endoscope, in accordance with yet another embodiment of the present specification.

FIG. 16X illustrates a closed loop vapor delivery system 1600*x* for use with an endoscope, in accordance with yet another embodiment of the present specification. A closed loop catheter 1601*x*, heating chamber 1602*x*, and fluid channel 1603*x* (from a fluid source 1606*x*) is provided. In various embodiments, the fluid channel 1603*x* comprises a solid tube or housing and acts as a handle to be held and manipulated by a physician. In this embodiment, the heating chamber 1602*x* is too big to be moved back and forth without support. Therefore, the system 1600*x* includes an endoscope handle attachment 1608*x*, similar to the handle 1686 shown in FIG. 16K. The catheter 1601*x* is configured to be inserted into the working channel of an endoscope, such as working channel 1643 of FIG. 16E, with the heating chamber 1602*x* and handle portion of the fluid channel 1603*x* being positioned within the endoscope handle attachment 1608*x*. In the embodiment depicted in FIG. 16X, the induction coil 1609*x* is attached to and wound about the heating chamber 1602*x* and is not included as a part of the endoscope handle attachment 1608*x*. The induction coil 1609*x* is in turn attached to driving circuitry via wire 1605*x* to power the coil 1609*x* and generate induction heating. Fluid is provided from fluid source 1606*x* through fluid channel 1603*x* and into heating chamber 1602*x* where it is converted into steam through induction heating provided by the induction coil 1609*x*. The steam travels through catheter 1601*x* and is delivered to a target tissue via one or more openings 1607*x* at the distal end of the catheter 1601*x*. In some embodiments, the catheter 1601*x* further includes one or more positioning elements, for example inflatable balloons, for positioning the catheter 1601*x* within a body cavity. The endoscope handle attachment 1608*x* does not move with the heating chamber 1602*x*, however, the heating chamber 1602*x* and induction coil 1609*x* do move together as they are physically attached to one another. A physician toggles a switch on the endoscope handle attachment 1608*x* which manipulates the fluid channel 1602*x*, which doubles as a handle, and moves the catheter 1601*x* as needed via the endoscope. In this embodiment, the closed loop system 1600*x* inserted into the endoscope is moved back and forth and the heating chamber 1602*x* and attached induction coil 1609*x* move together relative to the endoscope handle attachment 1608*x*.

Figure 16Y:
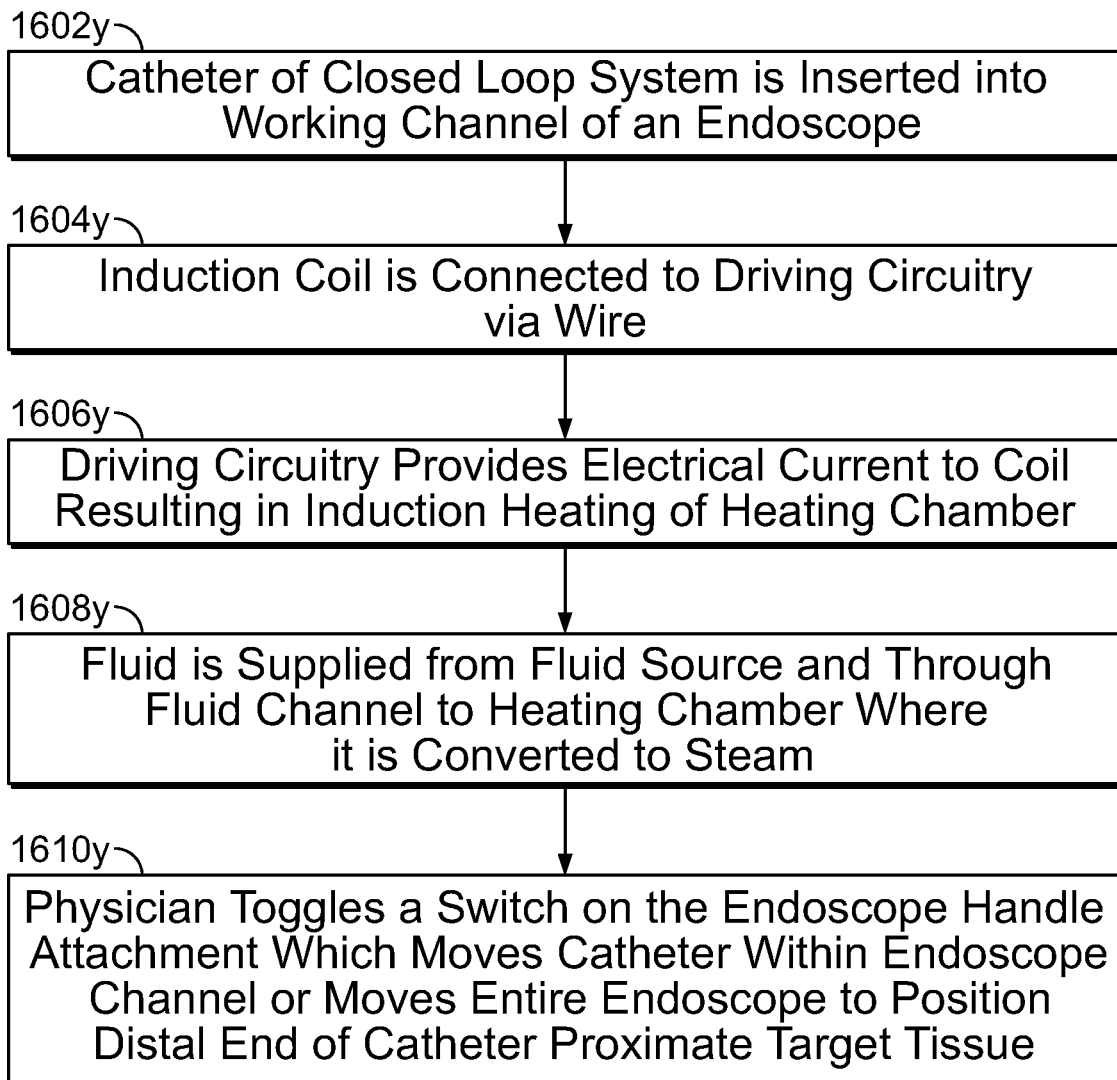
FIG. 16Y is a flowchart illustrating the steps involved in one embodiment of a method of providing vapor ablation therapy using the vapor delivery system of FIG. 16X.

FIG. 16Y is a flowchart illustrating the steps involved in one embodiment of a method of providing vapor ablation therapy using the vapor delivery system of FIG. 16X. At step 1602y, the catheter of the closed loop vapor delivery system in inserted into a working channel of an endoscope. The induction coil, attached to the heating chamber, is then connected to driving circuitry via a wire at step 1604y. The driving circuitry provides electrical current to the coil at step 1606y resulting in induction heating of the heating chamber. At step 1608y, fluid is supplied from the fluid source and through the fluid channel to the heating chamber where it is converted to steam. The physician toggles a switch on the endoscope handle attachment at step 1610y which moves the catheter within the endoscope channel or moves the entire endoscope to position the distal end of the catheter proximate a target tissue for vapor ablation.

Figure 17D:
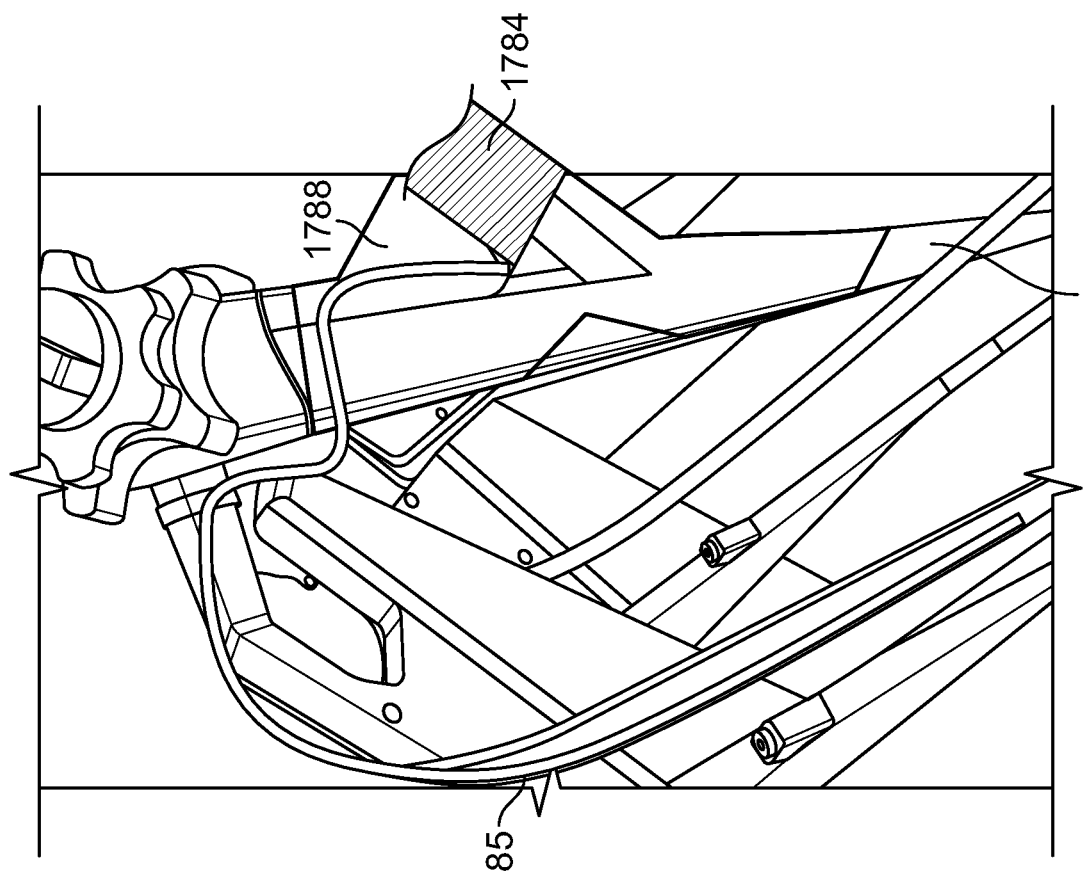
FIG. 17D illustrates the handle mechanism of FIG. 17C attached to an endoscope, in accordance with an embodiment.

In accordance with some aspects, the present specification provides a handle mechanism that may be used with in conjunction with an endoscope for maneuvering the ablation catheters disclosed in various embodiments. FIG. 17A provides an exemplary illustration of the handle 1780. Referring to FIG. 17A, handle 1780 comprises a port 1781 for receiving and holding an ablation catheter. The handle 1780 further comprises a clamp 1782 for securing to an endoscope (not shown). The handle also comprises clamps 1783 for securing or attaching a power cord 1785. The power cord is used to supply power to an RF coil 1784, which is located in a chamber or port 1786 within the handle 1780. In one embodiment, the RF coil is located within a port on the handle, which is in communication with the port 1781 that receives the ablation catheter.

When alternating current is supplied to the RF coil 1784 by means of the power cord, the RF coil which comprises a metal coil wound about a ferromagnetic core, creates a magnetic field. In one embodiment, the chamber 1786 is composed of a ferrous material, such as iron, stainless steel, or copper. This causes electrical currents known as eddy currents to flow in the chamber, owing to the presence of the alternating current and the magnetic field, as described earlier in the specification. The eddy currents cause localized heating of the chamber 1786. When the chamber 1786 is filled with a fluid, such as water, the heat is transferred from the chamber to the fluid inside, resulting in vaporization of said fluid. This vapor is supplied to the catheter by means of port 1781, for ablation. It may be noted that the configuration of the chamber and coil in FIG. 17A depicts only one possible embodiment and is not intended to be limiting. Those skilled in the art will understand that many different design configurations are possible with respect to the chamber and coil. In one embodiment, for example, the RF coil heats a fluid within a heating chamber of a catheter inserted into the handle, such that the fluid is converted to vapor for ablation. In this case, the heating chamber is included as a part of the catheter assembly.

FIG. 17B provides an illustration of the handle mechanism 1780 of FIG. 17A attached to an endoscope 1787. Referring to FIG. 17B, the RF coil 1784 of the handle is positioned within a port on the handle. In one embodiment, once the handle is clamped to an endoscope, the RF coil is positioned over and is in communication with another port on the endoscope configured to receive the ablation catheter.

In one embodiment, the handle 1780 is disposable. In another embodiment, the handle 1780 is reusable.

Figure 17C:
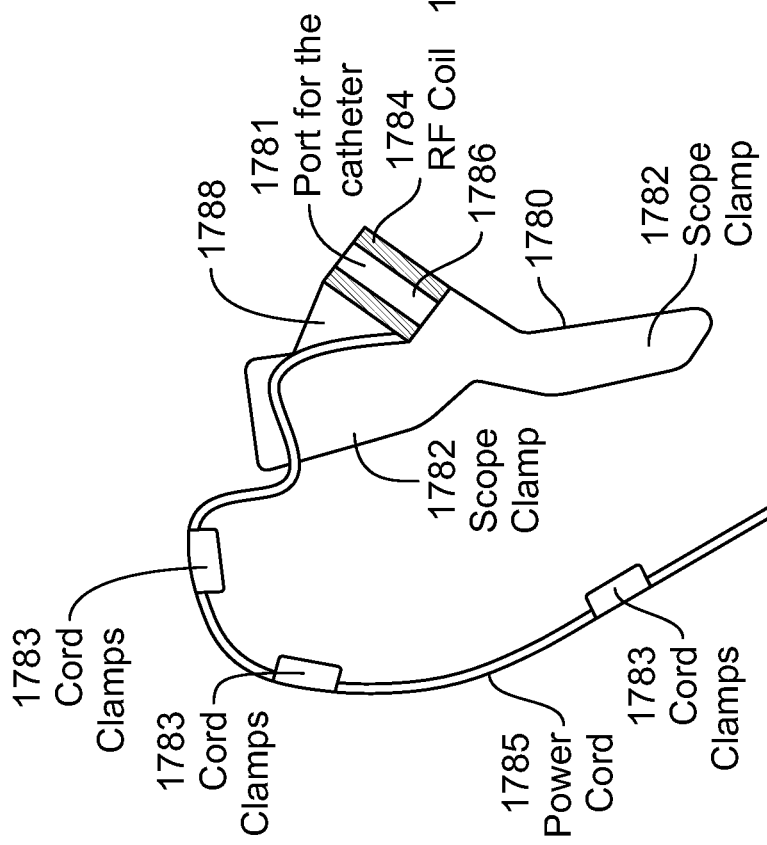
FIG. 17C illustrates another embodiment of a handle mechanism comprising an RF coil for use with the ablation catheters.

FIG. 17C illustrates an alternate embodiment of the handle mechanism, wherein the handle 1780 also includes a support component 1788 connecting the catheter port 1781 to a proximal portion 1789 of the handle. This provides the port and catheter with additional support once the catheter has been inserted. The support component 1788 can also be seen in FIG. 17D, where the handle 1780 is shown attached to an endoscope 1787.

Figure 17E:
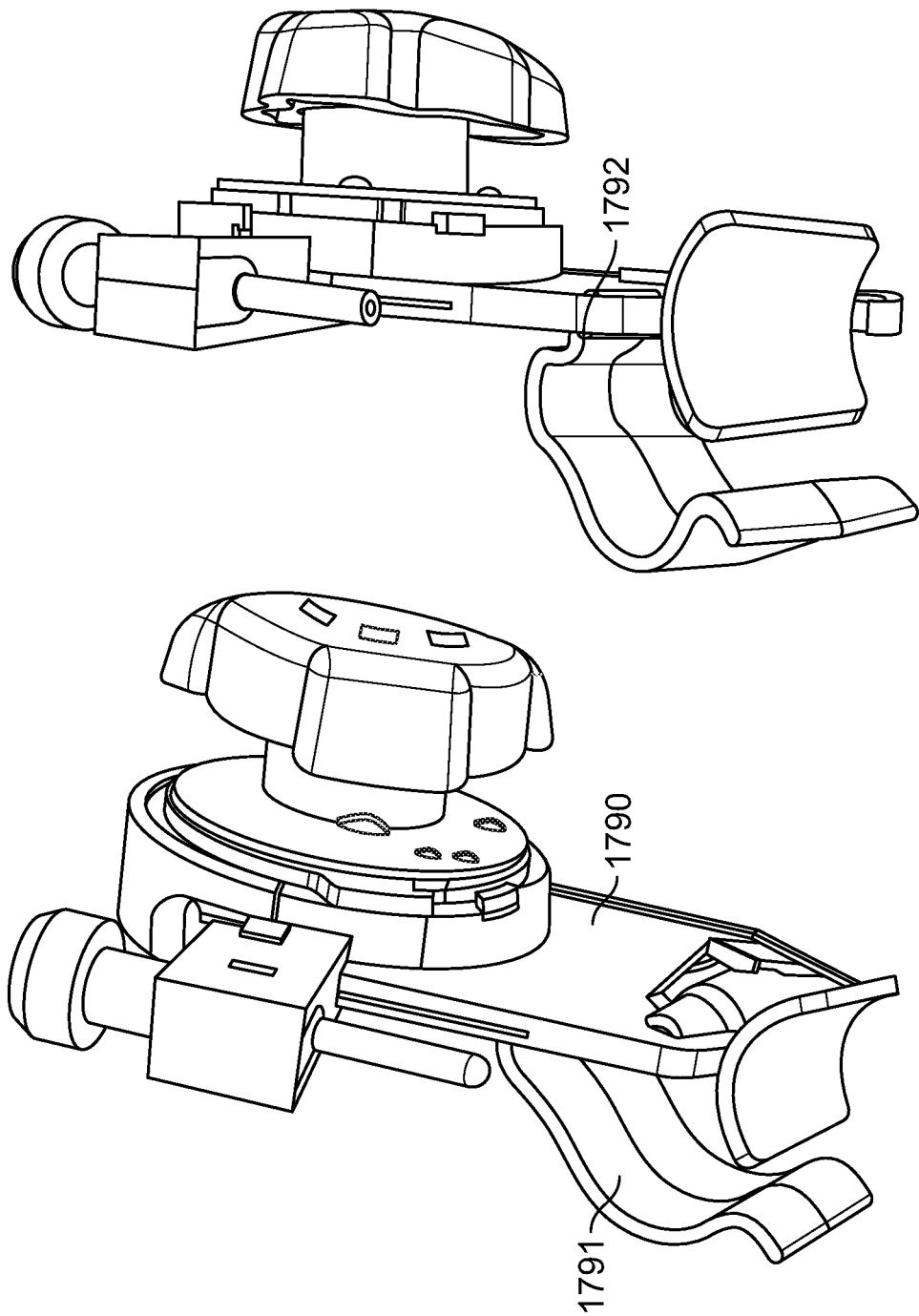
FIG. 17E illustrates another embodiment of a handle mechanism for use with the ablation catheters.
Figure 17F:
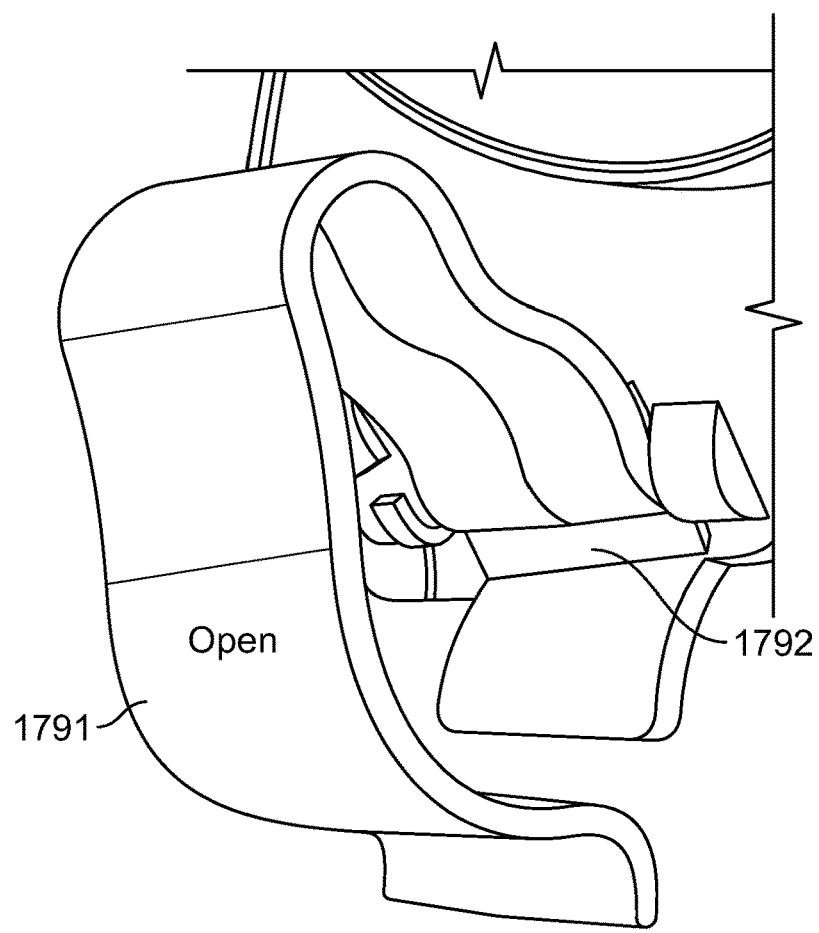
FIG. 17F illustrates a close view of a fastener used for securing the handle to the endoscope, in accordance with one embodiment.
Figure 17G:
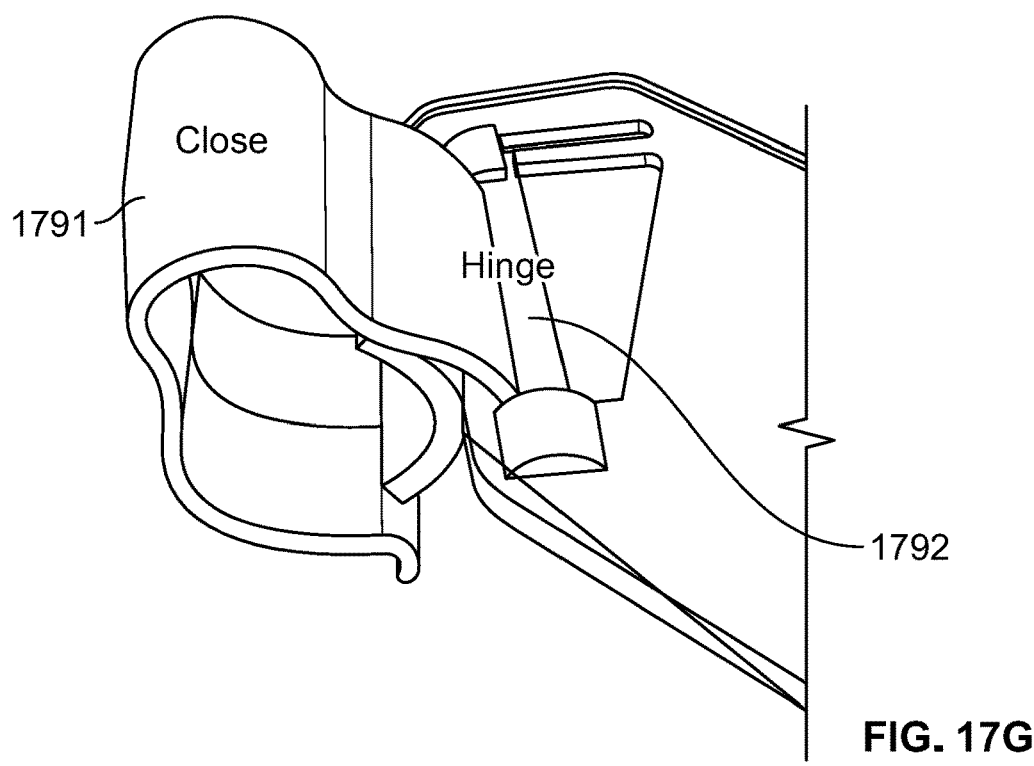
FIG. 17G illustrates another close view of a fastener used for securing the handle to the endoscope, in accordance with one embodiment.

FIG. 17E provides another illustration of the handle mechanism 1790. Referring to FIG. 17E, in one embodiment, the handle comprises a fastener 1791 such as a clamp or a bracket that is used to secure the handle to an endoscope. In one embodiment, the fastener 1791 can be snapped around an endoscope to attach the handle to the endoscope. In one embodiment, the clamp 1791 is attached to the handle unit by means of a hinge 1792. The hinge mechanism allows the clamp or the fastener to be easily opened as shown in FIG. 17F, and also to be easily closed, as shown in FIG. 17G.

Figure 17H:
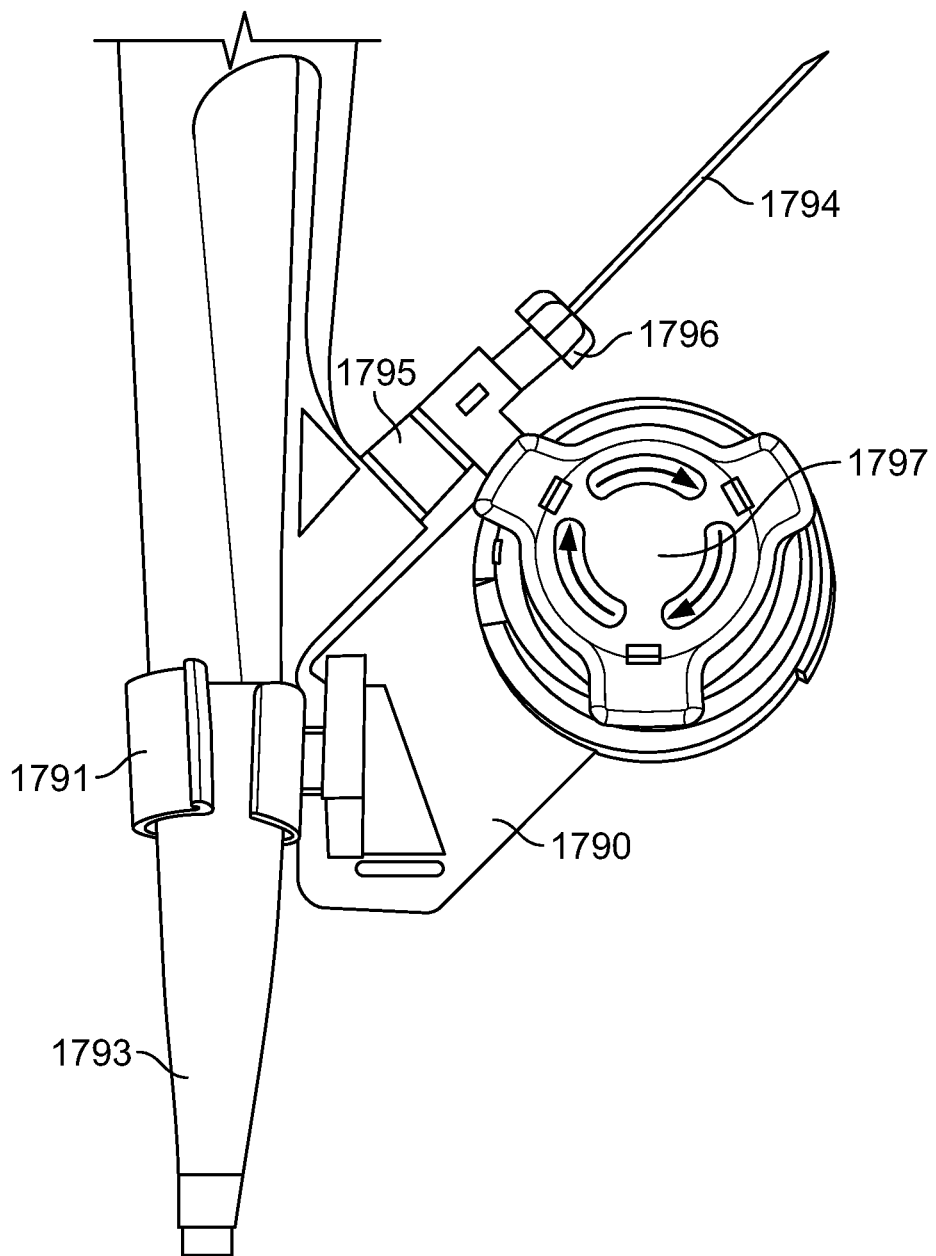
FIG. 17H illustrates the handle mechanism of FIG. 17E attached to an endoscope, in accordance with an embodiment.

FIG. 17H illustrates the handle 1790 attached to an endoscope 1793 via clamp 1791. Referring to FIG. 17H, in one embodiment, the handle is equipped with a catheter 1794 for the ablative fluid to flow through. Before clamping the handle to the endoscope, the catheter 1794 is inserted into the biopsy port 1795 of the endoscope, from where it is advanced through the working channel of the endoscope until it exits from the distal end of the endoscope. The fluid enters the heating chamber 1796, where it is heated and converted to vapor, through the catheter 1794 and passes as vapor through the distal end of the catheter at a distal end of the endoscope to ablate the desired tissue. The details of the heating chamber 1796 are provided in FIGS. 17A-D. The handle is also equipped with a knob 1797 for maneuvering the ablation catheter 1794 in and out of the endoscope without needing the operator to physically touch the catheter shaft.

Figure 18A:
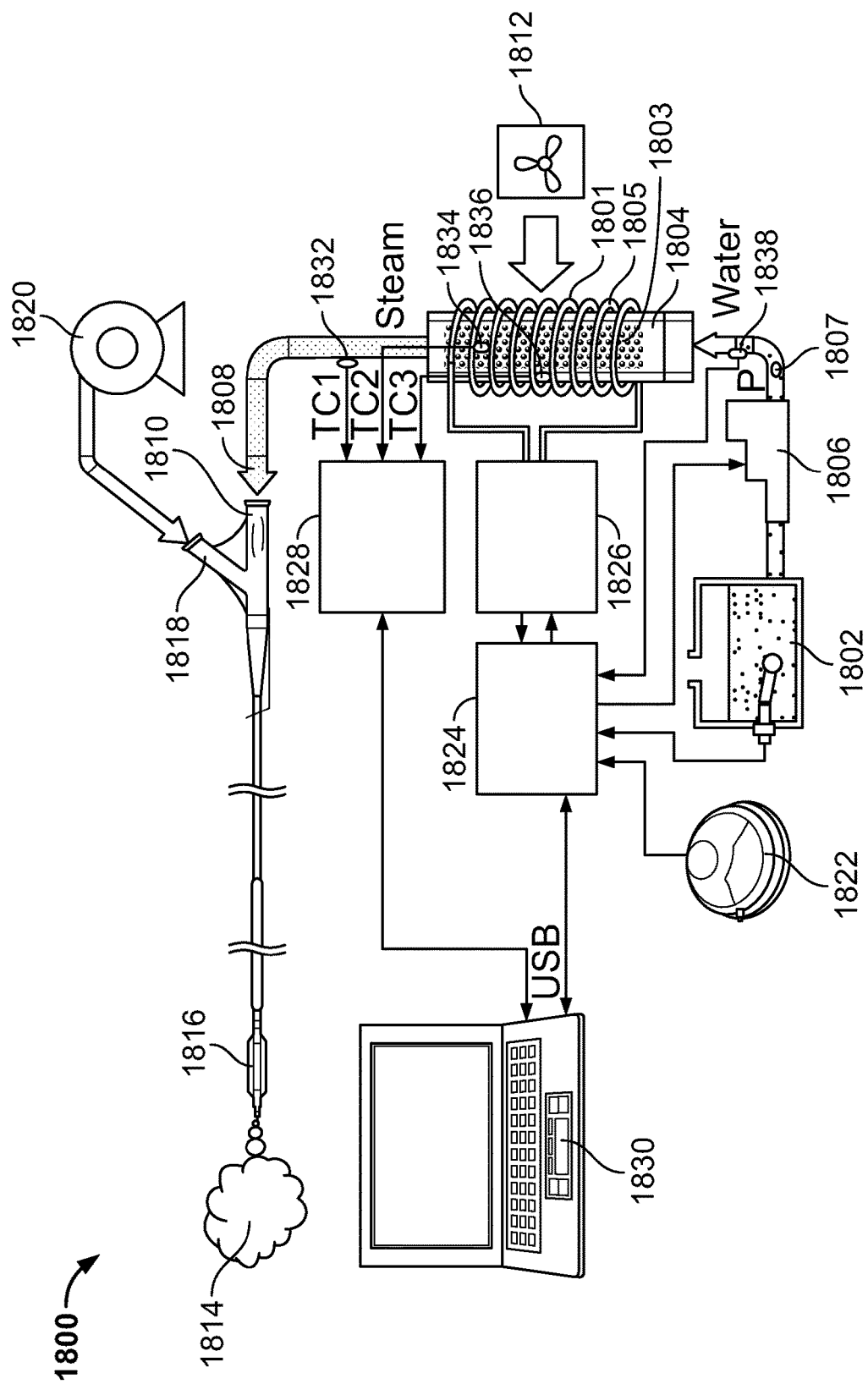
FIG. 18A is an illustration of a vapor ablation system using induction heating in accordance with one embodiment of the present specification.

FIG. 18A is an illustration of a vapor ablation system 1800 using induction heating in accordance with one embodiment of the present specification. The vapor ablation system 1800 comprises a fluid circuit including a water reservoir 1802, a heating chamber 1804, and a catheter 1810 connected by a contiguous fluid channel. In various embodiments, the contiguous fluid channel connecting the components of the fluid circuit comprises flexible tubing having an internal lumen. In various embodiments, one or more of the components of the fluid circuit are disposable such that the separate components are discarded and replaced after a single use or the entire fluid circuit is discarded after a single use. In one embodiment, prior to use, a portion of the fluid channel positioned between the water reservoir 1802 and the heating chamber 1804 is blocked by a barrier, thereby blocking water from passively flowing from the water reservoir 1802 to the heating chamber 1804. In one embodiment, a check valve or a fracture diaphragm 1807 is positioned in the contiguous fluid channel between the water reservoir 1802 and the heating chamber 1804 to prevent water from entering the heating chamber 1804 until force is applied to the water to direct it into the heating chamber 1804. During operation, the barrier, check valve, or fracture diaphragm 1807 is breached by an increase in water pressure as water is acted upon by a pump or driving mechanism, permitting water to flow from the water reservoir 1802 to the heating chamber 1804.

Water travels from the reservoir 1802 into the heating chamber 1804 where it is converted to steam. The resulting steam travels into the catheter 1810 and out its distal end as ablative agent. The only pathway for water and steam to travel is from the reservoir 1802, through the heating chamber 1804, and out the distal end of the catheter 1810. In various embodiments, there are no other inputs, ports, or openings for receiving fluid from an external source into the fluid circuit. In various embodiments, there are no other outputs, ports, or openings, for receiving or expelling fluid external to the fluid circuit. In various embodiments, the water reservoir 1802 comprises a pliable bag, a syringe, or any three dimensional enclosure configured to contain a predetermined volume of water.

The heating chamber 1804 is configured to be positioned within an induction coil 1805. In various embodiments, the heating chamber can be cylindrical, cuboid, or any other shape. In some embodiments, the induction coil 1805 comprises an induction chamber 1801 having a cylindrical volume around which a plurality of coils are positioned and a lumen 1803 within configured to receive the heating chamber 1804. In other embodiments, the induction coil 1805 comprises only the coil itself which is wrapped about the heating chamber 1804. The induction coil 1805 comprises a plurality of coils for receiving an electrical current and generating a magnetic field which leads to induction heating of a ferromagnetic portion of the heating chamber 1804. In various embodiments, the frequency of the electrical current provided to the induction coil is in a range of 100 Hz-200 kHz, more preferably 1 kHz-100 kHz, more preferably yet 10 kHz-50 kHz, and most preferably 25 kHz-35 kHz. In various embodiments, the heating chamber 1804 is insulated to prevent heat losses from the chamber and/or thermal injury to an operator.

Water is directed from the reservoir 1802 into the heating chamber 1804 via force applied by a pump, motor, or other mechanism. In various embodiments, water is directed into the heating chamber 1804 by a pump driven by a motor as described further below. In other embodiments, the water reservoir 1802 is elevated relative to the heating chamber 1804 and water from the reservoir 1802 is gravity fed into the heating chamber 1804. In other embodiments, the mechanism for delivering water from the reservoir 1802 to the heating chamber 1804 comprises a bladder tank. In one embodiment, the bladder tank comprises a diaphragm separating two compartments within one tank. A first compartment contains compressed air while the second compartment contains water. The compressed air pushes on the diaphragm, which forces water out of the second compartment and into a heating chamber. In another embodiment, the mechanism to deliver water from the reservoir 1802 to the heating chamber 1804 comprises an occluded water tank. The occluded water tank functions similarly to a toothpaste tube wherein a portion of the occluded water tank is compressible and is squeezed to force water out of the tank and into a heating chamber.

In various embodiments, fluid from the water reservoir 1802 is pumped with precise dosing into the heating chamber 1804. In one embodiment, the water reservoir 1802 is configured to contain 200 ml of water. A precisely controllable, positive displacement dosing pump 1806 delivers exact amounts of water on demand into the induction heater chamber 1804 for vaporization. Induction heating is preferred because it permits heating of an element inside a sterile catheter without comprising sterility and does not require complex electrical feed-throughs. In addition, the catheter itself can be disposable and therefore manufactured at a low cost. In one embodiment, the heating chamber includes 1804 a metal core and is mounted vertically. In one embodiment, the metal is steel. Water is introduced at the bottom of the heating chamber 1804 at an inlet port at its proximal end. As described further below, in one embodiment, the metal core is a smooth rod with a slightly smaller outer diameter than the inner diameter of a tube coaxially positioned over the core. An induction coil 1805 is wrapped about the tube of the heating chamber 1804. The core and the tube comprise the heating chamber 1804. Water introduced into the heating chamber 1804 passes through the space between the core and the tube. Therefore, all water is forced into close proximity of the core, contacting the metal surface, vaporizing and exiting the chamber entirely as steam as long as sufficient heating power is provided for a given flow rate. Steam created within the heating chamber 1804 exits via an outlet port at its distal end.

The generated steam is delivered to a luer lock connector 1808 connected to the input port of a catheter 1810. The catheter 1810 is designed such that all parts that come into direct contact with the steam are able to withstand temperatures in excess of 100° C., preventing melting and subsequent leaks or obstructions. The catheter 1810 includes one or more openings at its distal end for the delivery of steam 1814 to target tissues. In various embodiments, the catheter 1810 includes one or more positioning attachments 1816 proximate its distal end. In one embodiment, the positioning attachments 1816 comprise inflatable balloons and the catheter 1810 further comprises an insufflation port 1818 at its proximal end. An air pump 1820 connected to the insufflation port 1818 is used to inflate said balloons. In various embodiments, the positioning attachments, or balloons 1816, are inflated using air through the air pump 1820 and then the air expands once steam is generated by the system 1800. In some embodiments, the one or more balloons 1816 are first inflated to a positioning volume by the air pump 1820 and are then further expanded to an occlusive volume as the air is heated by the delivery of steam, establishing a non-puncturing seal. In one embodiment, the occlusive volume is less than 120% of the positioning volume. In various embodiments, the one or more balloons 1816 are comprised of silicone. The silicone is thermally insulating so heat generated from ablation in the area proximate the outside of the balloons 1816 will not transfer passively and expand the air inside the balloons 1816. Therefore, in some embodiments, the air used for insufflation must be actively heated from inside the catheter into the balloons 1816 to accomplish the desired heat expansion. In various embodiments, the catheter 1810 has a coaxial design such that heat energy from the steam is transferred to the air used for insufflation as they both travel along the catheter 1810. The coaxial design of the catheter 1810 allows for heat losses along the catheter to be captured and transferred to the air in the balloons 1816 to generate a treatment responsive seal. In other embodiments, the catheter 1810 includes a coaxial lumen for heating the air or the balloons 1816 include a conductive metal inside for conducting heat from vapors in the catheter to the air in the balloons 1816.

Figure 18B:
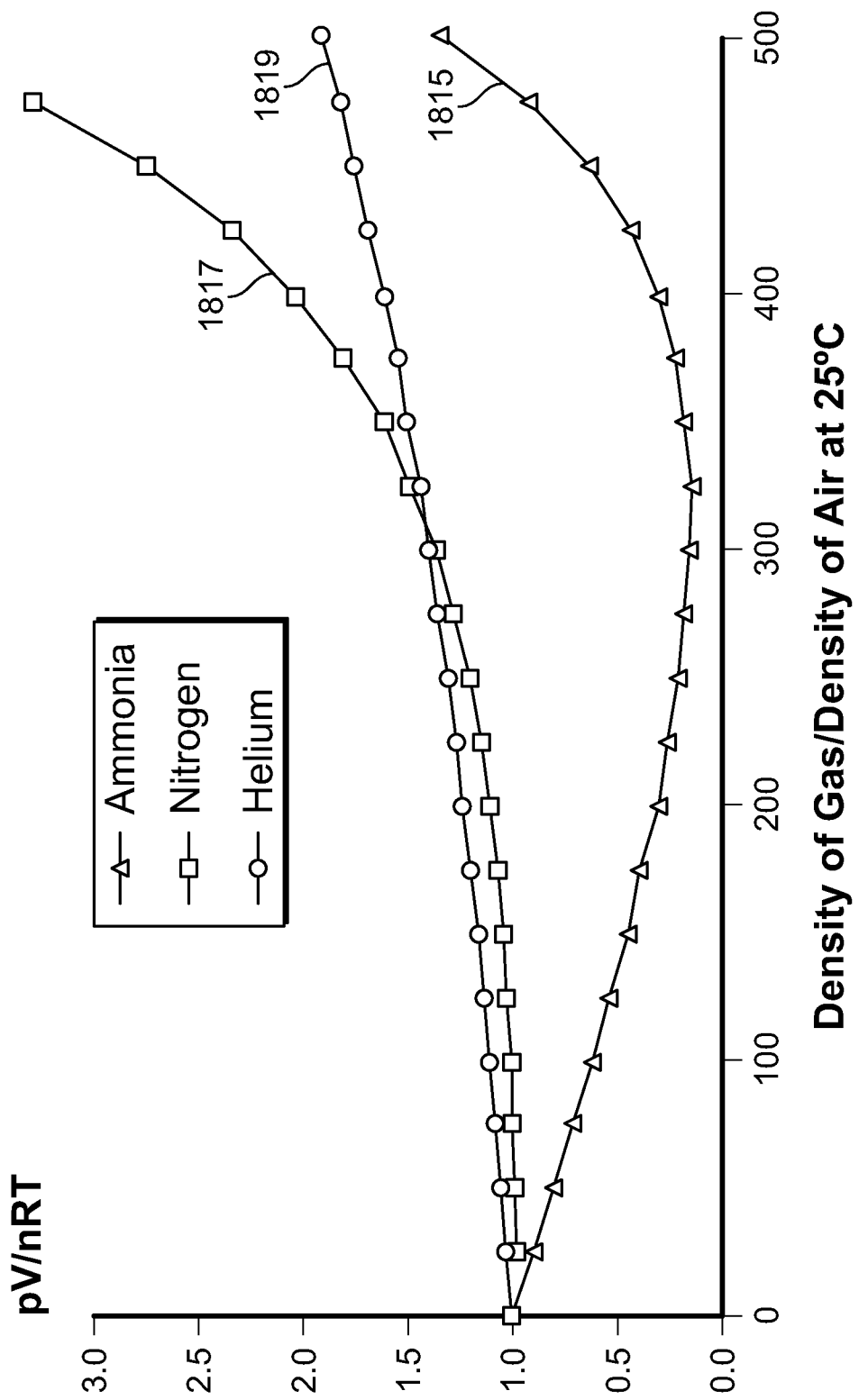
FIG. 18B is a graph illustrating the behavior, in relation to the ideal gas law, of a plurality of gases as they are heated to high temperatures.

When heating air from 37° C. (body temperature) to 100° C., the air will expand by approximately 20%. Therefore, in one embodiment, the one or more balloons 1816 are inflated to approximately 75% using the air pump 1820, allowing for the remainder of the volume expansion to be effectuated by heat transfer from the steam. Since the steam is not being directed into the balloons 1816, pressure within the balloons 1816 will not change significantly. The air used to inflate the one or more balloons 1816 behaves like an ideal gas at temperatures below 400° C., as depicted in FIG. 18B, and follows approximately the ideal gas law below:

$$PV=nRT$$

where P is the absolute pressure of the gas, V is the volume of the gas, n is the amount of gas, R is the ideal gas constant, and T is the absolute temperature of the gas expressed in degrees Kelvin (degrees C.+273). Referring to FIG. 18B, the air behaves less like an ideal gas as it is heated beyond approximately 400° C., where the curves for the density of ammonia 1815, nitrogen 1817, and helium 1819 become less linear at temperatures over 400° C. In various embodiments, the air used to inflate the balloons is defined by at least three different temperatures: starting temperature ($T_{start}$); ideal temperature ($T_{ideal}$); and, maximum temperature ($T_{max}$). In various embodiments, $T_{start}$ is equal to 25° C. (room temperature), $T_{ideal}$ is less than or equal to 75° C., and $T_{max}$ is equal to 125° C. In various embodiments, the volume expansion of the balloons relative to the volume at $T_{start}$ ranges from 2% to 40% at $T_{max}$ and from 1% to 20% for $T_{ideal}$. In various embodiments, the system has a maximum continuous operating time of less than or equal to 5 minutes and an ideal continuous operating time of less than or equal to 2 minutes. In various embodiments, the balloons are configured to have a maximum diameter change, or expansion, of less than or equal to 5 mm and an ideal diameter change, or expansion, of less than or equal to 3 mm. Different temperatures at a substantially fixed pressure provide a volume ratio equal to the temperature ratio. Therefore, in one embodiment having the operating parameters listed above, heating the air from 25° C. ($T_{start}$) to 125° C. ($T_{max}$) provides a temperature increase of 100 K (398K/298K) which translates to a volume expansion of less than or equal to 33%. In one embodiment having the operating parameters listed above, heating the air from 25° C. ($T_{start}$) to 75° C. ($T_{ideal}$) provides a temperature increase of 50 K (348K/298K) which translates to a volume expansion of less than or equal to 17%. In various embodiments, the balloons have a first positioning diameter when inflated by action of an air pump and a second occlusion diameter when the pumped air is heated by the steam generated by the system, as listed in Table 1 below:

TABLE 1

| Positioning Diameter | Occlusion Diameter | Percent Change in Volume |
|---|---|---|
| 18 mm | 21 mm | 36% |
| 20 mm | 23 mm | 32% |
| 22 mm | 25 mm | 29% |

Referring to Table 1, a balloon having a positioning diameter of 18 mm expands to have an occlusion diameter of 21 mm, a 36% increase, when the insufflation air is heated by the nearby steam. A balloon having a positioning diameter of 20 mm expands to have an occlusion diameter of 23 mm, a 32% increase, when the insufflation air is heated by the nearby steam. A balloon having a positioning diameter of 22 mm expands to have an occlusion diameter of 25 mm, a 29% increase, when the insufflation air is heated by the nearby steam.

In another embodiment, further volume expansion of the balloon is not desired and the volume of the balloons is kept constant by monitoring the pressure in the balloon and allowing a portion of expanded air to escape the balloon to keep the pressure, and therefore volume, constant.

Figure 19A:
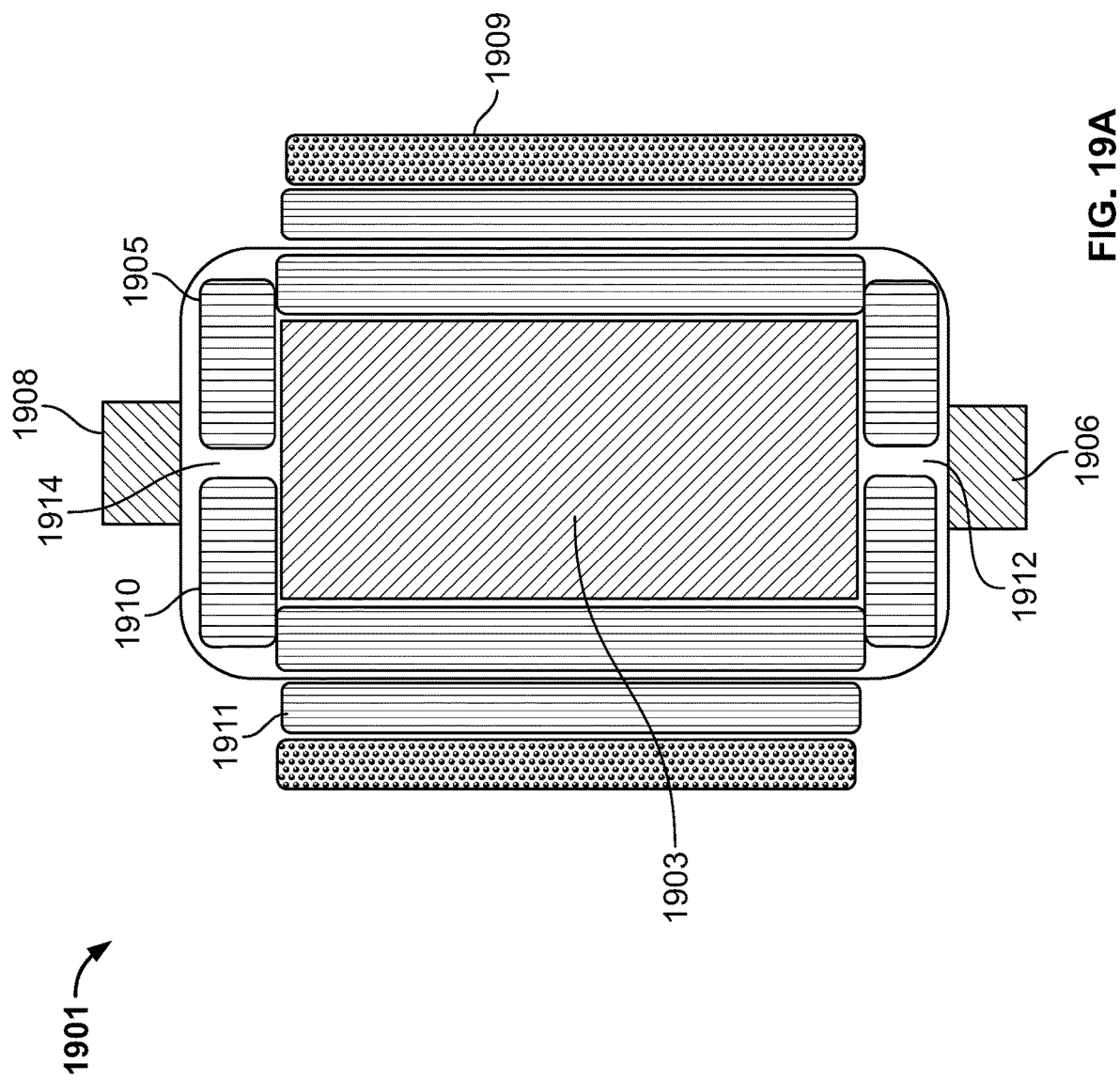
FIG. 19A is a vertical cross section illustration of an induction heating chamber in accordance with one embodiment of the present specification.
Figure 19B:
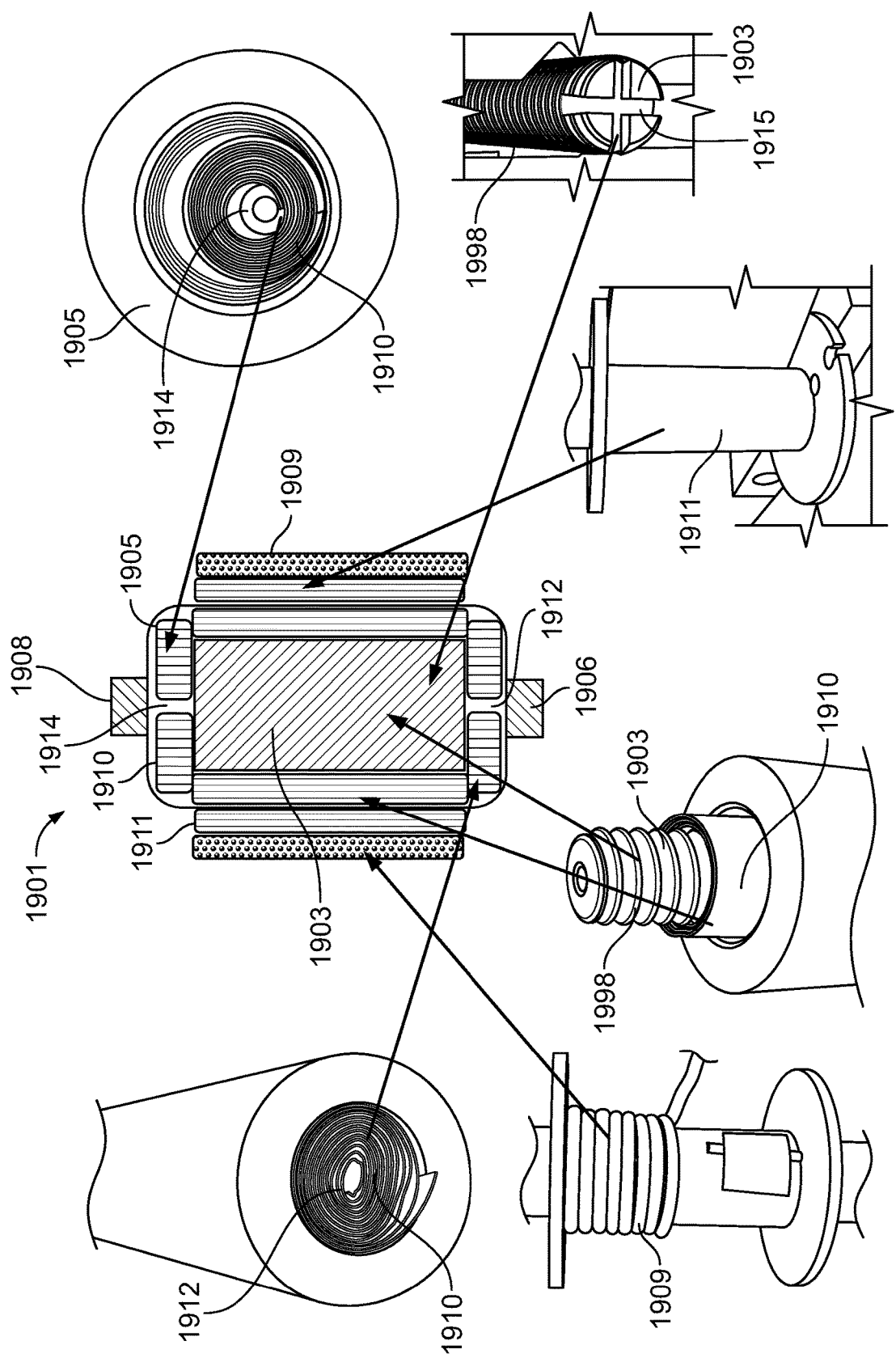
FIG. 19B is an illustration of the induction heating chamber of FIG. 16A depicting the various components of the chamber in further detail.

FIG. 19A is a vertical cross section illustration of an induction heating chamber 1901 in accordance with one embodiment of the present specification and FIG. 19B is an illustration of the induction heating chamber of FIG. 19A depicting the various components of the chamber in further detail. Referring to FIGS. 19A and 19B simultaneously, the heating chamber 1901 includes a ferromagnetic core 1903 contained within a non-ferromagnetic housing or thermoplastic container 1905. The thermoplastic container 1905 includes an inlet port 1906 at its proximal end and an outlet port 1908 at its distal end. An induction coil 1909 is wound about the thermoplastic container 1905. A first portion of non-thermoplastic insulation 1910 is positioned within the thermoplastic container 1905 and between the walls of the thermoplastic container 1905 and the ferromagnetic core 1903. A second portion of non-thermoplastic insulation 1911 is positioned between the walls of the thermoplastic container 1905 and the induction coil 1909.

In some embodiments, the thermoplastic container 1905 has a length ranging from 2.75 inches to 3.75 inches, an inner diameter ranging from 7/32 inches to 11/32 inches, and an outer diameter ranging from 3/8 inches to 0.5 inches. In some embodiments, the ferromagnetic core 1903 has a length ranging from 1.5 inches to 2.5 inches and a diameter ranging from 3/16 inches to 5/16 inches.

In various embodiments, the thermoplastic container 1905 is composed of PEEK, ABS, acetal, polyamide, or polyvinylidene difluoride (PVDF). In some embodiments, the first portion of non-thermoplastic insulation 1910 comprises a film of mica rolled to create a stand-off within the proximal end and distal end of the thermoplastic container 1905 to prevent the ferromagnetic core 1903 from contacting the PEEK. An outer perimeter of the mica roll also extends along the length within the thermoplastic container 1905 to prevent the ferromagnetic core from contacting the PEEK walls. A pair of central openings 1912, 1914 are positioned in the proximal and distal ends of the mica roll respectively, to allow water to flow into a space between the mica rolls and the ferromagnetic core 1903.

In some embodiments, the ferromagnetic core 1903 is a unitary member and includes grooves 1998 encircling its outer periphery. The grooves 1998 are configured to allow water or steam to flow along the core 1903. In an embodiment, the ferromagnetic core 1903 includes grooves or notches 1915 formed into its proximal end and distal end creating channels for water or steam to flow between the core 1903 and surrounding insulation 1910. In another embodiment, the proximal and distal ends of the ferromagnetic core are flat and the insulation 1910 includes grooves or notches formed into its surfaces contacting the proximal and distal ends of the ferromagnetic core to create channels for water and steam flow.

Figure 19C:
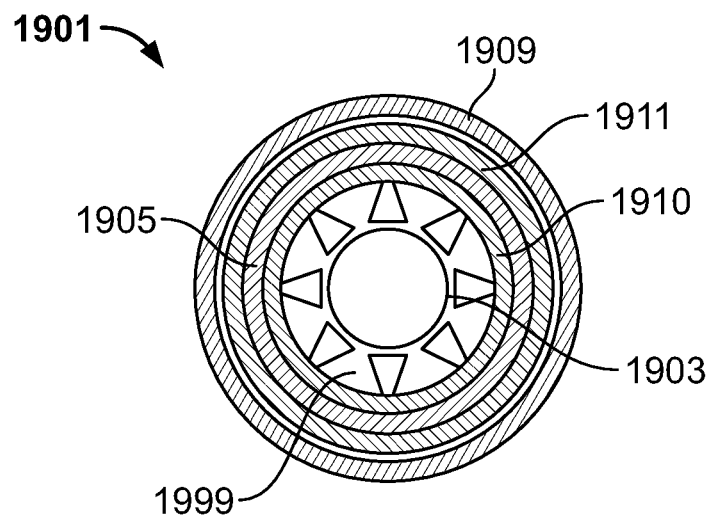
FIG. 19C is a horizontal cross section illustration of the induction heating chamber of FIG. 19A.

FIG. 19C is a horizontal cross section illustration of the induction heating chamber 1901 of FIG. 19A. The induction heating chamber 1901 includes a ferromagnetic core 1903 surrounded by a first portion of non-thermoplastic insulation 1910 which is surrounded by a thermoplastic container 1905 which, in turn, is surrounded by a second portion of non-thermoplastic insulation 1911. An induction coil 1909 is wound about the second portion of non-thermoplastic insulation 1911. In an embodiment, the ferromagnetic core 1903 is shaped such that a plurality of channels 1999 are formed along its outer surface to allow for the flow of water or steam in a proximal to distal direction between the ferromagnetic core 1903 and the first portion of non-thermoplastic insulation 1910.

Cardiac Ablation

Figure 20A:
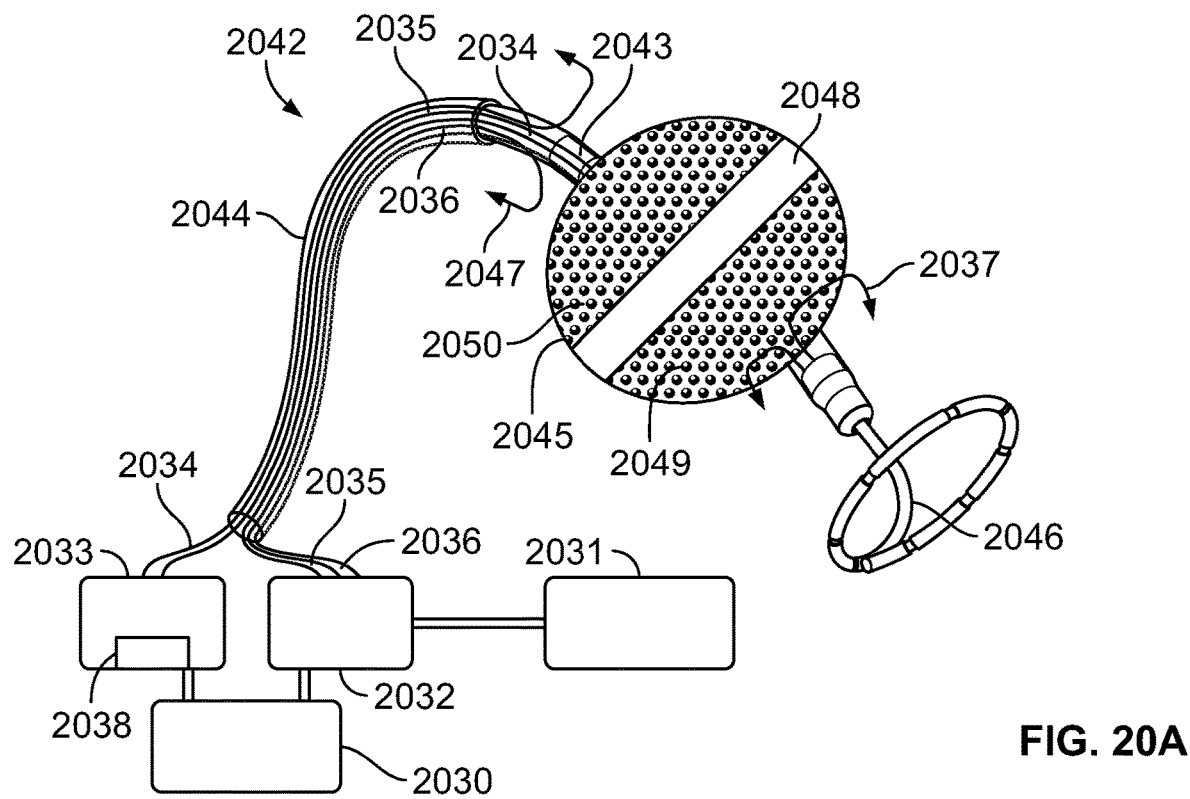
FIG. 20A illustrates a cardiac ablation catheter in accordance with one embodiment of the present specification.
Figure 20B:
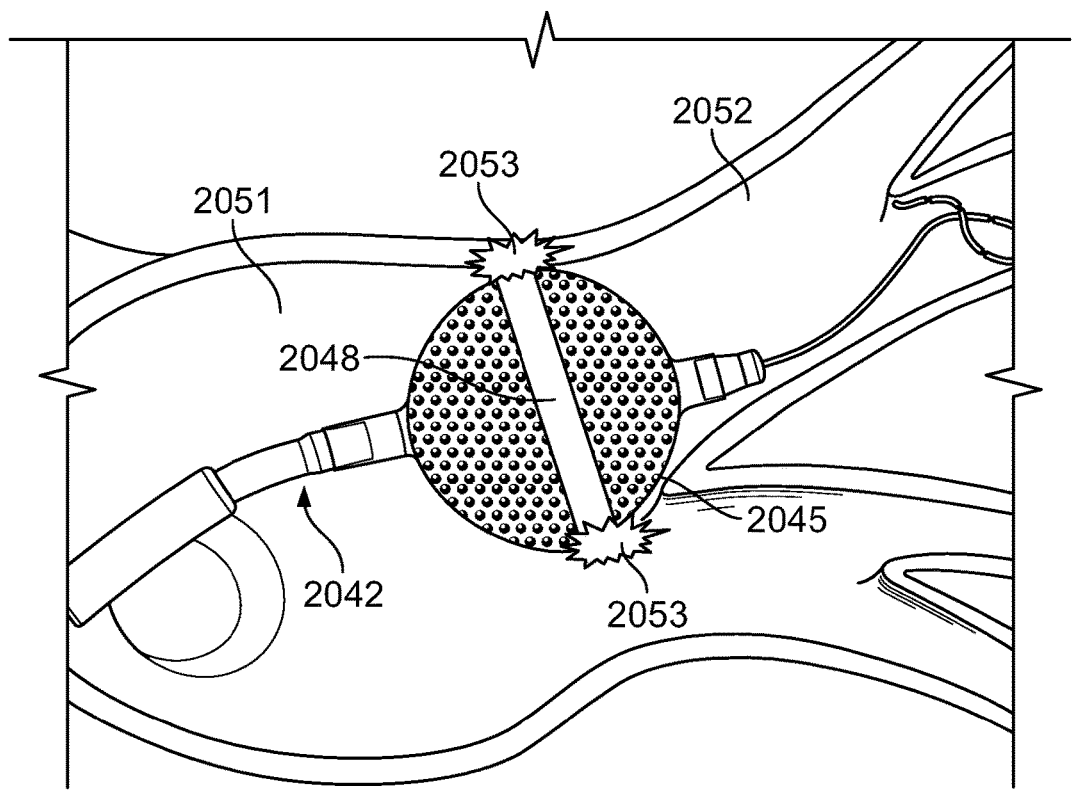
FIG. 20B illustrates cardiac ablation being performed by the cardiac ablation catheter of FIG. 20A.

FIG. 20A illustrates a cardiac ablation catheter 2042 in accordance with one embodiment of the present specification and FIG. 20B illustrates cardiac ablation being performed by the cardiac ablation catheter 2042 of FIG. 20A. The cardiac ablation catheter 2042 can be used to ablate cardiac tissue to treat an arrhythmia, such as atrial fibrillation. The catheter 2042 includes an elongate inner shaft 2043 covered by an outer shaft 2044. The inner shaft 2043 includes an inflatable balloon 2045 proximal its distal end. The inflatable balloon is in fluid communication with an air/vapor channel 2034 which extends through the inner shaft 2043 from the balloon 2045 to an air source, or first pump 2033, which is in data communication with, and controlled by, a controller 2030. The air source 2033 pulls air from the external environment through an optional filter 2038 to fill the balloon 2045. In an embodiment, the air source or first pump 2033 is reversible, thereby allowing air to be pumped into the balloon 2045 or out of the balloon 2045, as required and per instructions sent by the controller 2030. A mapping member 2046, which may be a radial extension, catheter, or any substrate comprising a plurality of sensors, detectors, or electrodes, is attached to the distal end of the inner shaft 2043 distal to the balloon 2045. The mapping member 2046 maps the area of cardiac tissue responsible for the arrhythmia. The distal end of the outer shaft 2044 ends a distance proximal to the balloon 2045 such that a portion of the inner shaft 2043 between the balloon 2045 and outer shaft 2044 is exposed. Water 2047 can be pumped from a sterile water reservoir 2031, via a second pump 2032, through a first water lumen 2035 in the outer shaft 2044, where it exits proximal to the balloon 2045 for cooling a space proximal to the balloon 2045. Water 2037 can also be pumped from the sterile water reservoir 2031, via the second pump 2032, through a second water lumen 2036 in the inner shaft 2043, where it exits distal to the balloon 2045 and proximal to the mapping member 2046 for cooling a space distal to the balloon 2045. The first water lumen 2035 extends within the outer shaft 2044 from the second pump 2032 to the distal end of the outer shaft 2044. The second water lumen 2036 extends within the inner shaft 2043 from the second pump 2032 to the distal end of the inner shaft 2043. The controller 2030 is in data communication with, and controls, the second pump 2032, wherein the second pump 2032 is configured to pass water 2047, 2037 from the sterile water reservoir 2031 into the first water lumen 2035 and/or second water lumen 2036 of the outer shaft 2044 and inner shaft 2043, respectively. The balloon 2045 includes an ablation or hot zone 2048 proximate its equator and a first cold zone in its top hemisphere 2049, cooled by water 2037 pumped through the inner shaft 2043, and a second cold zone in its bottom hemisphere 2050, cooled by water 2047 pumped through the outer shaft 2044. The temperature of the ablation or hot zone 2048 is typically between 60-100° C. and the temperature of the cold zones 2049, 2050 is typically between 35-60° C., with the temperature of the cold zones 2049, 2050 decreasing as the cold zones 2049, 2050 extend away from the hot zone 2048. The equatorial hot zone 2048 remains heated by vapor used to heat the inside of the balloon 2045 and is distant enough from the water 2037, 2047 pumped through the inner shaft 2043 and outer shaft 2044 such that it does not become cooled. Referring to FIG. 20B, the balloon 2045 of the catheter 2042 has been positioned in a heart 2051, proximate a pulmonary vein 2052. Heat supplied to the balloon 2045 by vapor is transferred from the hot zone 2048 to the target cardiac tissue 2053 to ablate the tissue 2053 and treat the arrhythmia. The hot zone 2048 is defined the portion of the balloon contacting the target cardiac tissue 2053 where the water for cooling does not contact the balloon surface, while the cold zones 2049, 2050 are defined by the portion of the balloon not contacting the target cardiac tissue 2053, allowing for the water to contact and cool the balloon surface. In some embodiments, the two temperature zones can also be defined by constructing the balloon with two different materials with different thermal conductivity.

Figure 20C:
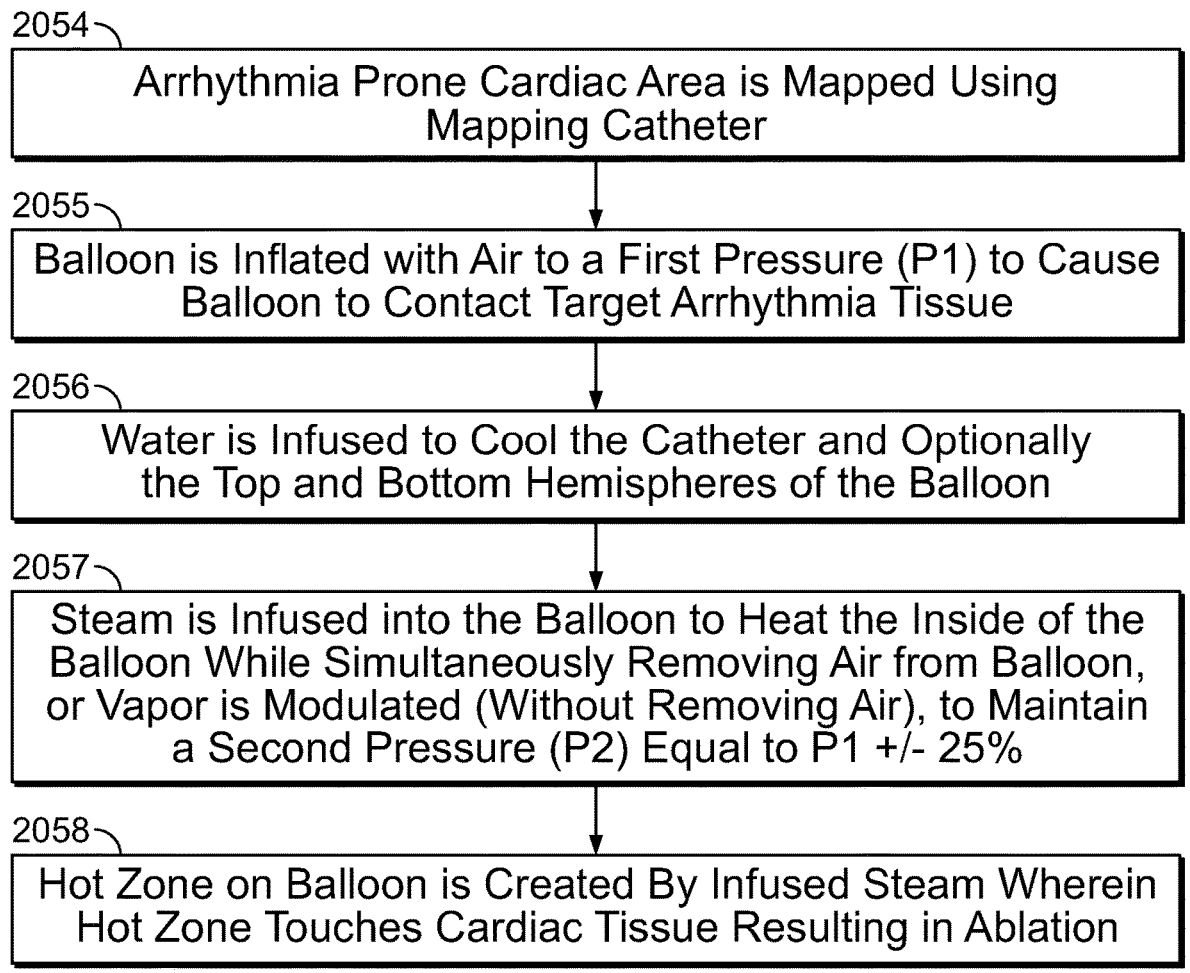
FIG. 20C is a flowchart illustrating the steps involved in one embodiment of a method of using the catheter of FIG. 20A to ablate cardiac tissue.

FIG. 20C is a flowchart illustrating the steps involved in one embodiment of a method of using the catheter of FIG. 20A to ablate cardiac tissue. At step 2054, an arrhythmia prone cardiac area is mapped using the mapping catheter. The balloon is inflated with air to a first pressure (P1) to cause the balloon to contact the target arrhythmia tissue at step 2055. At step 2056, water is infused to cool the catheter and optionally the top and bottom hemispheres of the balloon. In some embodiments, blood assists in cooling the top and bottom hemispheres of the balloon. At step 2057, steam is infused into the balloon to heat the inside of the balloon while simultaneously removing air from the balloon to maintain a second pressure (P2) equal to P1+/−25%. The amount of vapor being delivered to the balloon may also be modulated (without removing air) to maintain the second pressure (P2) equal to P1+/−25%. A hot zone on the balloon is created by the infused steam wherein the hot zone touches the cardiac tissue resulting in ablation at step 2058.

Figure 20D:
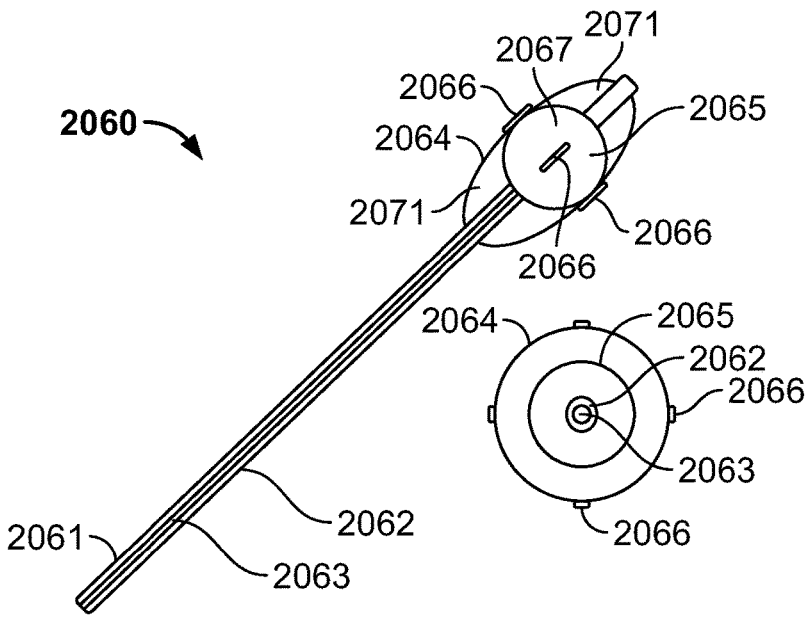
FIG. 20D illustrates a cardiac ablation catheter in accordance with another embodiment of the present specification.

FIG. 20D illustrates a cardiac ablation catheter 2060 in accordance with another embodiment of the present specification. The catheter 2060 includes an elongate body 2061, a proximal end, and a distal end with an air/water lumen 2062 and a vapor lumen 2063 supplied by ports at its proximal end. The air/water lumen 2062 is in fluid communication with a mapping balloon 2064 attached to the distal end of the catheter 2060. The mapping balloon 2064 includes a plurality of mapping electrodes 2066 within or attached to the outer surface of its walls. The mapping electrodes 2066 map the area of cardiac tissue responsible for an arrhythmia. The vapor lumen 2063 is in fluid communication with an ablation balloon 2065 attached to the distal end of the catheter 2060 and positioned within the mapping balloon 2064. Once both balloons 2064, 2065 are inflated, a length of the mapping balloon 2064 is greater than a length of the ablation balloon 2065 and a diameter of the ablation balloon 2065 approximates a diameter of the mapping balloon 2064. During use, the mapping balloon 2064 is inflated with water or air and the ablation balloon 2066 is inflated with vapor such that the ablation balloon 2065 comes into contact with the mapping balloon 2064 and the mapping balloon 2064 comes into contact with the target cardiac tissue proximate the equators of both balloons 2064, 2065. This creates a hot zone or ablation zone 2067 proximate the equator of the mapping balloon 2064. Cold zones 2071 are located on the mapping balloon 2064 where the inflated ablation balloon 2065 is not in contact with the inflated mapping balloon 2064. Heat is transferred from inside the ablation balloon 2065 through the mapping balloon 2064 and into the cardiac tissue to ablate the tissue and treat the arrhythmia.

Figure 20E:
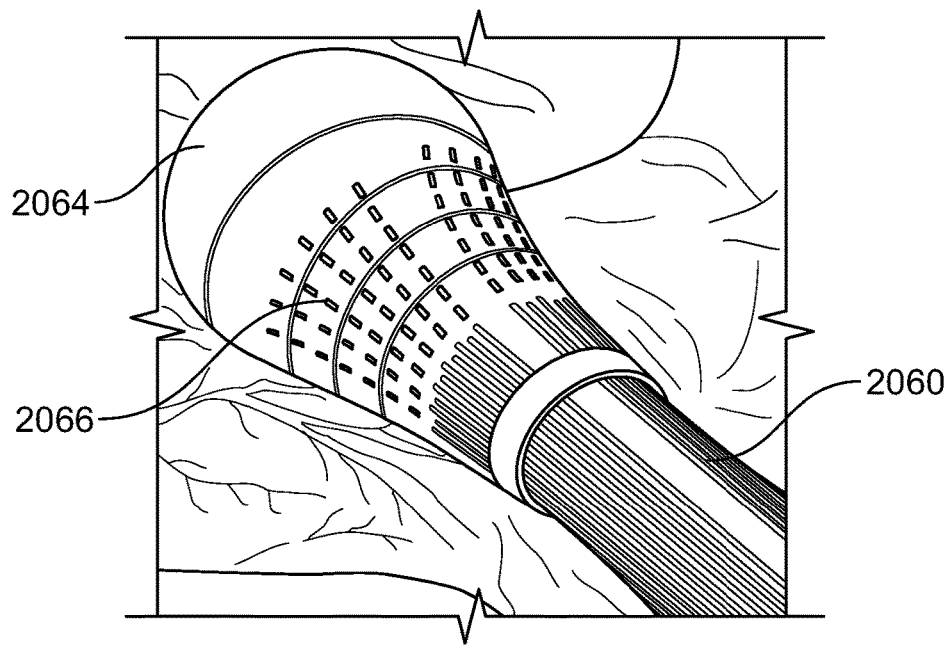
FIG. 20E illustrates the mapping balloon with mapping electrodes of the catheter of FIG. 20D.
Figure 20F:
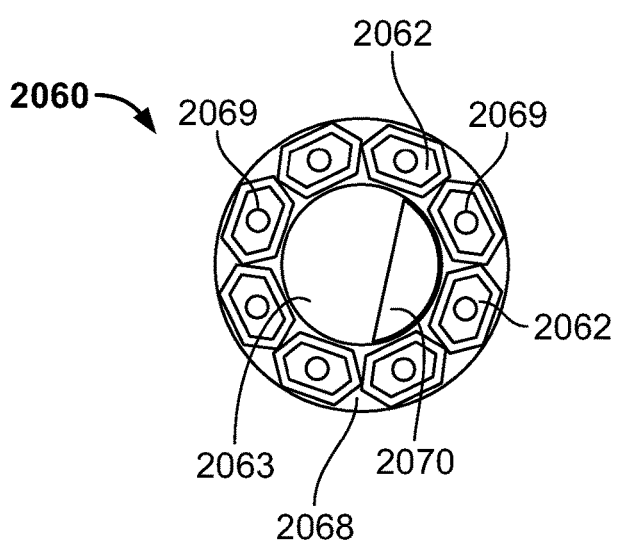
FIG. 20F illustrates a cross sectional view of a mid-shaft portion of the catheter of FIG. 20D.
Figure 20G:
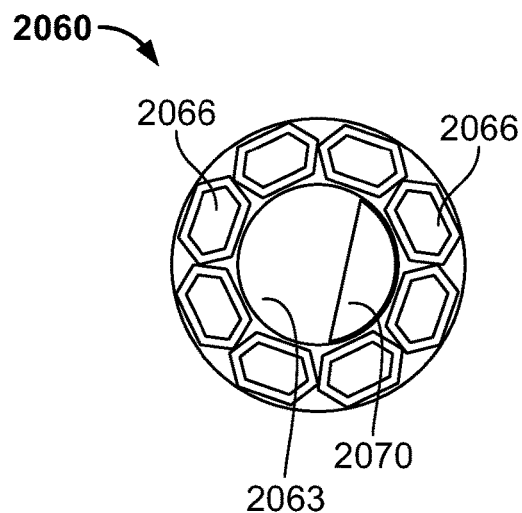
FIG. 20G illustrates a cross sectional view of a distal tip portion of the catheter of FIG. 20D.

FIG. 20E illustrates the mapping balloon 2064 with mapping electrodes 2066 of the catheter 2060 of FIG. 20D. FIG. 20F illustrates a cross sectional view of a mid-shaft portion of the catheter 2060 of FIG. 20D. The catheter 2060 includes a compartmentalized outer wall 2068 which includes the air/water lumen 2062 and wires 2069 for the mapping electrodes. The catheter 2060 also includes the vapor lumen 2063 and, in one embodiment, a guidewire lumen 2070. FIG. 20G illustrates a cross sectional view of a distal tip portion of the catheter 2060 of FIG. 20D. The catheter 2060 includes a plurality of mapping electrodes 2066 built into its outer wall or, in an embodiment, into the wall of the mapping balloon, the vapor lumen 2063, and a guidewire lumen 2070.

Figure 20H:
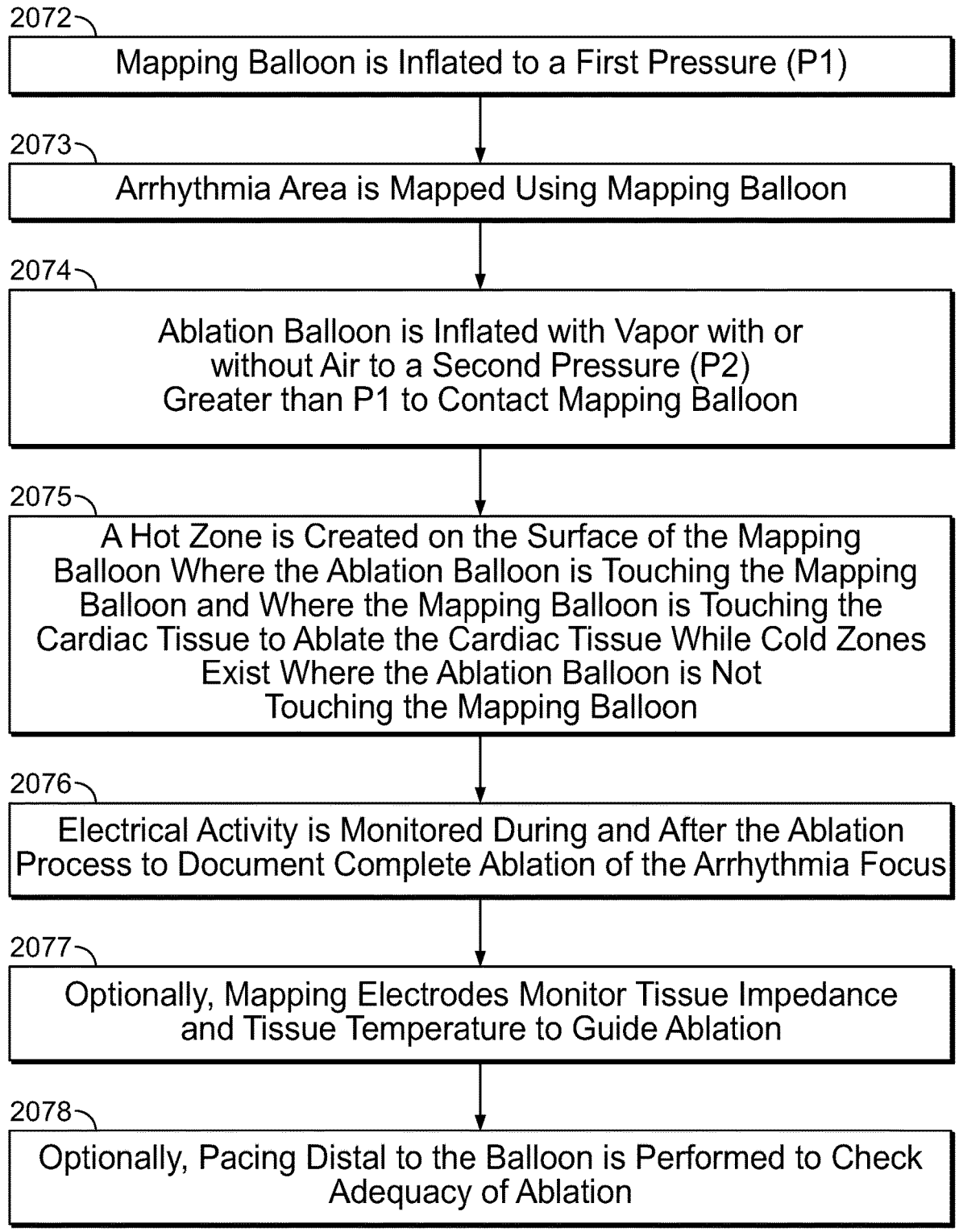
FIG. 20H is a flowchart illustrating the steps involved in one embodiment of a method of using the catheter of FIG. 20D to ablate cardiac tissue.

FIG. 20H is a flowchart illustrating the steps involved in one embodiment of a method of using the catheter of FIG. 20D to ablate cardiac tissue. At step 2072, the mapping balloon is inflated to a first pressure (P1). An arrhythmia area is mapped using the mapping balloon at step 2073. At step 2074, the ablation balloon is inflated with vapor with or without air to a second pressure (P2) greater than P1 to contact the mapping balloon. At step 2075, a hot zone is created on the surface of the mapping balloon where the ablation balloon is touching the mapping balloon and where the mapping balloon is touching the cardiac tissue to ablate the cardiac tissue while cold zones exist where the ablation balloon is not touching the mapping balloon. At step 2076, electrical activity is monitored during and after the ablation process to document complete ablation of the arrhythmia focus. Optionally, at step 2077, the mapping electrodes monitor tissue impedance and tissue temperature to guide the ablation. Optionally, at step 2078, pacing distal to the balloon is performed to check for adequacy of ablation.

Figure 20I:
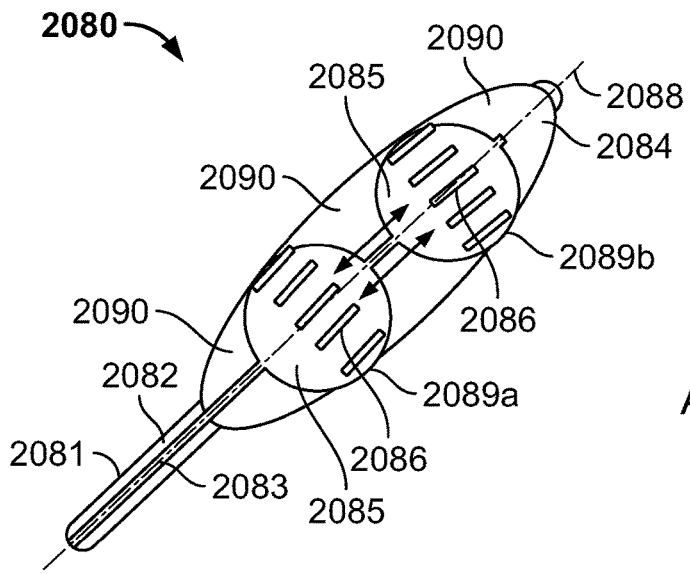
FIG. 20I illustrates a cardiac ablation catheter in accordance with yet another embodiment of the present specification.
Figure 20J:
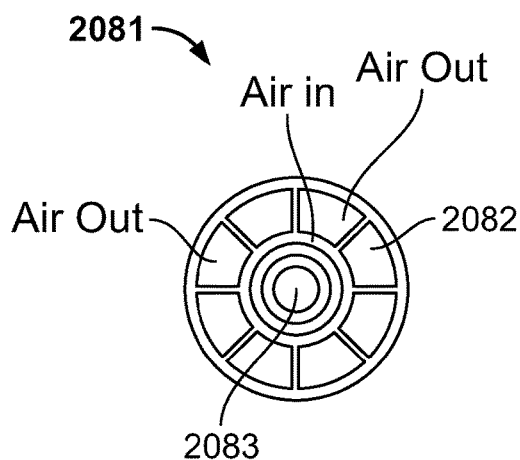
FIG. 20J is a cross sectional view of a mid-shaft portion of the catheter of FIG. 20I.
Figure 20K:
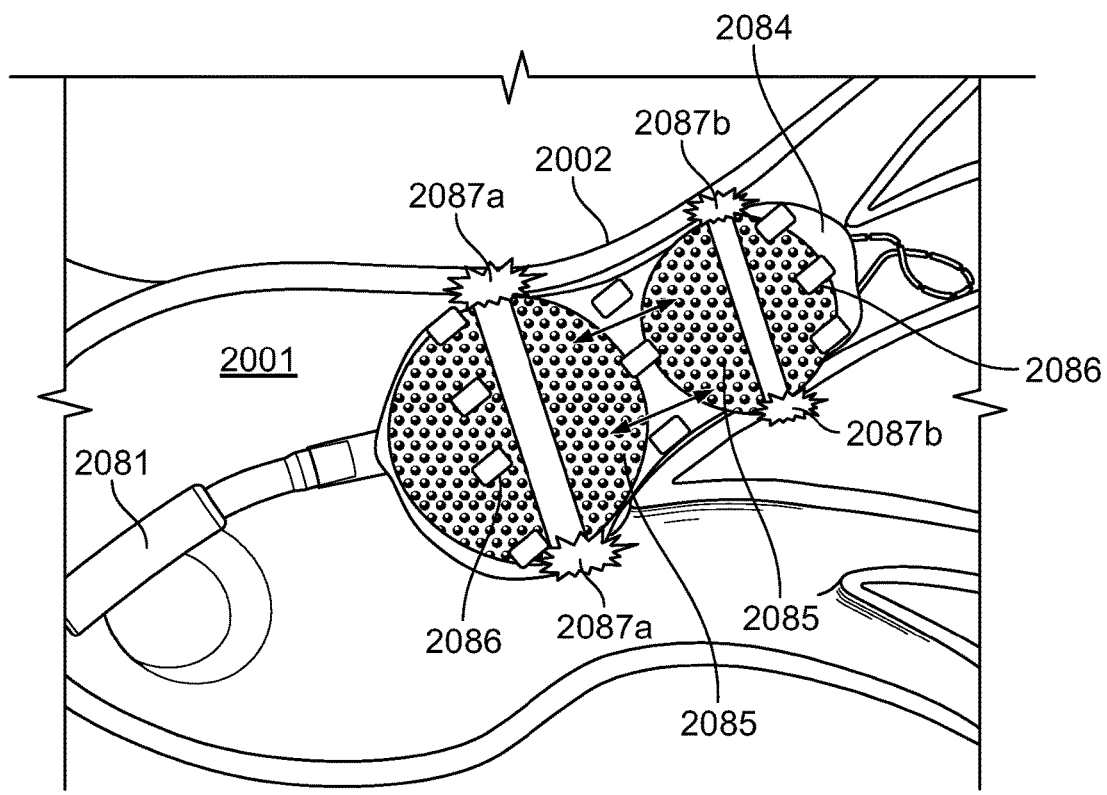
FIG. 20K illustrates cardiac ablation being performed by the cardiac ablation catheter of FIG. 20I.

FIG. 20I illustrates a cardiac ablation catheter 2080 in accordance with another embodiment of the present specification, FIG. 20J illustrates a cross-sectional view of a mid-portion of an elongate body 2081 of the catheter 2080 of FIG. 20I and FIG. 20K illustrates cardiac ablation being performed by the cardiac ablation catheter 2080 of FIG. 20I. Referring now to FIGS. 20I through 20K simultaneously, the catheter 2080 includes an elongate body 2081, a proximal end, and a distal end with an air/water lumen 2082 and a vapor lumen 2083 supplied by ports at its proximal end. The air/water lumen 2082 is in fluid communication with a mapping balloon 2084 attached to the distal end of the catheter 2080. The air/water lumen 2082 optionally comprises a plurality of sub-channels or lumens (along the length of the elongate body 2081) to allow air/water to enter and exit the lumen 2082 at the proximal end of the catheter 2080. The mapping balloon 2084 includes a plurality of mapping electrodes 2086 within or attached to the outer surface of its walls. The mapping electrodes 2086 map a plurality of areas of cardiac tissue responsible for arrhythmia. The vapor lumen 2083 is in fluid communication with an ablation balloon 2085 attached to the distal end of the catheter 2080, positioned within the mapping balloon 2084 and freely movable co-axially within the mapping balloon 2084 to be positioned at a plurality of positions along a longitudinal axis 2088. In accordance with an exemplary embodiment, the catheter 2080 illustrates the ablation balloon 2085 being moved from a first position 2089*a* to a second position 2089*b* along the longitudinal axis 2088.

Once both balloons 2084, 2085 are inflated, a length (along the longitudinal axis 2088) of the mapping balloon 2084 is greater than a length (along the longitudinal axis 2088) of the ablation balloon 2085 and a diameter of the ablation balloon 2085 approximates a diameter of the mapping balloon 2084. During use, the mapping balloon 2084 is inflated with water or air and the ablation balloon 2085 is inflated with vapor and placed at the first position 2089*a* (within the mapping balloon 2084) such that the ablation balloon 2085 comes into contact with the mapping balloon 2084 and the mapping balloon 2084 comes into contact with the target cardiac tissue proximate the first position 2089*a* in a heart 2001 proximate a pulmonary vein 2002. This creates a hot zone or ablation zone 2087*a* proximate the first position 2089*a*. Heat is transferred from inside the ablation balloon 2085 through the mapping balloon 2084 and into the cardiac tissue to ablate the tissue at the first position 2089*a*. The ablation balloon 2085 is thereafter moved to the second position 2089*b* (within the mapping balloon 2084) such that the ablation balloon contacts the mapping balloon 2084 and the mapping balloon 2084 comes into contact with the target cardiac tissue proximate the second position 2089*b* within the pulmonary vein 2002. This creates a hot zone or ablation zone 2087*b* proximate the second position 2089*b*. Heat is now transferred from inside the ablation balloon 2085 through the mapping balloon 2084 and into the cardiac tissue to ablate the tissue at the second position 2089*b*. Cold zones 2090 are located on the mapping balloon 2084 where the inflated ablation balloon 2085 is not in contact with the inflated mapping balloon 2084. It should be appreciated that the mapping balloon 2084 and the ablation balloon 2085 may have to be inflated differentially at the first and second positions 2089*a*, 2089*b* in order to conform to the space (associated with the first and second positions 2089*a*, 2089*b*) within the pulmonary vein 2002.

In accordance with an aspect, the mapping balloon 2084 is more flexible (compared to the ablation balloon 2085) and can free-form or conform to fit the shape of anatomical structure, such as the lumen of the pulmonary vein 2002, in order to create a contact sufficient for electrical contact between the electrodes 2086 and cardiac tissue. The ablation balloon 2085 is more firm and is meant to apply firm contact at the points (such as those corresponding to the first and second positions 2089*a*, 2089*b*) of its axial contact with the target tissue for ideal delivery of thermal energy to the target cardiac tissue.

Figure 20L:
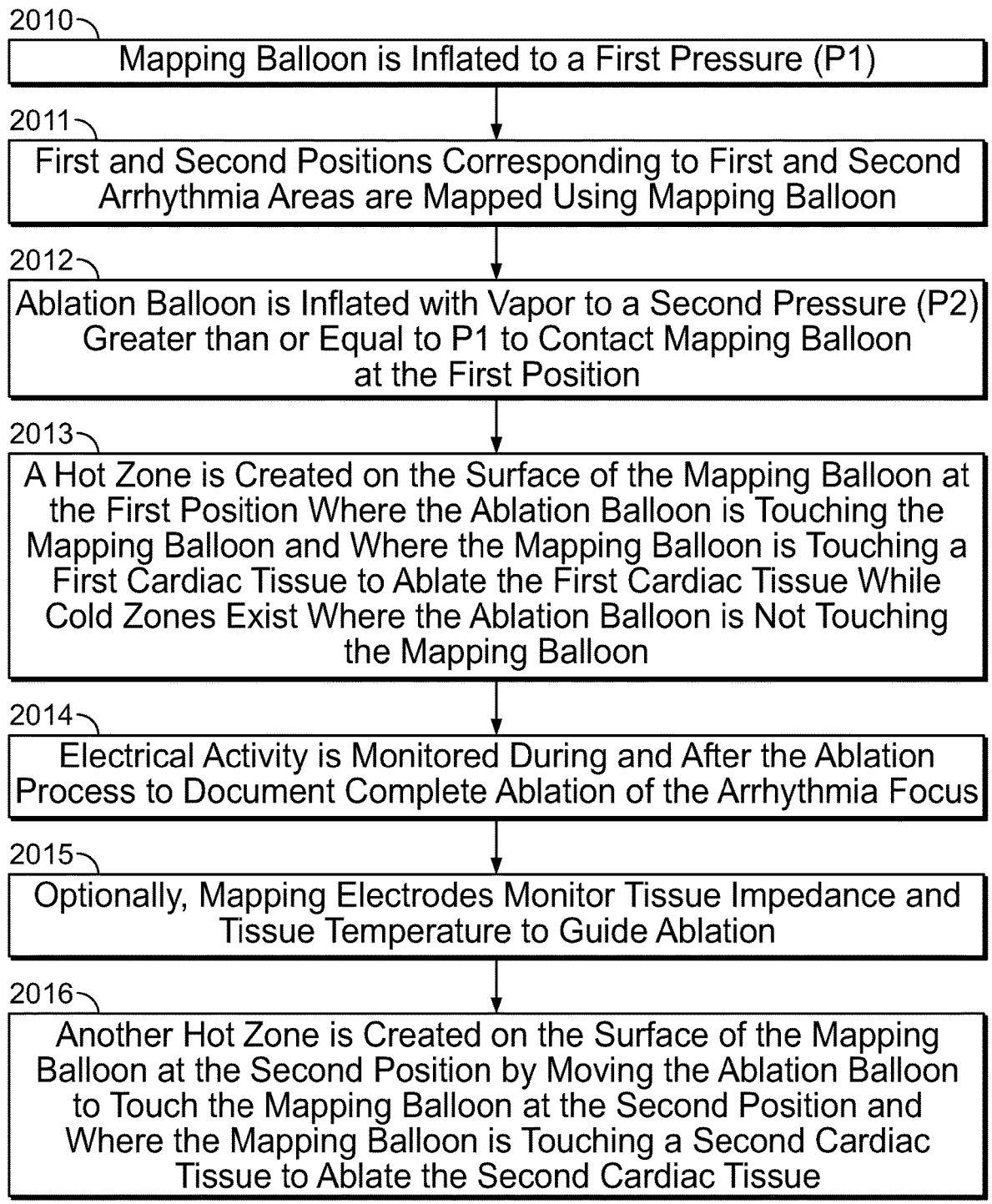
FIG. 20L is a flowchart illustrating the steps involved in one embodiment of a method of using the catheter of FIG. 20I to ablate cardiac tissue.

FIG. 20L is a flowchart illustrating the steps involved in one embodiment of a method of using the catheter of FIG. 20I to ablate cardiac tissue. At step 2010, the mapping balloon is inflated to a first pressure (P1) using air. The first and second positions corresponding to first and second arrhythmia areas are mapped using the mapping balloon at step 2011. At step 2012, the ablation balloon is inflated with vapor to a second pressure (P2) greater than or equal to P1 to contact the mapping balloon at the first position. In accordance with an embodiment, the air circulated into the mapping balloon maintains a temperature of less than 60 degrees C. while maintaining the pressure in the mapping balloon between 0.1×P1 and 10×P2. At step 2013, a hot zone is created on the surface of the mapping balloon at the first position where the ablation balloon is touching the mapping balloon and where the mapping balloon is touching a first cardiac tissue to ablate the first cardiac tissue while cold zones exist where the ablation balloon is not touching the mapping balloon. At step 2014, electrical activity is monitored during and after the ablation process to document complete ablation of the first arrhythmia focus. Optionally, at step 2015, the mapping electrodes monitor tissue impedance and tissue temperature to guide the ablation. Once ablation at the first position is completed, at step 2016, the ablation balloon is moved to create a hot zone on the surface of the mapping balloon at the second position where the ablation balloon has been moved to touch the mapping balloon and where the mapping balloon touches a second cardiac tissue to ablate the second cardiac tissue. Steps 2014 and 2015 are repeated for the ablation process at the second position. It should be appreciated that in various embodiments, the ablation balloon can be moved to multiple positions and therefore create multiple hot zones on the surface of the mapping balloon to ablate cardiac tissue corresponding to multiple positions.

Figure 21:
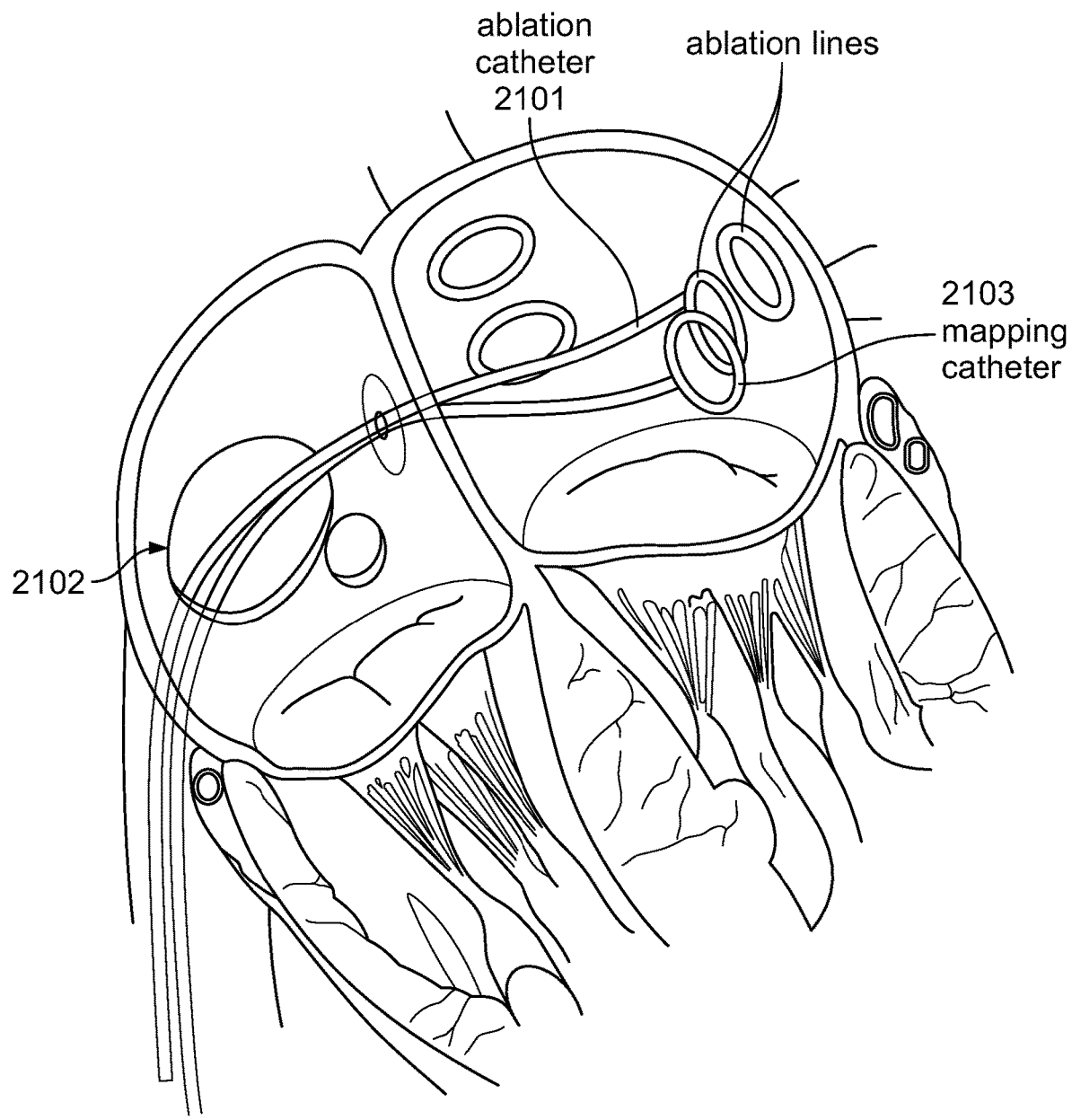
FIG. 21 illustrates a vapor ablation catheter introduced via a trans-septal approach into a left atrium of a heart in accordance with one embodiment of the present specification.

FIG. 21 illustrates a vapor ablation catheter 2101 introduced via a trans-septal approach into a left atrium of a heart 2102 in accordance with one embodiment of the present specification. In one embodiment, a flexible-tipped wire (not shown) is introduced through the lumen of the vapor ablation catheter 2101 and guided into the targeted pulmonary vein. A 20-40 mm vapor ablation balloon is located at the tip of the wire, which is then inflated in the chamber of the left atrium and guided over the wire to the antrum of the targeted pulmonary vein. A mapping catheter 2103 is also introduced at the site to guide the ablation.

FIG. 22A illustrates a cardiac ablation catheter 2201 in accordance with an embodiment of the present specification. The catheter includes a handle 2204. The catheter 2201 includes an elongate body 2202, a proximal end, and a distal end with an air, water or saline lumen 2209 and a vapor lumen 2206 supplied by ports at its proximal end. In some embodiments, air/water or preferably saline 2207 is circulated in the saline lumen 2209 to cool the body 2202 while vapor 2208 is being infused into the lumen 2206. The distal end of the body 2202 has a distal attachment, such as a retractable needle 2205 that is in fluid communication with the vapor lumen 2206. The retractable needle 2205 has at least one opening or infusion port at its distal end for allowing vapor 2208 to emanate therefrom to ablate target cardiac tissue, while the body 2202 is being cooled by the saline 2207 circulating in the saline lumen 2209. In various embodiments, the catheter 2201 includes a plurality of sensors, such as an electrical sensor, at the distal end of the catheter 2201, to monitor electrical activity during and after the ablation process and measure tissue impedance to document complete ablation of the target cardiac tissue, a pressure sensor to measure pressure in the vapor lumen 2206 and shut down vapor delivery once a predefined critical pressure is reached, and a temperature sensor to monitor tissue temperature to guide the ablation.

Figure 22B:
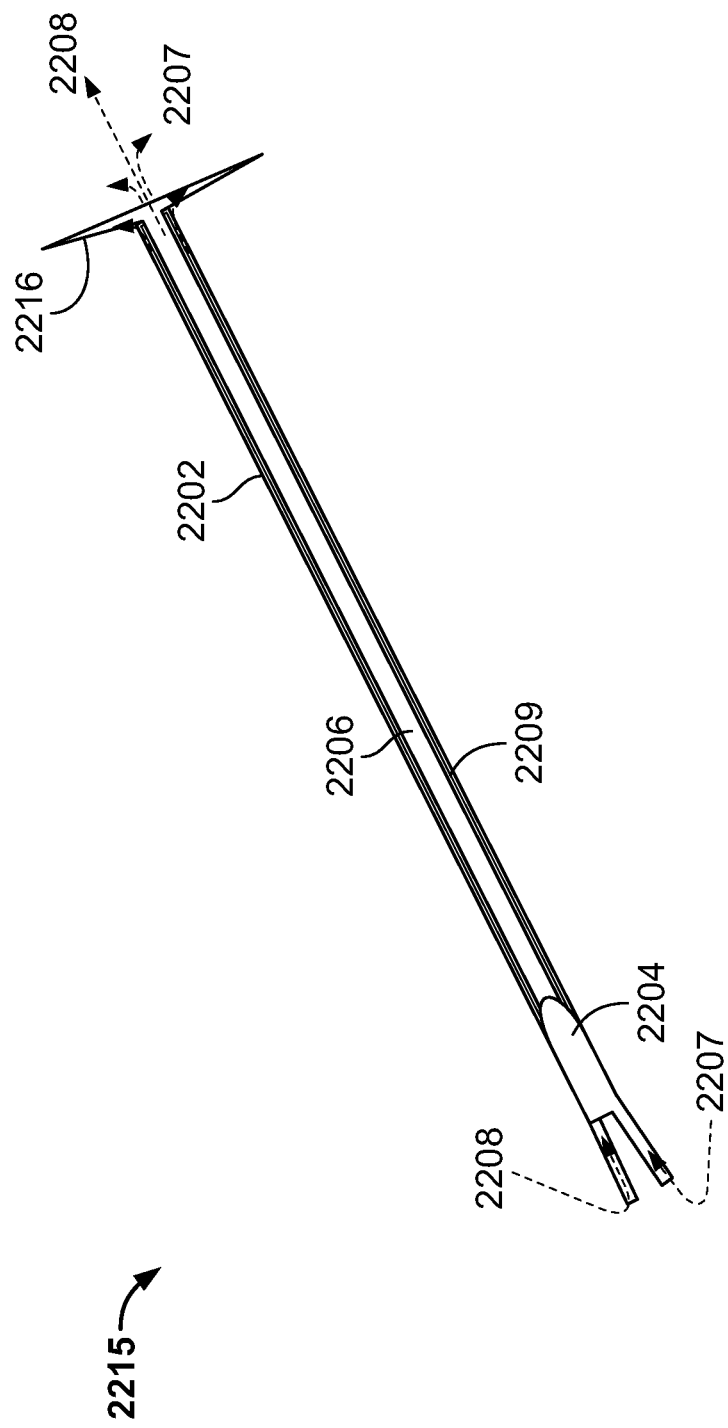
FIG. 22B illustrates a cardiac ablation catheter with a second distal attachment, in accordance with an embodiment.

It should be appreciated that the shape and size of the distal attachment is varied in various embodiments to adapt to a specific anatomy to be treated by ablation. For example, FIG. 22B illustrates another embodiment of a cardiac ablation catheter 2215 where the distal attachment is a retractable disc 2216 covered in a thermally insulated membrane and attached to the distal end of the elongate body 2202. The catheter includes a handle 2204. During use, vapor 2208 is delivered to the disc 2216 through the vapor lumen 2206 while saline 2207 is being circulated through the saline lumen 2209 to keep the elongate body 2202 and the outer surface of the disc 2216 cool. The vapor 2208 infuses out from at least one infusion port or opening at a distal surface of the retractable disc 2216 in order to ablate the target tissue. In various embodiments, the catheter 2215 includes a plurality of sensors, such as an electrical sensor, at the distal end of the catheter 2215, to monitor electrical activity during and after the ablation process and measure tissue impedance to document complete ablation of the target cardiac tissue, a pressure sensor to measure pressure in the vapor lumen 2206 and shut down vapor delivery once a predefined critical pressure is reached, and a temperature sensor to monitor tissue temperature to guide the ablation.

Figure 22C:
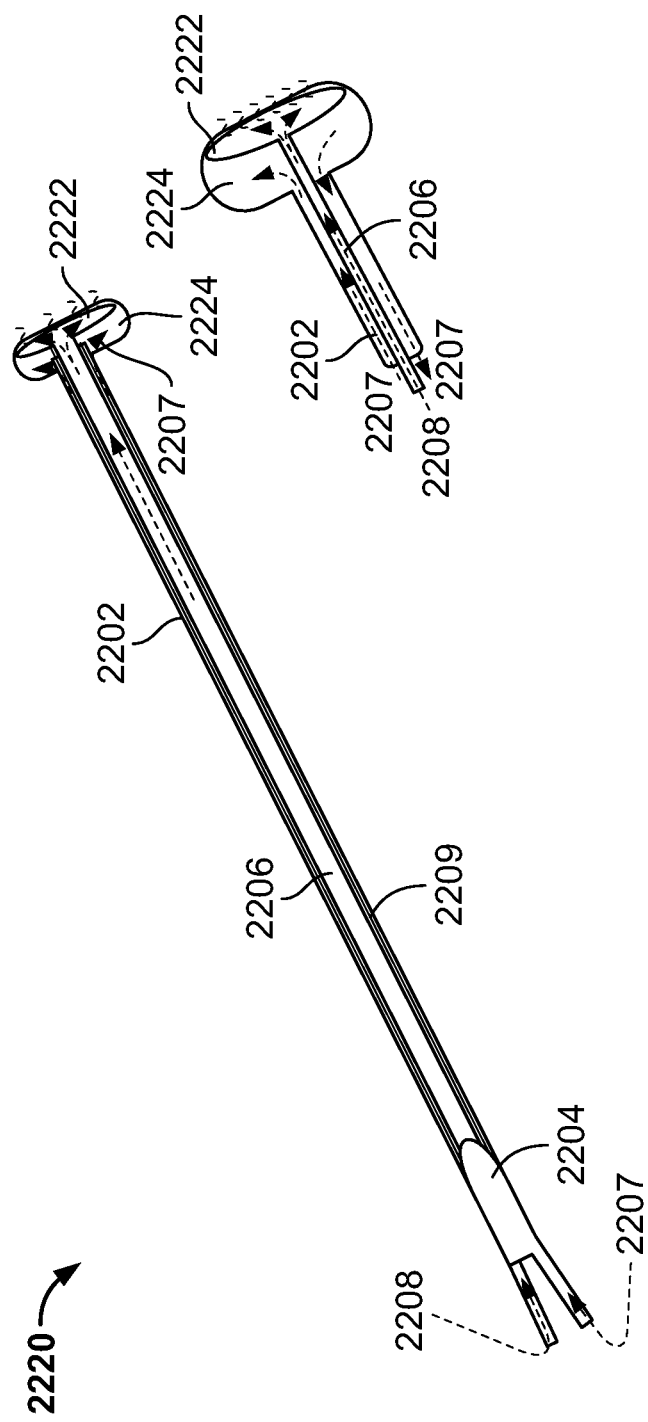
FIG. 22C illustrates a cardiac ablation catheter with a third distal attachment, in accordance with an embodiment.

FIG. 22C illustrates yet another embodiment of a cardiac ablation catheter 2220 where the distal attachment comprises an inner balloon 2222 lying within an outer balloon 2224 at the distal end of the catheter 2220. The catheter includes a handle 2204. The outer balloon 2224 is in fluid communication with the saline lumen 2209 while the inner balloon 2222 is in fluid communication with the vapor lumen 2206. During use, the outer balloon 2224 is inflated with saline 2207 (or air/water alternatively) to enable the outer balloon 2224 to contact an area of ablation comprising target tissue to be ablated. Vapor 2208 is passed into the inner balloon 2222 to inflate the inner balloon 2222 to contact the outer balloon 2224 proximate the area of ablation. In various embodiments, the area of contact between the inner balloon 2222 and the external balloon 2224 is between 5% and 95% and lies at a distal end or tip of the outer balloon 2224. In embodiments, the inner balloon 2222 is movable within the outer balloon 2224 and therefore contacts the outer balloon 2224 at different circumferential areas. A hot zone is created at the area of contact between the inner balloon 2222 and the external balloon 2224, such that thermal energy from the inner balloon 2222 passes through the outer balloon 2224 to the area of ablation proximate the distal end or tip of the outer balloon 2224. The elongate body 2202 and portions of the outer balloon 2224, excluding the hot zone, remain cool owing to the circulating saline 2207. In various embodiments, the catheter 2220 includes a plurality of sensors, such as an electrical sensor, at the distal end of the catheter 2220, to measure tissue impedance for mapping the target tissue and monitor electrical activity during and after the ablation process to document complete ablation of the target tissue, a pressure sensor to measure pressure in the vapor lumen 2206 and shut down vapor delivery once a predefined critical pressure is reached, and a temperature sensor to monitor tissue temperature to guide the ablation. It should be noted that in various embodiments, saline 2207 enters the saline lumen 2209 at the proximal end of the catheter and exits from the proximal end of the catheter after circulating through the outer balloon 2224.

Figure 23:
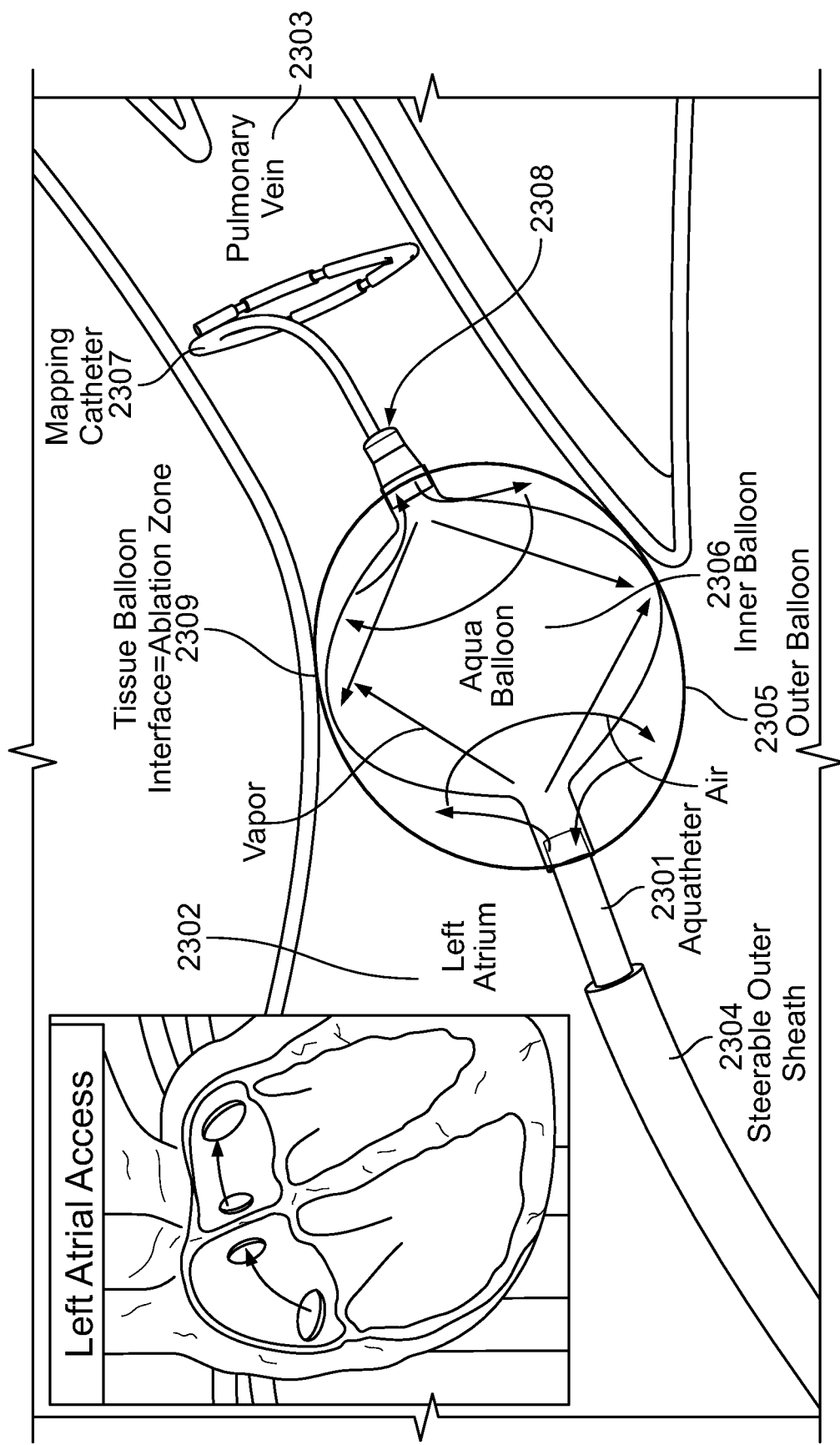
FIG. 23 illustrates one embodiment of a cardiac ablation catheter passing through a left atrium of a heart and into a pulmonary vein in accordance with one embodiment of the present specification.

FIG. 23 illustrates one embodiment of a cardiac ablation catheter 2301 passing through a left atrium 2302 of a heart and into a pulmonary vein 2303 in accordance with one embodiment of the present specification. In one embodiment, the catheter is encased in a steerable outer sheath 2304. At a distal end of the catheter is an outer balloon 2305 through which air circulates. Inside the outer balloon is an inner balloon 2306 filled with water vapor. It may be appreciated that the ablation zone 2309 here comprises the tissue-balloon interface. A mapping catheter 2307 is coupled to the balloon by means of a tip 2308.

In various embodiments, ablation therapy provided by the vapor ablation systems of the present specification is delivered to achieve the following therapeutic endpoints for cardiac ablation: maintain a tissue temperature at 100° C. or less; ablate a cardiac tissue without damaging an esophageal tissue; at least 10% of patients revert to normal sinus rhythm for at least 1 week; at least 10% of patients remain in normal sinus rhythm for at least 1 week; decrease the number of atrial arrhythmia episodes by at least 5% relative to the number of pre-treatment atrial arrhythmia episodes; decrease the number of supraventricular arrhythmia episodes by at least 5% relative to the number of pre-treatment supraventricular arrhythmia episodes; decrease the number of ventricular arrhythmia episodes by at least 5% relative to the number of pre-treatment ventricular arrhythmia episodes; and an increase in esophageal temperature at any time during or post treatment is less than 8° C. or an esophageal temperature at any time during or post treatment is less than 45° C.

Figure 24:
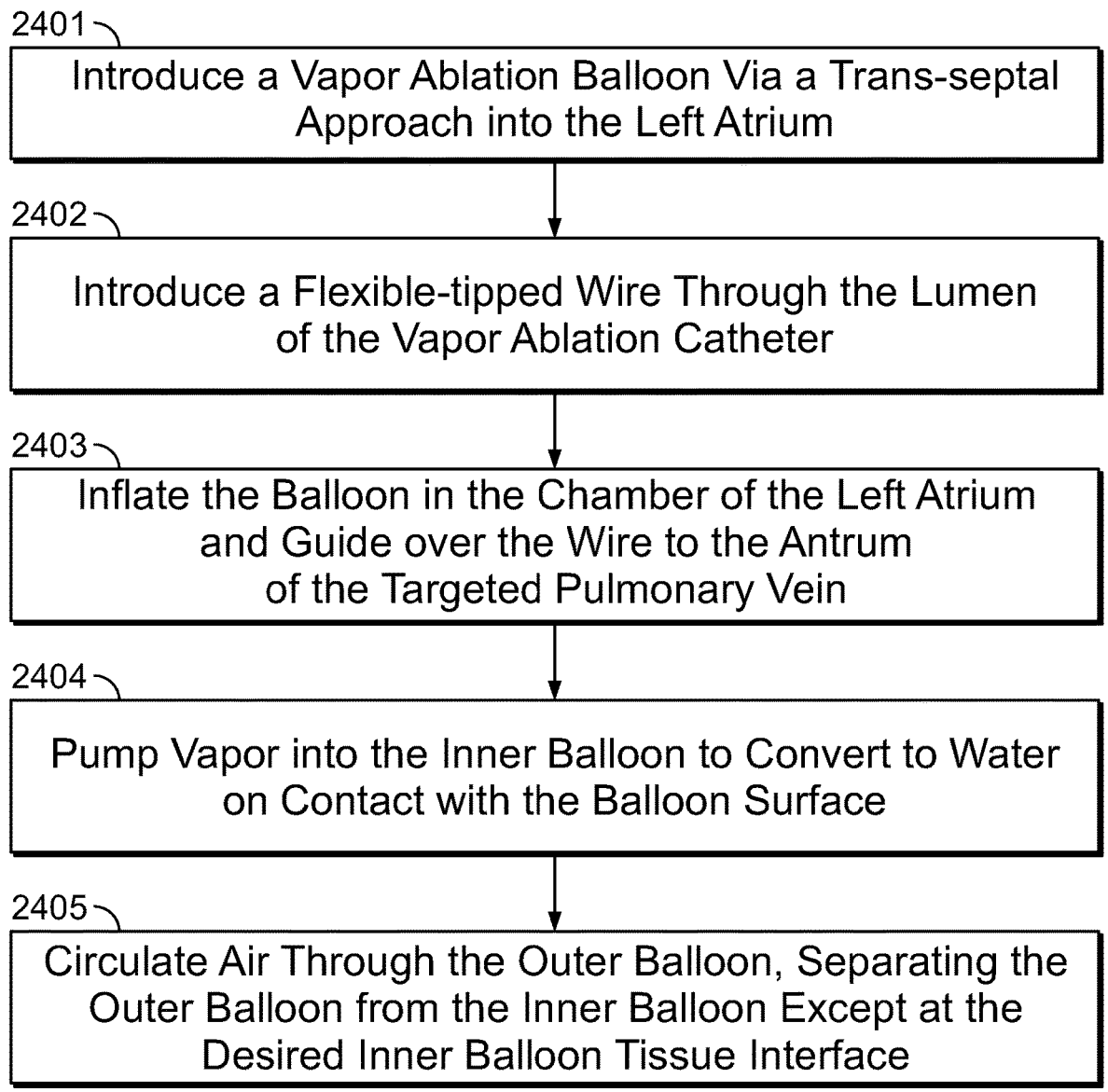
FIG. 24 is a flowchart listing the steps involved in one embodiment of a method of cardiac ablation.

FIG. 24 is a flowchart listing the steps involved in one embodiment of a method of cardiac ablation. The ablation device used is similar to that described with reference to FIG. 23. At step 2401, a 10-40 mm vapor ablation balloon is introduced via a trans-septal approach into the left atrium. Next, in step 2402, a flexible-tipped wire is introduced through the lumen of the vapor ablation catheter and guided into the targeted pulmonary vein. The balloon is then inflated in the chamber of the left atrium and guided over the wire to the antrum of the targeted pulmonary vein in 2403. Next, in 2404, vapor in a range of 95 to 105° C. is pumped into the inner balloon and converted to water on contact with the balloon surface due to the temperature change at the balloon/tissue/blood interface. This conversion of vapor to water is an exothermic reaction that delivers heat to the tissue, resulting in the balloon/tissue interface becoming extremely hot, for example, between 60 and 100° C. The extremely hot temperature at the balloon/tissue interface creates an irreversible injury to the pulmonary vein tissue, thereby ablating the tissue. Air is circulated through the outer balloon, separating the outer balloon from the inner balloon except at the desired inner balloon tissue interface, insulating the rest of the surface of the inner balloon from contacting the surrounding tissue or blood in 2405.

FIG. 25A illustrates a side cross section view of one embodiment of a cardiac ablation catheter 2502, where the distal attachment comprises an inner balloon 2504 lying within an outer balloon 2503 at the distal end of the catheter 2502. Cooling fluid is circulated through the outer balloon 2503, while the inner balloon 2504 is inflated with steam or water vapor. In one embodiment, the outer balloon 2503 is made up of a harder material, such as PET, while the inner balloon 2504 is made up of a more flexible material, such as latex.

At the proximal end 2502b of the catheter 2502 is a handle 2507, having channels or lumens 2508 extending there through for carrying steam and cooling water. During operation, water vapor/steam at a temperature of around 100-120 degrees C. is input from a luer connector 2510 and carried via the catheter 2502 to the inner balloon 2504. This allows the inner balloon 2504 to inflate and contact the outer balloon 2503 proximate the area of ablation. A hot zone 2509 is created at the area of contact between the inner balloon 2504 and the external balloon 2503, such that thermal energy from the inner balloon 2504 passes through the outer balloon 2503 to the area of ablation. The elongate body and portions of the outer balloon 2503, excluding the hot zone 2509, remain cool owing to the circulating water. As noted above, channels are provided in the catheter 2502 for carrying cooling fluid and steam. Cooling water enters the catheter 2502 from a tube 2511 at the proximal end of the catheter and exits from another tube 2512 at the proximal end of the catheter after circulating through the outer balloon 2503. Luer connectors 2513 are provided to enable cooling fluid to be supplied to and exit from the tubes 2511 and 2512, respectively. In one embodiment, the luer connector 2510 at the inlet of water vapor is a pressure resistant luer lock. In one embodiment the cooling fluid is water. In another embodiment, the cooling fluid is air.

In one embodiment, the length of the catheter 2502 between its distal end 2502a and proximal end 2502b is about 1800 mm, with a margin of ±500 mm. In one embodiment, the outer balloon 2502 is substantially cylindrical in shape, with tapering ends, while the inner balloon 2504 is substantially spherical in shape. In one embodiment, the total length of the outer balloon 2503 between its two ends is about 83 mm, while the length of the cylindrical portion is about 60 mm, with a margin of ±25 mm, and its width is about 24 mm with a margin of ±15 mm. In one embodiment, the diameter of the inner balloon 2504 is about 25 mm with a margin of ±15 mm.

FIG. 25B illustrates a detailed inside view of the catheter 2502 with various lumens. Referring to FIG. 25B, the central lumen 2501 is used to carry steam into the inner balloon 2504. The first outer lumen 2514 is used to carry cooling water from the tube 2511 into the outer balloon 2503, and the second outer lumen 2515 of the catheter is used to carry cooling water coming back from the outer balloon and is exit through the tube 2512. All the lumens are encased in another tube or handle 2505 for reinforcement.

Figure 25C:
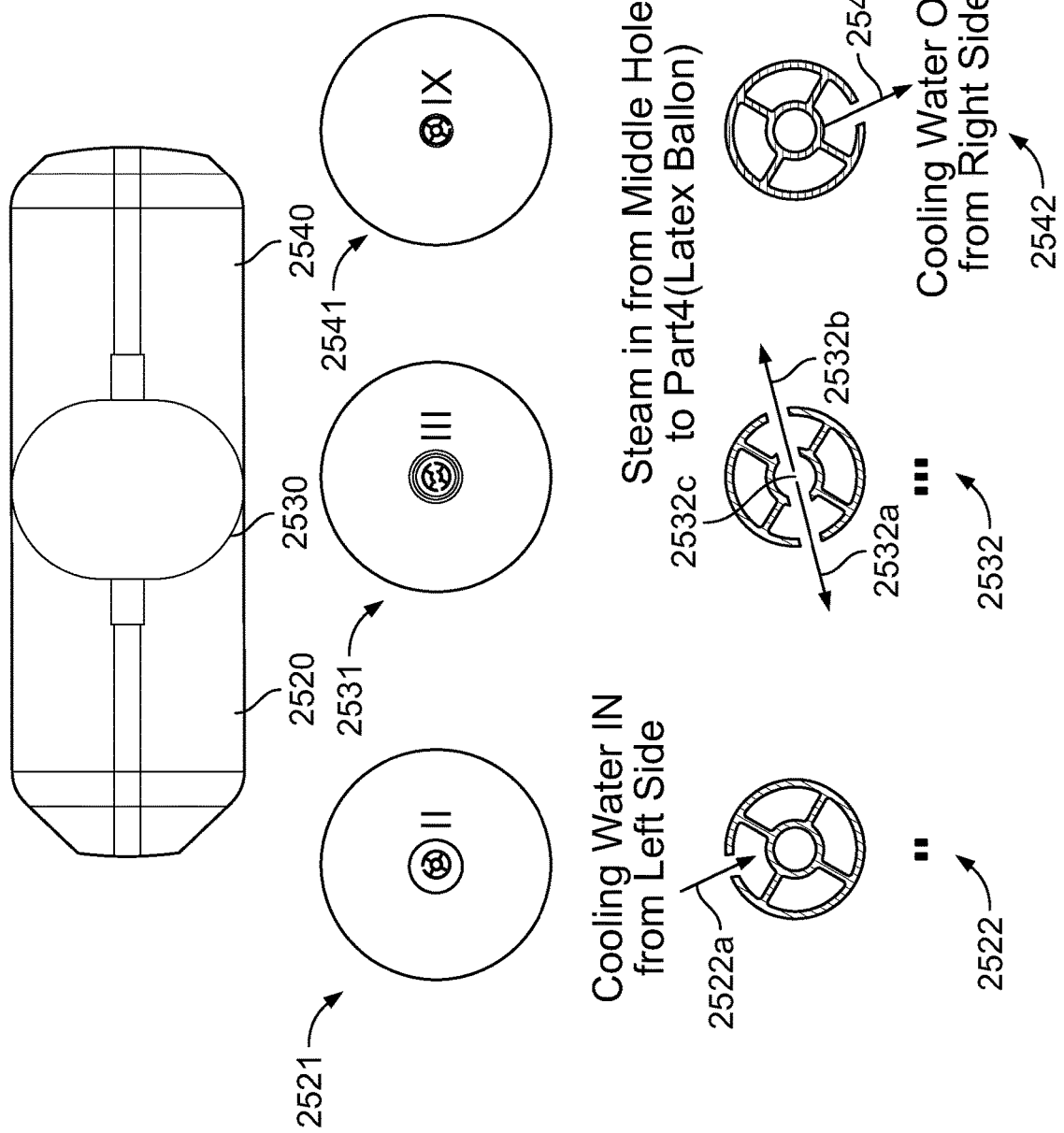
FIG. 25C illustrates the flow mechanism for a catheter, as it passes through the inner balloon and the outer balloon, in accordance with one embodiment.

In one embodiment, the channels or lumens of the catheter 2502, shown in FIG. 25B are designed with openings at appropriate places, to ensure correct flow of fluids—steam into the inner balloon and cooling water in and out of the outer balloon. FIG. 25C illustrates the flow mechanism for catheter 2502, as it passes through the inner balloon 2504 and the outer balloon 2503. Referring to FIG. 25C, the cross sectional views of the catheter lumens at locations 2520, 2530 and 2540, are illustrated as 2521, 2531 and 2541. Details of the cross section views can be seen in 2522, 2532 and 2542. As can be seen in 2522, there is an opening 2522a in the tube to allow cooling water into the channel from the outer balloon. This cooling water is carried by the lumen to the exit (vial tube 2512 in FIG. 25B). As can be seen in 2542, there is an opening 2542a in the tube to allow cooling water out of the channel into the outer balloon. This cooling water is supplied by tube 2511 (shown in FIG. 25B) and carried by the channel to the outer balloon. In 2532, two openings 2532a and 2532b can be seen in the channel, through which steam is supplied from the central lumen 2532c to the inner balloon.

FIG. 26A illustrates a side cross section 2601 and a perspective view 2602 of the inner balloon (shown as 2504 in FIGS. 25A, 25B and 25C), when the balloon is in an unexpanded state, that is, it is not inflated with steam. Referring to FIG. 26A, in one embodiment, the balloon 2603 in unexpanded form has a substantially cylindrical shape, and is tapered at both the ends 2604 and 2605. The ends extend into tube like structures 2606 and 2607, which help in keeping the catheter in place when it is passed through the balloon, as shown in FIG. 25A. In one embodiment, the total length of the balloon in the unexpanded state is about 28 mm with a margin of ±15 mm, while the length of the cylindrical portion 2609 is about 13.2 mm with a margin of ±10 mm. The length of each tubular segment 2606, 2607 is about 4.9 mm, while the length of the tapered portions 2604, 2605 is 2.5 mm on each side. In one embodiment, the inner diameter of each tubular segment is about 2.9 mm, while the outer diameter is 3.7 mm. The width of the widest portion of the balloon 2609 is about 5.6 mm with a margin of ±2.5 mm.

FIG. 26B illustrates a side cross section 2611 and a perspective view 2612 of the inner balloon (shown as 2504 in FIGS. 25A, 25B and 25C), when the balloon is in an expanded state, that is, it is inflated with steam. Referring to FIG. 26B, in one embodiment, the balloon 2613 in expanded form has a shape of an elongated spheroid. Tube like structures 2616 and 2617 extend from two opposite sides in the balloon, which help in keeping the catheter in place when it is passed through the balloon, as shown in FIG. 25A. In one embodiment, the total length of the balloon in expanded state, including the tubular segments 2616, 2617 is about 28 mm with a margin of ±15 mm, while the length of each individual tube segment is about 4.8 mm with a margin of ±2.0 mm. In one embodiment, the inner diameter of each tubular segment is about 2.9 mm, while the outer diameter is 3.3 mm with a margin of ±2.0 mm, when the balloon 2613 is in expanded state. In one embodiment, the length of the major axis 2619 of the elongated spheroid shaped balloon is about 23.8 mm with a margin of ±15 mm, when the balloon is inflated.

Figure 27:
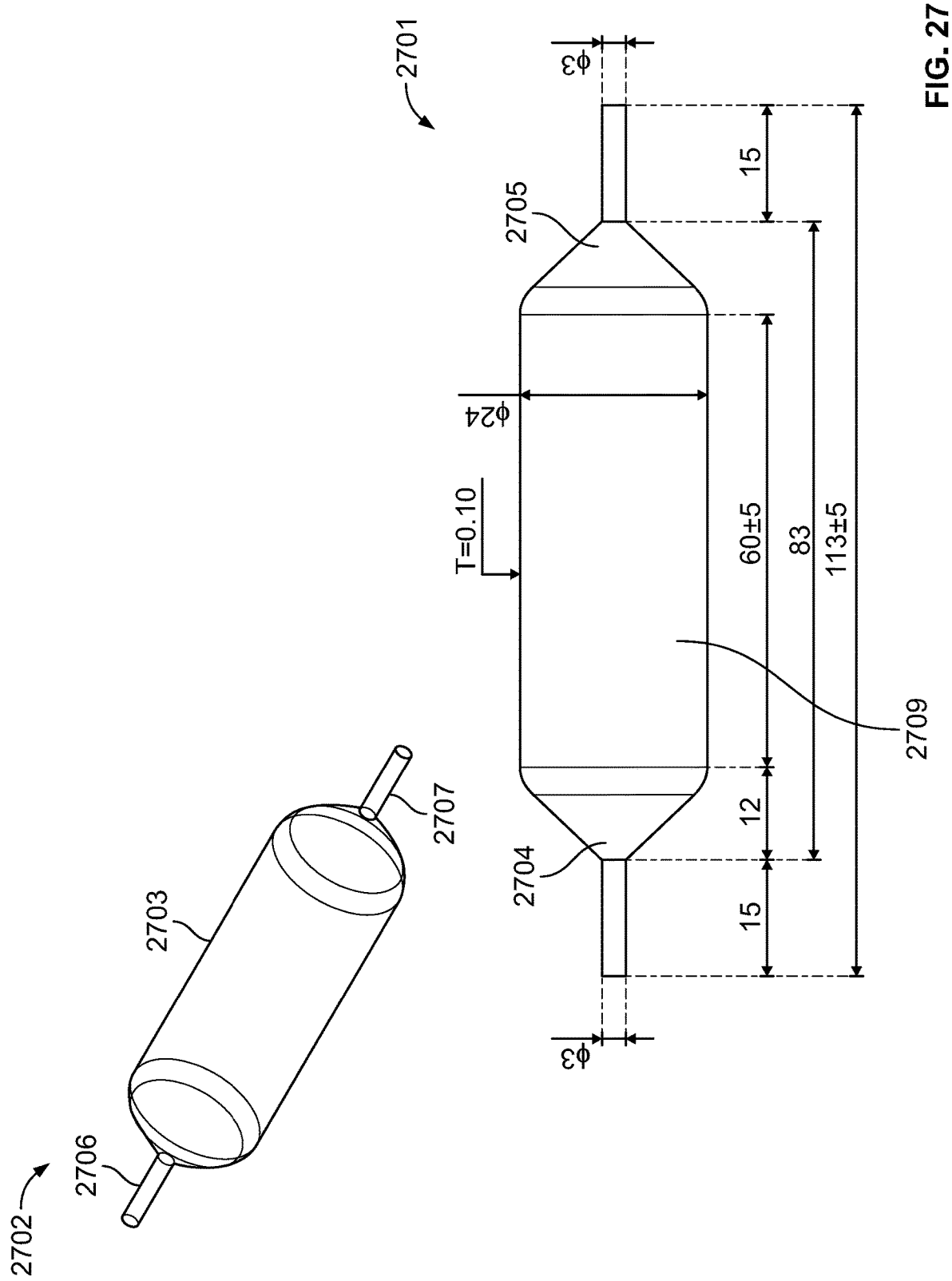
FIG. 27 illustrates a side cross section view and a perspective view of the outer balloon, in accordance with one embodiment.

FIG. 27 illustrates a side cross section 2701 and a perspective view 2702 of the outer balloon (shown as 2503 in FIGS. 25A, 25B and 25C) in an expanded state. Referring to FIG. 27, in one embodiment, the balloon 2703 has a substantially cylindrical shape, and is tapered at both the ends 2704 and 2705. The ends extend into tube like structures 2706 and 2707, which help in keeping the catheter in place when it is passed through the outer balloon, as shown in FIG. 25A. In one embodiment, the total length of the balloon including the tubular structures 2706, 2707 is about 113±35 mm, while the length of the cylindrical portion 2709 is about 60±25 mm. The length of each tubular segment 2706, 2707 is about 15 mm with a margin of ±15 mm, while the length of the tapered portions 2708 is 12 mm on each side with a margin of ±10 mm. In one embodiment, the diameter of each tubular segment is about 3 mm. The width of the cylindrical portion of the balloon 2709 is about 24 mm with a margin of ±15 mm, while the thickness of the material of the balloon is about 0.10 mm.

Figure 28:
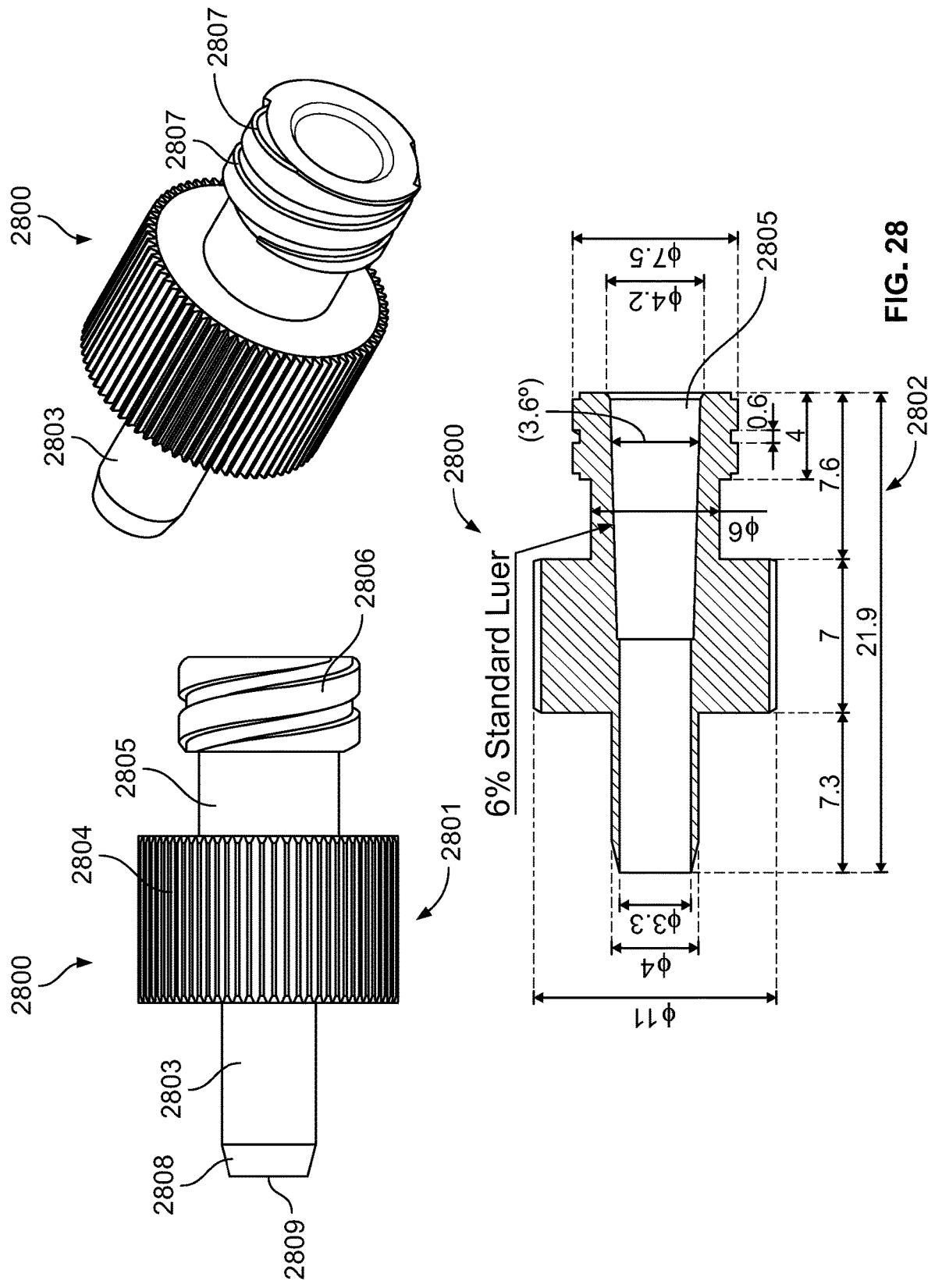
FIG. 28 illustrates a side view, a side cross section view, and a perspective view of a pressure resistant luer lock positioned at the proximal end of the catheter, in accordance with one embodiment of the present specification.

FIG. 28 illustrates a side view 2801, side cross section 2802, and perspective view 2803 of a pressure resistant luer lock 2800 positioned at the proximal end of the catheter, shown as 2510 in FIG. 25A. Referring to FIG. 28, in one embodiment, the luer lock 2803 comprises a grip 2804 in the center for handling the lock 2803, a male connector 2803 at its distal end 2809, and a female connector 2806 at its proximal end 2810. The male connector 2803 includes a tapered end 2808 and is configured to attach securely to the proximal end of handle 2507 in FIG. 25A to form a luer lock for the steam inlet in the catheter. The female connector 2806 includes an opening 2811 for receiving a tube of a steam source and grooves 2807 for securing said steam source tube. The grip 2804 is used for handling the lock 2800 when attaching the lock to a steam source. In one embodiment, the total length of the lock 2800 is about 21.9 mm. At the female connector 2806, the outer diameter is about 7.5 mm, while the inner diameter is about 4.2 mm. The width of the female connector 2806 is about 4 mm, in one embodiment. In one embodiment, grooves 2807 are etched on the female connector 2806, which have a uniform width of about 0.6 mm. The diameter of the male connector 2803 just before it tapers is about 4 mm, while the diameter is reduced to 3.3 mm at the distal end 2809. In one embodiment, the lock 2800 has a 6% standard taper.

In one embodiment, the grip 2804 of the luer lock 2800 has a width of about 7 mm and a diameter of about 11 mm.

Endometrial Ablation

Figure 29A:
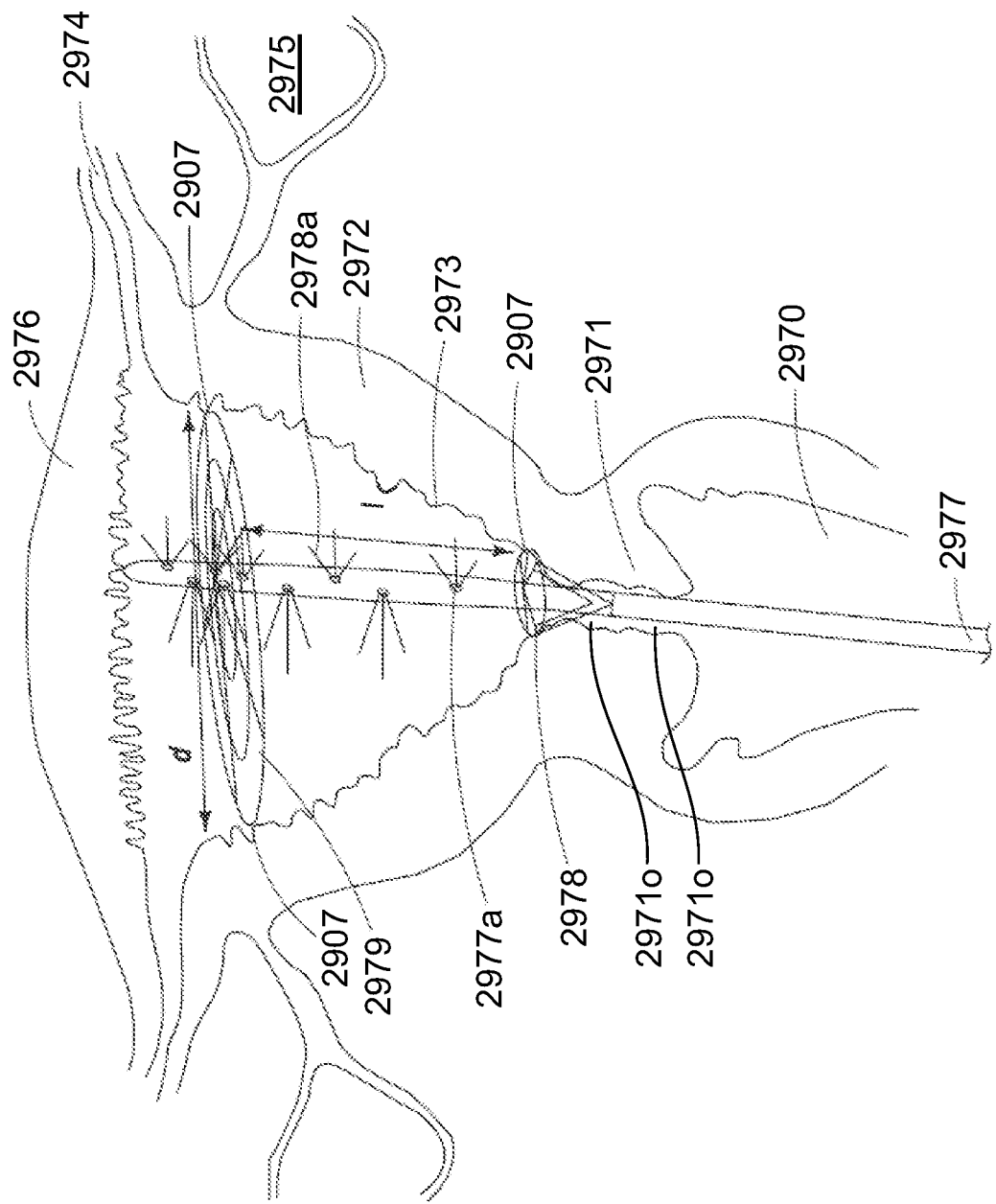
FIG. 29A illustrates endometrial ablation being performed in a female uterus by using the ablation device, in accordance with an embodiment of the present specification.

FIG. 29A illustrates endometrial ablation being performed in a female uterus by using the ablation device, in accordance with an embodiment of the present specification. A cross-section of the female genital tract comprising a vagina 2970, a cervix 2971, a uterus 2972, an endometrium 2973, fallopian tubes 2974, ovaries 2975 and the fundus of the uterus 2976 is illustrated. A catheter 2977 of the ablation device is inserted into the uterus 2972 through the cervix 2971 at the cervical os. In an embodiment, the catheter 2977 has two positioning elements, a conical positioning element 2978 and a disc shaped positioning element 2979. The positioning element 2978 is conical with an insulated membrane covering the conical positioning element 2978. The conical element 2978 positions the catheter 2977 in the center of the cervix 2971 and the insulated membrane prevents the escape of thermal energy or ablative agent out the cervix 2971 through the os 2971*o*. The second disc shaped positioning element 2979 is deployed close to the fundus of the uterus 2976 positioning the catheter 2977 in the middle of the cavity. An ablative agent 2978*a* is passed through infusion ports 2977*a* for uniform delivery of the ablative agent 2977*a* into the uterine cavity. Predetermined length 'l' of the ablative segment of the catheter and diameter 'd' of the positioning element 2979 allows for estimation of the cavity size and is used to calculate the amount of thermal energy needed to ablate the endometrial lining. In one embodiment, the positioning elements 2978, 2979 also act to move the endometrial tissue away from the infusion ports 2977*a* on the catheter 2977 to allow for the delivery of ablative agent. Optional temperature sensors 2907 deployed close to the endometrial surface are used to control the delivery of the ablative agent 2978*a*. Optional topographic mapping using multiple infrared, electromagnetic, acoustic or radiofrequency energy emitters and sensors can be used to define cavity size and shape in patients with an irregular or deformed uterine cavity due to conditions such as fibroids. Additionally, data from diagnostic testing can be used to ascertain the uterine cavity size, shape, or other characteristics.

In an embodiment, the ablative agent is vapor or steam which contracts on cooling. Steam turns to water which has a lower volume as compared to a cryogen that will expand or a hot fluid used in hydrothermal ablation whose volume stays constant. With both cryogens and hot fluids, increasing energy delivery is associated with increasing volume of the ablative agent which, in turn, requires mechanisms for removing the agent, otherwise the medical provider will run into complications, such as perforation. However, steam, on cooling, turns into water which occupies significantly less volume; therefore, increasing energy delivery is not associated with an increase in volume of the residual ablative agent, thereby eliminating the need for continued removal. This further decreases the risk of leakage of the thermal energy via the fallopian tubes 2974 or the cervix 2971, thus reducing any risk of thermal injury to adjacent healthy tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area. For endometrial ablation, 100% of the tissue does not need to be ablated to achieve the desired therapeutic effect.

In one embodiment, the preferred distal positioning attachment is an uncovered wire mesh that is positioned proximate to the mid body region. In one embodiment, the preferred proximal positioning device is a covered wire mesh that is pulled into the cervix, centers the device, and occludes the cervix. One or more such positioning devices may be helpful to compensate for the anatomical variations in the uterus. The proximal positioning device is preferably oval, with a long axis between 0.1 mm and 10 cm (preferably 1 cm to 5 cm) and a short axis between 0.1 mm and 5 cm (preferably 0.5 cm to 1 cm). The distal positioning device is preferably circular with a diameter between 0.1 mm and 10 cm, preferably 1 cm to 5 cm.

In another embodiment, the catheter is a coaxial catheter comprising an external catheter and an internal catheter wherein, upon insertion, the distal end of the external catheter engages and stops at the cervix while the internal extends into the uterus until its distal end contacts the fundus of the uterus. The length of the internal catheter that has passed into the uterus is then used to measure the depth of the uterine cavity and determines the amount of ablative agent to use. Ablative agent is then delivered to the uterine cavity via at least one port on the internal catheter. In one embodiment, during treatment, intracavitary pressure within the uterus is kept below 100 mm Hg. In one embodiment, the coaxial catheter further includes a pressure sensor to measure intracavitary pressure. In one embodiment, the coaxial catheter further includes a temperature sensor to measure intracavitary temperature. In one embodiment, the ablative agent is steam and the steam is released from the catheter at a pressure of less than 100 mm Hg. In one embodiment, the steam is delivered with a temperature between 90 and 100° C.

Figure 29B:
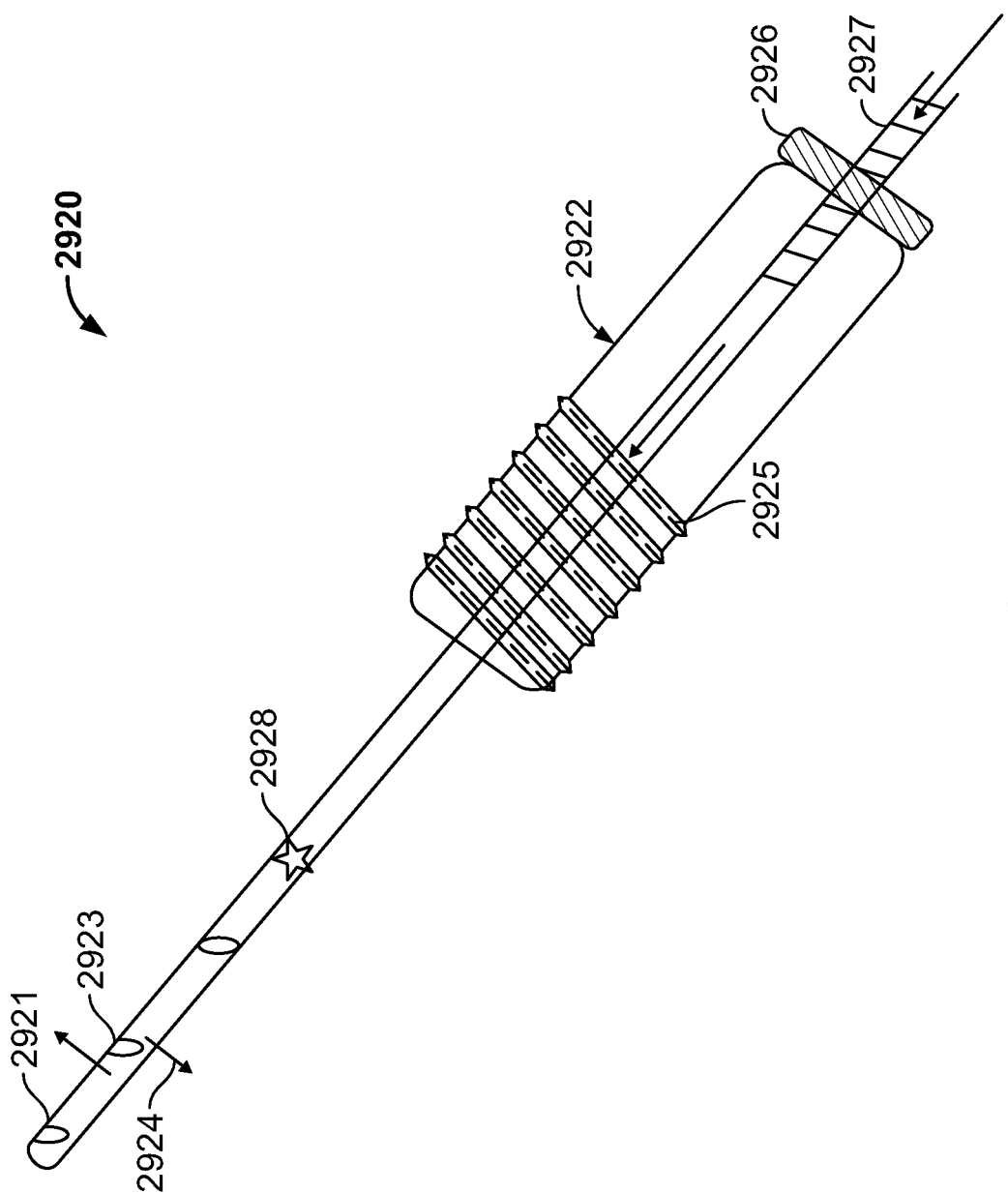
FIG. 29B is an illustration of a coaxial catheter used in endometrial tissue ablation, in accordance with one embodiment of the present specification.

FIG. 29B is an illustration of a coaxial catheter 2920 used in endometrial tissue ablation, in accordance with one embodiment of the present specification. The coaxial catheter 2920 comprises an inner catheter 2921 and outer catheter 2922. In one embodiment, the inner catheter 2921 has one or more ports 2923 for the delivery of an ablative agent 2924. In one embodiment, the ablative agent is steam. In one embodiment, the outer catheter 2922 has multiple fins 2925 to engage the cervix to prevent the escape of vapor out of the uterus and into the vagina. In one embodiment, the fins are composed of silicone. In one embodiment, the outer catheter 2922 includes a luer lock 2926 to prevent the escape of vapor between the inner catheter 2921 and outer catheter 2922. In one embodiment, the inner catheter 2921 includes measurement markings 2927 to measure the depth of insertion of the inner catheter 2921 beyond the tip of the outer catheter 2922. Optionally, in various embodiments, one or more sensors 2928 are incorporated into the inner catheter 2921 to measure intracavitary pressure or temperature.

Figure 29C:
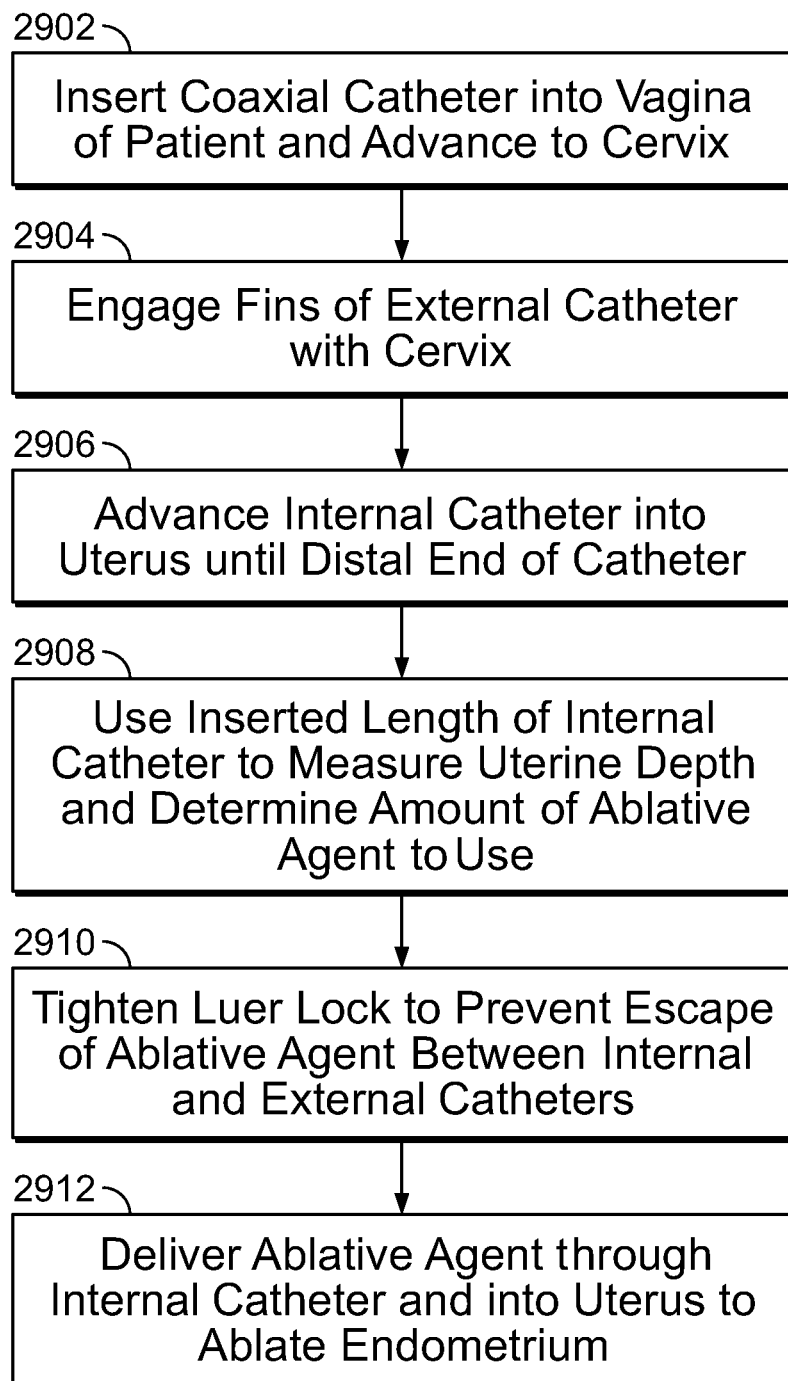
FIG. 29C is a flow chart listing the steps involved in an endometrial tissue ablation process using a coaxial ablation catheter, in accordance with one embodiment of the present specification.

FIG. 29C is a flow chart listing the steps involved in an endometrial tissue ablation process using a coaxial ablation catheter, in accordance with one embodiment of the present specification. At step 2902, the coaxial catheter is inserted into the patient's vagina and advanced to the cervix. Then, at step 2904, the coaxial catheter is advanced such that the fins of the outer catheter engage the cervix, effectively stopping advancement of the outer catheter at that point. The inner catheter is then advanced, at step 2906, until the distal end of the internal catheter contacts the fundus of the uterus. The depth of insertion is then measured using the measurement markers on the internal catheter at step 2908, thereby determining the amount of ablative agent to use in the procedure. At step 2910, the luer lock is tightened to prevent any escape of vapor between the two catheters. The vapor is then delivered, at step 2912, through the lumen of the inner catheter and into the uterus via the delivery ports on the internal catheter to ablate the endometrial tissue.

Figure 29D:
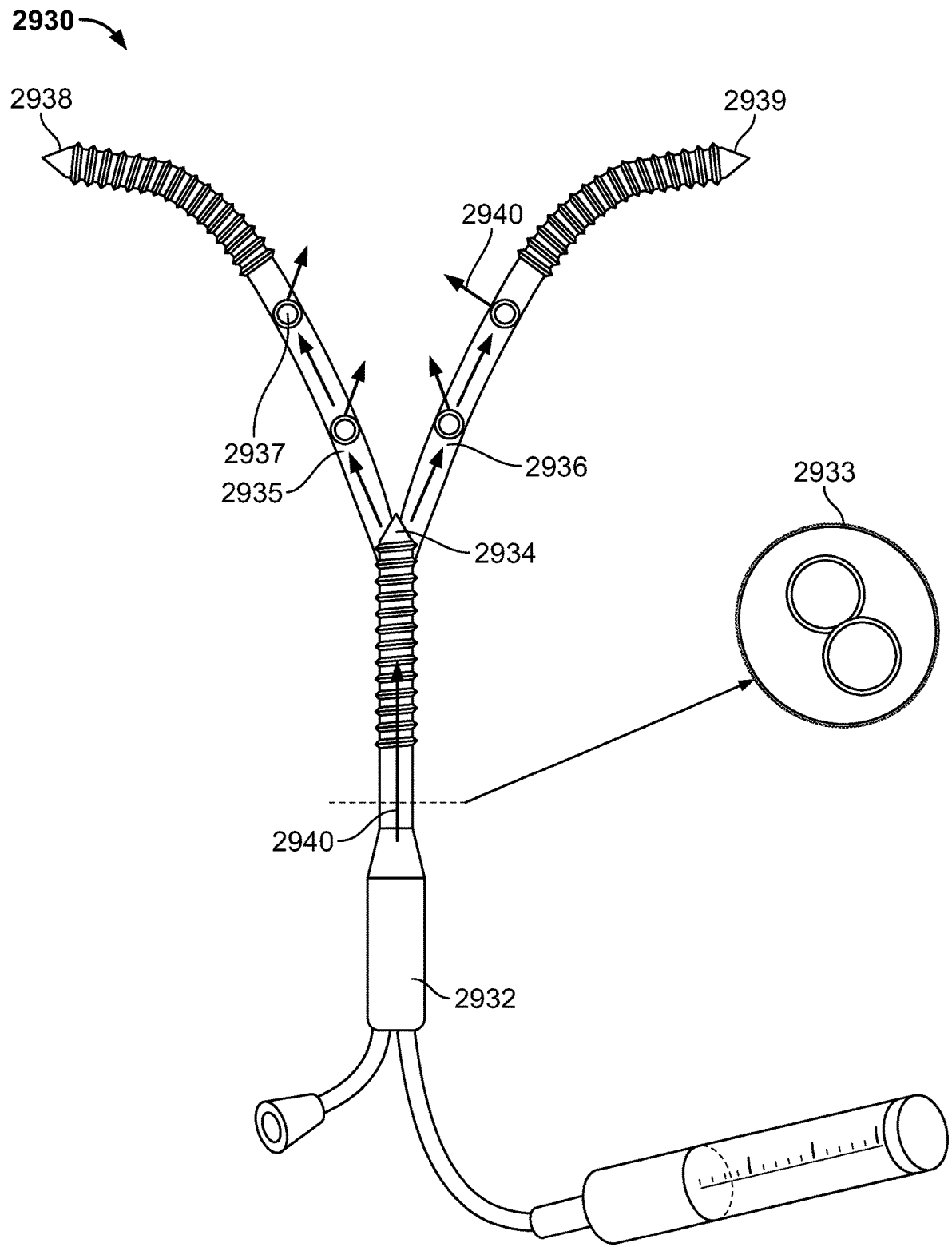
FIG. 29D is an illustration of a bifurcating coaxial catheter used in endometrial tissue ablation, in accordance with one embodiment of the present specification.

FIG. 29D is an illustration of a bifurcating coaxial catheter 2930 used in endometrial tissue ablation, in accordance with one embodiment of the present specification. The catheter 2930 includes a first elongate shaft 2932 having a proximal end, a distal end and a first lumen within. The first lumen splits in the distal end to create a coaxial shaft 2933. The distal end of the first shaft 2932 also includes a first positioning element, or cervical plug 2934, that occludes a patient's cervix. The catheter 2930 bifurcates as it extends distally from the cervical plug 2934 to form a second catheter shaft 2935 and a third catheter shaft 2936. The second and third catheter shafts 2935, 2936 each include a proximal end, a distal end, and a shaft body having one or more vapor delivery ports 2937. The second and third catheter shafts 2935, 2936 include second and third lumens respectively, for the delivery of ablative agent. The distal ends of the second and third catheter shafts 2935, 2936 include second and third positioning elements, or fallopian tube plugs 2938, 2939 respectively, designed to engage a patient's fallopian tubes during an ablation therapy procedure and prevent the escape of ablative energy. The fallopian tube plugs 2938, 2939 also serve to position the second and third shafts 2935, 2936 respectively, in an intramural portion or isthmus of a patient's fallopian tube. The second and third catheter shafts 2935, 2936 are independently coaxially extendable and the length of each shaft 2935, 2936 is used to determine the dimension of a patient's endometrial cavity. An ablative agent 2940 travels through the first catheter shaft 2932, through both second and third catheter shaft 2935, 2936, and out the vapor delivery ports 2937 and into the endometrial cavity to ablate endometrial tissue.

Figure 29E:
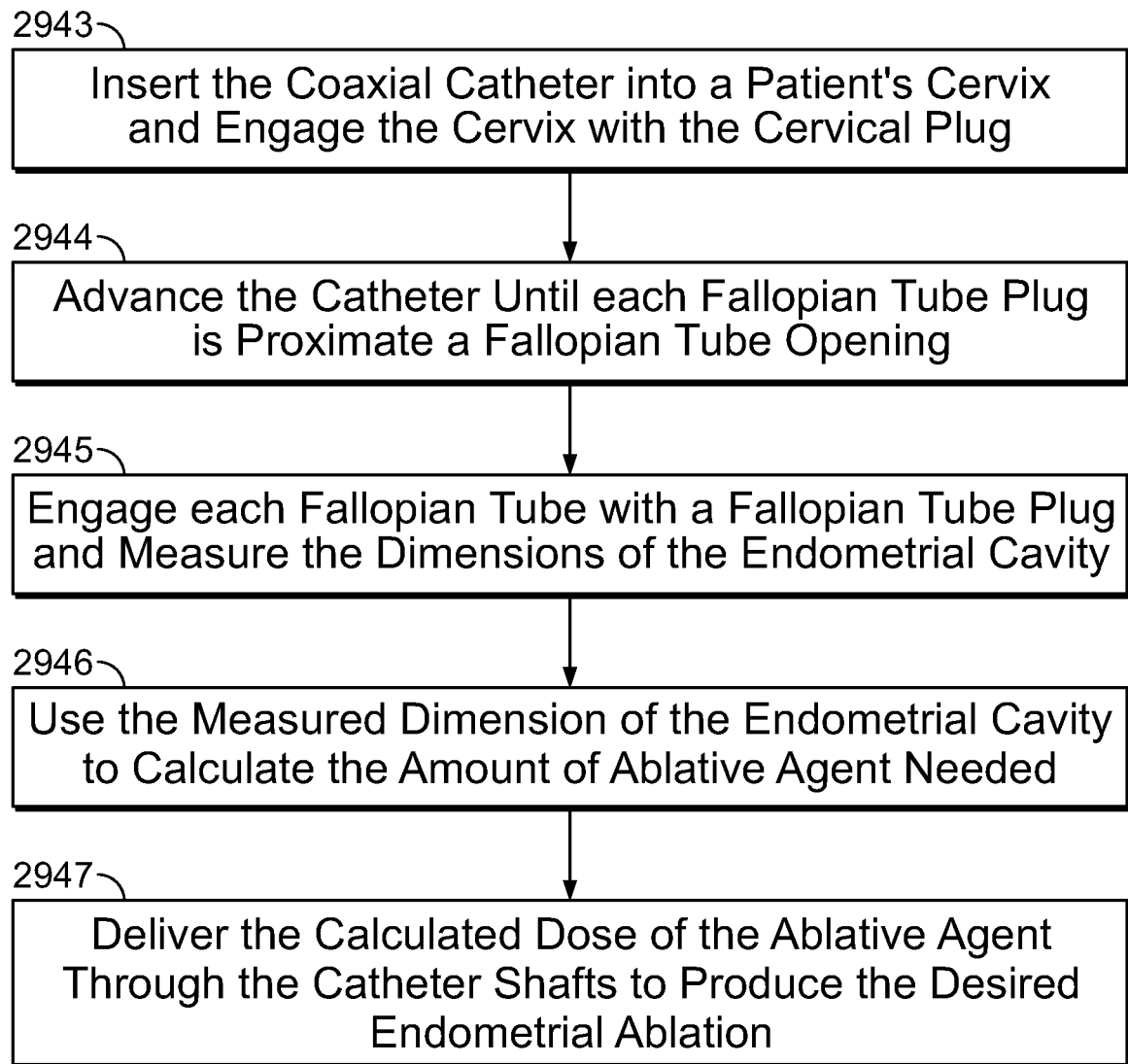
FIG. 29E is a flowchart listing the steps of a method of using the ablation catheter of FIG. 29D to ablate endometrial tissue, in accordance with one embodiment of the present specification.

FIG. 29E is a flowchart listing the steps of a method of using the ablation catheter of FIG. 29D to ablate endometrial tissue, in accordance with one embodiment of the present specification. At step 2943, the coaxial catheter is inserted into a patient's cervix and the cervix is engaged with the cervical plug. The catheter is then advanced until each fallopian tube plug is proximate a fallopian tube opening at step 2944. Each fallopian tube is then engaged with a fallopian tube plug at step 2945 and the dimensions of the endometrial cavity are measured. The measurements are based on the length of each catheter shaft that has been advanced. At step 2946, the measured dimensions are used to calculate the amount of ablative agent needed to carry out the ablation. The calculated dose of ablative agent is then delivered through the catheter shafts and into the endometrial cavity to produce the desired endometrial ablation at step 2947.

Figure 29F:
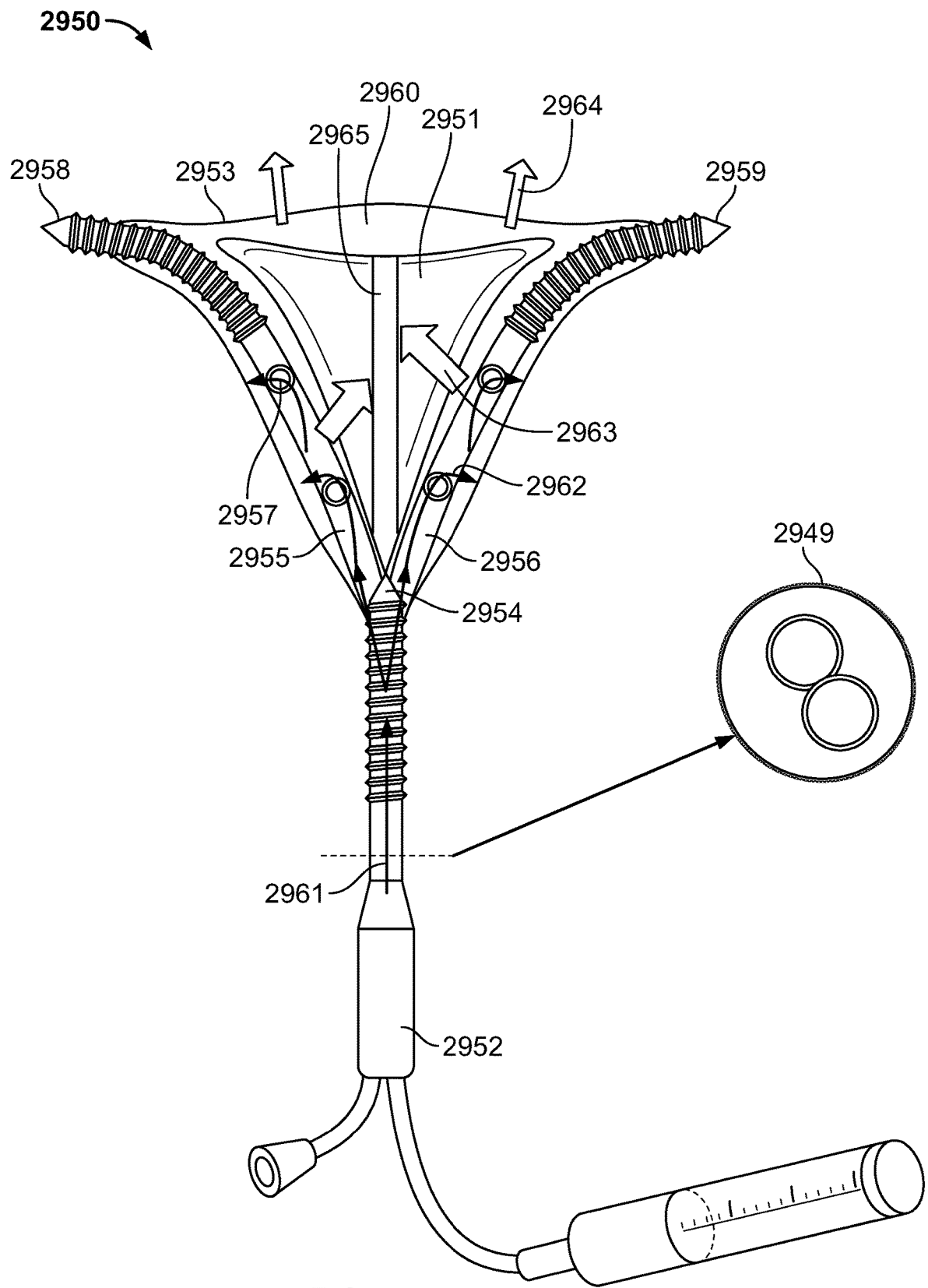
FIG. 29F is an illustration of a bifurcating coaxial catheter with expandable elements used in endometrial tissue ablation, in accordance with one embodiment of the present specification.

FIG. 29F is an illustration of a bifurcating coaxial catheter 2950 with expandable elements 2951, 2953 used in endometrial tissue ablation, in accordance with one embodiment of the present specification. Similar to the catheter 2930 of FIG. 29D, the catheter 2950 depicted in FIG. 29F includes a first elongate coaxial shaft 2952 having a proximal end, a distal end and a first lumen within. The first lumen splits in the distal end to create a coaxial shaft 2949. The distal end of the first shaft 2952 also includes a first positioning element, or cervical plug 2954, that occludes a patient's cervix. The catheter 2950 bifurcates as it extends distally from the cervical plug 2954 to form a second catheter shaft 2955 and a third catheter shaft 2956. The second and third catheter shafts 2955, 2956 each include a proximal end, a distal end, and a catheter shaft body having one or more vapor delivery ports 2957. The second and third catheter shafts 2955, 2956 include second and third lumens respectively, for the delivery of ablative agent. The distal ends of the second and third catheter shafts 2955, 2956 include second and third positioning elements, or fallopian tube plugs 2958, 2959 respectively, designed to engage a patient's fallopian tubes during an ablation therapy procedure and prevent the escape of ablative energy. The fallopian tube plugs 2958, 2959 also serve to position the second and third shafts 2955, 2956 respectively, in an intramural portion or isthmus of a patient's fallopian tube. The second and third catheter shafts 2955, 2956 are independently coaxially extendable and the length of each catheter shaft 2955, 2956 is used to determine the dimension of a patient's endometrial cavity.

The catheter 2950 further includes a first expandable member or balloon 2951 and a second expandable member or balloon 2953 comprising a coaxial balloon structure. In one embodiment, the first balloon 2951 is a compliant balloon structure and the second balloon 2953 is a non-compliant balloon structure shaped to approximate the uterine cavity shape, size or volume. In another embodiment, the second balloon 2953 is partially compliant. In another embodiment, the compliance of the two balloons 2951, 2953 is substantially equivalent. The balloons 2951, 2953 are attached to the second and third catheter shafts 2955, 2956 along an inner surface of each shaft 2955, 2956. The first, inner balloon 2951 is positioned within the second, outer balloon 2953. The inner balloon 2951 is designed to be inflated with air and a first volume of the inner balloon 2951 is used to measure a dimension of a patient's endometrial cavity. An ablative agent 2961 is introduced into the catheter 2950 at its proximal end and travels through the first catheter shaft 2952 and into the second and third catheter shafts 2955, 2956. The second and third catheter shafts 2955, 2956 are designed to release ablative energy 2962 through delivery ports 2957 and into a space 2960 between the two balloons 2951, 2953. Some of the ablative energy 2963 is transferred to the air in the inner balloon 2951, expanding its volume from said first volume to a second volume, resulting in further expansion of said inner balloon 2951 to further occlude the patient's endometrial cavity for ideal vapor delivery. In one embodiment, the second volume is less than 25% greater than the first volume. The expansion also forces the fallopian tube plugs 2958, 2959 to further engage the openings of the fallopian tubes. A portion of the ablative agent or ablative energy 2964 diffuses out of the thermally permeable outer balloon 2953 and into the endometrial cavity, ablating the endometrial tissue. In various embodiments, the thermal heating of the air in the balloon occurs either through the walls of the inner balloon, through the length of the catheter, or through both. In one embodiment, the catheter 2950 includes an optional fourth catheter shaft 2965 extending from the first catheter shaft 2952 and between the second and third catheter shaft 2955, 2956 within the inner balloon 2951. Thermal energy from within the fourth catheter shaft 2965 is used to further expand the inner balloon 2951 and assist with ablation.

In one embodiment, the volume of the inner balloon 2951 is used to control the pressure exerted by the outer balloon 2953 on the wall of the uterus. The pressure in the inner balloon 2951 is monitored and air is added to or removed from the inner balloon 2951 to maintain a desirable therapeutic pressure in the outer balloon 2953.

Figure 29G:
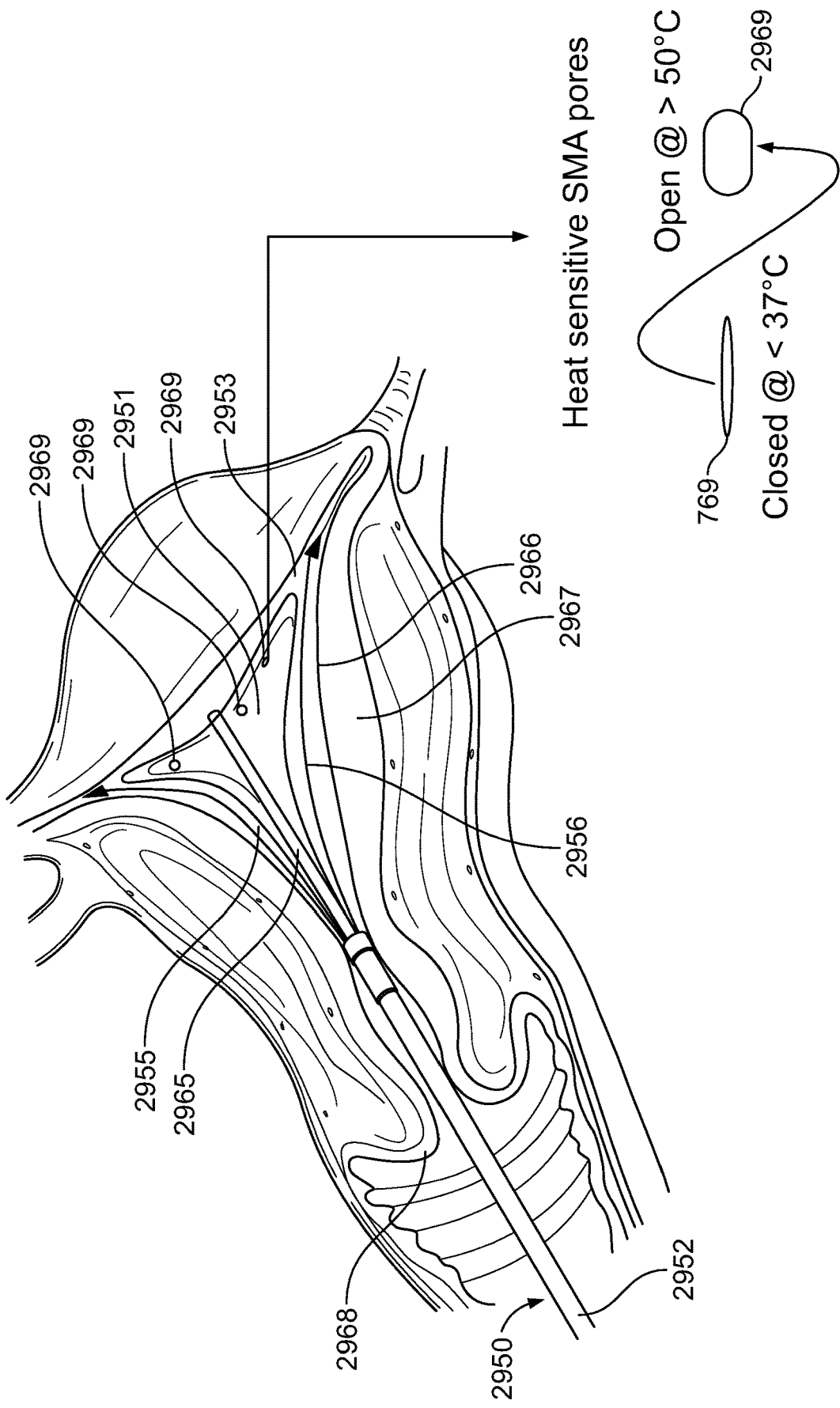
FIG. 29G is an illustration of the catheter of FIG. 29F inserted into a patient's uterine cavity for endometrial tissue ablation.

FIG. 29G is an illustration of the catheter 2950 of FIG. 29F inserted into a patient's uterine cavity 2966 for endometrial tissue 2967 ablation, in accordance with one embodiment of the present specification. The catheter 2950 has been inserted with the first shaft 2952 extending through the patient's cervix 2968 such that the second shaft 2955 is positioned along a first side of the patient's uterine cavity 2966 and the third shaft 2956 is positioned along a second side opposite said first side. This positioning deploys the inner balloon 2951 and outer balloon 2953 between the second and third shafts 2955, 2956. In the pictured embodiment, the catheter 2950 includes an optional fourth shaft 2965 to further expand the inner balloon 2951 with thermal energy and assist with ablation of endometrial tissue 2967. In one embodiment, the inner balloon 2951 is optional and the outer balloon 2953 performs the function of both sizing and delivery of the ablative agent. In one embodiment, the outer balloon includes heat sensitive pores 2969 which are closed at room temperature and open at a temperature higher than the body temperature. In one embodiment, the pores are composed of a shape memory alloy (SMA). In one embodiment, the SMA is Nitinol. In one embodiment, the austenite finish (Af) temperature, or temperature at which the transformation from martensite to austenite finishes on heating (alloy undergoes a shape change to become an open pore 2969), of the SMA is greater than 37° C. In other embodiments, the Af temperature of the SMA is greater than 50° C. but less than 100° C.

Figure 29H:
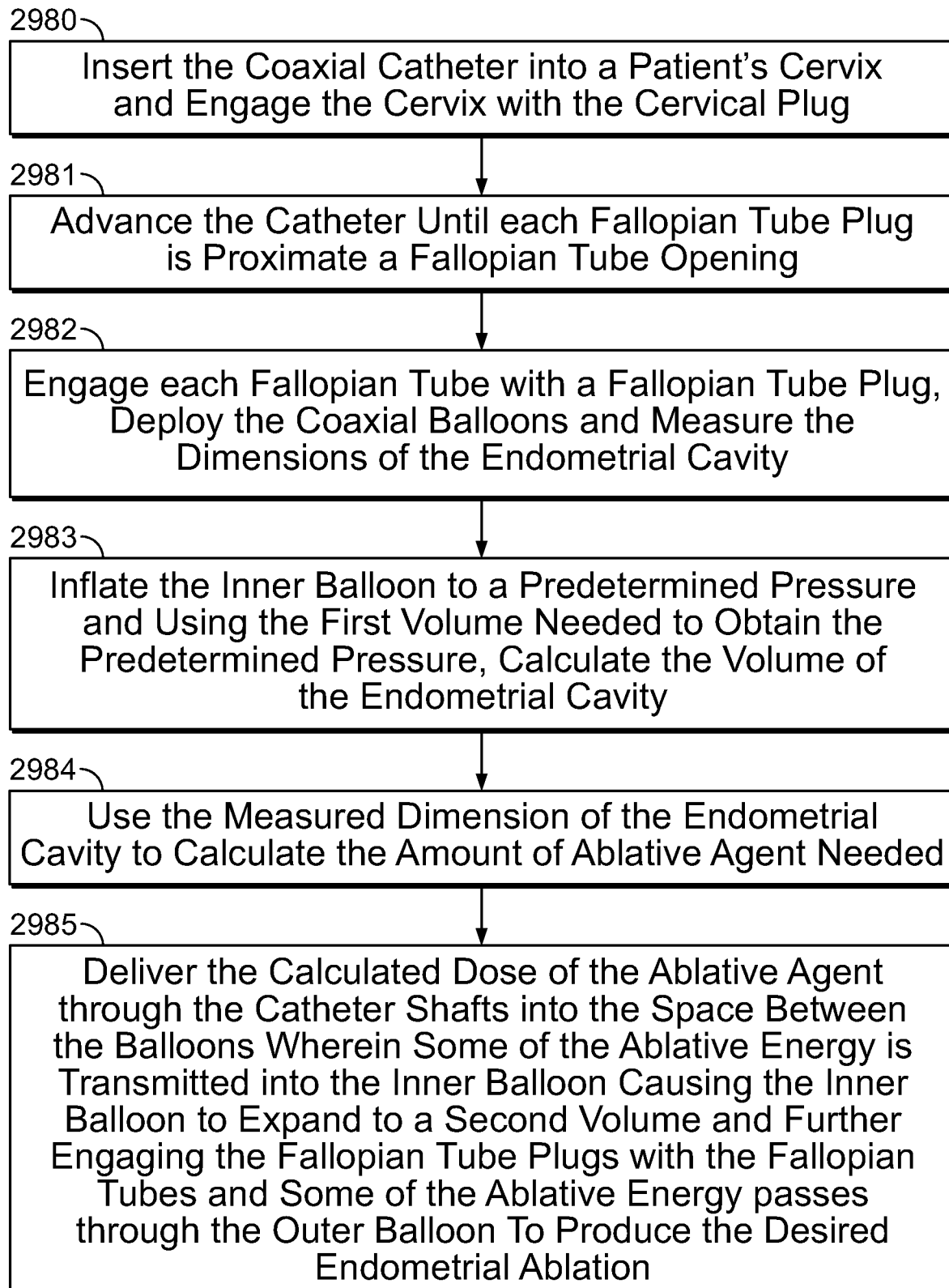
FIG. 29H is a flowchart listing the steps of a method of using the ablation catheter of FIG. 20F to ablate endometrial tissue, in accordance with one embodiment of the present specification.

FIG. 29H is a flowchart listing the steps of a method of using the ablation catheter of FIG. 29F to ablate endometrial tissue, in accordance with one embodiment of the present specification. At step 2980, the coaxial catheter is inserted into a patient's cervix and the cervix is engaged with the cervical plug. The catheter is then advanced until each fallopian tube plug is proximate a fallopian tube opening at step 2981. Each fallopian tube is then engaged with a fallopian tube plug at step 2982, which also deploys the coaxial balloons in the endometrial cavity, and the dimensions of the endometrial cavity are measured. The measurements are based on the length of each catheter shaft that has been advanced and a first volume needed to expand the inner balloon to a predetermined pressure. At step 2983, the inner balloon is inflated to said predetermined pressure and a first volume of the inner balloon at said pressure is used to calculate the volume of the endometrial cavity. The measured dimensions are then used at step 2984 to calculate the amount of ablative agent needed to carry out the ablation. The calculated dose of ablative agent is then delivered through the catheter shafts and into the space between the coaxial balloons at step 2985. Some of the ablative energy is transmitted into the inner balloon to expand the inner balloon to a second volume which further expands the endometrial cavity and, optionally, further pushes the fallopian tube plugs into the fallopian tube openings to prevent the escape of thermal energy. Another portion of the ablative energy passes through the thermally permeable outer balloon to produce the desired endometrial ablation.

In another embodiment, a vapor ablation device for ablation of endometrial tissue comprises a catheter designed to be inserted through a cervical os and into an endometrial cavity, wherein the catheter is connected to a vapor generator for generation of vapor and includes at least one port positioned in the endometrial cavity to deliver the vapor into the endometrial cavity. The vapor is delivered through the port and heats and expands the air in the endometrial cavity to maintain the endometrial cavity pressure below 200 mm Hg and ideally below 50 mm of Hg. In one embodiment, an optional pressure sensor measures the pressure and maintains the intracavitary pressure at the desired therapeutic level, wherein the endometrial cavity is optimally expanded to allow for uniform distribution of ablative energy without the risk of significant leakage of the ablative energy beyond the endometrial cavity and damage to the adjacent normal tissue.

Figure 29I:
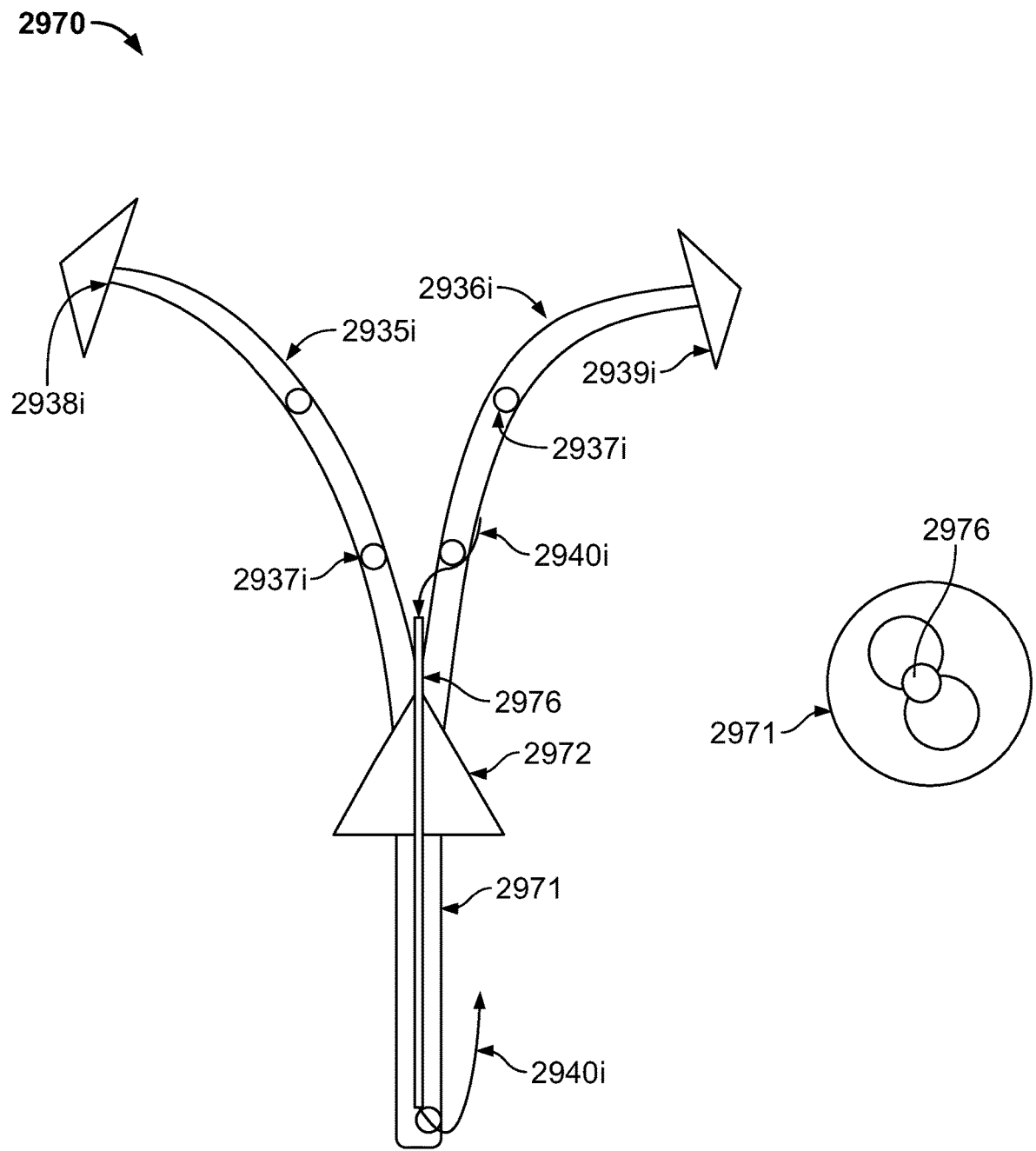
FIG. 29I is an illustration of a bifurcating coaxial catheter used in endometrial tissue ablation, in accordance with another embodiment of the present specification.

FIG. 29I is an illustration of a bifurcating coaxial catheter 2970 used in endometrial tissue ablation, in accordance with another embodiment of the present specification. Forming a seal at the cervix is undesirable as it creates a closed cavity, resulting in a rise of pressure when vapor is delivered into the uterus. This increases the temperature of the intrauterine air, causing a thermal expansion and further rise of intracavitary pressure. This rise in pressure may force the vapor or hot air to escape out of the fallopian tubes, causing thermal injury to the abdominal viscera. This requires for continuous measurement of intracavitary pressure and active removal of the ablative agent to prevent leakage of thermal energy outside the cavity. Referring to FIG. 29I, the catheter 2970 includes a coaxial handle 2971, a first positioning element 2972, a first bifurcated catheter arm 2935*i* with a second positing element 2938*i* at its distal end, a second bifurcated catheter arm 2936*i* with a third positioning element 2939*i* at its distal end, and a plurality of infusion ports 2937*i* along each bifurcated catheter arm 2935*i*, 2936*i*. The catheter 2970 also includes a venting tube 2976 which extends through the coaxial handle 2971 and through the first positioning element 2972 such that the lumen of a patient's uterus is in fluid communication with the outside of the patient's body when the first positioning element 2972 is in place positioned against a cervix. This prevents formation of a tight seal when the catheter 2970 is inserted into the cervix. Since the cervix is normally in a closed position, insertion of any device will inadvertently result in formation of an undesirable seal. The venting tube allows for heated air or extra vapor 2940i to vent out as it expands with delivery of vapor and the intracavitary pressure rises. In some embodiments, the venting tube includes a valve for unidirectional flow of air.

Figure 29J:
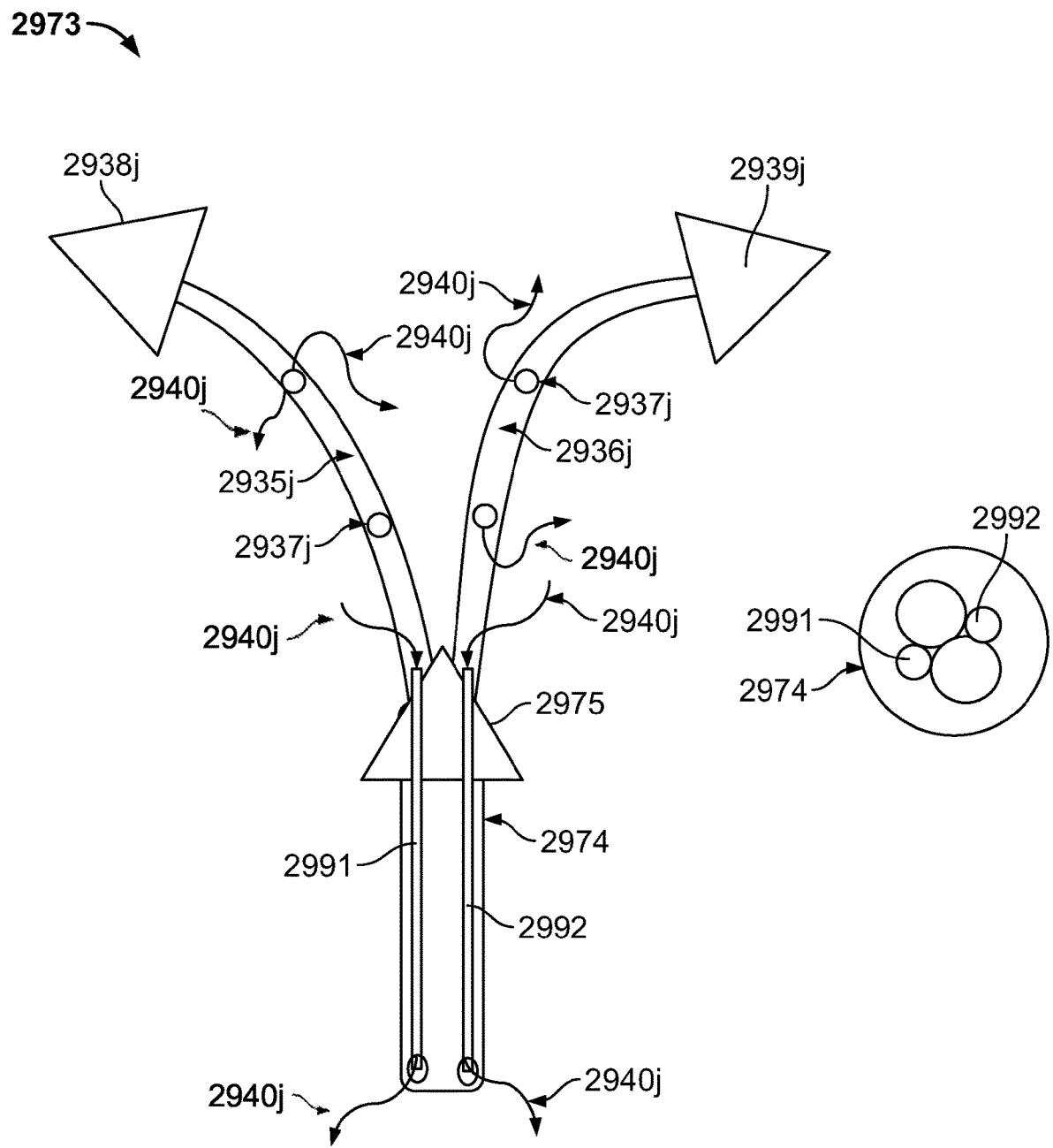
FIG. 29J is an illustration of a bifurcating coaxial catheter used in endometrial tissue ablation, in accordance with yet another embodiment of the present specification.

FIG. 29J is an illustration of a bifurcating coaxial catheter 2973 used in endometrial tissue ablation, in accordance with yet another embodiment of the present specification. The catheter 2973 includes a coaxial handle 2974, a first positioning element 2975, a first bifurcated catheter arm 2935j with a second positing element 2938j at its distal end, a second bifurcated catheter arm 2936j with a third positioning element 2939j at its distal end, and a plurality of infusion ports 2937j along each bifurcated catheter arm 2935j, 2936j. The catheter 2973 also includes two venting tubes 2991, 2992 which extend through the coaxial handle 2974 and through the first positioning element 2975 such that the lumen of a patient's uterus is in fluid communication with the outside of the patient's body when the first positioning element 2975 is in place positioned against a cervix. This prevents formation of a tight seal when the catheter 2973 is inserted into the cervix. The venting tubes 2991, 2992 allow for heated air or extra vapor 2940j to vent out as it expands with delivery of vapor and the intracavitary pressure rises. In some embodiments, the venting tubes 2991, 2992 include a valve for unidirectional flow of air.

Figure 29K:
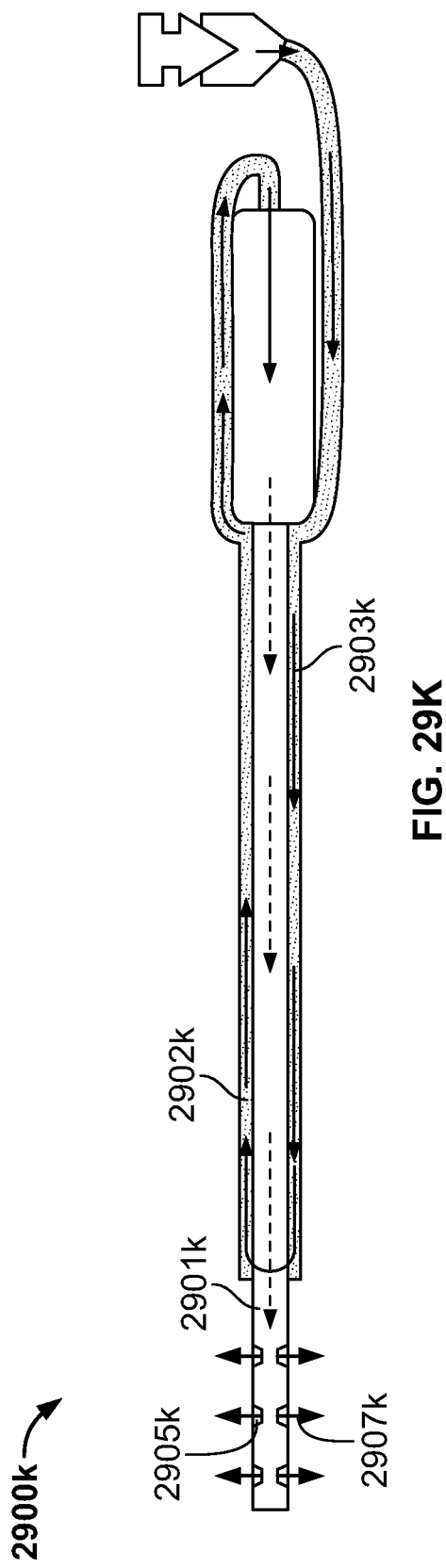
FIG. 29K is an illustration of a water cooled catheter used in endometrial tissue ablation, in accordance with one embodiment of the present specification.

FIG. 29K is an illustration of a water cooled catheter 2900k used in endometrial tissue ablation, in accordance with one embodiment of the present specification. The catheter 2900k comprises an elongate body 2901k having a proximal end and a distal end. The distal end includes a plurality of ports 2905k for the delivery of vapor 2907k for tissue ablation. A sheath 2902k extends along the body 2901k of the catheter 2900k to a point proximal to the ports 2905k. During use, water 2903k is circulated through the sheath 2902k to cool the catheter 2900k. Vapor 2907k for ablation and water 2903k for cooling are supplied to the catheter 2900k at its proximal end.

Figure 29L:
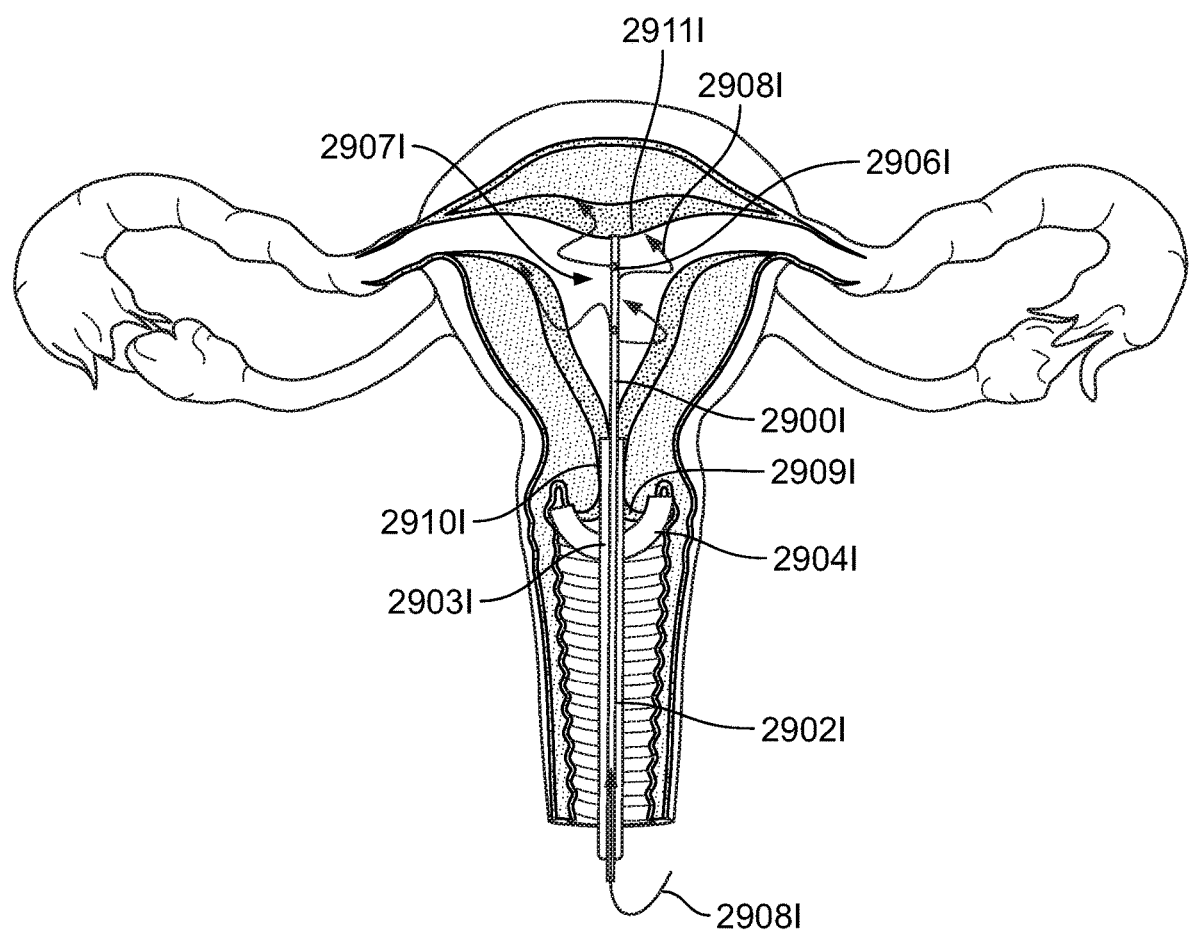
FIG. 29L is an illustration of a water cooled catheter used in endometrial tissue ablation and positioned in a uterus of a patient, in accordance with another embodiment of the present specification.

FIG. 29L is an illustration of a water cooled catheter 29001 used in endometrial tissue ablation and positioned in a uterus 29071 of a patient, in accordance with another embodiment of the present specification. The catheter 29001 comprises an elongate body 29011, a proximal end, distal end, and a sheath 29021 covering a proximal portion of the body 29011. Extending from, and in fluid communication with, the sheath 29021 is a cervical cup 29041. The catheter 29001 further includes a plurality of ports 29061 at its distal end configured to deliver ablative vapor 29081 to the uterus 29071. Vapor 29081 is supplied to the proximal end of the catheter 29001. The ports 29061 are positioned on the catheter body 29011 distal to the sheath 29021. The cervical cup 29041 is configured to cover the cervix 29091 and a distal end of the sheath 29021 extends into the cervical canal 29101. Water 29031 is circulated through the sheath 29021 and cervical cup 29041 to cool the cervical canal 29101 and/or cervix 29091 while vapor 29081 is delivered through the vapor delivery ports 29061 to ablate the endometrial lining 29111.

In various embodiments, ablation therapy provided by the vapor ablation systems of the present specification is delivered to achieve the following therapeutic endpoints for uterine ablation: maintain a tissue temperature at 100° C. or less; increase patient's hemoglobin by at least 5% or at least 1 gm % relative to pre-treatment hemoglobin; decrease menstrual blood flow by at least 5% as measured by menstrual pad weight relative to pre-treatment menstrual blood flow; ablation of endometrial tissue in a range of 10% to 99%; decrease in duration of menstrual flow by at least 5% relative to pre-treatment menstrual flow; decrease in amenorrhea rate by at least 10% relative to pre-treatment amenorrhea rate; and patient reported satisfaction with uterine ablation procedure of greater than 25%.

Figure 29N:
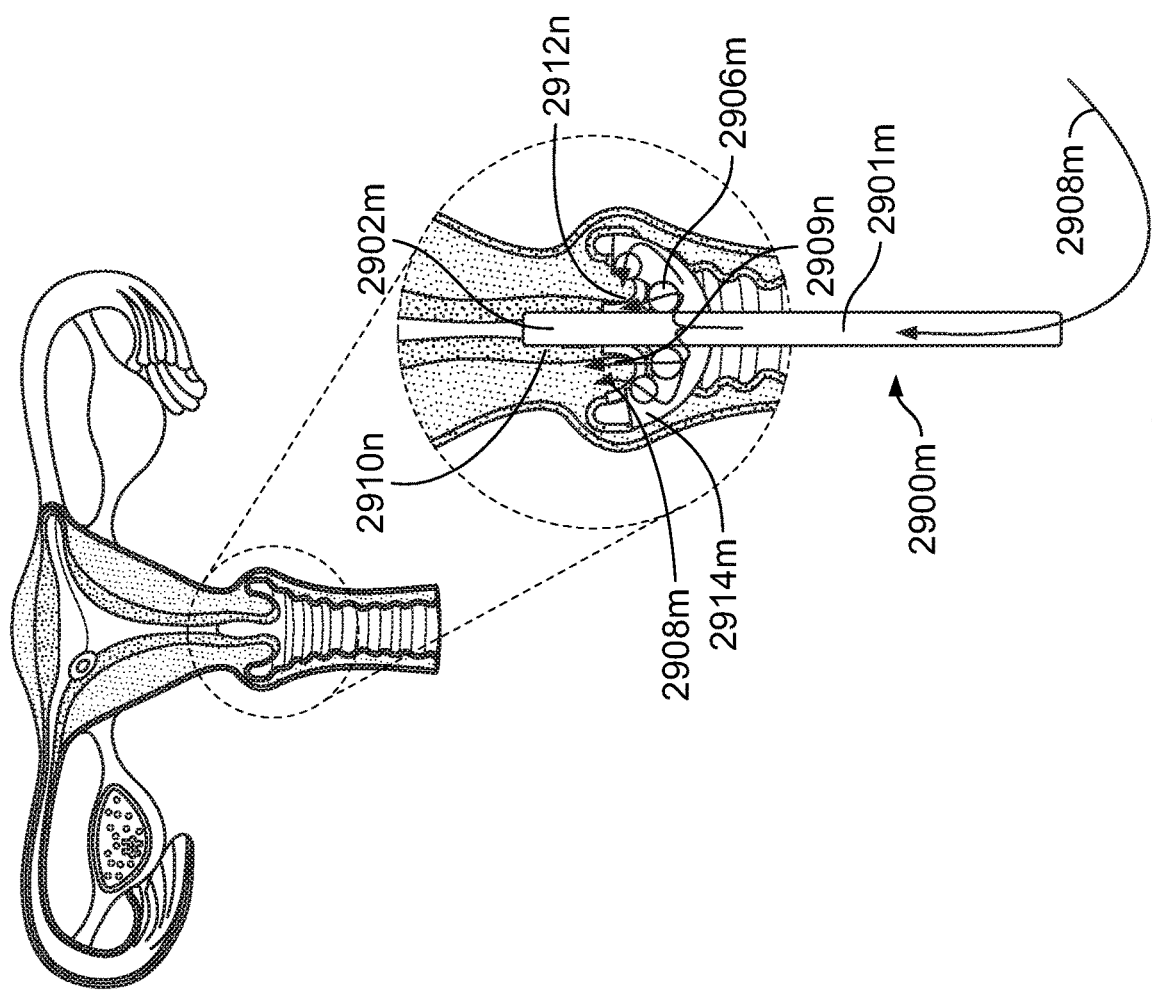
FIG. 29N is an illustration of the catheter of FIG. 29M positioned in a cervix of a patient.
Figure 29M:
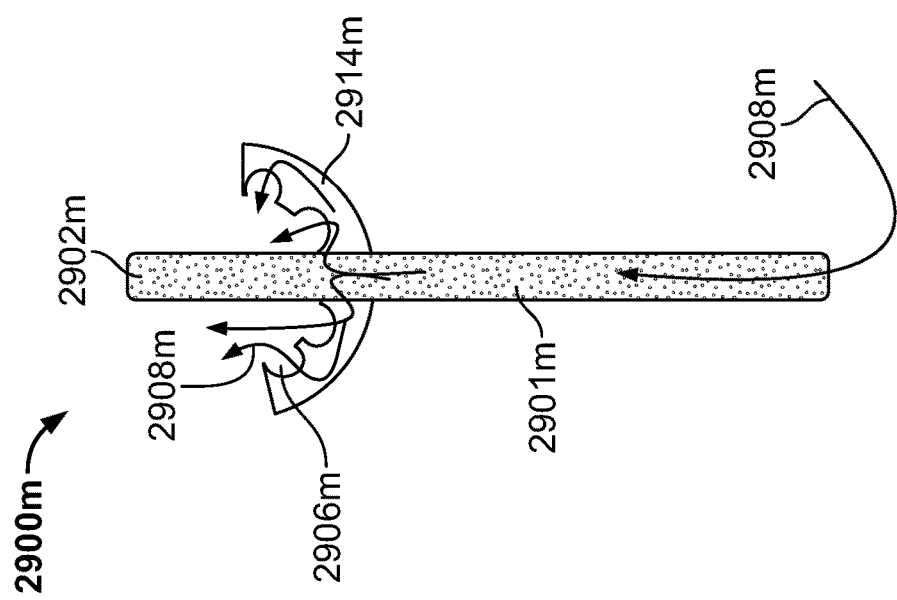
FIG. 29M is an illustration of a water cooled catheter used in cervical ablation, in accordance with one embodiment of the present specification.

FIG. 29M is an illustration of a water cooled catheter 2900m used in cervical ablation, in accordance with one embodiment of the present specification, and FIG. 29N is an illustration of the catheter 2900m of FIG. 29M positioned in a cervix 2909n of a patient. Referring to FIGS. 29M and 29N simultaneously, the catheter 2900m comprises an elongate body 2901m, a proximal end, a distal end, and a water cooled tip 2902m at its distal end. A cervical cup 2914m is attached to the catheter body 2901m and includes a plurality of ports 2906m which are in fluid communication with the proximal end of the catheter 2900m. Vapor 2908m is provided at the proximal end of the catheter 2900m and is delivered to the cervix 2909n via ports 2906m. In an embodiment, the vapor 2908m ablates the transformation zone 2912n at the cervix 2909n. The water cooled tip 2902m of the catheter 2900m cools the cervical canal 2910n during ablation.

Figure 29O:
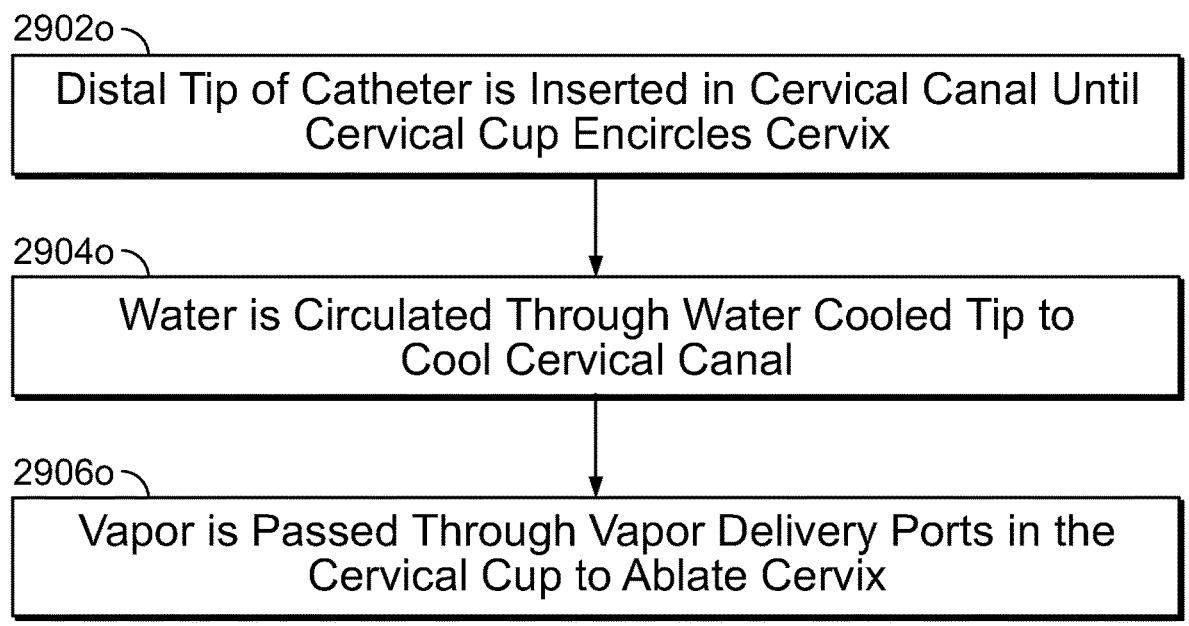
FIG. 29O is a flowchart listing the steps involved in cervical ablation performed using the catheter of FIG. 29M.

FIG. 29O is a flowchart listing the steps involved in cervical ablation performed using the catheter of FIG. 29M. At step 2902o the distal tip of the catheter is inserted into the cervical canal until the cervical cup of the catheter encircles the cervix. Water is circulated through the water cooled tip to cool the cervical canal at step 2904o. At step 2906o vapor is passed through the vapor delivery ports in the cervical cup to ablate the cervix.

In various embodiments, ablation therapy provided by the vapor ablation systems of the present specification is delivered to achieve the following therapeutic endpoints for cervical ablation: maintain a tissue temperature at 100° C. or less; ablate a cervical mucosa without significant injury to the cervical canal; ablate at least 50% of a surface area of a targeted abnormal cervical mucosa such that, upon healing, said abnormal cervical mucosa is replaced by normal cervical mucosa; elimination of more than 25% of abnormal cervical mucosa as assessed by colposcopy; and ablate more than 25% of abnormal cervical mucosa and less than 25% of a total length of a cervical canal.

Figure 30A:
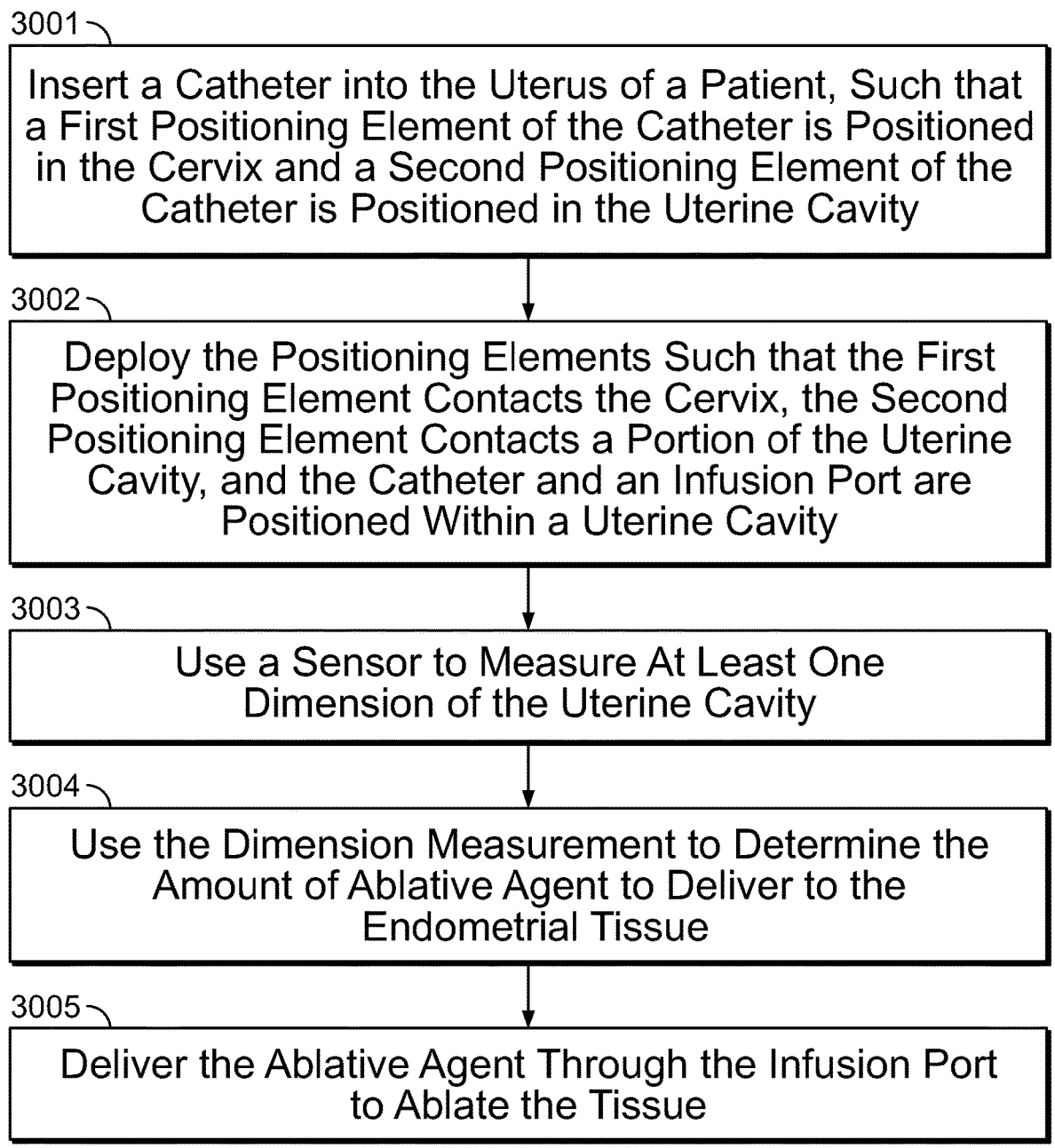
FIG. 30A is a flowchart illustrating a method of ablation of endometrial tissue in accordance with one embodiment of the present specification.

FIG. 30A is a flowchart illustrating a method of ablation of endometrial tissue in accordance with one embodiment of the present specification. Referring to FIG. 30A, the first step 3001 includes inserting a catheter of an ablation device through a cervix and into a uterus of a patient, wherein the catheter includes a hollow shaft through which an ablative agent can travel, at least one first positioning element, at least one second positioning element positioned distal to the at least one first positioning element, and at least one infusion port for delivering the ablative agent. In an embodiment, the ablation device includes a controller comprising a microprocessor for controlling the delivery of the ablative agent. The catheter is passed through the cervix such that a first positioning element is positioned in the cervix and a second positioning element is positioned in the uterine cavity. In one embodiment, the second positioning element is positioned proximate the fundus of the uterus. The two positioning elements are deployed such that the first positioning element contacts the cervix, the second positioning element contacts a portion of the uterine cavity, and the catheter and an infusion port are positioned within a uterine cavity of the patient in step 3002. Finally, in step 3005, an ablative agent is delivered through the infusion port to ablate the endometrial tissue.

Optionally, a sensor is used to measure at least one dimension of the uterine cavity in step 3003 and the measurement is used to determine the amount of ablative agent to be delivered in step 3004.

Figure 30B:
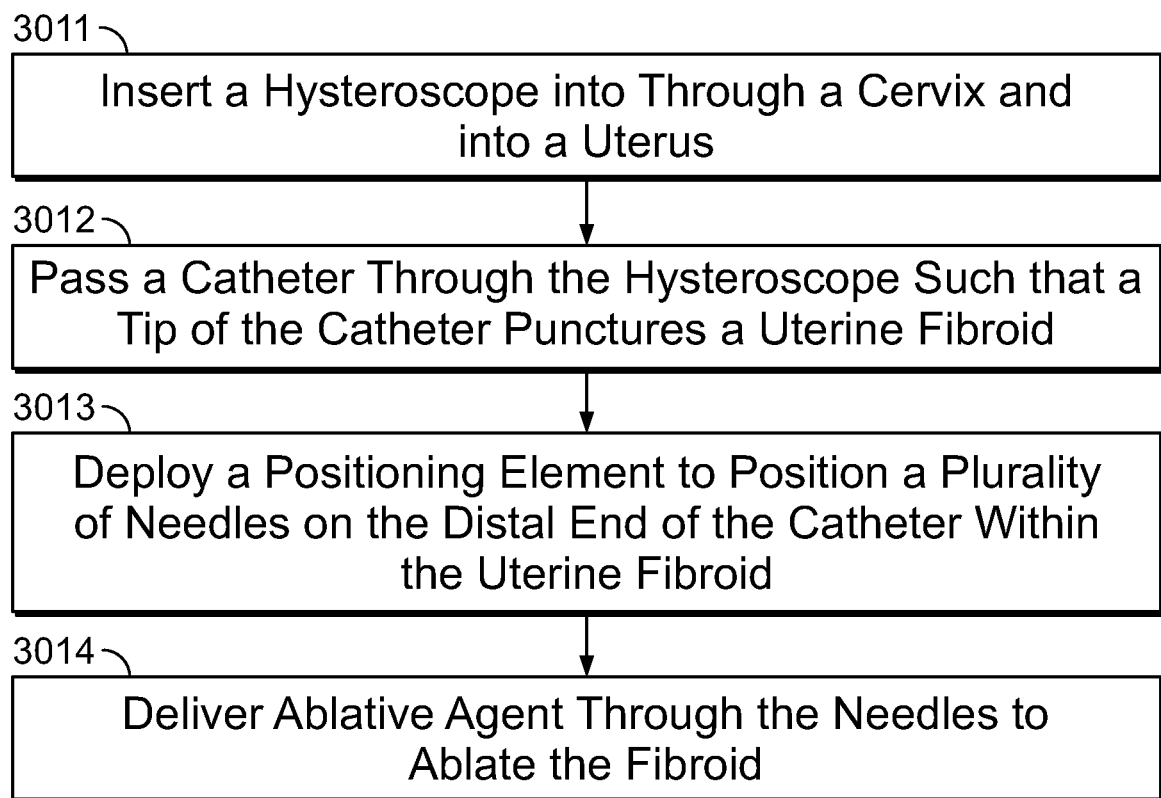

FIG. 30B is a flowchart illustrating a method of ablating a uterine fibroid. Referring to FIG. 30B, the first step 3011 includes inserting a hysteroscope through the cervix and into a uterus of a patient. Next, in step 3012 a catheter of an ablation device is passed through the hysteroscope, wherein the catheter includes a hollow shaft through which an ablative agent can travel, a puncturing tip at its distal end, at least one positioning element, and a plurality of needles on a distal end of the catheter and configured to deliver ablative agent to said uterine fibroid. In an embodiment, the ablation device includes a controller comprising a microprocessor for controlling the delivery of the ablative agent. The catheter is passed through said hysteroscope such that the puncturing tip of the catheter punctures the uterine fibroid. In the next step 3013, the at least one positioning element is deployed to position the catheter within the uterine fibroid such that the plurality of needles on the distal end of said catheter are positioned within the uterine fibroid. Finally, in step 3014, an ablative agent is delivered through the needles to ablate the fibroid.

Prostate

Figure 31A:
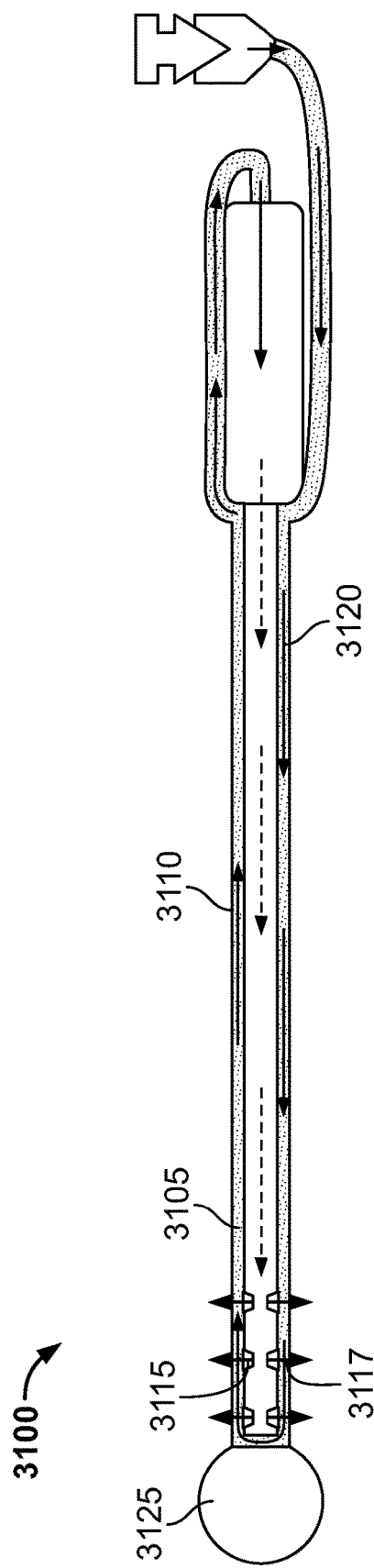
Figure 31B:
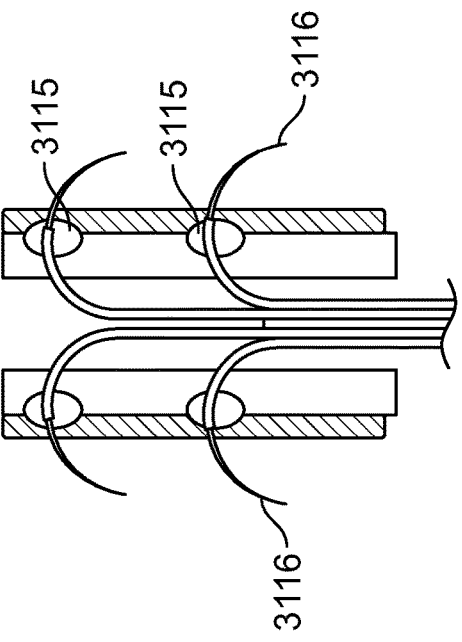

FIG. 31A is an illustration of a water cooled catheter 3100 while FIG. 31B is a cross-section of the tip of the catheter 3100, in accordance with another embodiment of the present specification. Referring now to FIGS. 31A and 31B, the catheter 3100 comprises an elongate body 3105 having a proximal end and a distal end. The distal end includes a positioning element 3125, such as an inflatable balloon. A plurality of openings 3115 are located proximate the distal end for enabling a plurality of associated thermally conductive elements 3116, such as needles, to be extended (at an angle from the catheter 3100, wherein the angle ranges between 30 to 90 degrees) and deployed or retracted through the plurality of openings 3115. In accordance with an aspect, the plurality of retractable needles 3116 are hollow and include at least one opening to allow delivery of an ablative agent, such as steam or vapor 3117, through the needles 3116 when the needles 3116 are extended and deployed through the plurality of openings 3115. A sheath 3110 extends along the body 3105 of the catheter 3100, including the plurality of openings 3115, to the distal end. The plurality of openings 3115 extend from the body 3105 and through the sheath 3110 to enable the plurality of needles 3116 to be extended beyond the sheath 3110 when deployed. During use, cooling fluid such as water or air 3120 is circulated through the sheath 3110 to cool the catheter 3100. Vapor 3117 for ablation and cooling fluid 3120 for cooling are supplied to the catheter 3100 at its proximal end.

It should be noted that alternate embodiments may include two positioning elements or balloons—one at the distal end and the other proximate the openings 3115 such that the openings 3115 are located between the two balloons.

Figure 32A:
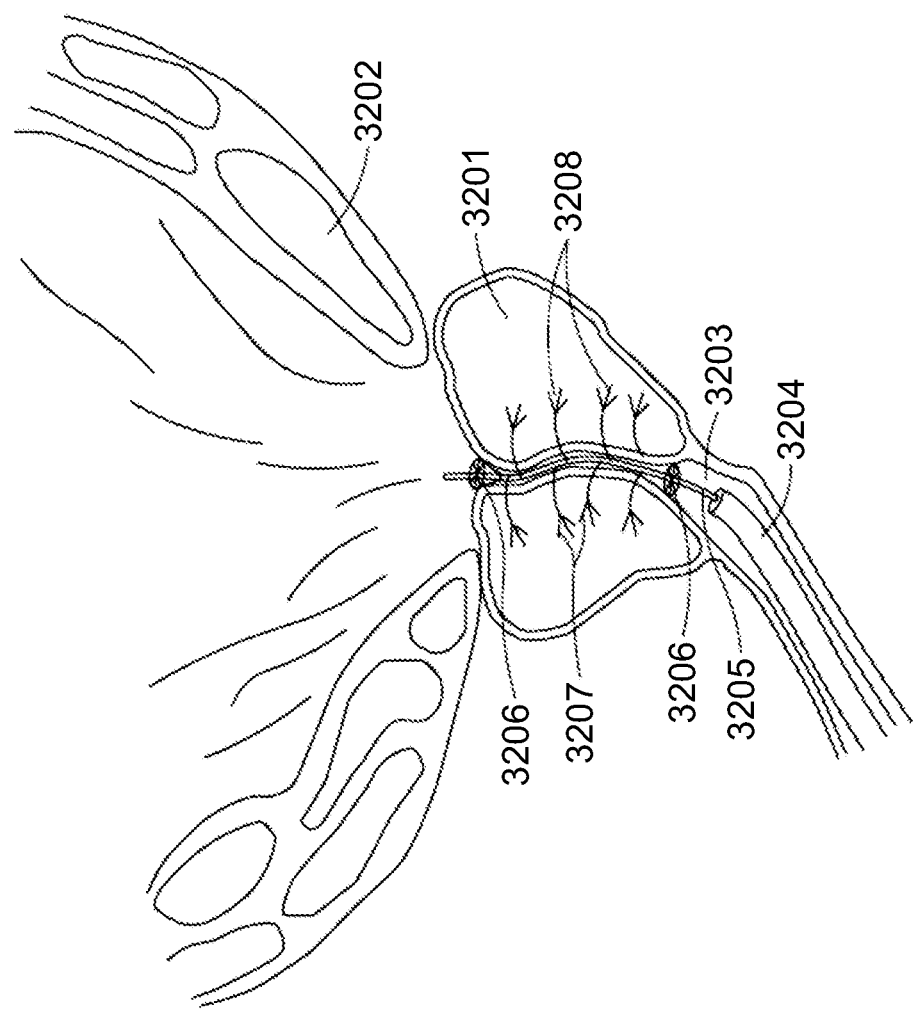

FIG. 32A illustrates prostate ablation being performed on an enlarged prostrate in a male urinary system by using a catheter (such as the catheter 3100 of FIG. 31A—with two positioning elements), in accordance with an embodiment of the present specification. A cross-section of a male genitourinary tract having an enlarged prostate 3201, bladder 3202, and urethra 3203 is illustrated. The urethra 3203 is compressed by the enlarged prostate 3201. The ablation catheter 3205 is passed through the cystoscope 3204 positioned in the urethra 3203 distal to the obstruction. The positioning elements 3206 are deployed to center the catheter in the urethra 3203 and one or more insulated needles 3207 are passed to pierce the prostate 3201. The vapor ablative agent 3208 is passed through the insulated needles 3207 thus causing ablation of the diseased prostatic tissue resulting in shrinkage of the prostate.

The size of the enlarged prostate could be calculated by using the differential between the extra-prostatic and intra-prostatic urethra. Normative values could be used as baseline. Additional ports for infusion of a cooling fluid into the urethra can be provided to prevent damage to the urethra while the ablative energy is being delivered to the prostrate for ablation, thus preventing complications such as stricture formation.

In one embodiment, the positioning attachment must be separated from the ablation region by a distance of greater than 0.1 mm, preferably 1 mm to 5 mm and no more than 2 cm. In another embodiment, the positioning attachment can be deployed in the bladder and pulled back into the urethral opening/neck of the bladder thus fixing the catheter. In one embodiment, the positioning device is between 0.1 mm and 10 cm in diameter.

Figure 32C:
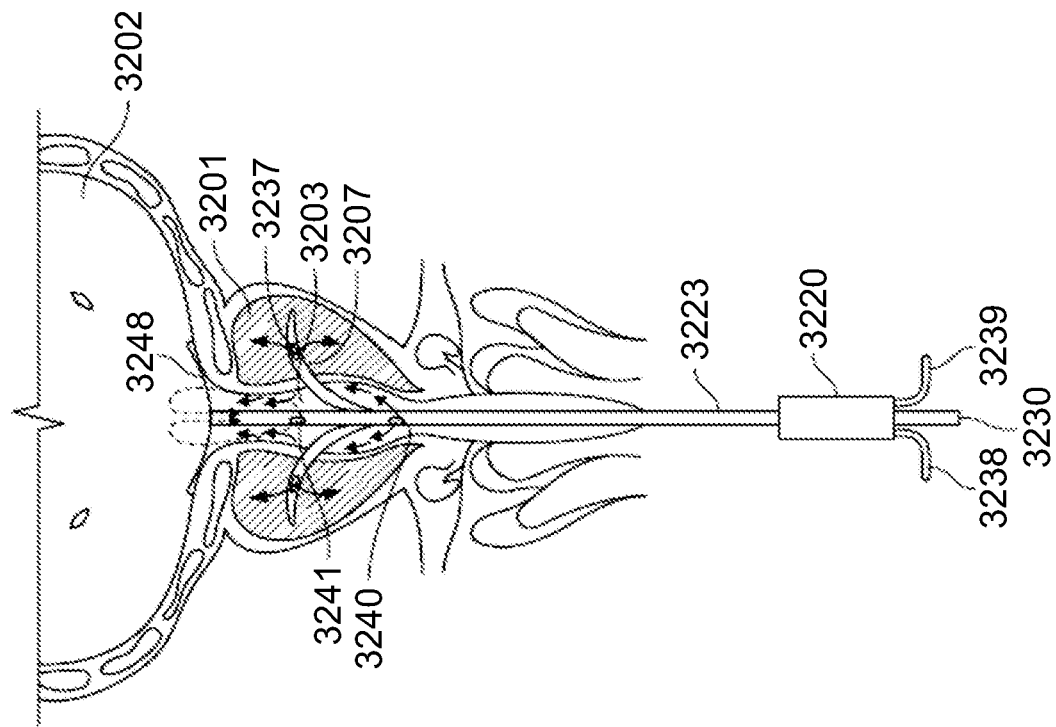
Figure 32B:
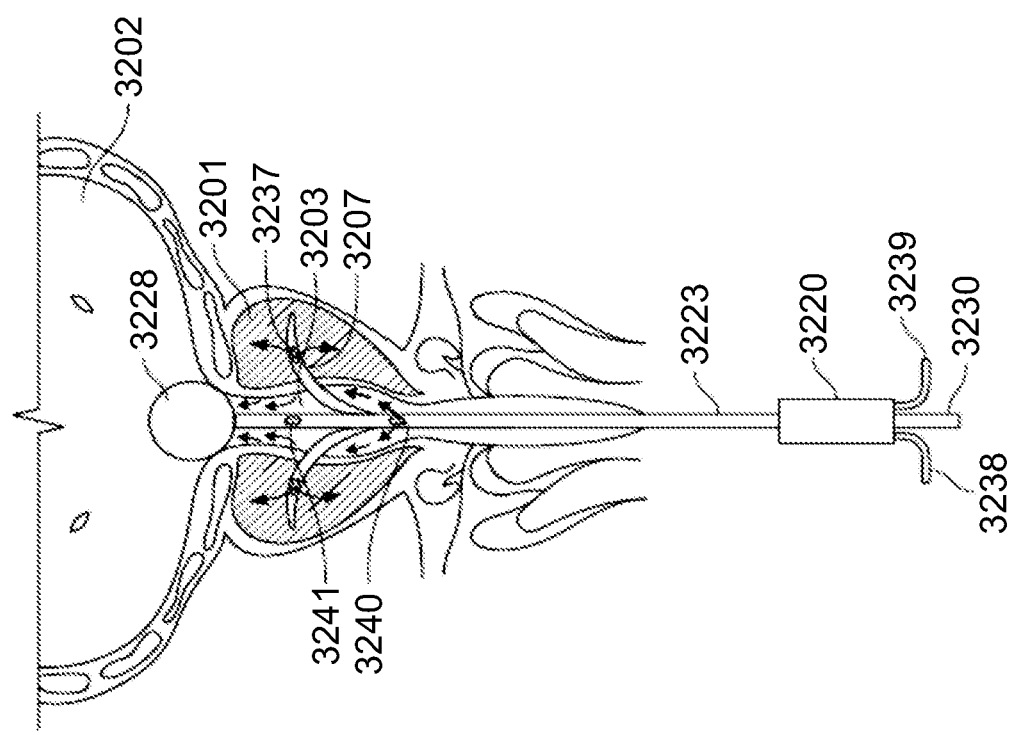

FIG. 32B is an illustration of transurethral prostate ablation being performed on an enlarged prostrate 3201 in a male urinary system using an ablation device (such as the catheter 3100 of FIG. 31A—with one positioning element), in accordance with one embodiment of the present specification. Also depicted in FIG. 32B are the urinary bladder 3202 and prostatic urethra 3203. An ablation catheter 3223 with a handle 3220 and a positioning element 3228 is inserted into the urethra 3203 and advanced into the bladder 3202. The position element 3228 is inflated and pulled to the junction of the bladder with the urethra, thus positioning needles 3207 at a predetermined distance from the junction. Using a pusher 3230, the needles 3207 are then pushed out at an angle between 30 and 90 degree from the catheter 3223 through the urethra 3203 into the prostate 3201. Vapor is administered through a port 3238 that travels through the shaft of the catheter 3223 and exits from openings 3237 in the needles 3207 into the prostatic tissue, thus ablating the prostatic tissue. In one embodiment, the needles 3207 are insulated. Optional port 3239 allows for insertion of cool fluid at a temperature <37 degree C. through opening 3240 to cool the prostatic urethra. Optional temperature sensors 3241 can be installed to detect the temperature of the prostatic urethra and modulate the delivery of vapor.

FIG. 32C is an illustration of transurethral prostate ablation being performed on an enlarged prostrate 3201 in a male urinary system using an ablation device, in accordance with another embodiment of the present specification. Also depicted in FIG. 32C are the urinary bladder 3202 and prostatic urethra 3203. An ablation catheter 3223 with a handle 3220 and a positioning element 3248 is inserted into the urethra 3203 and advanced into the bladder 3202. The positioning element 3248 is a compressible disc that is expanded in the bladder 3202 and pulled to the junction of the bladder with the urethra, thus positioning needles 3207 at a predetermined distance from the junction. Using a pusher 3230, the needles 3207 are then pushed out at an angle between 30 and 90 degree from the catheter 3223 through the urethra 3203 into the prostate 3201. Vapor is administered through a port 3238 that travels through the shaft of the catheter 3223 and exits through openings 3237 in the needles 3207 into the prostatic tissue, thus ablating the prostatic tissue. In one embodiment, the needles 3207 are insulated. Optional port 3239 allows for insertion of cool fluid at a temperature <37 degree C. through opening 3240 to cool the prostatic urethra. Optional temperature sensors 3241 can be installed to detect the temperature of the prostatic urethra and modulate the delivery of vapor.

Figure 32D:
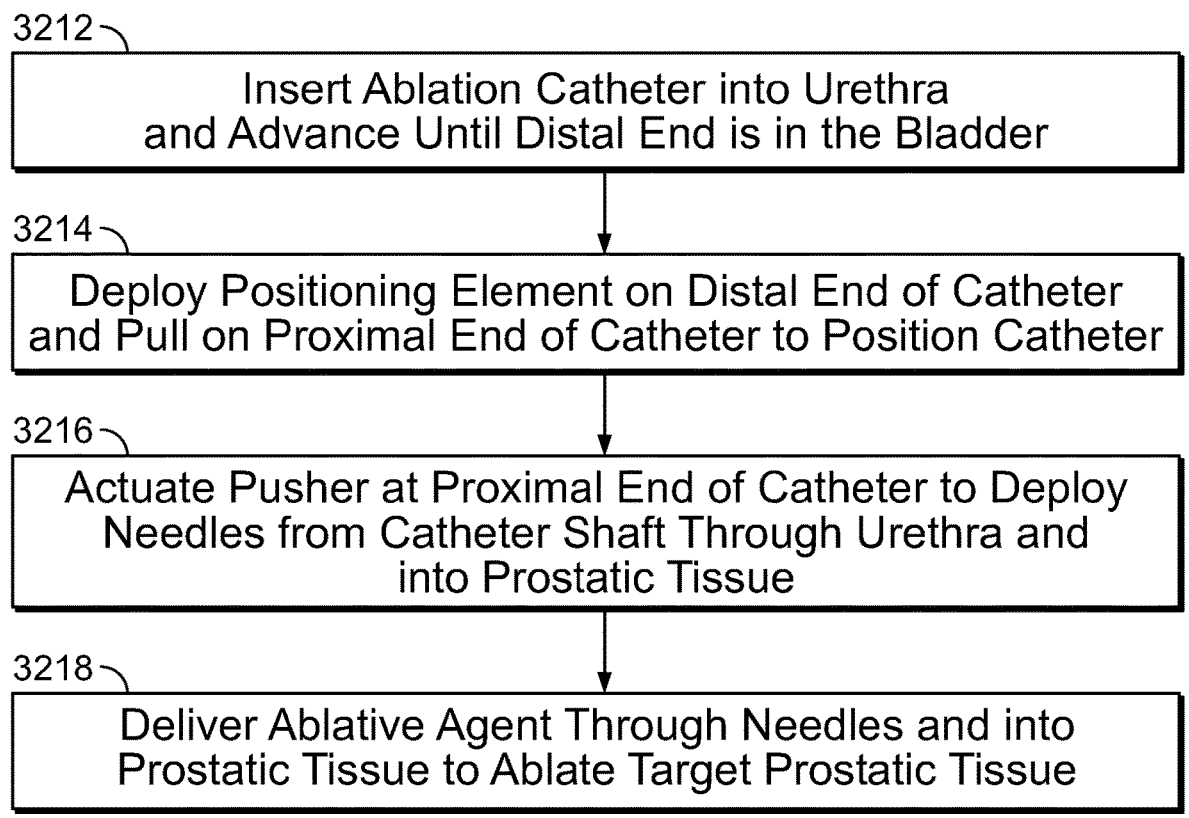

FIG. 32D is a flow chart listing the steps involved in a transurethral enlarged prostate ablation process using an ablation catheter, in accordance with one embodiment of the present specification. At step 3212, an ablation catheter (such as the catheter 3100 of FIG. 31A) is inserted into the urethra and advanced until its distal end is in the bladder. A positioning element is then deployed on the distal end of the catheter, at step 3214, and the proximal end of the catheter is pulled so that the positioning element abuts the junction of the bladder with the urethra, thereby positioning the catheter shaft within the urethra. A pusher at the proximal end of the catheter is actuated to deploy needles from the catheter shaft through the urethra and into the prostatic tissue at step 3216. At step 3218, an ablative agent is delivered through the needles and into the prostate to ablate the target prostatic tissue.

Figure 32E:
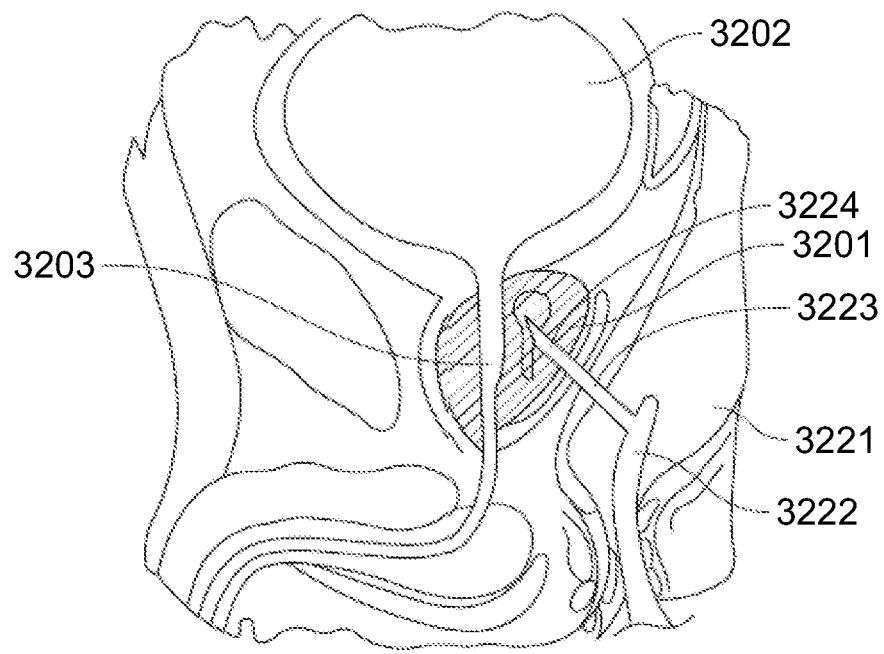

FIG. 32E is an illustration of transrectal prostate ablation being performed on an enlarged prostrate in a male urinary system using an ablation device, in accordance with one embodiment of the present specification. Also depicted in FIG. 32E are the urinary bladder 3202 and prostatic urethra 3203. The ablation device comprises a catheter 3223 with a needle tip 3224. An endoscope 3222 is inserted into the rectum 3221 for the visualization of the enlarged prostate 3201. In various embodiments, the endoscope 3222 is an echoendoscope or a transrectal ultrasound such that the endoscope can be visualized using radiographic techniques. The catheter 3223 with needle tip 3224 is passed through a working channel of the endoscope and the needle tip 3224 is passed transrectally into the prostate 3201. A close-up illustration of the distal end of the catheter 3223 and needle tip 3204 is depicted in FIG. 32G. An ablative agent is then delivered through the needle tip 3224 into the prostatic tissue for ablation. In one embodiment, the catheter 3223 and needle tip 3224 are composed of a thermally insulated material. In various embodiments, the needle tip 3224 is an echotip or sonolucent tip that can be observed using radiologic techniques for accurate localization in the prostate tissue. In one embodiment, an optional catheter (not shown) can be placed in the urethra to insert fluid to cool the prostatic urethra 3203. In one embodiment, the inserted fluid has a temperature less than 37° C.

Figure 32F:
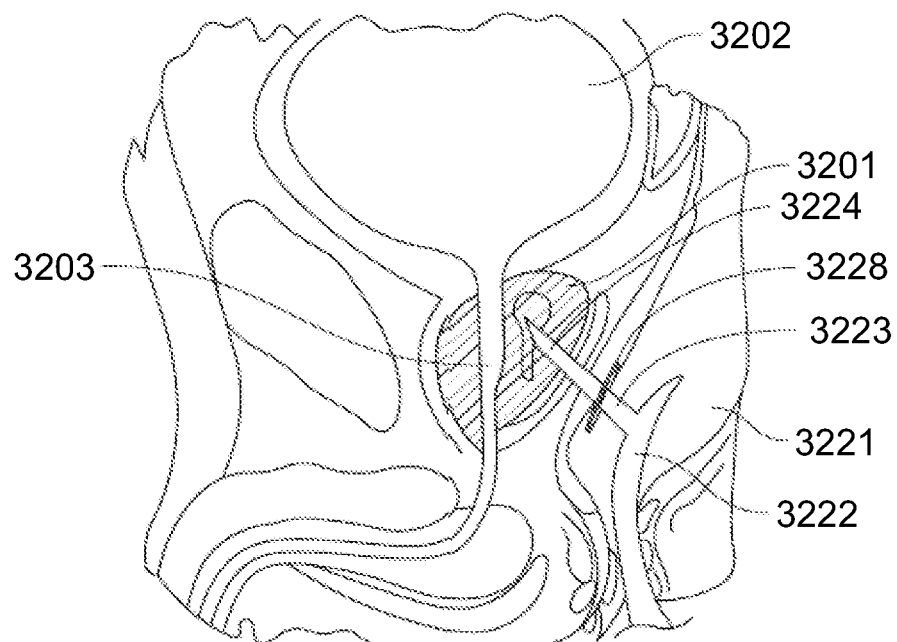
Figure 32G:
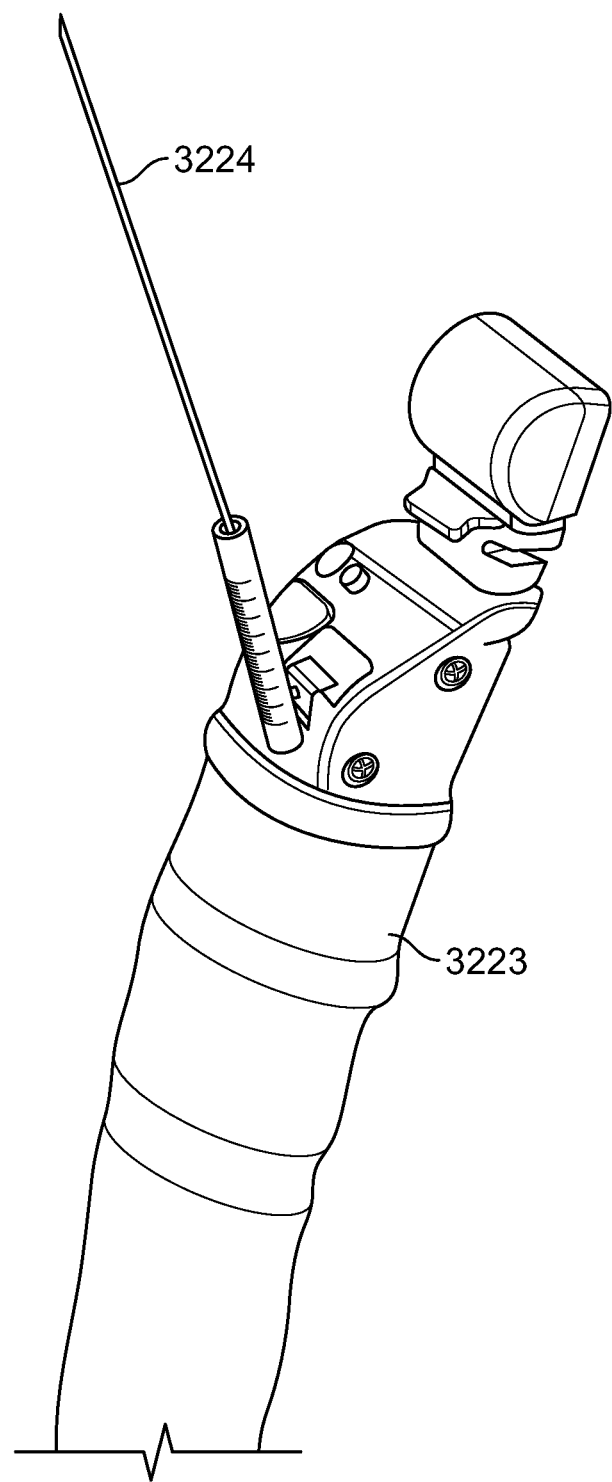

FIG. 32F is an illustration of transrectal prostate ablation being performed on an enlarged prostrate in a male urinary system using a coaxial ablation device having a positioning element, in accordance with another embodiment of the present specification. Also depicted in FIG. 32F are the urinary bladder 3202 and prostatic urethra 3203. The ablation device comprises a coaxial catheter 3223 having an internal catheter with a needle tip 3224 and an external catheter with a positioning element 3228. An endoscope 3222 is inserted into the rectum 3221 for the visualization of the enlarged prostate 3201. In various embodiments, the endoscope 3222 is an echoendoscope or a transrectal ultrasound such that the endoscope can be visualized using radiographic techniques. The coaxial catheter 3223 with needle tip 3224 and positioning element 3228 is passed through a working channel of the endoscope such that the positioning element 3228 comes to rest up against the rectal wall and the internal catheter is advanced transrectally, thereby positioning the needle tip 3224 at a predetermined depth in the prostate 3201. A close-up illustration of the distal end of the catheter 3223 and needle tip 3204 is depicted in FIG. 32G. In one embodiment, the positioning element is a compressible disc that has a first, compressed pre-employment configuration and a second, expanded deployed configuration once it has passed beyond the distal end of the endoscope 3222. An ablative agent is then delivered through the needle tip 3224 into the prostatic tissue for ablation. In one embodiment, the coaxial catheter 3223, needle tip 3224, and positioning element 3228 are composed of a thermally insulated material. In various embodiments, the needle tip 3224 is an echotip or sonolucent tip that can be observed using radiologic techniques for accurate localization in the prostate tissue. In one embodiment, an optional catheter (not shown) can be placed in the urethra to insert fluid to cool the prostatic urethra 3203. In one embodiment, the inserted fluid has a temperature less than 37° C.

Figure 32H:
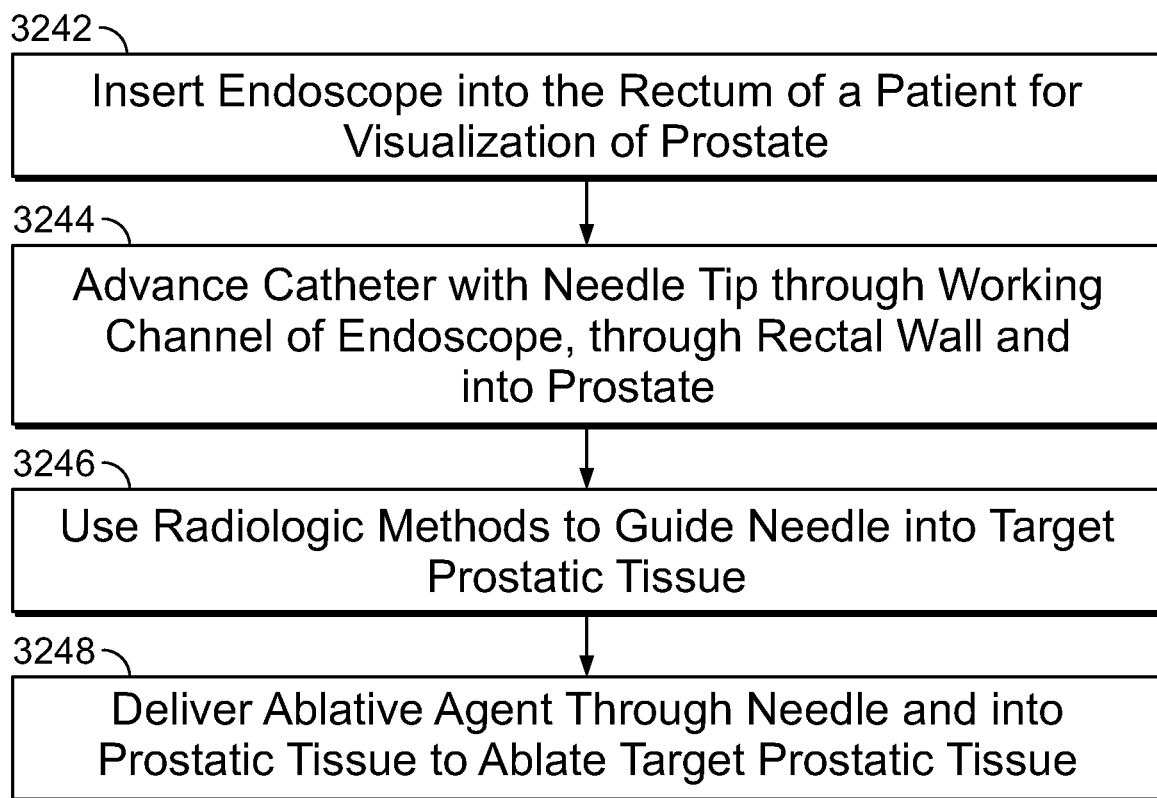

FIG. 32H is a flow chart listing the steps involved in a transrectal enlarged prostate ablation process using an ablation catheter, in accordance with one embodiment of the present specification. At step 3242, an endoscope is inserted into the rectum of a patient for visualization of the prostate. A catheter with a needle tip is then advanced, at step 3244, through a working channel of the endoscope and through the rectal wall and into the prostate. Radiologic methods are used to guide the needle into the target prostatic tissue at step 3246. At step 3248, an ablative agent is delivered through the needle and into the prostate to ablate the target prostatic tissue.

FIG. 33A illustrates an ablation catheter 3300 while FIG. 33B is a cross-section of the tip of the catheter 3300, in accordance with an embodiment of the present specification. Referring now to FIGS. 33A and 33B, the catheter 3300 comprises an elongate body 3305 having a proximal end and a distal end. A plurality of openings 3315 and an inflatable balloon 3325 are located proximate the distal end. The plurality of openings 3315 enable a plurality of associated thermally conductive elements 3316, such as needles, to be extended (at an angle from the catheter 3300, wherein the angle ranges between 30 to 90 degrees) or retracted through the plurality of openings 3315. In accordance with an aspect, the plurality of retractable needles 3316 are hollow and include at least one opening to allow delivery of an ablative agent, such as steam or vapor 3317, through the needles 3316 when the needles are extended and deployed through the plurality of openings 3315. The plurality of openings 3315 extend from the body 3305 and through the balloon 3325 to enable the plurality of needles 3316 to be extended beyond the balloon 3325 when deployed.

A heating chamber 3310 is located at the proximal end of the catheter 3300. The heating chamber 3310 comprises a metal coil wound about a ferromagnetic core. The chamber 3310 is filled with water via a water inlet port 3311 at a proximal end of the chamber 3310. Alternating current is provided to the coil creating a magnetic field that induces electric current flow in the ferromagnetic core thereby heating the chamber 3310 and causing the water within to vaporize. The resulting steam or vapor 3317 exits the needles 3316 to ablate target tissue. The balloon 3325 is inflated by filling it with a coolant that is supplied to the balloon 3325 through a coolant port 3312 at the proximal end of the chamber 3310. During use, the balloon 3325 is inflated with the coolant while vapor or steam 3317, generated in the chamber 3310, is delivered through the plurality of needles 3316. Since the needles 3316 pierce into the target tissue during use, the steam or vapor 3317 delivered through the pierced needles 3316 cause ablation of tissue located deep within the target tissue. The coolant filled inflated balloon 3325 contacts the surface of the non-target tissue and maintains the ambient temperature on the surface of the non-target tissue to a desired level, such as below 60 degrees C. in some embodiments. This enables the vapor 3317 to ablate deeper target tissue without circumferentially ablating the non-target tissue at the surface.

FIG. 33C is an illustration of prostate ablation being performed on an enlarged prostrate in a male urinary system using the ablation catheter 3300 of FIG. 33A, in accordance with an embodiment of the present specification. Also depicted in FIG. 33C are the prostate 3330 and prostatic urethra 3332. Referring now to FIGS. 33A and 33C, the ablation catheter 3300 with the heating chamber 3310 and the inflatable cooling balloon 3325 is inserted into the patient's urethra and advanced into the prostatic urethra 3332 so as to position the plurality of openings 3315 proximate the tissue to be ablated. The cooling balloon 3325 is inflated by filling it with coolant supplied from the coolant port 3312, so that the inflated cool balloon 3325 abuts the surface of the prostatic urethra proximate to the prostatic tissue to be ablated. Using a pusher, the needles 3316 are then pushed out at an angle (ranging between 30 and 90 degrees, in various embodiments) from the catheter 3300 into the prostate 3330. Water (through the water inlet port 3311) is administered into the chamber 3310 where it is converted into steam or vapor 3317. The steam or vapor 3317 travels through the body 3305 of the catheter and exits from openings in the needles 3316 into the prostatic tissue, thus ablating the prostatic tissue. In one embodiment, the needles 3316 are insulated. The coolant filled inflated balloon 3325 maintains the ambient temperature on the surface of the prostatic urethra tissue to a desired level, such as below 60 degree C. in some embodiments. This enables the vapor 3317 to ablate deeper prostatic tissue without circumferentially ablating the prostatic urethra tissue at the surface. Optional temperature sensors can be installed to detect the temperature of the prostatic urethra and modulate the delivery of vapor.

FIG. 33D is a flow chart listing the steps involved in a transurethral enlarged prostate ablation process using the ablation catheter 3300 of FIG. 33A, in accordance with one embodiment of the present specification. Referring now to FIGS. 33A and 33D, at step 3340, the ablation catheter 3300 is inserted into the urethra and advanced until the plurality of openings 3315 are positioned proximate the prostatic tissue to be ablated within the prostatic urethra. At step 3342, the cooling balloon 3325 is inflated, with coolant supplied from the coolant port 3312, to fix the catheter 3300 within the prostatic urethra and maintain ambient temperature on the surface of the tissue to be ablated. Using a pusher, at step 3344, the needles 3316 are then pushed out at an angle (between 30 and 90 degrees, in various embodiments) from the catheter 3300 through the prostatic urethra and into the prostate up to a desirable depth. Vapor is delivered, from openings in the needles 3316, into the prostatic tissue at the desirable depth, thus ablating the prostatic tissue, without ablating the surface of the prostatic urethra. An optional temperature sensor is utilized to monitor the temperature of the surface of the prostatic urethra and control or modulate the flow of the coolant to maintain the temperature of the surface of the prostatic urethra below, say, 60 degrees C.

FIG. 34A illustrates an ablation catheter 3400 while FIG. 34B is a cross-section of the tip of the catheter 3400, in accordance with an embodiment of the present specification. Referring now to FIGS. 34A and 34B, the catheter 3400 comprises an elongate body 3405 having a proximal end and a distal end. A first plurality of openings 3415, a second plurality of openings 3418, and a silicone or Teflon membrane 3425, covering the first and second pluralities of openings, are located proximate the distal end. The first plurality of openings 3415 enables a plurality of associated thermally conductive elements 3416, such as needles, to be extended (at an angle from the catheter 3400, wherein the angle ranges between 30 to 90 degrees) or retracted through the plurality of openings 3415. The second plurality of openings 3418 enables a coolant 3419, supplied via coolant port 3412 at the proximal end of the catheter 3400, to be delivered to the ablation zone. In accordance with an aspect, the plurality of retractable needles 3416 are hollow and include at least one opening to allow delivery of an ablative agent, such as steam or vapor 3417, through the needles 3416 when the needles are extended and deployed through the first plurality of openings 3415. The plurality of openings 3415 extend from the body 3405 and through the balloon 3425 to enable the plurality of needles 3416 to be extended beyond the membrane 3425 when deployed. The needles 3416 pierce through the membrane 3425, when deployed, such that the membrane 3425 insulates the needles 3416 as these are being deployed and pierced into a target tissue.

A heating chamber 3410 is located at the proximal end of the catheter 3400. The heating chamber 3410 comprises a metal coil wound about a ferromagnetic core. The chamber 3410 is filled with water via a water inlet port 3411 at a proximal end of the chamber 3410. Alternating current is provided to the coil creating a magnetic field that induces electric current flow in the ferromagnetic core thereby heating the chamber 3410 and causing the water within to vaporize. The resulting steam or vapor 3417 exits the needles 3416 to ablate target tissue. The coolant port 3412, at the proximal end of the chamber 3410, supplies coolant 3419 for delivery through the second plurality of openings 3418 into the prostatic urethra. During use, the coolant 3419 is delivered to the ablation zone through coolant openings 3418, while vapor or steam 3417, generated in the chamber 3410, is delivered through the plurality of needles 3416.

Since the needles 3416 pierce into the target tissue during use, the steam or vapor 3417 delivered through the pierced needles 3416 cause ablation of tissue located deep within the target tissue. The coolant 3419 directly contacts the surface of the non-target urethral tissue and maintains the ambient temperature on the surface of the non-target tissue to a desired level, such as below 60 degrees C. in some embodiments, preventing or diminishing clinically significant thermal injury to the non-target tissue. This enables the vapor 3417 to ablate deeper prostatic tissue without circumferentially ablating the urethral tissue at the surface. Also, the membrane 3425 insulates the piercing needles 3416 and prevents the coolant 3419 from significantly cooling the needles 3416.

FIG. 34C is an illustration of prostate ablation being performed on an enlarged prostrate in a male urinary system using the ablation catheter 3400 of FIG. 34A, in accordance with an embodiment of the present specification. Also depicted in FIG. 34C are the prostate 3430 and prostatic urethra 3432. Referring now to FIGS. 34A and 34C, the ablation catheter 3400 with the heating chamber 3410 and the inflatable cooling balloon 3425 is inserted into the patient's urethra and advanced into the prostatic urethra 3432 so as to position the first plurality of openings 3415 and second plurality of openings 3418 proximate the prostatic tissue to be ablated. The coolant 3419 is delivered, through the second plurality of openings 3418, to the prostatic urethra 3432. Using a pusher, the needles 3416 are then pushed out at an angle (ranging between 30 and 90 degrees, in various embodiments) from the catheter 3400 into the prostate 3430. The pushed out needles 3416 also perforate the insulating membrane 3425 covering the openings 3415.

Water (through the water inlet port 3411) is administered into the chamber 3410 where it is converted into steam or vapor 3417. The steam or vapor 3417 travels through the body 3405 of the catheter and exits from openings in the needles 3416 into the prostatic tissue, thus ablating the prostatic tissue. The needles 3416 are insulated by the membrane 3421 while the needles 3416 perforate the membrane 3425. The coolant filled inflated balloon 3425, as well as the coolant 3419 delivered to the prostatic urethra 3432, via the second plurality of openings 3418, maintain the ambient temperature on the surface of the prostatic tissue to a desired level, such as below 60 degree C. in some embodiments. This enables the vapor 3417 to ablate deeper prostatic tissue without ablating the prostatic urethra tissue at the surface. Optional temperature sensors can be installed to detect the temperature of the prostatic urethra and modulate the delivery of vapor 3417 and/or coolant 3419.

FIG. 34D is a flow chart listing the steps involved in a transurethral enlarged prostate ablation process using the ablation catheter 3400 of FIG. 34A, in accordance with one embodiment of the present specification. Referring now to FIGS. 34A and 34D, at step 3440, the ablation catheter 3400 is inserted into the urethra and advanced until the first plurality of openings 3415 is positioned proximate the prostatic tissue to be ablated within the prostatic urethra. At step 3442, the cooling balloon 3425 is inflated, with coolant supplied from the coolant port 3412, to fix the catheter 3400 within the prostatic urethra and maintain ambient temperature on the surface of the prostatic tissue to be ablated. Using a pusher, at step 3444, the needles 3416 are then pushed out at an angle (between 30 and 90 degrees, in various embodiments) from the catheter 3400 to pierce through the insulating membrane 3421, through the prostatic urethra and into the prostate up to a desirable depth. Vapor 3417 is delivered, from openings in the needles 3416, into the prostatic tissue at the desirable depth, thus ablating the prostatic tissue, without ablating the surface of the prostatic tissue. At step 3446, coolant 3419 is administered into the prostatic urethra, via the second plurality of openings 3418, to maintain ambient temperature on the surface of the prostatic tissue to be ablated. The membrane 3421 insulates the piercing needles 3416 from the coolant 3419 administered into the prostatic urethra. An optional temperature sensor is utilized to monitor the temperature of the surface of the prostatic tissue and control or modulate the flow of the coolant to maintain the temperature of the surface of the prostatic tissue below a specific temperature, which, in some embodiments, is 60 degree C.

Referring back to FIGS. 33A and 34A, in accordance with some embodiments, a pump, such as a syringe pump, is used to control the flow of water to the heating chamber 3310, 3410.

In various embodiments, the catheters of the present specification further include at least one thermally conducting element attached to the positioning element. The at least one thermally conducting element is configured to physically contact, and, in some embodiments, penetrate, a target tissue and enhance the delivery of thermal energy into the target tissue for ablation. FIG. 35A is an illustration of one embodiment of a positioning element 3571 of an ablation catheter 3570, depicting a plurality of thermally conducting elements 3572 attached thereto. In various embodiments, the positioning element 3571 is an inflatable balloon. The positioning element, or balloon 3571, is inflated to a first volume to bring the thermally conducting elements 3572 into contact with a target tissue. An ablative agent is then delivered to the target tissue through the catheter 3570 and out via at least one delivery port at the distal end of the catheter 3570. Thermal energy from the ablative agent is transferred from the lumen of the catheter 3570 into the air in the balloon 3571, further expanding the volume of the balloon 3571 and pushing the thermally conducting elements 3572 further into the target tissue. Thermal energy from the air in the balloon 3571 is transferred to the thermally conducting elements 3572 and is released into the target tissue for ablation. In various embodiments, the thermally conducting elements 3572 comprise solid or hollow metal spikes or needles. In various embodiments, the balloon 3571 is composed of a thermally insulating material so that ablative thermal energy is predominantly transferred from the thermally conducting elements 3572 into the target tissue.

FIG. 35B is an illustration of one embodiment of a positioning element 3571 of an ablation catheter 3570, depicting a plurality of hollow thermally conducting elements 3573 attached thereto. In one embodiment, each hollow thermally conducting element 3573 includes a valve 3583 at the inlet from a lumen of the positioning element 3571 to a lumen of the hollow thermally conducting element 3573. In various embodiments, the positioning element 3571 is an inflatable balloon. The positioning element, or balloon 3571, is inflated to a first volume to bring the thermally conducting elements 3572 into contact with a target tissue. An ablative agent is then delivered to the target tissue through the catheter 3570 and out via at least one delivery port at the distal end of the catheter 3570. Thermal energy from the ablative agent is transferred from the lumen of the catheter 3570 into the air in the balloon 3571, further expanding the volume of the balloon 3571 and pushing the thermally conducting elements 3573 further into the target tissue. Thermal energy from the air in the balloon 3571 is transferred to the thermally conducting elements 3573 and is released into the target tissue for ablation. In various embodiments, the thermally conducting elements 3573 comprise hollow metal spikes or needles. The thermally conducting elements 3573 include at least one opening at their distal ends which are in fluid communication with a lumen of the thermally conducting elements 3573, which, in turn, is in fluid communication with the interior of the balloon 3571. As seen in the cross section of the catheter 3570, vapor follows a first pathway 3584 to pass from the interior of the balloon 3571, through the thermally conducting elements 3573, and out to the target tissue. In one embodiment, each thermally conducting element 3573 includes a valve 3583 positioned at its junction with the balloon 3571 to control the flow of vapor into each hollow thermally conducting element 3573. In one embodiment, the vapor also follows a second pathway 3585 into the interior of the balloon 3571 to transmit thermal energy and assist in balloon expansion 3571. In another embodiment, flexible tubes 3586 connect the lumen of each thermally conducting element 3573 with a lumen of the catheter 3570, bypassing the interior of the balloon 3571. In one embodiment, the tubes 3586 are composed of silicone. In this embodiment, the vapor can only travel via the first pathway 3584 and air 3587 is used to expand the balloon 3571. In various embodiments, the balloon 3571 is composed of a thermally insulating material so that ablative thermal energy is predominantly transferred from the thermally conducting elements 3573 into the target tissue. In various embodiments, the thermally conducting elements 3573 possess shape memory properties such that they change shape from being generally parallel to the catheter 3570 at a temperature below a patient's body temperature to being generally perpendicular to the catheter 3570 at temperatures above the patient's body temperature.

FIG. 36 is a flowchart illustrating one embodiment of a method of ablation of a tissue using a needle catheter device as described above. The device includes a thermally insulated catheter having a hallow shaft and a retractable needle through which an ablative agent can travel, at least one infusion port on the needle for delivery of the ablative agent, at least one positioning element on a distal end of the catheter, and a controller comprising a microprocessor for controlling the delivery of ablative agent. Referring to FIG. 36, in the first step 3601, a catheter is inserted such that a positioning element is positioned proximate to the tissue to be ablated. The next step 3602 involves extending the needle through the catheter such that the infusion port is positioned proximate to the tissue. Finally in step 3603, an ablative agent is delivered through the infusion port to ablate the tissue. In another embodiment, the device does not include a positioning element and the method does not include a step of positioning the positioning element proximate the tissue to be ablated.

In one embodiment, the needle catheter device described in FIGS. 35A and 35B is also used for vapor ablation of submucosal tissue.

FIG. 37 is a flowchart illustrating a method of ablation of a submucosal tissue using a needle catheter device similar to those as described above. Referring to FIG. 37, in the first step 3701, an endoscope is inserted into a body lumen with its distal end proximate a tissue to be ablated. Next, in step 3702, the submucosal space is punctured using a vapor delivery needle, which is passed by means of a catheter through a working channel of the endoscope. Next, in step 3703, vapor is delivered into a submucosal space, predominantly ablating the submucosa and/or mucosa without irreversibly or significantly ablating the deep muscularis or the serosa. In one embodiment, the mucosa can be optionally resected with a snare or a needle knife for histological evaluation in step 3704.

In another embodiment, the present specification discloses shape changing needles for ablation of prostatic tissue. FIG. 38 is an exemplary illustration of shape changing needles. Referring to FIG. 38, needle 3801a is made up of a flexible material, such as nitinol, and has a curvature in the range of −30 to 120°. In one embodiment, when heat is applied to the needle 3801a, its curvature increases, as shown by 3801b. In one embodiment, for an increase in temperature in the range of 25 degrees C. to 75 degrees C., the increase in the curvature of the needle ranges from −30 to 120°. In accordance with an aspect, the needle 3801a is hollow and includes at least one opening to allow delivery of an ablative agent, such as steam or vapor through the needle.

FIG. 39 is an illustration of transurethral prostate ablation being performed on an enlarged prostate 3901 in a male urinary system using an ablation device, which makes use of shape changing needles, in accordance with one embodiment of the present specification. Also depicted in FIG. 39 are the urinary bladder 3902 and prostatic urethra 3903. An ablation catheter 3923 with a handle 3920 and a positioning element 3928 is inserted into the urethra 3903 and advanced into the bladder 3902. In one embodiment, the positioning element 3928 is inflated and pulled to the junction of the bladder with the urethra, thus positioning needles 3907a at a predetermined distance from the junction. Using a pusher (not shown) coupled to the handle 3920, the needles 3907a are then pushed out at an angle between 10 and 45 degrees from the catheter 3923 through the urethra 3903 into the prostate 3901. Vapor is administered through a port (not shown) that travels through the shaft of the catheter 3923 and exits from openings 3937 in the needles 3907a into the prostatic tissue, thus ablating the prostatic tissue. According to an embodiment, vapor delivery heats the needles and the needles change shape from substantially straight 3907a to curved in 3907b, while vapor is being delivered. On cessation of vapor delivery, the needles revert back to their original straight shape, which allows for easy retraction into the catheter. The mechanical shape change of needles allows for more effective distribution of the ablative energy within the prostatic tissue.

FIG. 40A is an illustration of one embodiment of a positioning element 4001 of an ablation catheter 4070 with needles 4073 attached to the catheter body. In various embodiments, the positioning element 4001 is an inflatable balloon. The positioning element, or balloon 4001, is inflated to a first volume, thus positioning needles 4073 at a predetermined distance from the bladder neck 4050 and bringing them into contact with the target tissue. In one embodiment, an ablative agent, such as steam or vapor, is delivered to the target tissue through the catheter 4070. Travelling through the shaft 4071 of the catheter, the vapor exits from openings (not shown) in the needles 4073 into the prostatic tissue, thus ablating the prostatic tissue. In one embodiment, the balloon 4001 is capable of being expanded to different sizes. This feature is used, in one embodiment, to progressively or sequentially inflate the balloon 4001 to different sizes, thereby positioning the needles at various fixed distances 4051, 4052 from the bladder neck 4050, allowing for treatment of discrete regions of the prostate tissue. In one embodiment, the predetermined distance at which the balloon may be used to place the needles ranges from 1 mm to 50 mm from the bladder neck.

In another embodiment shown in FIG. 40B, a plurality of inflatable balloons 4011, 4012, 4013 are employed as positioning elements. These balloons may be used to position the needles 4083 at various fixed distances 4061, 4062 from the bladder neck 4060, allowing for treatment of discrete regions of the prostate tissue. It may be noted that any one of the plurality of balloons may be inflated, depending on the region of tissue to be ablated. The balloons may also be ablated in a sequential manner, to allow comprehensive coverage of target tissue. In one embodiment, the number of balloons ranges from one to five.

FIG. 40C illustrates a cross section of the distal tip of a catheter 4091, in accordance with an embodiment of the present specification. In one embodiment, for ablation of prostatic tissue, an inner diameter (ID) of the catheter employed is about 4 mm, and an outer diameter (OD) is about 6 mm. A plurality of thermally conductive elements 4090, such as needles, extend at an angle from the catheter 4091, wherein the angle ranges between 30 to 90 degrees. In one embodiment, the needles may be retracted into the catheter after ablation.

In one embodiment, the balloon is inflated prior to ablation. In another embodiment, the ablative agent, such as steam or vapor also transmits thermal energy and assists in balloon expansion. That is, thermal energy from the ablative agent is transferred from the lumen of the catheter into the air in the balloon, further expanding the volume of the balloon and pushing the needles further into the target tissue. In yet another embodiment, the balloon is inflated by filling it with a coolant that is supplied to the balloon through a coolant port at the proximal end of catheter. During use, the balloon is inflated with the coolant while vapor or steam is delivered through the plurality of needles. Since the needles pierce into the target tissue during use, the steam or vapor delivered through the pierced needles cause ablation of tissue located deep within the target tissue. The coolant filled inflated balloon contacts the surface of the target tissue and maintains the ambient temperature on the surface of the target tissue to a desired level, such as below 60 degrees C. in some embodiments. This enables the vapor to ablate deeper tissue without ablating the tissue at the surface.

FIG. 41 illustrates one embodiment of a handle mechanism 4100 that may be used for deployment and retrieval of needles at variable depths of insertion, when ablating prostatic tissue. Referring to FIG. 41, in one embodiment, the handle 4100 is shaped like a handheld gun or pistol, which allows it to be conveniently operated by a physician for the treatment of prostatic tissue. The tip 4101 of the handle is equipped with a slot, into which an ablation catheter 4102 may be inserted for passing into the urethra of the patient. Ablation needles are coupled to the catheter, as explained in the embodiments above, and are used to deliver steam vapor to target tissue. On the top of the handle 4100, markers 4103 are placed, which indicate the depth of insertion of the needles. The markers may be placed by printing, etching, painting, engraving, or by using any other means known in the art suitable for the purpose. In one embodiment, the ablation needles may be inserted or retracted in increments of a fixed distance—such as 5 mm, and therefore markers are placed correspondingly to reflect the increments. A button 4105 is provided on the markers, which advances or retracts by a mark, each time the catheter and the needles are advanced or retracted by the preset distance. In one embodiment, a trigger 4104 is provided on the handle mechanism, which may be pressed to advance the needles for the preset increment of distance. In one embodiment, once the needles are advanced to the maximum distance by repeatedly pressing the trigger—as indicated by the button 4105 on the markers, further pressing of the trigger results in retraction of the needles, one increment of distance at a time. It may be noted that as explained in the embodiments above, the catheter is also equipped with a positioning element, such as a balloon, which does not allow the catheter and the needles to be advanced beyond a fixed distance in the urethra.

In one embodiment, a knob or a button 4106 is provided which may be turned or pressed to control the direction of movement of the catheter and the needles. That is, the knob 4106 may be used to determine whether the catheter and needles are moved forward (advanced) or backward (retracted), each time the trigger 4104 is pressed.

In one embodiment, the handle mechanism 4100 also comprises a heating chamber 4110, which is used to generate steam or vapor for supplying to the catheter 4102. The heating chamber 4110 comprises a metal coil 4112 wound about a ferromagnetic core. The chamber is filled with water via a water inlet port 4111 located at a proximal end of the handle mechanism 4100. In one embodiment, sterile water is supplied from a water source into the handle for conversion into vapor. The handle is also equipped with an electrical connection 4108 to supply the coil 4112 with electrical current from a current generator. Alternating current is provided to the coil 4112, thereby creating a magnetic field that induces electric current flow in the ferromagnetic core. This causes heating in the chamber 4110 and causes the water within to vaporize. The resulting steam or vapor, generated in the chamber 4110, is delivered through the needles placed at the appropriate location to ablate target tissue.

In an embodiment, a start/stop button 4107 is also provided on the handle 4100 to initiate or stop ablation therapy as required.

FIG. 42A is a flowchart illustrating a method of ablation of prostatic tissue in accordance with one embodiment of the present specification. Referring to FIG. 42A, the first step 4201 includes passing a catheter of an ablation device into a patient's urethra, wherein the catheter includes a hollow shaft through which an ablative agent can travel, at least one first positioning element, at least one second positioning element positioned distal to said at least one first positioning element, at least one input port for receiving an ablative agent, and a plurality of needles positioned on said catheter between said first and second positioning elements and configured to deliver ablative agent to a prostatic tissue. In an embodiment, the ablation device includes a controller comprising a microprocessor for controlling the delivery of the ablative agent. The catheter is passed through the urethra such that the first positioning element is positioned proximal to the prostatic tissue to be ablated and the second positioning element is positioned distal to the prostatic tissue to be ablated. Next, in step 4202, the positioning elements are deployed such that they contact the urethra and the catheter is positioned within the urethra, proximate the prostatic tissue to be ablated. In the next step 4203, the plurality of needles is passed through the urethra into the prostatic tissue to be ablated. Finally, in step 4204, an ablative agent is delivered through the needles to ablate the prostatic tissue. Optionally, a sensor is used to measure a parameter of the prostate in step 4205 and the measurement is used to increase or decrease the flow of ablative agent being delivered in step 4206. Optionally, in an embodiment, a cystoscope is first inserted in the patient's urethra and the catheter is inserted through the cystoscope.

FIG. 42B is a flowchart illustrating a method of ablation of prostatic tissue in accordance with another embodiment of the present specification. Referring to FIG. 42B, the first step 4211 includes passing a catheter into a patient's urethra, wherein the catheter includes a hollow shaft through which an ablative agent can travel, at least one first positioning element, at least one second positioning element positioned distal to said at least one first positioning element, at least one input port for receiving an ablative agent, and a plurality of needles positioned on said catheter between said first and second positioning elements and configured to deliver ablative agent to a prostatic tissue. In an embodiment, the ablation device includes a controller comprising a microprocessor for controlling the delivery of the ablative agent. The catheter is passed through the urethra such that the first positioning element is positioned proximate the prostatic tissue to be ablated and the second positioning element is positioned within the bladder of the patient. Next, in step 4212, the second positioning element is deployed and the catheter is pulled back such that the second positioning element abuts a urethral opening at the neck of the bladder. The first positioning element is deployed such that the catheter is positioned within the urethra proximate to the prostatic tissue to be ablated in 4213. In the next step 4214, the plurality of needles is passed through the urethra into the prostatic tissue to be ablated. Finally, in step 4215, an ablative agent is delivered through the needles to ablate the prostatic tissue. Optionally, in an embodiment, a cystoscope is first inserted in the patient's urethra and the catheter is inserted through the cystoscope. In various embodiments, the order of deployment of the positioning elements can be reversed. In other embodiments, only one of the two positioning elements may be deployed to deliver the therapy.

In various embodiments, ablation therapy provided by the vapor ablation systems of the present specification is delivered to achieve the following therapeutic endpoints for prostate ablation: maintain a tissue temperature at 100° C. or less; improve patient urine flow by at least 5% relative to pre-treatment urine flow; decrease prostate volume by at least 5% relative to pre-treatment prostate volume; ablate the prostate tissue without circumferentially ablating a urethral tissue; improve International Prostate Symptom Score (IPSS) by at least 5% relative to a pre-treatment IPSS score, wherein the IPSS questionnaire, depicted in FIG. 43A, comprises a series of questions 4380 regarding a patient's urinary habits with numerical scores 4381 for each question; improve Benign Prostatic Hypertrophy Impact Index Questionnaire (BPHIIQ) score by at least 10% relative to a pre-treatment BPHIIQ score, wherein the BPHIIQ, depicted in FIG. 43B, comprises a series of questions 4385 regarding a patient's urinary problems with numerical scores 4386 for each question; and patient reported satisfaction with the ablation procedure of greater than 25%.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A catheter adapted to ablate a body tissue comprising:
   an outer balloon integrated into the catheter and having an exterior surface defining an interior volume;
   an inner balloon integrated into the catheter and configured to expand within the interior volume of the outer balloon;
   a first lumen within the catheter and in fluid communication with an interior volume of the inner balloon, wherein the first lumen is configured to direct an ablative agent to the interior volume of the inner balloon and wherein the ablative agent is defined by a first temperature; and
   a second lumen within the catheter and in fluid communication with the interior volume of the outer balloon, wherein the second lumen is configured to direct a fluid to the interior volume of the outer balloon and wherein the fluid is defined by a second temperature that is different from the first temperature, wherein, when said fluid inflates the interior volume of the outer balloon and the ablative agent inflates the interior volume of the inner balloon, an ablative zone is created at an area of contact between said outer balloon and inner balloon such that ablative zone is at a temperature sufficient to ablate the body tissue while portions of said outer balloon excluding said ablative zone remain a temperature different from the ablative zone.

2. The catheter of claim 1, wherein the ablative agent comprises at least one of water vapor or steam.

3. The catheter of claim 1, wherein the fluid comprises at least one of water or air.

4. The catheter of claim 1, wherein the inner balloon comprises a first material, the outer balloon comprises a second material, and wherein the first material is more flexible than the second material.

5. The catheter of claim 4, wherein said first material is latex and said second material is PET.

6. The catheter of claim 1, further comprising a first opening or inlet at a proximal end of the catheter and configured to direct the cooling fluid to the second lumen.

7. The catheter of claim 1, further comprising a second opening or inlet at a proximal end of the catheter and configured to direct the fluid out of the catheter.

8. The catheter of claim 1, wherein the outer balloon has a predominantly cylindrical shape when the fluid inflates the interior volume of the outer balloon.

9. The catheter of claim 1, wherein, when the interior volume of the outer balloon is inflated, the outer balloon has a tapered shape at its proximal end and a tapered shape at its distal end.

10. The catheter of claim 9, wherein, when the interior volume of the outer balloon is inflated, a length of a central cylindrical portion of the outer balloon is 60 mm±25 mm, a length of a tapered section at the proximal end 12 mm±10 mm, and a length of a tapered section at the distal end 12 mm±10 mm.

11. The catheter of claim 1, wherein, when the interior volume of the outer balloon is inflated, a width of a central cylindrical portion of said outer balloon is 24 mm±15 mm.

12. The catheter of claim 1, wherein the inner balloon has a spherical shape when inflated with the ablative agent.

13. The catheter of claim 1, wherein the inner balloon further comprises structures at its proximal end and distal end to correctly position the inner balloon in the catheter.

14. The catheter of claim 1, further comprising:
   a first opening positioned at a first location in the catheter and configured to allow the fluid to flow from the second lumen into the outer balloon; and
   at least one second opening positioned at a second location in the catheter and configured to allow saline to flow through the first lumen toward the inner balloon, wherein the first and second locations are different.

15. The catheter of claim 1, wherein a shape of the ablation zone is determined by a shape of the inner balloon when inflated and a shape of the outer balloon when inflated.

16. The catheter of claim 1, wherein a size of the ablation zone is determined by a shape of the inner balloon when inflated and a shape of the outer balloon when inflated.

17. The catheter of claim 1, further comprising a mapping member distal to the outer balloon, wherein the mapping member comprises a plurality of electrodes configured to record cardiac pacing.

18. The catheter of claim 1, wherein the inner balloon is movable along a longitudinal axis of the catheter within and along a length of the outer balloon.

19. The catheter of claim 1, further comprising a plurality of mapping electrodes within or attached to an outer surface of the outer balloon configured to record cardiac signals to map areas of cardiac tissue responsible for an arrhythmia.

20. The catheter of claim 1, further comprising at least one temperature sensor configured to monitor temperature.

* * * * *